United States Patent
Nabel et al.

(10) Patent No.: US 11,617,780 B2
(45) Date of Patent: Apr. 4, 2023

(54) ANTIGENIC EPSTEIN BARR VIRUS POLYPEPTIDES

(71) Applicant: Sanofi, Paris (FR)

(72) Inventors: Gary J. Nabel, Bridgewater, NJ (US);
Chih-Jen Wei, Bridgewater, NJ (US);
Laura Nguyen, Bridgewater, NJ (US);
Kurt Swanson, Bridgewater, NJ (US);
Te-Hui Chou, Bridgewater, NJ (US);
Stefan Koester, Bridgewater, NJ (US)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 17/061,146

(22) Filed: Oct. 1, 2020

(65) Prior Publication Data
US 2021/0015896 A1   Jan. 21, 2021

Related U.S. Application Data

(63) Continuation of application No. PCT/US2019/025419, filed on Apr. 2, 2019.

(60) Provisional application No. 62/652,201, filed on Apr. 3, 2018.

(51) Int. Cl.
| | |
|---|---|
| *A61K 39/245* | (2006.01) |
| *A61K 39/12* | (2006.01) |
| *C07K 14/05* | (2006.01) |
| *A61K 38/16* | (2006.01) |
| *A61K 47/00* | (2006.01) |

(52) U.S. Cl.
CPC ............ *A61K 38/162* (2013.01); *A61K 47/00* (2013.01); *C07K 14/05* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,406,705 B1 | 6/2002 | Davis et al. | |
| 6,429,199 B1 | 8/2002 | Krieg et al. | |
| 8,562,996 B2 | 10/2013 | Spits et al. | |
| 9,703,095 B2 | 7/2017 | Pakhchyan | |
| 10,961,283 B2 * | 3/2021 | Kwong | C07K 14/11 |
| 2014/0072958 A1 | 3/2014 | Nabel et al. | |
| 2014/0348865 A1 | 11/2014 | Kwong et al. | |
| 2016/0303224 A1 | 10/2016 | Kanekiyo et al. | |
| 2020/0282047 A1 * | 9/2020 | Ciaramella | A61P 31/22 |

FOREIGN PATENT DOCUMENTS

| | | |
|---|---|---|
| WO | 2002016421 A2 | 2/2002 |
| WO | 2011143623 A1 | 11/2011 |
| WO | 2012006180 A1 | 1/2012 |
| WO | 2013039792 A1 | 3/2013 |
| WO | 2013044203 A2 | 3/2013 |
| WO | 2014018858 A2 | 1/2014 |
| WO | 2014160463 A1 | 10/2014 |
| WO | 2015054639 A1 | 4/2015 |
| WO | 2015169271 A1 | 11/2015 |
| WO | 2015183969 A1 | 12/2015 |
| WO | 2016138160 A1 | 9/2016 |
| WO | 2017172890 A1 | 10/2017 |
| WO | 2017211886 A1 | 12/2017 |
| WO | 2017218819 A1 | 12/2017 |
| WO | 2018005558 A1 | 1/2018 |
| WO | 2019195276 A1 | 10/2019 |
| WO | 2019195284 A1 | 10/2019 |
| WO | 2019195291 A1 | 10/2019 |
| WO | 2019195314 A2 | 10/2019 |
| WO | 2019195316 A1 | 10/2019 |

OTHER PUBLICATIONS

Alvarez-Cienfuegos et al., "Intramolecular trimerization, a novel strategy for making multispecific antibodies with controlled orientation of the antigen binding domains", Scientific Reports 2016; 6:28643 (Jun. 2016).
Aslam et al., "The accuracy of protein structure alignment servers", Electronic Journal of Biotechnology, 20, pp. 9-13 (2016).
Bordoli et al., "Protein structure homology modeling using SWISS-MODEL workspace", Nature Protocols, 4(1), pp. 1-13 (2009).
Bu et al., "Immunization with Components of the Viral Fusion Apparatus Elicits Antibodies That Neutralize Epstein-Barr Virus in B Cells and Epithelial Cells", Immunity, 50, pp. 1305-1316 (2019).
Carter et al., "Design and Characterization of a Computationally Optimized Broadly Reactive Hemagglutinin Vaccine tor H1N1 Influenza Viruses", J Virol, 90(9), pp. 4720-4734 (May 1, 2016).
Chapter 4 of Holtzhauer, M., Basic Methods for the Biochemical Lab, Springer 2006, ISBN 978-3-540-32785-1, available from www.springer.com.
Cui et al., "Rabbits immunized with Epstein-Barr virus gH/gL or gB recombinant proteins elicit higher serum virus neutralizing activity than gp350" Vaccine, 34(34), pp. 4050-4055 (Jul. 25, 2016).
Danilchanka et al., "Cyclic Dinucleotides and the Innate Immune Response", Cell, 154, pp. 962-970 (Aug. 29, 2013).
DiLillo et al, "Broadly neutralizing hemagglutinin stalk-specific antibodies require FcγR interactions for protection against influenza virus in vivo". Nature Medicine 20(2), pp. 143-151 (2014).
Faloon et al., "An Adjuvanted, Postfusion F Protein-Based Vaccine Did Not Prevent Respiratory Syncytial Virus Illness in Older Adults", J Infect Dis., 216, pp. 1362-1370 (Dec. 1, 2017).
Gaydos et al., "Swine Influenza A Outbreak, Fort Dix, New Jersey, 1976", Emerg Infect Dis, 12(1), pp. 23-28 (1976).
GenBank Accession Nos. CEQ35765.1 (Sep. 24, 2015) (2 pages).
GenBank Accession Nos. YP_001129472.1 (Aug. 13, 2018) (2 pages).

(Continued)

*Primary Examiner* — Nianxiang Zou
(74) *Attorney, Agent, or Firm* — McNeill Baur PLLC

(57) ABSTRACT

This disclosure relates to antigenic EBV polypeptides and their use in eliciting antibodies against EBV. Also disclosed are antigenic polypeptides comprising an EBV polypeptide and a ferritin protein.

17 Claims, 58 Drawing Sheets

Specification includes a Sequence Listing.

(56) References Cited

OTHER PUBLICATIONS

Gomes et al., "Harnessing Nanoparticles for Immunomodulation and Vaccines", Vaccines, 5(1), p. 6, (Feb. 14, 2017).
Gross et al., "Identification of LFA-1 as a candidate autoantigen in treatment-resistant Lyme arthritis", Science, 281(5377), pp. 703-706 (1998).
Hein et al., "Click Chemistry, a Powerful Tool for Pharmaceutical Sciences", Pharm Res, 25(10), pp. 2216-2230 (Oct. 2008).
Hu et al., "Towards the next generation of biomedicines by site-selective conjugation", Chemical Society Reviews, 45(6), pp. 1691-1719 (Mar. 21, 2016).
Hurwitz, J., "Respiratory syncytial virus vaccine development", Expert Rev Vaccines, 10(10), pp. 1415-1433 (Oct. 2011).
International Search Report issued in PCT Application No. PCT/US2019/025422 dated Sep. 4, 2019 (8 pages).
Kanekiyo et al., "Rational Design of an Epstein-Barr Virus Vaccine Targeting the Receptor-Binding Site", CELL, 162(5), pp. 1090-1100 (Aug. 27, 2015).
Kanekiyo et al., "Self-assembling influenza nanoparticle vaccines elicit broadly neutralizing H1N1 antibodies", Nature, 499(7456), pp. 102-106 (Jul. 4, 2013).
Khazina et al., "Non-LTR retrotransposons encode noncanonical RRMdomains in their first open reading frame", Proc Natl Acad Sci U S A; 106(3), pp. 731-736 (Jan. 20, 2009).
Kim et al., "Efficient Site-Specific Labeling of Proteins via Cysteines", Bioconjugate Chemistry, 19(3), pp. 786-791 (Mar. 1, 2008).
Kitahara, et al., "A Delicate Interplay of Structure, Dynamics, and Thermodynamics for Function: A High Pressure NMR Study of Outer Surface Protein A", Biophys J 102(4), pp. 916-926 (2012).
Klucker et al., "AF03, An Alternative Squalene Emulsion-Based Vaccine Adjuvant Prepared by a Phase Inversion Temperature Method", J Pharm Sci., 101(12), pp. 4490-4500 (Dec. 2012).
Lander, et al., "Appion: an integrated, database-driven pipeline to facilitate EM image processing", J Struct Biol, 166(1), pp. 95-102 (2009).
Li et al., "Ferritin nanoparticle technology . . . A new platform for antigen presentation and vaccine development", Industrial Biotechnology, 2(2), pp. 143-147 (Jul. 17, 2006).
Livey et al., "A New Approach to a Lyme Disease Vaccine", Clinical Infectious Diseases, vol. 52, Supplement 3, pp. S266-S270 (Feb. 1, 2011).
Lopez-Sagaseta et al., "Self-assembling protein nanoparticles in the design of vaccines", Computational and Structural Biotechnology Journal, vol. 14, pp. 58-68 (Jan. 1, 2016).
Lynn et al., "In vivo characterization of the physicochemical properties of polymer-linked TLR agonists that enhance vaccine immunogenicity", Nat Biotechnol, 33(11), pp. 1201-1210 (Nov. 2015).
McLellan et al., "Structure-Based Design of a Fusion Glycoprotein Vaccine for Respiratory Syncytial Virus", Science, 342(6158), pp. 592-598 (Nov. 1, 2013).
McLellan et al., "Structure of RSV Fusion Glycoprotein Trimer Bound to a Prefusion-Specific Neutralizing Antibody", Science, 340(6136), pp. 1113-1117 (2013).
McLellan, et al., "Structure of Respiratory Syncytial Virus Fusion Glycoprotein in the Postfusion Conformation Reveals Preservation of Neutralizing Epitopes", J Virol 85(15), pp. 7788-7796 (2011).
Notification of Transmittal of the International Search Report and the Written Opinion of The International Searching Authority, or the Declaration, issued in PCT Application No. PCT/US2019/025377 dated Jul. 10, 2019 (16 pages).
Notification of Transmittal of the International Search Report and the Written Opinion of The International Searching Authority, or the Declaration, issued in PCT Application No. PCT/US2019/025387 dated Jul. 9, 2019 (20 pages).
Notification of Transmittal of the International Search Report and the Written Opinion of The International Searching Authority, or the Declaration, issued in PCT Application No. PCT/US2019/025419 dated Oct. 18, 2019 (21 pages).
Notification of Transmittal of the International Search Report and the Written Opinion of The International Searching Authority, or the Declaration, issued in PCT Application No. PCT/US2019/025367 dated Jul. 9, 2019 (20 pages).
Perez et al., "Novel Epstein-Barr virus-like particles incorporating gH/gL-EBNA1 or gB-LMP2 induce high neutralizing antibody titers and EBV-specific T-cell responses in immunized mice", ONCOTARGET, 8(12), (Mar. 21, 2017).
Ra et al., "Lumazine synthase protein cage nanoparticles as antigen delivery nanoplatforms for dendritic cell-based vaccine development", Clin Exp Vaccine Res, 3, pp. 227-234 (2014).
Rosa et al. "The burgeoning molecular genetics of the Lyme disease spirochaete", Nat Rev Microbiol 3(2), pp. 129-143 (2005).
Sashihara et al., "Human Antibody Titers to Epstein-Barr Virus (EBV) gp350 Correlate with Neutralization of Infectivity Better than Antibody Titers to EBV gp42 Using a Rapid Flow Cytometry-Based EBV Neutralization Assay", Virology, 391(2), pp. 249-256 (Sep. 1, 2009).
Sliepen et al., "Presenting native-like HIV-1 envelope trimers on ferritin nanoparticles improves their immunogenicity", Retrovirology, 11(1), p. e1004767 (Sep. 26, 2015).
Sorzano et al., XMIPP: a new generation of an open-source image processing package for electron microscopy, J Struct Biol, 148(2), pp. 194-204 (2004).
Steff et al., "Pre-fusion RSV F strongly boosts pre-fusion specific neutralizing responses in cattle pre-exposed to bovine RSV", Nature Communications, 8(1) (Oct. 20, 2017) (abstract).
Swanson et al., "Structural basis for immunization with postfusion respiratory syncytial virus fusion F glycoprotein (RSV F) to elicit high neutralizing antibody titers", Proc Natl Acad Sci, 108(23), pp. 9619-9624 (2011).
Trikha, J., et al. "High Resolution Crystal Structures of Amphibian Red-Cell L Ferritin: Potential Roles for Structural Plasticity and Solvation in Function", J Mol Biol, 248(5), pp. 949-967 (1995).
Tripp et al., "Respiratory Syncytial Virus: Targeting the G Protein Provides a New Approach for an Old Problem", Journal of Virology, 92(3), pp. 1-8 (Nov. 8, 2017).
Uchida et al., "Targeting of Cancer Cells with Ferrimagnetic Ferritin Cage Nanoparticles", Journal of the American Chemical Society, 128(51), pp. 16626-16633 (Dec. 1, 2006).
Van Geel et al., "Chemoenzymatic Conjugation of Toxic Payloads to the Globally Conserved N-Glycan of Native mAbs Provides Homogeneous and Highly Efficacious Antibody—Drug Conjugates", Bioconjugate Chem., 26, pp. 2233-2242 (2015).
Wang et al., "Functional ferritin nanoparticles for biomedical applications", Frontiers of Chemical Science and Engineering, 11(4), pp. 633-646 (Feb. 15, 2017).
Wille-Reece et al., "HIV Gag protein conjugated to a Toll-like receptor 7/8 agonist improves the magnitude and quality of Th1 and CD8+ T cell responses in nonhuman primates", Proc Natl Acad Sci, 102(42), pp. 15190-15194 (2005).
Wilske et al., "An OspA Serotyping System for Borrelia burgdorferi Based on Reactivity with Monoclonal Antibodies and OspA Sequence Analysis", J Clin Microbio, 31(2), pp. 340-350 (1993).
Wressnigg et al., "A Novel Multivalent OspA Vaccine against Lyme Borreliosis Is Safe and Immunogenic in an Adult Population Previously Infected with Borrelia burgdorferi Sensu Lato", Clinical and Vaccine Immunology, 21(11), pp. 1490-1499 (Nov. 2014).
Written Opinion of the International Searching Authority issued in PCT Application No. PCT/US2019/025422 dated Sep. 4, 2019 (13 pages).
Wu, Tom Y.-H., "Strategies for designing synthetic immune agonists", Immunology, 148(4), pp. 315-325 (Jul. 11, 2016).
Xu et al., "Trispecific broadly neutralizing HIV antibodies mediate potent SHIV protection in macaques", Science 358(6359), pp. 85-90 (2017).
Yassine et al., "Hemagglutinin-stem nanoparticles generate heterosubtypic influenza protection", Nature Medicine 21(9), pp. 1065-1071 (2015).
Zhang et al., "Challenges of glycosylation analysis and control: an integrated approach to producing optimal and consistent therapeutic drugs", Drug Discovery Today, 21(5), pp. 740-765 (May 2016).

(56) References Cited

OTHER PUBLICATIONS

Lawson et al., "Solving the structure of human H ferritin by genetically engineering intermolecular crystal contacts", Nature, 349, pp. 541-544 (1991).

* cited by examiner

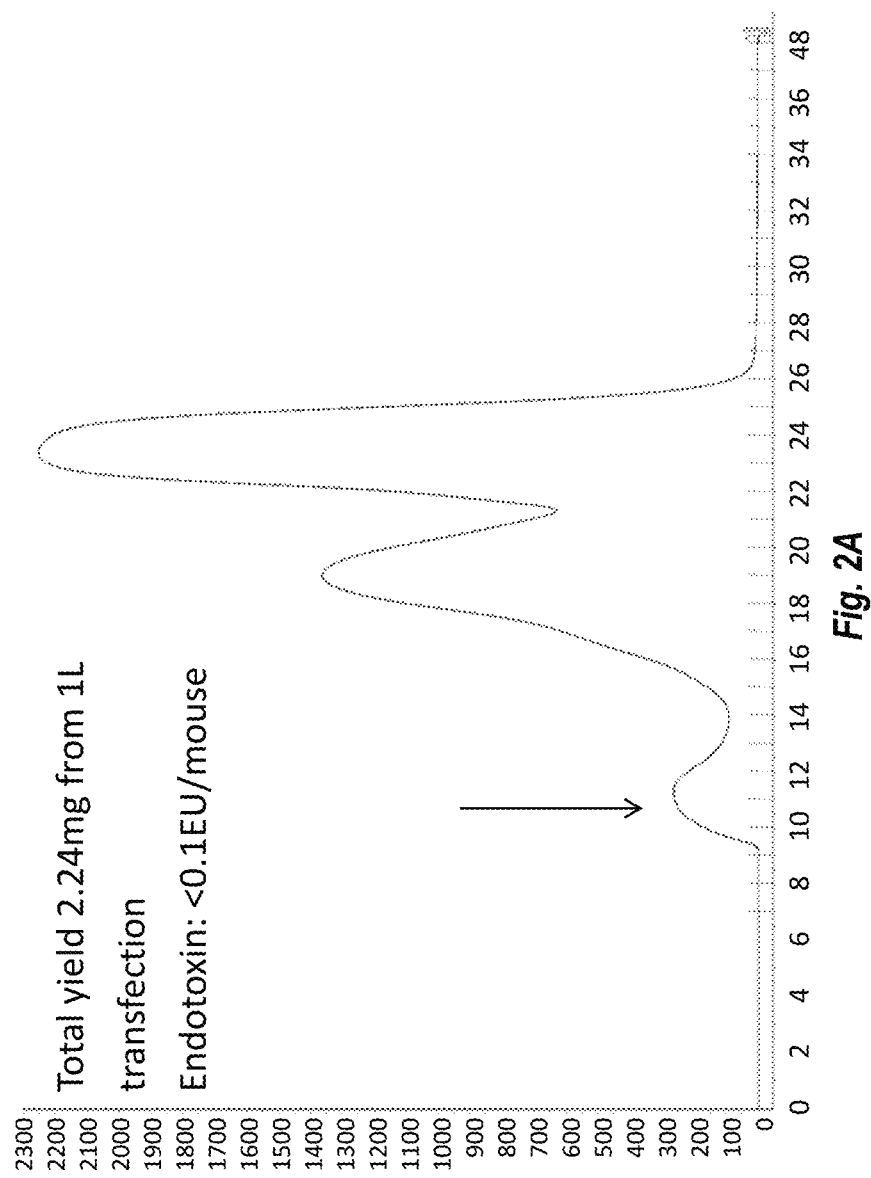

Negative stain EM image of gL and gH nanoparticle

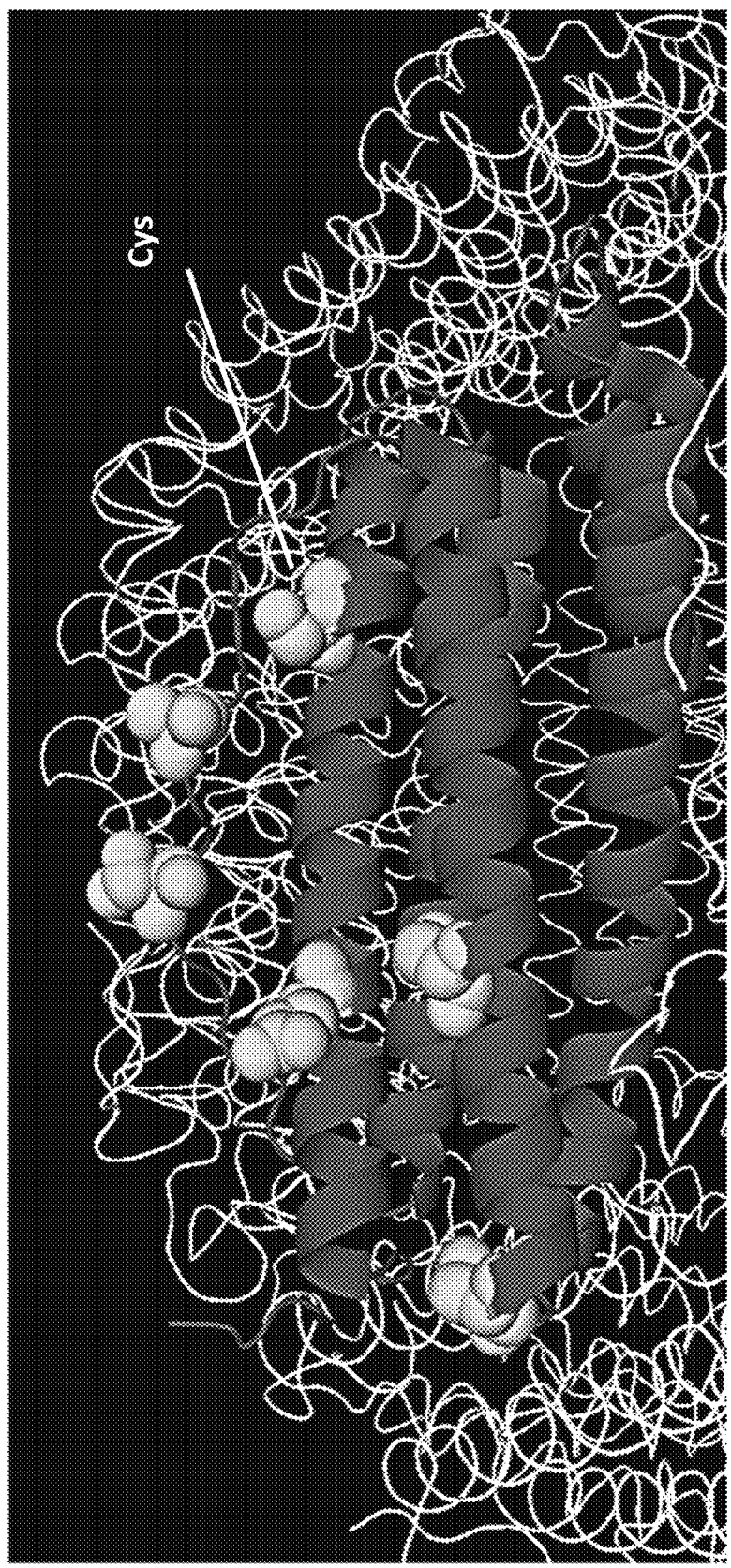

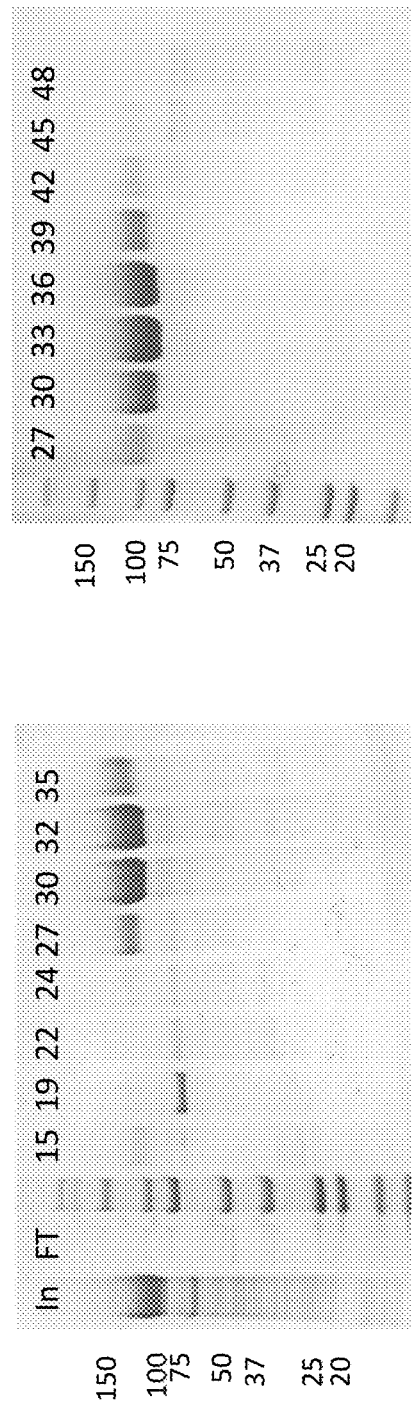
*Fig. 24D*
*Fig. 24C*
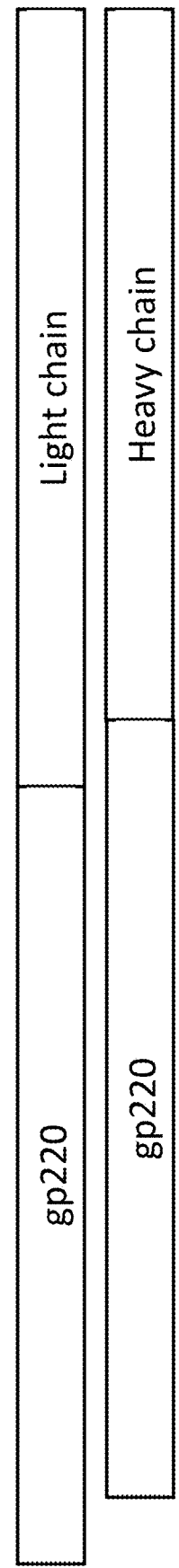
*Fig. 24E*

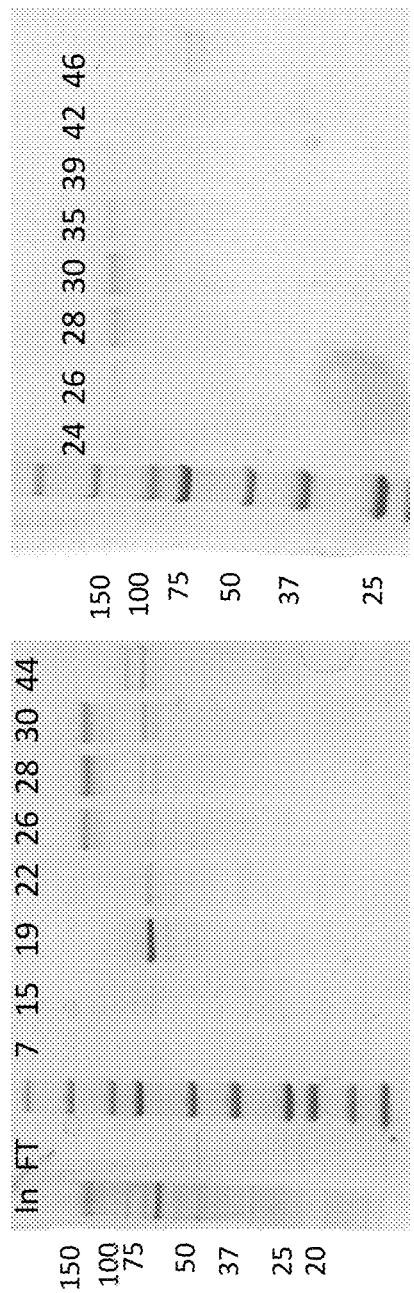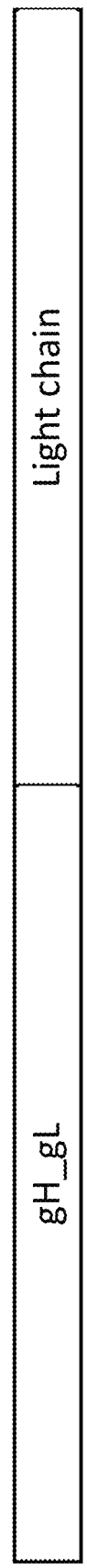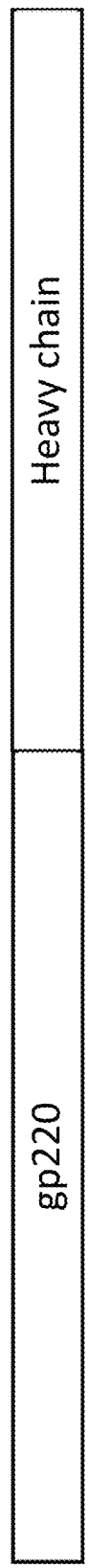
Fig. 25C
Fig. 25D
Fig. 25E

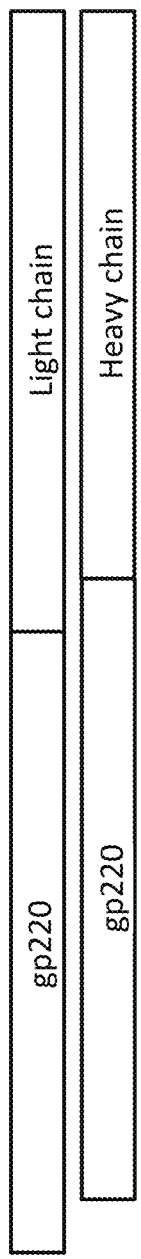
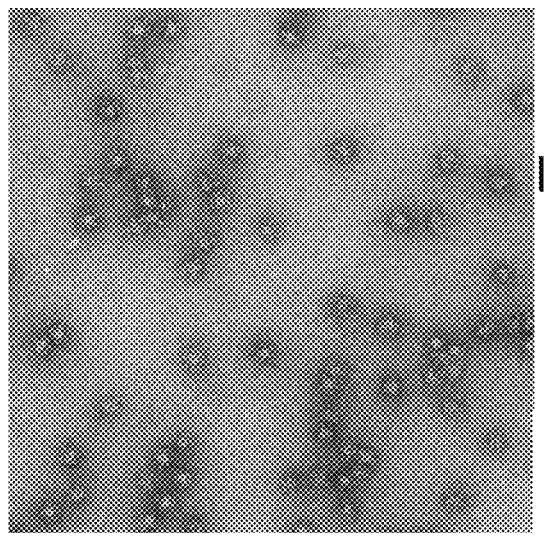
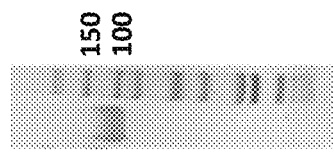
Fig. 26A
Fig. 26B
Fig. 26C

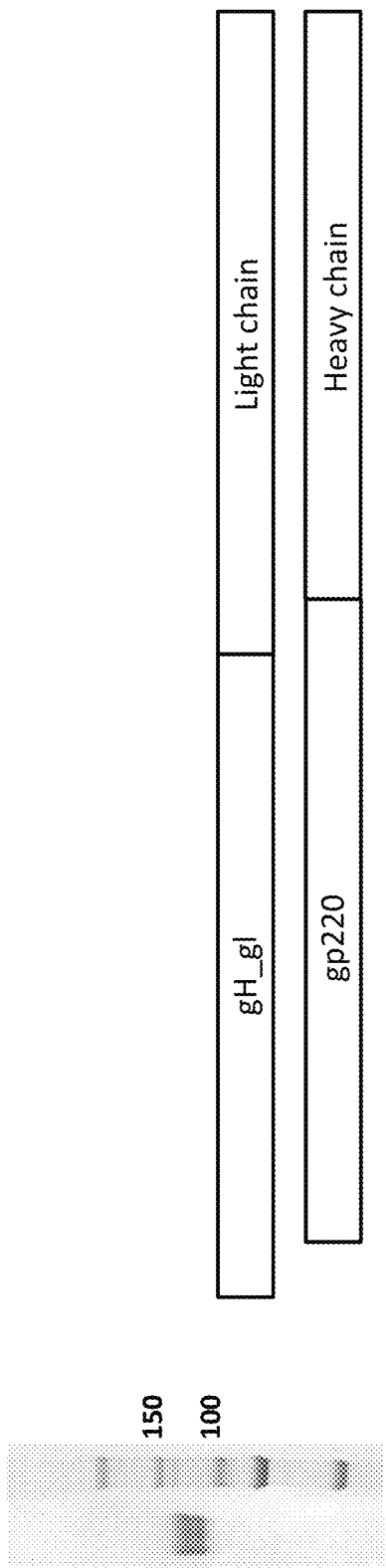
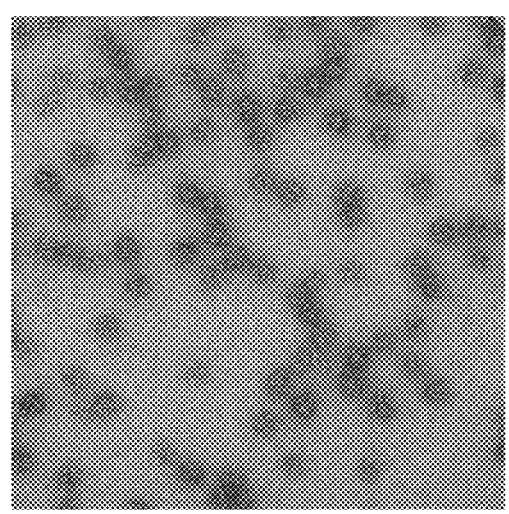
Fig. 26E
Fig. 26F
Fig. 26G

Ferret sera binding to gHgL monomer

*Fig. 30C*

Ferret sera binding to gp220 monomer

*Fig. 30D*

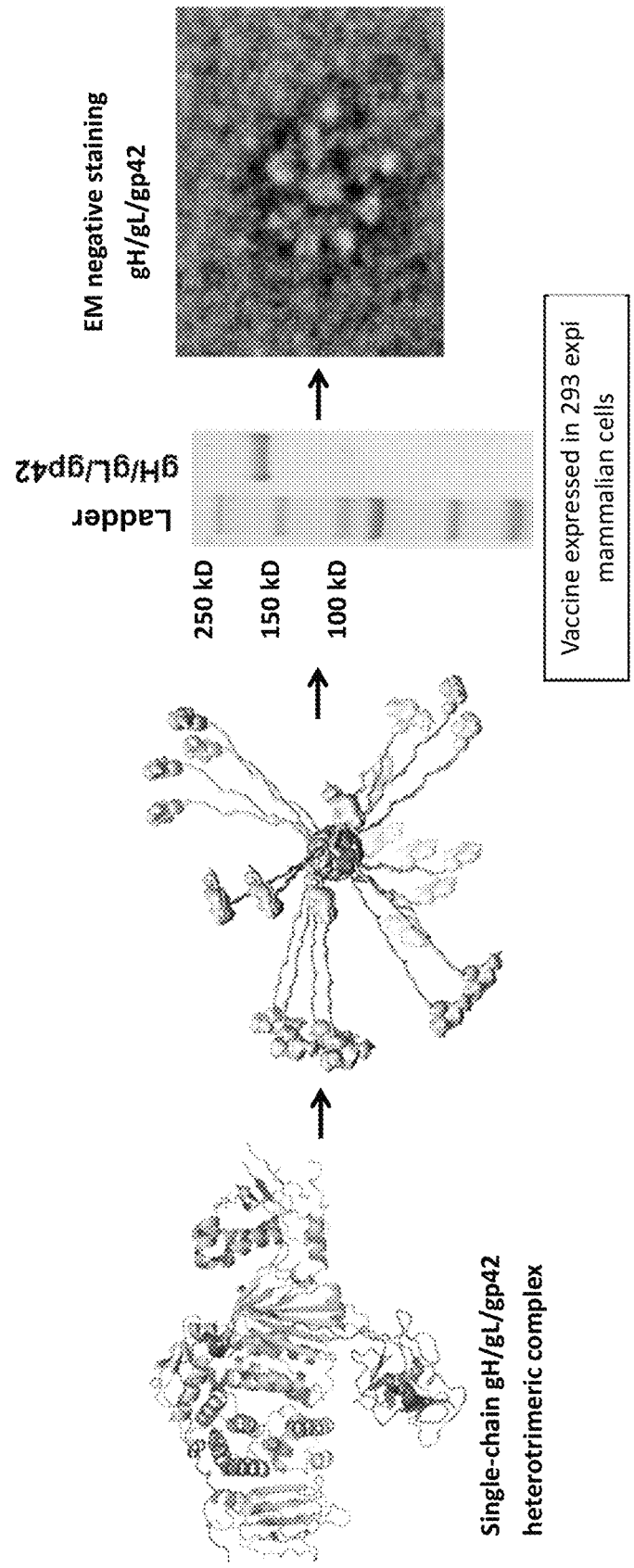
Fig. 35A
Fig. 35B
Fig. 35C
Fig. 35D
Fig. 35E

SEQUENCE LISTING

```
<160> NUMBER OF SEQ ID NOS: 247

<210> SEQ ID NO 1
<211> LENGTH: 630
<212> TYPE: PRT
<213> ORGANISM: Artificial Sequence
```

<220> FEATURE:
<223> OTHER INFORMATION: Synthetic polypeptide

<400> SEQUENCE: 1

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Glu Ala
            20                  25                  30

Ala Leu Leu Val Cys Gln Tyr Thr Ile Gln Ser Leu Ile His Leu Thr
        35                  40                  45

Gly Glu Asp Pro Gly Phe Phe Asn Val Glu Ile Pro Glu Phe Pro Phe
50                  55                  60

Tyr Pro Thr Cys Asn Val Cys Thr Ala Asp Val Asn Val Thr Ile Asn
65                  70                  75                  80

Phe Asp Val Gly Gly Lys Lys His Gln Leu Asp Leu Asp Phe Gly Gln
                85                  90                  95

Leu Thr Pro His Thr Lys Ala Val Tyr Gln Pro Arg Gly Ala Phe Gly
            100                 105                 110

Gly Ser Glu Asn Ala Thr Asn Leu Phe Leu Leu Glu Leu Leu Gly Ala
        115                 120                 125

Gly Glu Leu Ala Leu Thr Met Arg Ser Lys Lys Leu Pro Ile Asn Val
130                 135                 140

Thr Thr Gly Glu Glu Gln Gln Val Ser Leu Glu Ser Val Asp Val Tyr
145                 150                 155                 160

Phe Gln Asp Val Phe Gly Thr Met Trp Cys His His Ala Glu Met Gln
                165                 170                 175

Asn Pro Val Tyr Leu Ile Pro Glu Thr Val Pro Tyr Ile Lys Trp Asp
            180                 185                 190

Asn Cys Asn Ser Thr Asn Ile Thr Ala Val Val Arg Ala Gln Gly Leu
        195                 200                 205

Asp Val Thr Leu Pro Leu Ser Leu Pro Thr Ser Ala Gln Asp Ser Asn
210                 215                 220

Phe Ser Val Lys Thr Glu Met Leu Gly Asn Glu Ile Asp Ile Glu Cys
225                 230                 235                 240

Ile Met Glu Asp Gly Glu Ile Ser Gln Val Leu Pro Gly Asp Asn Lys
                245                 250                 255

Phe Asn Ile Thr Cys Ser Gly Tyr Glu Ser His Val Pro Ser Gly Gly
            260                 265                 270

Ile Leu Thr Ser Thr Ser Pro Val Ala Thr Pro Ile Pro Gly Thr Gly
        275                 280                 285

Tyr Ala Tyr Ser Leu Arg Leu Thr Pro Arg Pro Val Ser Arg Phe Leu
290                 295                 300

Gly Asn Asn Ser Ile Leu Tyr Val Phe Tyr Ser Gly Asn Gly Pro Lys
305                 310                 315                 320

Ala Ser Gly Gly Asp Tyr Cys Ile Gln Ser Asn Ile Val Phe Ser Asp
            325                 330                 335

Glu Ile Pro Ala Ser Gln Asp Met Pro Thr Asn Thr Thr Asp Ile Thr
        340                 345                 350

Tyr Val Gly Asp Asn Ala Thr Tyr Ser Val Pro Met Val Thr Ser Glu
            355                 360                 365

Asp Ala Asn Ser Pro Asn Val Thr Val Thr Ala Phe Trp Ala Trp Pro
370                 375                 380

Asn Asn Thr Glu Thr Asp Phe Lys Cys Lys Trp Thr Leu Thr Ser Gly
385                 390                 395                 400

```
Thr Pro Ser Gly Cys Glu Asn Ile Ser Gly Ala Phe Ala Ser Asn Arg
            405                 410                 415

Thr Phe Asp Ile Thr Val Ser Gly Leu Gly Thr Ala Pro Lys Thr Leu
            420                 425                 430

Ile Ile Thr Arg Thr Ala Thr Asn Ala Thr Thr Thr His Lys Val
            435                 440                 445

Ile Phe Ser Lys Ala Pro Glu Gly Ser Glu Ser Gln Val Arg Gln Gln
450                 455                 460

Phe Ser Lys Asp Ile Glu Lys Leu Leu Asn Glu Gln Val Asn Lys Glu
465                 470                 475                 480

Met Gln Ser Ser Asn Leu Tyr Met Ser Met Ser Trp Ser Tyr Thr
            485                 490                 495

His Ser Leu Asp Gly Ala Gly Leu Phe Leu Phe Asp His Ala Ala Glu
            500                 505                 510

Glu Tyr Glu His Ala Lys Lys Leu Ile Ile Phe Leu Asn Glu Asn Asn
            515                 520                 525

Val Pro Val Gln Leu Thr Ser Ile Ser Ala Pro Glu His Lys Phe Glu
            530                 535                 540

Gly Leu Thr Gln Ile Phe Gln Lys Ala Tyr Glu His Glu Gln His Ile
545                 550                 555                 560

Ser Glu Ser Ile Asn Asn Ile Val Asp His Ala Ile Lys Cys Lys Asp
                565                 570                 575

His Ala Thr Phe Asn Phe Leu Gln Trp Tyr Val Ala Glu Gln His Glu
            580                 585                 590

Glu Glu Val Leu Phe Lys Asp Ile Leu Asp Lys Ile Glu Leu Ile Gly
                595                 600                 605

Asn Glu Asn His Gly Leu Tyr Leu Ala Asp Gln Tyr Val Lys Gly Ile
            610                 615                 620

Ala Lys Ser Arg Lys Ser
625                 630

<210> SEQ ID NO 2
<211> LENGTH: 1032
<212> TYPE: PRT
<213> ORGANISM: Artificial Sequence
<220> FEATURE:
<223> OTHER INFORMATION: Synthetic polypeptide

<400> SEQUENCE: 2

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125
```

```
Asn Arg Gly Gly Ser Gly Ser Ala Ser Ser Gly Ala Ser Ala Ser Gly
    130                 135                 140

Ser Ser Asn Gly Ser Gly Ser Gly Ser Gly Ser Asn Ser Ser Ala Ser
145                 150                 155                 160

Ser Gly Ala Ser Ser Gly Gly Ala Ser Gly Gly Ser Gly Gly Ser Gly
                165                 170                 175

Ala Ala Ser Leu Ser Glu Val Lys Leu His Leu Asp Ile Glu Gly His
            180                 185                 190

Ala Ser His Tyr Thr Ile Pro Trp Thr Glu Leu Met Ala Lys Val Pro
        195                 200                 205

Gly Leu Ser Pro Glu Ala Leu Trp Arg Glu Ala Asn Val Thr Glu Asp
    210                 215                 220

Leu Ala Ser Met Leu Asn Arg Tyr Lys Leu Ile Tyr Lys Thr Ser Gly
225                 230                 235                 240

Thr Leu Gly Ile Ala Leu Ala Glu Pro Val Asp Ile Pro Ala Val Ser
                245                 250                 255

Glu Gly Ser Met Gln Val Asp Ala Ser Lys Val His Pro Gly Val Ile
            260                 265                 270

Ser Gly Leu Asn Ser Pro Ala Cys Met Leu Ser Ala Pro Leu Glu Lys
        275                 280                 285

Gln Leu Phe Tyr Tyr Ile Gly Thr Met Leu Pro Asn Thr Arg Pro His
    290                 295                 300

Ser Tyr Val Phe Tyr Gln Leu Arg Cys His Leu Ser Tyr Val Ala Leu
305                 310                 315                 320

Ser Ile Asn Gly Asp Lys Phe Gln Tyr Thr Gly Ala Met Thr Ser Lys
                325                 330                 335

Phe Leu Met Gly Thr Tyr Lys Arg Val Thr Glu Lys Gly Asp Glu His
            340                 345                 350

Val Leu Ser Leu Val Phe Gly Lys Thr Lys Asp Leu Pro Asp Leu Arg
        355                 360                 365

Gly Pro Phe Ser Tyr Pro Ser Leu Thr Ser Ala Gln Ser Gly Asp Tyr
    370                 375                 380

Ser Leu Val Ile Val Thr Thr Phe Val His Tyr Ala Asn Phe His Asn
385                 390                 395                 400

Tyr Phe Val Pro Asn Leu Lys Asp Met Phe Ser Arg Ala Val Thr Met
                405                 410                 415

Thr Ala Ala Ser Tyr Ala Arg Tyr Val Leu Gln Lys Leu Val Leu Leu
            420                 425                 430

Glu Met Lys Gly Gly Cys Arg Glu Pro Glu Leu Asp Thr Glu Thr Leu
        435                 440                 445

Thr Thr Met Phe Glu Val Ser Val Ala Phe Phe Lys Val Gly His Ala
    450                 455                 460

Val Gly Glu Thr Gly Asn Gly Cys Val Asp Leu Arg Trp Leu Ala Lys
465                 470                 475                 480

Ser Phe Phe Glu Leu Thr Val Leu Lys Asp Ile Ile Gly Ile Cys Tyr
                485                 490                 495

Gly Ala Thr Val Lys Gly Met Gln Ser Tyr Gly Leu Glu Arg Leu Ala
            500                 505                 510

Ala Met Leu Met Ala Thr Val Lys Met Glu Glu Leu Gly His Leu Thr
        515                 520                 525

Thr Glu Lys Gln Glu Tyr Ala Leu Arg Leu Ala Thr Val Gly Tyr Pro
    530                 535                 540
```

-continued

Lys Ala Gly Val Tyr Ser Gly Leu Ile Gly Ala Thr Ser Val Leu
545                 550                 555                 560

Leu Ser Ala Tyr Asn Arg His Pro Leu Phe Gln Pro Leu His Thr Val
            565                 570                 575

Met Arg Glu Thr Leu Phe Ile Gly Ser His Val Val Leu Arg Glu Leu
        580                 585                 590

Arg Leu Asn Val Thr Thr Gln Gly Pro Asn Leu Ala Leu Tyr Gln Leu
    595                 600                 605

Leu Ser Thr Ala Leu Cys Ser Ala Leu Glu Ile Gly Glu Val Leu Arg
610                 615                 620

Gly Leu Ala Leu Gly Thr Glu Ser Gly Leu Phe Ser Pro Cys Tyr Leu
625                 630                 635                 640

Ser Leu Arg Phe Asp Leu Thr Arg Asp Lys Leu Leu Ser Met Ala Pro
            645                 650                 655

Gln Glu Ala Thr Leu Asp Gln Ala Ala Val Ser Asn Ala Val Asp Gly
        660                 665                 670

Phe Leu Gly Arg Leu Ser Leu Glu Arg Glu Asp Arg Asp Ala Trp His
    675                 680                 685

Leu Pro Ala Tyr Lys Cys Val Asp Arg Leu Asp Lys Val Leu Met Ile
690                 695                 700

Ile Pro Leu Ile Asn Val Thr Phe Ile Ile Ser Ser Asp Arg Glu Val
705                 710                 715                 720

Arg Gly Ser Ala Leu Tyr Glu Ala Ser Thr Thr Tyr Leu Ser Ser Ser
            725                 730                 735

Leu Phe Leu Ser Pro Val Ile Met Asn Lys Cys Ser Gln Gly Ala Val
        740                 745                 750

Ala Gly Glu Pro Arg Gln Ile Pro Lys Ile Gln Asn Phe Thr Arg Thr
    755                 760                 765

Gln Lys Ser Cys Ile Phe Cys Gly Phe Ala Leu Leu Ser Tyr Asp Glu
770                 775                 780

Lys Glu Gly Leu Glu Thr Thr Thr Tyr Ile Thr Ser Gln Glu Val Gln
785                 790                 795                 800

Asn Ser Ile Leu Ser Ser Asn Tyr Phe Asp Phe Asp Asn Leu His Val
            805                 810                 815

His Tyr Leu Leu Leu Thr Thr Asn Gly Thr Val Met Glu Ile Ala Gly
        820                 825                 830

Leu Tyr Glu Glu Arg Ala Ser Gly Gly Ser Gly Gly Ser Gly
    835                 840                 845

Gly Gly Ser Gly Gly Ser Gly Gly Gly Ser Glu Ser Gln Val Arg
850                 855                 860

Gln Gln Phe Ser Lys Asp Ile Glu Lys Leu Leu Asn Glu Gln Val Asn
865                 870                 875                 880

Lys Glu Met Gln Ser Ser Asn Leu Tyr Met Ser Met Ser Ser Trp Ser
            885                 890                 895

Tyr Thr His Ser Leu Asp Gly Ala Gly Leu Phe Leu Phe Asp His Ala
        900                 905                 910

Ala Glu Glu Tyr Glu His Ala Lys Lys Leu Ile Ile Phe Leu Asn Glu
    915                 920                 925

Asn Asn Val Pro Val Gln Leu Thr Ser Ile Ser Ala Pro Glu His Lys
930                 935                 940

Phe Glu Gly Leu Thr Gln Ile Phe Gln Lys Ala Tyr Glu His Glu Gln
945                 950                 955                 960

His Ile Ser Glu Ser Ile Asn Asn Ile Val Asp His Ala Ile Lys Cys

-continued

```
                965                 970                 975
Lys Asp His Ala Thr Phe Asn Phe Leu Gln Trp Tyr Val Ala Glu Gln
            980                 985                 990

His Glu Glu Val Leu Phe Lys Asp Ile Leu Asp Lys Ile Glu Leu
        995                 1000                1005

Ile Gly Asn Glu Asn His Gly Leu Tyr Leu Ala Asp Gln Tyr Val
    1010                1015                1020

Lys Gly Ile Ala Lys Ser Arg Lys Ser
    1025                1030

<210> SEQ ID NO 3
<211> LENGTH: 1001
<212> TYPE: PRT
<213> ORGANISM: Artificial Sequence
<220> FEATURE:
<223> OTHER INFORMATION: Synthetic polypeptide

<400> SEQUENCE: 3

Met Glu Thr Asp Thr Leu Leu Leu Trp Val Leu Leu Leu Trp Val Pro
1               5                   10                  15

Gly Ser Thr Gly Asn Trp Ala Tyr Pro Cys Cys His Val Thr Gln Leu
            20                  25                  30

Arg Ala Gln His Leu Leu Ala Leu Glu Asn Ile Ser Asp Ile Tyr Leu
        35                  40                  45

Val Ser Asn Gln Thr Cys Asp Gly Phe Ser Leu Ala Ser Leu Asn Ser
    50                  55                  60

Pro Lys Asn Gly Ser Asn Gln Leu Val Ile Ser Arg Cys Ala Asn Gly
65                  70                  75                  80

Leu Asn Val Val Ser Phe Phe Ile Ser Ile Leu Lys Arg Ser Ser Ser
                85                  90                  95

Ala Leu Thr Gly His Leu Arg Glu Leu Leu Thr Thr Leu Glu Thr Leu
            100                 105                 110

Tyr Gly Ser Phe Ser Val Glu Asp Leu Phe Gly Ala Asn Leu Asn Arg
        115                 120                 125

Gly Gly Gly Ser Gly Gly Gly Ser Gly Gly Gly Ser Gly Gly Gly Ser
    130                 135                 140

Gly Ala Ala Ser Leu Ser Glu Val Lys Leu His Leu Asp Ile Glu Gly
145                 150                 155                 160

His Ala Ser His Tyr Thr Ile Pro Trp Thr Glu Leu Met Ala Lys Val
                165                 170                 175

Pro Gly Leu Ser Pro Glu Ala Leu Trp Arg Glu Ala Asn Val Thr Glu
            180                 185                 190

Asp Leu Ala Ser Met Leu Asn Arg Tyr Lys Leu Ile Tyr Lys Thr Ser
        195                 200                 205

Gly Thr Leu Gly Ile Ala Leu Ala Glu Pro Val Asp Ile Pro Ala Val
    210                 215                 220

Ser Glu Gly Ser Met Gln Val Asp Ala Ser Lys Val His Pro Gly Val
225                 230                 235                 240

Ile Ser Gly Leu Asn Ser Pro Ala Cys Met Leu Ser Ala Pro Leu Glu
                245                 250                 255

Lys Gln Leu Phe Tyr Tyr Ile Gly Thr Met Leu Pro Asn Thr Arg Pro
            260                 265                 270

His Ser Tyr Val Phe Tyr Gln Leu Arg Cys His Leu Ser Tyr Val Ala
        275                 280                 285

Leu Ser Ile Asn Gly Asp Lys Phe Gln Tyr Thr Gly Ala Met Thr Ser
```

```
            290                 295                 300
Lys Phe Leu Met Gly Thr Tyr Lys Arg Val Thr Glu Lys Gly Asp Glu
305                 310                 315                 320

His Val Leu Ser Leu Val Phe Gly Lys Thr Lys Asp Leu Pro Asp Leu
                325                 330                 335

Arg Gly Pro Phe Ser Tyr Pro Ser Leu Thr Ser Ala Gln Ser Gly Asp
                340                 345                 350

Tyr Ser Leu Val Ile Val Thr Thr Phe Val His Tyr Ala Asn Phe His
                355                 360                 365

Asn Tyr Phe Val Pro Asn Leu Lys Asp Met Phe Ser Arg Ala Val Thr
                370                 375                 380

Met Thr Ala Ala Ser Tyr Ala Arg Tyr Val Leu Gln Lys Leu Val Leu
385                 390                 395                 400

Leu Glu Met Lys Gly Gly Cys Arg Glu Pro Glu Leu Asp Thr Glu Thr
                405                 410                 415

Leu Thr Thr Met Phe Glu Val Ser Val Ala Phe Phe Lys Val Gly His
                420                 425                 430

Ala Val Gly Glu Thr Gly Asn Gly Cys Val Asp Leu Arg Trp Leu Ala
                435                 440                 445

Lys Ser Phe Phe Glu Leu Thr Val Leu Lys Asp Ile Ile Gly Ile Cys
                450                 455                 460

Tyr Gly Ala Thr Val Lys Gly Met Gln Ser Tyr Gly Leu Glu Arg Leu
465                 470                 475                 480

Ala Ala Met Leu Met Ala Thr Val Lys Met Glu Glu Leu Gly His Leu
                485                 490                 495

Thr Thr Glu Lys Gln Glu Tyr Ala Leu Arg Leu Ala Thr Val Gly Tyr
                500                 505                 510

Pro Lys Ala Gly Val Tyr Ser Gly Leu Ile Gly Ala Thr Ser Val
                515                 520                 525

Leu Leu Ser Ala Tyr Asn Arg His Pro Leu Phe Gln Pro Leu His Thr
                530                 535                 540

Val Met Arg Glu Thr Leu Phe Ile Gly Ser His Val Val Leu Arg Glu
545                 550                 555                 560

Leu Arg Leu Asn Val Thr Thr Gln Gly Pro Asn Leu Ala Leu Tyr Gln
                565                 570                 575

Leu Leu Ser Thr Ala Leu Cys Ser Ala Leu Glu Ile Gly Glu Val Leu
                580                 585                 590

Arg Gly Leu Ala Leu Gly Thr Glu Ser Gly Leu Phe Ser Pro Cys Tyr
                595                 600                 605

Leu Ser Leu Arg Phe Asp Leu Thr Arg Asp Lys Leu Leu Ser Met Ala
                610                 615                 620

Pro Gln Glu Ala Thr Leu Asp Gln Ala Ala Val Ser Asn Ala Val Asp
625                 630                 635                 640

Gly Phe Leu Gly Arg Leu Ser Leu Glu Arg Glu Asp Arg Asp Ala Trp
                645                 650                 655

His Leu Pro Ala Tyr Lys Cys Val Asp Arg Leu Asp Lys Val Leu Met
                660                 665                 670

Ile Ile Pro Leu Ile Asn Val Thr Phe Ile Ser Ser Asp Arg Glu
                675                 680                 685

Val Arg Gly Ser Ala Leu Tyr Glu Ala Ser Thr Thr Tyr Leu Ser Ser
                690                 695                 700

Ser Leu Phe Leu Ser Pro Val Ile Met Asn Lys Cys Ser Gln Gly Ala
705                 710                 715                 720
```

```
Val Ala Gly Glu Pro Arg Gln Ile Pro Lys Ile Gln Asn Phe Thr Arg
                725                 730                 735

Thr Gln Lys Ser Cys Ile Phe Cys Gly Phe Ala Leu Leu Ser Tyr Asp
            740                 745                 750

Glu Lys Glu Gly Leu Glu Thr Thr Thr Tyr Ile Thr Ser Gln Glu Val
        755                 760                 765

Gln Asn Ser Ile Leu Ser Ser Asn Tyr Phe Asp Phe Asp Asn Leu His
    770                 775                 780

Val His Tyr Leu Leu Leu Thr Thr Asn Gly Thr Val Met Glu Ile Ala
785                 790                 795                 800

Gly Leu Tyr Glu Glu Arg Ala Ser Gly Gly Ser Gly Gly Ser
                805                 810                 815

Gly Gly Gly Ser Gly Gly Gly Ser Gly Gly Gly Ser Glu Ser Gln Val
            820                 825                 830

Arg Gln Gln Phe Ser Lys Asp Ile Glu Lys Leu Leu Asn Glu Gln Val
            835                 840                 845

Asn Lys Glu Met Gln Ser Ser Asn Leu Tyr Met Ser Met Ser Ser Trp
    850                 855                 860

Ser Tyr Thr His Ser Leu Asp Gly Ala Gly Leu Phe Leu Phe Asp His
865                 870                 875                 880

Ala Ala Glu Glu Tyr Glu His Ala Lys Lys Leu Ile Ile Phe Leu Asn
                885                 890                 895

Glu Asn Asn Val Pro Val Gln Leu Thr Ser Ile Ser Ala Pro Glu His
            900                 905                 910

Lys Phe Glu Gly Leu Thr Gln Ile Phe Gln Lys Ala Tyr Glu His Glu
        915                 920                 925

Gln His Ile Ser Glu Ser Ile Asn Asn Ile Val Asp His Ala Ile Lys
    930                 935                 940

Cys Lys Asp His Ala Thr Phe Asn Phe Leu Gln Trp Tyr Val Ala Glu
945                 950                 955                 960

Gln His Glu Glu Glu Val Leu Phe Lys Asp Ile Leu Asp Lys Ile Glu
                965                 970                 975

Leu Ile Gly Asn Glu Asn His Gly Leu Tyr Leu Ala Asp Gln Tyr Val
            980                 985                 990

Lys Gly Ile Ala Lys Ser Arg Lys  Ser
        995                 1000
```

<210> SEQ ID NO 4
<211> LENGTH: 892
<212> TYPE: PRT
<213> ORGANISM: Artificial Sequence
<220> FEATURE:
<223> OTHER INFORMATION: Synthetic polypeptide

<400> SEQUENCE: 4

```
Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80
```

```
Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Gly Gly Ser Gly Ser Ala Ser Ser Gly Ala Ser Ala Ser Gly
    130                 135                 140

Ser Ser Asn Gly Ser Gly Ser Gly Ser Gly Ser Asn Ser Ser Ala Ser
145                 150                 155                 160

Ser Gly Ala Ser Ser Gly Gly Ala Ser Gly Gly Ser Gly Gly Ser Gly
                165                 170                 175

Ala Ala Ser Leu Ser Glu Val Lys Leu His Leu Asp Ile Glu Gly His
            180                 185                 190

Ala Ser His Tyr Thr Ile Pro Trp Thr Glu Leu Met Ala Lys Val Pro
        195                 200                 205

Gly Leu Ser Pro Glu Ala Leu Trp Arg Glu Ala Asn Val Thr Glu Asp
    210                 215                 220

Leu Ala Ser Met Leu Asn Arg Tyr Lys Leu Ile Tyr Lys Thr Ser Gly
225                 230                 235                 240

Thr Leu Gly Ile Ala Leu Ala Glu Pro Val Asp Ile Pro Ala Val Ser
                245                 250                 255

Glu Gly Ser Met Gln Val Asp Ala Ser Lys Val His Pro Gly Val Ile
            260                 265                 270

Ser Gly Leu Asn Ser Pro Ala Cys Met Leu Ser Ala Pro Leu Glu Lys
        275                 280                 285

Gln Leu Phe Tyr Tyr Ile Gly Thr Met Leu Pro Asn Thr Arg Pro His
    290                 295                 300

Ser Tyr Val Phe Tyr Gln Leu Arg Cys His Leu Ser Tyr Val Ala Leu
305                 310                 315                 320

Ser Ile Asn Gly Asp Lys Phe Gln Tyr Thr Gly Ala Met Thr Ser Lys
                325                 330                 335

Phe Leu Met Gly Thr Tyr Lys Arg Val Thr Glu Lys Gly Asp Glu His
            340                 345                 350

Val Leu Ser Leu Val Phe Gly Lys Thr Lys Asp Leu Pro Asp Leu Arg
        355                 360                 365

Gly Pro Phe Ser Tyr Pro Ser Leu Thr Ser Ala Gln Ser Gly Asp Tyr
    370                 375                 380

Ser Leu Val Ile Val Thr Thr Phe Val His Tyr Ala Asn Phe His Asn
385                 390                 395                 400

Tyr Phe Val Pro Asn Leu Lys Asp Met Phe Ser Arg Ala Val Thr Met
                405                 410                 415

Thr Ala Ala Ser Tyr Ala Arg Tyr Val Leu Gln Lys Leu Val Leu Leu
            420                 425                 430

Glu Met Lys Gly Gly Cys Arg Glu Pro Glu Leu Asp Thr Glu Thr Leu
        435                 440                 445

Thr Thr Met Phe Glu Val Ser Val Ala Phe Lys Val Gly His Ala
    450                 455                 460

Val Gly Glu Thr Gly Asn Gly Cys Val Asp Leu Arg Trp Leu Ala Lys
465                 470                 475                 480

Ser Phe Phe Glu Leu Thr Val Leu Lys Asp Ile Ile Gly Ile Cys Tyr
                485                 490                 495
```

```
Gly Ala Thr Val Lys Gly Met Gln Ser Tyr Gly Leu Glu Arg Leu Ala
                500                 505                 510
Ala Met Leu Met Ala Thr Val Lys Met Glu Glu Leu Gly His Leu Thr
            515                 520                 525
Thr Glu Lys Gln Glu Tyr Ala Leu Arg Leu Ala Thr Val Gly Tyr Pro
        530                 535                 540
Lys Ala Gly Val Tyr Ser Gly Leu Ile Gly Gly Ala Thr Ser Val Leu
545                 550                 555                 560
Leu Ser Ala Tyr Asn Arg His Pro Leu Phe Gln Pro Leu His Thr Val
                565                 570                 575
Met Arg Glu Thr Leu Phe Ile Gly Ser His Val Val Leu Arg Glu Leu
            580                 585                 590
Arg Leu Asn Val Thr Thr Gln Gly Pro Asn Leu Ala Leu Tyr Gln Leu
        595                 600                 605
Leu Ser Thr Ala Leu Cys Ser Ala Leu Glu Ile Gly Glu Val Leu Arg
    610                 615                 620
Gly Leu Ala Leu Gly Thr Glu Ser Gly Leu Phe Ser Pro Cys Tyr Leu
625                 630                 635                 640
Ser Leu Arg Phe Asp Leu Thr Arg Asp Lys Leu Leu Ser Met Ala Pro
                645                 650                 655
Gln Glu Ala Thr Leu Asp Gln Ala Ala Val Ser Asn Ala Val Asp Gly
            660                 665                 670
Phe Leu Gly Arg Leu Ser Leu Glu Arg Glu Asp Arg Asp Ala Trp His
        675                 680                 685
Leu Pro Ala Tyr Lys Cys Val Asp Arg Leu Asp Lys Val Leu Met Ile
    690                 695                 700
Ile Pro Leu Ile Asn Val Thr Phe Ile Ile Ser Ser Asp Arg Glu Val
705                 710                 715                 720
Arg Gly Ser Ala Leu Tyr Glu Ala Ser Thr Thr Tyr Leu Ser Ser Ser
                725                 730                 735
Leu Phe Leu Ser Pro Val Ile Met Asn Lys Cys Ser Gln Gly Ala Val
            740                 745                 750
Ala Gly Glu Pro Arg Gln Ile Pro Lys Ile Gln Asn Phe Thr Arg Thr
        755                 760                 765
Gln Lys Ser Cys Ile Phe Cys Gly Phe Ala Leu Leu Ser Tyr Asp Glu
    770                 775                 780
Lys Glu Gly Leu Glu Thr Thr Tyr Ile Thr Ser Gln Glu Val Gln
785                 790                 795                 800
Asn Ser Ile Leu Ser Ser Asn Tyr Phe Asp Phe Asp Asn Leu His Val
                805                 810                 815
His Tyr Leu Leu Leu Thr Thr Asn Gly Thr Val Met Glu Ile Ala Gly
            820                 825                 830
Leu Tyr Glu Glu Arg Ala Ser Gly Ser Gly Tyr Ile Pro Glu Ala Pro
        835                 840                 845
Arg Asp Gly Gln Ala Tyr Val Arg Lys Asp Gly Glu Trp Val Leu Leu
    850                 855                 860
Ser Thr Phe Leu Gly Ser Gly Ser Gly Leu Val Pro Arg Gly
865                 870                 875                 880
Ser Gly Ala Gly Gly Gly His His His His His
                885                 890

<210> SEQ ID NO 5
<211> LENGTH: 861
<212> TYPE: PRT
```

<213> ORGANISM: Artificial Sequence
<220> FEATURE:
<223> OTHER INFORMATION: Synthetic polypeptide

<400> SEQUENCE: 5

```
Met Glu Thr Asp Thr Leu Leu Leu Trp Val Leu Leu Leu Trp Val Pro
1               5                   10                  15

Gly Ser Thr Gly Asn Trp Ala Tyr Pro Cys Cys His Val Thr Gln Leu
            20                  25                  30

Arg Ala Gln His Leu Leu Ala Leu Glu Asn Ile Ser Asp Ile Tyr Leu
        35                  40                  45

Val Ser Asn Gln Thr Cys Asp Gly Phe Ser Leu Ala Ser Leu Asn Ser
    50                  55                  60

Pro Lys Asn Gly Ser Asn Gln Leu Val Ile Ser Arg Cys Ala Asn Gly
65                  70                  75                  80

Leu Asn Val Val Ser Phe Phe Ile Ser Ile Leu Lys Arg Ser Ser Ser
                85                  90                  95

Ala Leu Thr Gly His Leu Arg Glu Leu Leu Thr Thr Leu Glu Thr Leu
            100                 105                 110

Tyr Gly Ser Phe Ser Val Glu Asp Leu Phe Gly Ala Asn Leu Asn Arg
        115                 120                 125

Gly Gly Gly Ser Gly Gly Gly Ser Gly Gly Ser Gly Gly Gly Ser
    130                 135                 140

Gly Ala Ala Ser Leu Ser Glu Val Lys Leu His Leu Asp Ile Glu Gly
145                 150                 155                 160

His Ala Ser His Tyr Thr Ile Pro Trp Thr Glu Leu Met Ala Lys Val
                165                 170                 175

Pro Gly Leu Ser Pro Glu Ala Leu Trp Arg Glu Ala Asn Val Thr Glu
            180                 185                 190

Asp Leu Ala Ser Met Leu Asn Arg Tyr Lys Leu Ile Tyr Lys Thr Ser
        195                 200                 205

Gly Thr Leu Gly Ile Ala Leu Ala Glu Pro Val Asp Ile Pro Ala Val
    210                 215                 220

Ser Glu Gly Ser Met Gln Val Asp Ala Ser Lys Val His Pro Gly Val
225                 230                 235                 240

Ile Ser Gly Leu Asn Ser Pro Ala Cys Met Leu Ser Ala Pro Leu Glu
                245                 250                 255

Lys Gln Leu Phe Tyr Tyr Ile Gly Thr Met Leu Pro Asn Thr Arg Pro
            260                 265                 270

His Ser Tyr Val Phe Tyr Gln Leu Arg Cys His Leu Ser Tyr Val Ala
        275                 280                 285

Leu Ser Ile Asn Gly Asp Lys Phe Gln Tyr Thr Gly Ala Met Thr Ser
    290                 295                 300

Lys Phe Leu Met Gly Thr Tyr Lys Arg Val Thr Glu Lys Gly Asp Glu
305                 310                 315                 320

His Val Leu Ser Leu Val Phe Gly Lys Thr Lys Asp Leu Pro Asp Leu
                325                 330                 335

Arg Gly Pro Phe Ser Tyr Pro Ser Leu Thr Ser Ala Gln Ser Gly Asp
            340                 345                 350

Tyr Ser Leu Val Ile Val Thr Thr Phe Val His Tyr Ala Asn Phe His
        355                 360                 365

Asn Tyr Phe Val Pro Asn Leu Lys Asp Met Phe Ser Arg Ala Val Thr
    370                 375                 380

Met Thr Ala Ala Ser Tyr Ala Arg Tyr Val Leu Gln Lys Leu Val Leu
```

-continued

```
        385                 390                 395                 400
Leu Glu Met Lys Gly Gly Cys Arg Glu Pro Glu Leu Asp Thr Glu Thr
                    405                 410                 415
Leu Thr Thr Met Phe Glu Val Ser Val Ala Phe Phe Lys Val Gly His
                420                 425                 430
Ala Val Gly Glu Thr Gly Asn Gly Cys Val Asp Leu Arg Trp Leu Ala
            435                 440                 445
Lys Ser Phe Phe Glu Leu Thr Val Leu Lys Asp Ile Ile Gly Ile Cys
        450                 455                 460
Tyr Gly Ala Thr Val Lys Gly Met Gln Ser Tyr Gly Leu Glu Arg Leu
465                 470                 475                 480
Ala Ala Met Leu Met Ala Thr Val Lys Met Glu Leu Gly His Leu
                485                 490                 495
Thr Thr Glu Lys Gln Glu Tyr Ala Leu Arg Leu Ala Thr Val Gly Tyr
                500                 505                 510
Pro Lys Ala Gly Val Tyr Ser Gly Leu Ile Gly Gly Ala Thr Ser Val
            515                 520                 525
Leu Leu Ser Ala Tyr Asn Arg His Pro Leu Phe Gln Pro Leu His Thr
        530                 535                 540
Val Met Arg Glu Thr Leu Phe Ile Gly Ser His Val Val Leu Arg Glu
545                 550                 555                 560
Leu Arg Leu Asn Val Thr Thr Gln Gly Pro Asn Leu Ala Leu Tyr Gln
                565                 570                 575
Leu Leu Ser Thr Ala Leu Cys Ser Ala Leu Glu Ile Gly Glu Val Leu
                580                 585                 590
Arg Gly Leu Ala Leu Gly Thr Glu Ser Gly Leu Phe Ser Pro Cys Tyr
            595                 600                 605
Leu Ser Leu Arg Phe Asp Leu Thr Arg Asp Lys Leu Leu Ser Met Ala
        610                 615                 620
Pro Gln Glu Ala Thr Leu Asp Gln Ala Ala Val Ser Asn Ala Val Asp
625                 630                 635                 640
Gly Phe Leu Gly Arg Leu Ser Leu Glu Arg Glu Asp Arg Asp Ala Trp
                645                 650                 655
His Leu Pro Ala Tyr Lys Cys Val Asp Arg Leu Asp Lys Val Leu Met
                660                 665                 670
Ile Ile Pro Leu Ile Asn Val Thr Phe Ile Ile Ser Ser Asp Arg Glu
            675                 680                 685
Val Arg Gly Ser Ala Leu Tyr Glu Ala Ser Thr Thr Tyr Leu Ser Ser
        690                 695                 700
Ser Leu Phe Leu Ser Pro Val Ile Met Asn Lys Cys Ser Gln Gly Ala
705                 710                 715                 720
Val Ala Gly Glu Pro Arg Gln Ile Pro Lys Ile Gln Asn Phe Thr Arg
                725                 730                 735
Thr Gln Lys Ser Cys Ile Phe Cys Gly Phe Ala Leu Leu Ser Tyr Asp
                740                 745                 750
Glu Lys Glu Gly Leu Glu Thr Thr Tyr Ile Thr Ser Gln Glu Val
            755                 760                 765
Gln Asn Ser Ile Leu Ser Asn Tyr Phe Asp Phe Asp Asn Leu His
        770                 775                 780
Val His Tyr Leu Leu Leu Thr Thr Asn Gly Thr Val Met Glu Ile Ala
785                 790                 795                 800
Gly Leu Tyr Glu Glu Arg Ala Ser Gly Ser Gly Tyr Ile Pro Glu Ala
                805                 810                 815
```

```
Pro Arg Asp Gly Gln Ala Tyr Val Arg Lys Asp Gly Glu Trp Val Leu
            820                 825                 830

Leu Ser Thr Phe Leu Gly Ser Gly Ser Gly Leu Val Pro Arg
        835                 840                 845

Gly Ser Gly Ala Gly Gly His His His His His His
    850                 855                 860

<210> SEQ ID NO 6
<211> LENGTH: 863
<212> TYPE: PRT
<213> ORGANISM: Artificial Sequence
<220> FEATURE:
<223> OTHER INFORMATION: Synthetic polypeptide

<400> SEQUENCE: 6

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Gly Gly Ser Gly Ser Ala Ser Ser Gly Ala Ser Ala Ser Gly
    130                 135                 140

Ser Ser Asn Gly Ser Gly Ser Gly Ser Gly Ser Asn Ser Ser Ala Ser
145                 150                 155                 160

Ser Gly Ala Ser Ser Gly Gly Ala Ser Gly Gly Ser Gly Gly Ser Gly
                165                 170                 175

Ala Ala Ser Leu Ser Glu Val Lys Leu His Leu Asp Ile Glu Gly His
            180                 185                 190

Ala Ser His Tyr Thr Ile Pro Trp Thr Glu Leu Met Ala Lys Val Pro
        195                 200                 205

Gly Leu Ser Pro Glu Ala Leu Trp Arg Glu Ala Asn Val Thr Glu Asp
    210                 215                 220

Leu Ala Ser Met Leu Asn Arg Tyr Lys Leu Ile Tyr Lys Thr Ser Gly
225                 230                 235                 240

Thr Leu Gly Ile Ala Leu Ala Glu Pro Val Asp Ile Pro Ala Val Ser
                245                 250                 255

Glu Gly Ser Met Gln Val Asp Ala Ser Lys Val His Pro Gly Val Ile
            260                 265                 270

Ser Gly Leu Asn Ser Pro Ala Cys Met Leu Ser Ala Pro Leu Glu Lys
        275                 280                 285

Gln Leu Phe Tyr Tyr Ile Gly Thr Met Leu Pro Asn Thr Arg Pro His
    290                 295                 300

Ser Tyr Val Phe Tyr Gln Leu Arg Cys His Leu Ser Tyr Val Ala Leu
305                 310                 315                 320
```

```
Ser Ile Asn Gly Asp Lys Phe Gln Tyr Thr Gly Ala Met Thr Ser Lys
                325                 330                 335

Phe Leu Met Gly Thr Tyr Lys Arg Val Thr Glu Lys Gly Asp Glu His
            340                 345                 350

Val Leu Ser Leu Val Phe Gly Lys Thr Lys Asp Leu Pro Asp Leu Arg
        355                 360                 365

Gly Pro Phe Ser Tyr Pro Ser Leu Thr Ser Ala Gln Ser Gly Asp Tyr
    370                 375                 380

Ser Leu Val Ile Val Thr Thr Phe Val His Tyr Ala Asn Phe His Asn
385                 390                 395                 400

Tyr Phe Val Pro Asn Leu Lys Asp Met Phe Ser Arg Ala Val Thr Met
                405                 410                 415

Thr Ala Ala Ser Tyr Ala Arg Tyr Val Leu Gln Lys Leu Val Leu Leu
            420                 425                 430

Glu Met Lys Gly Gly Cys Arg Glu Pro Glu Leu Asp Thr Glu Thr Leu
        435                 440                 445

Thr Thr Met Phe Glu Val Ser Val Ala Phe Phe Lys Val Gly His Ala
    450                 455                 460

Val Gly Glu Thr Gly Asn Gly Cys Val Asp Leu Arg Trp Leu Ala Lys
465                 470                 475                 480

Ser Phe Phe Glu Leu Thr Val Leu Lys Asp Ile Ile Gly Ile Cys Tyr
                485                 490                 495

Gly Ala Thr Val Lys Gly Met Gln Ser Tyr Gly Leu Glu Arg Leu Ala
            500                 505                 510

Ala Met Leu Met Ala Thr Val Lys Met Glu Glu Leu Gly His Leu Thr
        515                 520                 525

Thr Glu Lys Gln Glu Tyr Ala Leu Arg Leu Ala Thr Val Gly Tyr Pro
    530                 535                 540

Lys Ala Gly Val Tyr Ser Gly Leu Ile Gly Gly Ala Thr Ser Val Leu
545                 550                 555                 560

Leu Ser Ala Tyr Asn Arg His Pro Leu Phe Gln Pro Leu His Thr Val
                565                 570                 575

Met Arg Glu Thr Leu Phe Ile Gly Ser His Val Val Leu Arg Glu Leu
            580                 585                 590

Arg Leu Asn Val Thr Thr Gln Gly Pro Asn Leu Ala Leu Tyr Gln Leu
        595                 600                 605

Leu Ser Thr Ala Leu Cys Ser Ala Leu Glu Ile Gly Glu Val Leu Arg
    610                 615                 620

Gly Leu Ala Leu Gly Thr Glu Ser Gly Leu Phe Ser Pro Cys Tyr Leu
625                 630                 635                 640

Ser Leu Arg Phe Asp Leu Thr Arg Asp Lys Leu Leu Ser Met Ala Pro
                645                 650                 655

Gln Glu Ala Thr Leu Asp Gln Ala Ala Val Ser Asn Ala Val Asp Gly
            660                 665                 670

Phe Leu Gly Arg Leu Ser Leu Glu Arg Glu Asp Arg Asp Ala Trp His
        675                 680                 685

Leu Pro Ala Tyr Lys Cys Val Asp Arg Leu Asp Lys Val Leu Met Ile
    690                 695                 700

Ile Pro Leu Ile Asn Val Thr Phe Ile Ile Ser Ser Asp Arg Glu Val
705                 710                 715                 720

Arg Gly Ser Ala Leu Tyr Glu Ala Ser Thr Thr Tyr Leu Ser Ser Ser
                725                 730                 735
```

```
Leu Phe Leu Ser Pro Val Ile Met Asn Lys Cys Ser Gln Gly Ala Val
            740                 745                 750

Ala Gly Glu Pro Arg Gln Ile Pro Lys Ile Gln Asn Phe Thr Arg Thr
            755                 760                 765

Gln Lys Ser Cys Ile Phe Cys Gly Phe Ala Leu Leu Ser Tyr Asp Glu
            770                 775                 780

Lys Glu Gly Leu Glu Thr Thr Thr Tyr Ile Thr Ser Gln Glu Val Gln
785                 790                 795                 800

Asn Ser Ile Leu Ser Ser Asn Tyr Phe Asp Phe Asp Asn Leu His Val
            805                 810                 815

His Tyr Leu Leu Leu Thr Thr Asn Gly Thr Val Met Glu Ile Ala Gly
            820                 825                 830

Leu Tyr Glu Glu Arg Ala Ser Gly Ser Gly Ser Gly Ser Gly Leu Val
            835                 840                 845

Pro Arg Gly Ser Gly Ala Gly Gly His His His His His His
            850                 855                 860

<210> SEQ ID NO 7
<211> LENGTH: 832
<212> TYPE: PRT
<213> ORGANISM: Artificial Sequence
<220> FEATURE:
<223> OTHER INFORMATION: Synthetic polypeptide

<400> SEQUENCE: 7

Met Glu Thr Asp Thr Leu Leu Leu Trp Val Leu Leu Leu Trp Val Pro
1               5                   10                  15

Gly Ser Thr Gly Asn Trp Ala Tyr Pro Cys Cys His Val Thr Gln Leu
                20                  25                  30

Arg Ala Gln His Leu Leu Ala Leu Glu Asn Ile Ser Asp Ile Tyr Leu
            35                  40                  45

Val Ser Asn Gln Thr Cys Asp Gly Phe Ser Leu Ala Ser Leu Asn Ser
        50                  55                  60

Pro Lys Asn Gly Ser Asn Gln Leu Val Ile Ser Arg Cys Ala Asn Gly
65                  70                  75                  80

Leu Asn Val Val Ser Phe Phe Ile Ser Ile Leu Lys Arg Ser Ser Ser
                85                  90                  95

Ala Leu Thr Gly His Leu Arg Glu Leu Leu Thr Thr Leu Glu Thr Leu
            100                 105                 110

Tyr Gly Ser Phe Ser Val Glu Asp Leu Phe Gly Ala Asn Leu Asn Arg
        115                 120                 125

Gly Gly Gly Ser Gly Gly Gly Ser Gly Gly Gly Ser Gly Gly Gly Ser
        130                 135                 140

Gly Ala Ala Ser Leu Ser Glu Val Lys Leu His Leu Asp Ile Glu Gly
145                 150                 155                 160

His Ala Ser His Tyr Thr Ile Pro Trp Thr Glu Leu Met Ala Lys Val
                165                 170                 175

Pro Gly Leu Ser Pro Glu Ala Leu Trp Arg Glu Ala Asn Val Thr Glu
            180                 185                 190

Asp Leu Ala Ser Met Leu Asn Arg Tyr Lys Leu Ile Tyr Lys Thr Ser
        195                 200                 205

Gly Thr Leu Gly Ile Ala Leu Ala Glu Pro Val Asp Ile Pro Ala Val
        210                 215                 220

Ser Glu Gly Ser Met Gln Val Asp Ala Ser Lys Val His Pro Gly Val
225                 230                 235                 240
```

-continued

```
Ile Ser Gly Leu Asn Ser Pro Ala Cys Met Leu Ser Ala Pro Leu Glu
            245                 250                 255

Lys Gln Leu Phe Tyr Tyr Ile Gly Thr Met Leu Pro Asn Thr Arg Pro
        260                 265                 270

His Ser Tyr Val Phe Tyr Gln Leu Arg Cys His Leu Ser Tyr Val Ala
    275                 280                 285

Leu Ser Ile Asn Gly Asp Lys Phe Gln Tyr Thr Gly Ala Met Thr Ser
290                 295                 300

Lys Phe Leu Met Gly Thr Tyr Lys Arg Val Thr Glu Lys Gly Asp Glu
305                 310                 315                 320

His Val Leu Ser Leu Val Phe Gly Lys Thr Lys Asp Leu Pro Asp Leu
            325                 330                 335

Arg Gly Pro Phe Ser Tyr Pro Ser Leu Thr Ser Ala Gln Ser Gly Asp
        340                 345                 350

Tyr Ser Leu Val Ile Val Thr Thr Phe Val His Tyr Ala Asn Phe His
    355                 360                 365

Asn Tyr Phe Val Pro Asn Leu Lys Asp Met Phe Ser Arg Ala Val Thr
370                 375                 380

Met Thr Ala Ala Ser Tyr Ala Arg Tyr Val Leu Gln Lys Leu Val Leu
385                 390                 395                 400

Leu Glu Met Lys Gly Gly Cys Arg Glu Pro Glu Leu Asp Thr Glu Thr
            405                 410                 415

Leu Thr Thr Met Phe Glu Val Ser Val Ala Phe Phe Lys Val Gly His
        420                 425                 430

Ala Val Gly Glu Thr Gly Asn Gly Cys Val Asp Leu Arg Trp Leu Ala
    435                 440                 445

Lys Ser Phe Phe Glu Leu Thr Val Leu Lys Asp Ile Ile Gly Ile Cys
450                 455                 460

Tyr Gly Ala Thr Val Lys Gly Met Gln Ser Tyr Gly Leu Glu Arg Leu
465                 470                 475                 480

Ala Ala Met Leu Met Ala Thr Val Lys Met Glu Glu Leu Gly His Leu
            485                 490                 495

Thr Thr Glu Lys Gln Glu Tyr Ala Leu Arg Leu Ala Thr Val Gly Tyr
        500                 505                 510

Pro Lys Ala Gly Val Tyr Ser Gly Leu Ile Gly Gly Ala Thr Ser Val
    515                 520                 525

Leu Leu Ser Ala Tyr Asn Arg His Pro Leu Phe Gln Pro Leu His Thr
530                 535                 540

Val Met Arg Glu Thr Leu Phe Ile Gly Ser His Val Val Leu Arg Glu
545                 550                 555                 560

Leu Arg Leu Asn Val Thr Thr Gln Gly Pro Asn Leu Ala Leu Tyr Gln
            565                 570                 575

Leu Leu Ser Thr Ala Leu Cys Ser Ala Leu Glu Ile Gly Glu Val Leu
        580                 585                 590

Arg Gly Leu Ala Leu Gly Thr Glu Ser Gly Leu Phe Ser Pro Cys Tyr
    595                 600                 605

Leu Ser Leu Arg Phe Asp Leu Thr Arg Asp Lys Leu Leu Ser Met Ala
610                 615                 620

Pro Gln Glu Ala Thr Leu Asp Gln Ala Ala Val Ser Asn Ala Val Asp
625                 630                 635                 640

Gly Phe Leu Gly Arg Leu Ser Leu Glu Arg Glu Asp Arg Asp Ala Trp
            645                 650                 655

His Leu Pro Ala Tyr Lys Cys Val Asp Arg Leu Asp Lys Val Leu Met
```

```
                660             665             670
Ile Ile Pro Leu Ile Asn Val Thr Phe Ile Ser Ser Asp Arg Glu
            675             680             685

Val Arg Gly Ser Ala Leu Tyr Glu Ala Ser Thr Thr Tyr Leu Ser Ser
690             695             700

Ser Leu Phe Leu Ser Pro Val Ile Met Asn Lys Cys Ser Gln Gly Ala
705             710             715             720

Val Ala Gly Glu Pro Arg Gln Ile Pro Lys Ile Gln Asn Phe Thr Arg
            725             730             735

Thr Gln Lys Ser Cys Ile Phe Cys Gly Phe Ala Leu Leu Ser Tyr Asp
            740             745             750

Glu Lys Glu Gly Leu Glu Thr Thr Thr Tyr Ile Thr Ser Gln Glu Val
            755             760             765

Gln Asn Ser Ile Leu Ser Ser Asn Tyr Phe Asp Phe Asp Asn Leu His
            770             775             780

Val His Tyr Leu Leu Leu Thr Thr Asn Gly Thr Val Met Glu Ile Ala
785             790             795             800

Gly Leu Tyr Glu Glu Arg Ala Ser Gly Ser Gly Ser Gly Ser Gly Leu
            805             810             815

Val Pro Arg Gly Ser Gly Ala Gly Gly His His His His His His
            820             825             830
```

<210> SEQ ID NO 8
<211> LENGTH: 870
<212> TYPE: PRT
<213> ORGANISM: Artificial Sequence
<220> FEATURE:
<223> OTHER INFORMATION: Synthetic polypeptide

<400> SEQUENCE: 8

```
Met Arg Ala Val Gly Val Phe Leu Ala Ile Cys Leu Val Thr Ile Phe
1               5               10              15

Val Leu Pro Thr Trp Gly Asn Trp Ala Tyr Pro Cys Cys His Val Thr
            20              25              30

Gln Leu Arg Ala Gln His Leu Leu Ala Leu Glu Asn Ile Ser Asp Ile
            35              40              45

Tyr Leu Val Ser Asn Gln Thr Cys Asp Gly Phe Ser Leu Ala Ser Leu
50              55              60

Asn Ser Pro Lys Asn Gly Ser Asn Gln Leu Val Ile Ser Arg Cys Ala
65              70              75              80

Asn Gly Leu Asn Val Val Ser Phe Phe Ile Ser Ile Leu Lys Arg Ser
            85              90              95

Ser Ser Ala Leu Thr Gly His Leu Arg Glu Leu Leu Thr Thr Leu Glu
            100             105             110

Thr Leu Tyr Gly Ser Phe Ser Val Glu Asp Leu Phe Gly Ala Asn Leu
            115             120             125

Asn Arg Tyr Ala Trp His Arg Gly Gly Gly Ser Gly Ser Ala Ser
            130             135             140

Ser Gly Ala Ser Ala Ser Gly Ser Asn Gly Ser Gly Ser Gly Ser
145             150             155             160

Gly Ser Asn Ser Ser Ala Ser Ser Gly Ala Ser Ser Gly Ala Ser
            165             170             175

Gly Gly Ser Gly Gly Ser Gly Ala Ala Ser Leu Ser Glu Val Lys Leu
            180             185             190

His Leu Asp Ile Glu Gly His Ala Ser His Tyr Thr Ile Pro Trp Thr
```

```
            195                 200                 205
Glu Leu Met Ala Lys Val Pro Gly Leu Ser Pro Glu Ala Leu Trp Arg
210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
                245                 250                 255

Val Asp Ile Pro Ala Val Ser Glu Gly Ser Met Gln Val Asp Ala Ser
            260                 265                 270

Lys Val His Pro Gly Val Ile Ser Gly Leu Asn Ser Pro Ala Cys Met
        275                 280                 285

Leu Ser Ala Pro Leu Glu Lys Gln Leu Phe Tyr Tyr Ile Gly Thr Met
290                 295                 300

Leu Pro Asn Thr Arg Pro His Ser Tyr Val Phe Tyr Gln Leu Arg Cys
305                 310                 315                 320

His Leu Ser Tyr Val Ala Leu Ser Ile Asn Gly Asp Lys Phe Gln Tyr
                325                 330                 335

Thr Gly Ala Met Thr Ser Lys Phe Leu Met Gly Thr Tyr Lys Arg Val
            340                 345                 350

Thr Glu Lys Gly Asp Glu His Val Leu Ser Leu Val Phe Gly Lys Thr
        355                 360                 365

Lys Asp Leu Pro Asp Leu Arg Gly Pro Phe Ser Tyr Pro Ser Leu Thr
370                 375                 380

Ser Ala Gln Ser Gly Asp Tyr Ser Leu Val Ile Val Thr Thr Phe Val
385                 390                 395                 400

His Tyr Ala Asn Phe His Asn Tyr Phe Val Pro Asn Leu Lys Asp Met
                405                 410                 415

Phe Ser Arg Ala Val Thr Met Thr Ala Ala Ser Tyr Ala Arg Tyr Val
            420                 425                 430

Leu Gln Lys Leu Val Leu Leu Glu Met Lys Gly Gly Cys Arg Glu Pro
        435                 440                 445

Glu Leu Asp Thr Glu Thr Leu Thr Thr Met Phe Glu Val Ser Val Ala
450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
                485                 490                 495

Asp Ile Ile Gly Ile Cys Tyr Gly Ala Thr Val Lys Gly Met Gln Ser
            500                 505                 510

Tyr Gly Leu Glu Arg Leu Ala Ala Met Leu Met Ala Thr Val Lys Met
        515                 520                 525

Glu Glu Leu Gly His Leu Thr Thr Glu Lys Gln Glu Tyr Ala Leu Arg
530                 535                 540

Leu Ala Thr Val Gly Tyr Pro Lys Ala Gly Val Tyr Ser Gly Leu Ile
545                 550                 555                 560

Gly Gly Ala Thr Ser Val Leu Leu Ser Ala Tyr Asn Arg His Pro Leu
                565                 570                 575

Phe Gln Pro Leu His Thr Val Met Arg Glu Thr Leu Phe Ile Gly Ser
            580                 585                 590

His Val Val Leu Arg Glu Leu Arg Leu Asn Val Thr Thr Gln Gly Pro
        595                 600                 605

Asn Leu Ala Leu Tyr Gln Leu Leu Ser Thr Ala Leu Cys Ser Ala Leu
610                 615                 620
```

Glu Ile Gly Glu Val Leu Arg Gly Leu Ala Leu Gly Thr Glu Ser Gly
625                 630                 635                 640

Leu Phe Ser Pro Cys Tyr Leu Ser Leu Arg Phe Asp Leu Thr Arg Asp
            645                 650                 655

Lys Leu Leu Ser Met Ala Pro Gln Glu Ala Thr Leu Asp Gln Ala Ala
        660                 665                 670

Val Ser Asn Ala Val Asp Gly Phe Leu Gly Arg Leu Ser Leu Glu Arg
        675                 680                 685

Glu Asp Arg Asp Ala Trp His Leu Pro Ala Tyr Lys Cys Val Asp Arg
690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
            725                 730                 735

Thr Thr Tyr Leu Ser Ser Ser Leu Phe Leu Ser Pro Val Ile Met Asn
        740                 745                 750

Lys Cys Ser Gln Gly Ala Val Ala Gly Glu Pro Arg Gln Ile Pro Lys
        755                 760                 765

Ile Gln Asn Phe Thr Arg Thr Gln Lys Ser Cys Ile Phe Cys Gly Phe
770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
            805                 810                 815

Asp Phe Asp Asn Leu His Val His Tyr Leu Leu Leu Thr Thr Asn Gly
        820                 825                 830

Thr Val Met Glu Ile Ala Gly Leu Tyr Glu Glu Arg Ala Ser Gly Ser
        835                 840                 845

Gly Ser Gly Ser Gly Leu Val Pro Arg Gly Ser Gly Ala Gly Gly Gly
    850                 855                 860

His His His His His His
865                 870

<210> SEQ ID NO 9
<211> LENGTH: 852
<212> TYPE: PRT
<213> ORGANISM: Artificial Sequence
<220> FEATURE:
<223> OTHER INFORMATION: Synthetic polypeptide

<400> SEQUENCE: 9

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
            85                  90                  95

Ser Ser Ala Leu Thr Gly His Leu Arg Glu Leu Leu Thr Thr Leu Glu
        100                 105                 110

```
Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Gly Ser
130                 135                 140

Asn Ser Ser Ala Ser Ser Gly Ala Ser Gly Gly Ala Ser Gly Gly
145                 150                 155                 160

Ser Gly Gly Ser Gly Ala Ala Ser Leu Ser Glu Val Lys Leu His Leu
                165                 170                 175

Asp Ile Glu Gly His Ala Ser His Tyr Thr Ile Pro Trp Thr Glu Leu
            180                 185                 190

Met Ala Lys Val Pro Gly Leu Ser Pro Glu Ala Leu Trp Arg Glu Ala
        195                 200                 205

Asn Val Thr Glu Asp Leu Ala Ser Met Leu Asn Arg Tyr Lys Leu Ile
        210                 215                 220

Tyr Lys Thr Ser Gly Thr Leu Gly Ile Ala Leu Ala Glu Pro Val Asp
225                 230                 235                 240

Ile Pro Ala Val Ser Glu Gly Ser Met Gln Val Asp Ala Ser Lys Val
                245                 250                 255

His Pro Gly Val Ile Ser Gly Leu Asn Ser Pro Ala Cys Met Leu Ser
            260                 265                 270

Ala Pro Leu Glu Lys Gln Leu Phe Tyr Tyr Ile Gly Thr Met Leu Pro
        275                 280                 285

Asn Thr Arg Pro His Ser Tyr Val Phe Tyr Gln Leu Arg Cys His Leu
        290                 295                 300

Ser Tyr Val Ala Leu Ser Ile Asn Gly Asp Lys Phe Gln Tyr Thr Gly
305                 310                 315                 320

Ala Met Thr Ser Lys Phe Leu Met Gly Thr Tyr Lys Arg Val Thr Glu
                325                 330                 335

Lys Gly Asp Glu His Val Leu Ser Leu Val Phe Gly Lys Thr Lys Asp
            340                 345                 350

Leu Pro Asp Leu Arg Gly Pro Phe Ser Tyr Pro Ser Leu Thr Ser Ala
        355                 360                 365

Gln Ser Gly Asp Tyr Ser Leu Val Ile Val Thr Thr Phe Val His Tyr
        370                 375                 380

Ala Asn Phe His Asn Tyr Phe Val Pro Asn Leu Lys Asp Met Phe Ser
385                 390                 395                 400

Arg Ala Val Thr Met Thr Ala Ala Ser Tyr Ala Arg Tyr Val Leu Gln
                405                 410                 415

Lys Leu Val Leu Leu Glu Met Lys Gly Gly Cys Arg Glu Pro Glu Leu
            420                 425                 430

Asp Thr Glu Thr Leu Thr Thr Met Phe Glu Val Ser Val Ala Phe Phe
        435                 440                 445

Lys Val Gly His Ala Val Gly Glu Thr Gly Asn Gly Cys Val Asp Leu
        450                 455                 460

Arg Trp Leu Ala Lys Ser Phe Phe Glu Leu Thr Val Leu Lys Asp Ile
465                 470                 475                 480

Ile Gly Ile Cys Tyr Gly Ala Thr Val Lys Gly Met Gln Ser Tyr Gly
                485                 490                 495

Leu Glu Arg Leu Ala Ala Met Leu Met Ala Thr Val Lys Met Glu Glu
            500                 505                 510

Leu Gly His Leu Thr Thr Glu Lys Gln Glu Tyr Ala Leu Arg Leu Ala
        515                 520                 525
```

```
Thr Val Gly Tyr Pro Lys Ala Gly Val Tyr Ser Gly Leu Ile Gly Gly
    530                 535                 540

Ala Thr Ser Val Leu Leu Ser Ala Tyr Asn Arg His Pro Leu Phe Gln
545                 550                 555                 560

Pro Leu His Thr Val Met Arg Glu Thr Leu Phe Ile Gly Ser His Val
                565                 570                 575

Val Leu Arg Glu Leu Arg Leu Asn Val Thr Thr Gln Gly Pro Asn Leu
            580                 585                 590

Ala Leu Tyr Gln Leu Leu Ser Thr Ala Leu Cys Ser Ala Leu Glu Ile
        595                 600                 605

Gly Glu Val Leu Arg Gly Leu Ala Leu Gly Thr Glu Ser Gly Leu Phe
    610                 615                 620

Ser Pro Cys Tyr Leu Ser Leu Arg Phe Asp Leu Thr Arg Asp Lys Leu
625                 630                 635                 640

Leu Ser Met Ala Pro Gln Glu Ala Thr Leu Asp Gln Ala Ala Val Ser
                645                 650                 655

Asn Ala Val Asp Gly Phe Leu Gly Arg Leu Ser Leu Glu Arg Glu Asp
            660                 665                 670

Arg Asp Ala Trp His Leu Pro Ala Tyr Lys Cys Val Asp Arg Leu Asp
        675                 680                 685

Lys Val Leu Met Ile Ile Pro Leu Ile Asn Val Thr Phe Ile Ile Ser
    690                 695                 700

Ser Asp Arg Glu Val Arg Gly Ser Ala Leu Tyr Glu Ala Ser Thr Thr
705                 710                 715                 720

Tyr Leu Ser Ser Ser Leu Phe Leu Ser Pro Val Ile Met Asn Lys Cys
                725                 730                 735

Ser Gln Gly Ala Val Ala Gly Glu Pro Arg Gln Ile Pro Lys Ile Gln
            740                 745                 750

Asn Phe Thr Arg Thr Gln Lys Ser Cys Ile Phe Cys Gly Phe Ala Leu
        755                 760                 765

Leu Ser Tyr Asp Glu Lys Glu Gly Leu Glu Thr Thr Thr Tyr Ile Thr
    770                 775                 780

Ser Gln Glu Val Gln Asn Ser Ile Leu Ser Ser Asn Tyr Phe Asp Phe
785                 790                 795                 800

Asp Asn Leu His Val His Tyr Leu Leu Leu Thr Thr Asn Gly Thr Val
                805                 810                 815

Met Glu Ile Ala Gly Leu Tyr Glu Glu Arg Ala Ser Gly Ser Gly Ser
            820                 825                 830

Gly Ser Gly Leu Val Pro Arg Gly Ser Gly Ala Gly Gly Gly His His
        835                 840                 845

His His His His
    850

<210> SEQ ID NO 10
<211> LENGTH: 1007
<212> TYPE: PRT
<213> ORGANISM: Artificial Sequence
<220> FEATURE:
<223> OTHER INFORMATION: Synthetic polypeptide

<400> SEQUENCE: 10

Met Glu Thr Asp Thr Leu Leu Leu Trp Val Leu Leu Leu Trp Val Pro
1               5                   10                  15

Gly Ser Thr Gly Asn Trp Ala Tyr Pro Cys Cys His Val Thr Gln Leu
            20                  25                  30
```

```
Arg Ala Gln His Leu Leu Ala Leu Glu Asn Ile Ser Asp Ile Tyr Leu
         35                  40                  45

Val Ser Asn Gln Thr Cys Asp Gly Phe Ser Leu Ala Ser Leu Asn Ser
 50                  55                  60

Pro Lys Asn Gly Ser Asn Gln Leu Val Ile Ser Arg Cys Ala Asn Gly
 65                  70                  75                  80

Leu Asn Val Val Ser Phe Phe Ile Ser Ile Leu Lys Arg Ser Ser Ser
                 85                  90                  95

Ala Leu Thr Gly His Leu Arg Glu Leu Leu Thr Thr Leu Glu Thr Leu
            100                 105                 110

Tyr Gly Ser Phe Ser Val Glu Asp Leu Phe Gly Ala Asn Leu Asn Arg
        115                 120                 125

Tyr Ala Trp His Arg Gly Gly Gly Gly Ser Gly Gly Gly Gly
130                 135                 140

Ser Gly Gly Gly Gly Ser Gly Ala Ala Ser Leu Ser Glu Val Lys Leu
145                 150                 155                 160

His Leu Asp Ile Glu Gly His Ala Ser His Tyr Thr Ile Pro Trp Thr
                165                 170                 175

Glu Leu Met Ala Lys Val Pro Gly Leu Ser Pro Glu Ala Leu Trp Arg
            180                 185                 190

Glu Ala Asn Val Thr Glu Asp Leu Ala Ser Met Leu Asn Arg Tyr Lys
        195                 200                 205

Leu Ile Tyr Lys Thr Ser Gly Thr Leu Gly Ile Ala Leu Ala Glu Pro
    210                 215                 220

Val Asp Ile Pro Ala Val Ser Glu Gly Ser Met Gln Val Asp Ala Ser
225                 230                 235                 240

Lys Val His Pro Gly Val Ile Ser Gly Leu Asn Ser Pro Ala Cys Met
                245                 250                 255

Leu Ser Ala Pro Leu Glu Lys Gln Leu Phe Tyr Tyr Ile Gly Thr Met
            260                 265                 270

Leu Pro Asn Thr Arg Pro His Ser Tyr Val Phe Tyr Gln Leu Arg Cys
        275                 280                 285

His Leu Ser Tyr Val Ala Leu Ser Ile Asn Gly Asp Lys Phe Gln Tyr
    290                 295                 300

Thr Gly Ala Met Thr Ser Lys Phe Leu Met Gly Thr Tyr Lys Arg Val
305                 310                 315                 320

Thr Glu Lys Gly Asp Glu His Val Leu Ser Leu Val Phe Gly Lys Thr
                325                 330                 335

Lys Asp Leu Pro Asp Leu Arg Gly Pro Phe Ser Tyr Pro Ser Leu Thr
            340                 345                 350

Ser Ala Gln Ser Gly Asp Tyr Ser Leu Val Ile Val Thr Thr Phe Val
        355                 360                 365

His Tyr Ala Asn Phe His Asn Tyr Phe Val Pro Asn Leu Lys Asp Met
    370                 375                 380

Phe Ser Arg Ala Val Thr Met Thr Ala Ala Ser Tyr Ala Arg Tyr Val
385                 390                 395                 400

Leu Gln Lys Leu Val Leu Leu Glu Met Lys Gly Gly Cys Arg Glu Pro
                405                 410                 415

Glu Leu Asp Thr Glu Thr Leu Thr Thr Met Phe Glu Val Ser Val Ala
            420                 425                 430

Phe Phe Lys Val Gly His Ala Val Gly Glu Thr Gly Asn Gly Cys Val
        435                 440                 445

Asp Leu Arg Trp Leu Ala Lys Ser Phe Phe Glu Leu Thr Val Leu Lys
```

-continued

```
            450                 455                 460
Asp Ile Ile Gly Ile Cys Tyr Gly Ala Thr Val Lys Gly Met Gln Ser
465                 470                 475                 480

Tyr Gly Leu Glu Arg Leu Ala Ala Met Leu Met Ala Thr Val Lys Met
                    485                 490                 495

Glu Glu Leu Gly His Leu Thr Thr Glu Lys Gln Glu Tyr Ala Leu Arg
                500                 505                 510

Leu Ala Thr Val Gly Tyr Pro Lys Ala Gly Val Tyr Ser Gly Leu Ile
                515                 520                 525

Gly Gly Ala Thr Ser Val Leu Leu Ser Ala Tyr Asn Arg His Pro Leu
            530                 535                 540

Phe Gln Pro Leu His Thr Val Met Arg Glu Thr Leu Phe Ile Gly Ser
545                 550                 555                 560

His Val Val Leu Arg Glu Leu Arg Leu Asn Val Thr Thr Gln Gly Pro
                565                 570                 575

Asn Leu Ala Leu Tyr Gln Leu Leu Ser Thr Ala Leu Cys Ser Ala Leu
                580                 585                 590

Glu Ile Gly Glu Val Leu Arg Gly Leu Ala Leu Gly Thr Glu Ser Gly
            595                 600                 605

Leu Phe Ser Pro Cys Tyr Leu Ser Leu Arg Phe Asp Leu Thr Arg Asp
610                 615                 620

Lys Leu Leu Ser Met Ala Pro Gln Glu Ala Thr Leu Asp Gln Ala Ala
625                 630                 635                 640

Val Ser Asn Ala Val Asp Gly Phe Leu Gly Arg Leu Ser Leu Glu Arg
                645                 650                 655

Glu Asp Arg Asp Ala Trp His Leu Pro Ala Tyr Lys Cys Val Asp Arg
                660                 665                 670

Leu Asp Lys Val Leu Met Ile Ile Pro Leu Ile Asn Val Thr Phe Ile
            675                 680                 685

Ile Ser Ser Asp Arg Glu Val Arg Gly Ser Ala Leu Tyr Glu Ala Ser
            690                 695                 700

Thr Thr Tyr Leu Ser Ser Ser Leu Phe Leu Ser Pro Val Ile Met Asn
705                 710                 715                 720

Lys Cys Ser Gln Gly Ala Val Ala Gly Glu Pro Arg Gln Ile Pro Lys
                725                 730                 735

Ile Gln Asn Phe Thr Arg Thr Gln Lys Ser Cys Ile Phe Cys Gly Phe
                740                 745                 750

Ala Leu Leu Ser Tyr Asp Glu Lys Glu Gly Leu Glu Thr Thr Thr Tyr
            755                 760                 765

Ile Thr Ser Gln Glu Val Gln Asn Ser Ile Leu Ser Ser Asn Tyr Phe
770                 775                 780

Asp Phe Asp Asn Leu His Val His Tyr Leu Leu Leu Thr Asn Gly
785                 790                 795                 800

Thr Val Met Glu Ile Ala Gly Leu Tyr Glu Glu Arg Ala Ser Gly Gly
                805                 810                 815

Gly Ser Gly Gly Gly Ser Gly Gly Ser Gly Gly Ser Gly Gly
            820                 825                 830

Gly Ser Glu Ser Gln Val Arg Gln Gln Phe Ser Lys Asp Ile Glu Lys
            835                 840                 845

Leu Leu Asn Glu Gln Val Asn Lys Glu Met Gln Ser Ser Asn Leu Tyr
            850                 855                 860

Met Ser Met Ser Ser Trp Ser Tyr Thr His Ser Leu Asp Gly Ala Gly
865                 870                 875                 880
```

```
Leu Phe Leu Phe Asp His Ala Glu Glu Tyr Glu His Ala Lys Lys
            885                 890                 895

Leu Ile Ile Phe Leu Asn Glu Asn Asn Val Pro Val Gln Leu Thr Ser
            900                 905                 910

Ile Ser Ala Pro Glu His Lys Phe Glu Gly Leu Thr Gln Ile Phe Gln
            915                 920                 925

Lys Ala Tyr Glu His Glu Gln His Ile Ser Glu Ser Ile Asn Asn Ile
            930                 935                 940

Val Asp His Ala Ile Lys Cys Lys Asp His Ala Thr Phe Asn Phe Leu
945                 950                 955                 960

Gln Trp Tyr Val Ala Glu Gln His Glu Glu Val Leu Phe Lys Asp
                965                 970                 975

Ile Leu Asp Lys Ile Glu Leu Ile Gly Asn Glu Asn His Gly Leu Tyr
            980                 985                 990

Leu Ala Asp Gln Tyr Val Lys Gly  Ile Ala Lys Ser Arg  Lys Ser
            995                 1000                1005

<210> SEQ ID NO 11
<211> LENGTH: 881
<212> TYPE: PRT
<213> ORGANISM: Artificial Sequence
<220> FEATURE:
<223> OTHER INFORMATION: Synthetic polypeptide

<400> SEQUENCE: 11

Met Arg Ala Val Gly Val Phe Leu Ala Ile Cys Leu Val Thr Ile Phe
1               5                  10                  15

Val Leu Pro Thr Trp Gly Asn Trp Ala Tyr Pro Cys Cys His Val Thr
                20                  25                  30

Gln Leu Arg Ala Gln His Leu Leu Ala Leu Glu Asn Ile Ser Asp Ile
            35                  40                  45

Tyr Leu Val Ser Asn Gln Thr Cys Asp Gly Phe Ser Leu Ala Ser Leu
        50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Gly Ser
    130                 135                 140

Asn Ser Ser Ala Ser Gly Ala Ser Ser Gly Gly Ala Ser Gly Gly
145                 150                 155                 160

Ser Gly Gly Ser Gly Ala Ala Ser Leu Ser Glu Val Lys Leu His Leu
                165                 170                 175

Asp Ile Glu Gly His Ala Ser His Tyr Thr Ile Pro Trp Thr Glu Leu
            180                 185                 190

Met Ala Lys Val Pro Gly Leu Ser Pro Glu Ala Leu Trp Arg Glu Ala
        195                 200                 205

Asn Val Thr Glu Asp Leu Ala Ser Met Leu Asn Arg Tyr Lys Leu Ile
    210                 215                 220

Tyr Lys Thr Ser Gly Thr Leu Gly Ile Ala Leu Ala Glu Pro Val Asp
225                 230                 235                 240
```

-continued

Ile Pro Ala Val Ser Glu Gly Ser Met Gln Val Asp Ala Ser Lys Val
                245                 250                 255

His Pro Gly Val Ile Ser Gly Leu Asn Ser Pro Ala Cys Met Leu Ser
            260                 265                 270

Ala Pro Leu Glu Lys Gln Leu Phe Tyr Tyr Ile Gly Thr Met Leu Pro
            275                 280                 285

Asn Thr Arg Pro His Ser Tyr Val Phe Tyr Gln Leu Arg Cys His Leu
        290                 295                 300

Ser Tyr Val Ala Leu Ser Ile Asn Gly Asp Lys Phe Gln Tyr Thr Gly
305                 310                 315                 320

Ala Met Thr Ser Lys Phe Leu Met Gly Thr Tyr Lys Val Arg Val Thr Glu
                325                 330                 335

Lys Gly Asp Glu His Val Leu Ser Leu Val Phe Gly Lys Thr Lys Asp
            340                 345                 350

Leu Pro Asp Leu Arg Gly Pro Phe Ser Tyr Pro Ser Leu Thr Ser Ala
            355                 360                 365

Gln Ser Gly Asp Tyr Ser Leu Val Ile Val Thr Thr Phe Val His Tyr
        370                 375                 380

Ala Asn Phe His Asn Tyr Phe Val Pro Asn Leu Lys Asp Met Phe Ser
385                 390                 395                 400

Arg Ala Val Thr Met Thr Ala Ala Ser Tyr Ala Arg Tyr Val Leu Gln
                405                 410                 415

Lys Leu Val Leu Leu Glu Met Lys Gly Gly Cys Arg Glu Pro Glu Leu
            420                 425                 430

Asp Thr Glu Thr Leu Thr Thr Met Phe Glu Val Ser Val Ala Phe Phe
            435                 440                 445

Lys Val Gly His Ala Val Gly Glu Thr Gly Asn Gly Cys Val Asp Leu
450                 455                 460

Arg Trp Leu Ala Lys Ser Phe Phe Glu Leu Thr Val Leu Lys Asp Ile
465                 470                 475                 480

Ile Gly Ile Cys Tyr Gly Ala Thr Val Lys Gly Met Gln Ser Tyr Gly
                485                 490                 495

Leu Glu Arg Leu Ala Ala Met Leu Met Ala Thr Val Lys Met Glu Glu
            500                 505                 510

Leu Gly His Leu Thr Thr Glu Lys Gln Glu Tyr Ala Leu Arg Leu Ala
            515                 520                 525

Thr Val Gly Tyr Pro Lys Ala Gly Val Tyr Ser Gly Leu Ile Gly Gly
        530                 535                 540

Ala Thr Ser Val Leu Leu Ser Ala Tyr Asn Arg His Pro Leu Phe Gln
545                 550                 555                 560

Pro Leu His Thr Val Met Arg Glu Thr Leu Phe Ile Gly Ser His Val
                565                 570                 575

Val Leu Arg Glu Leu Arg Leu Asn Val Thr Thr Gln Gly Pro Asn Leu
            580                 585                 590

Ala Leu Tyr Gln Leu Leu Ser Thr Ala Leu Cys Ser Ala Leu Glu Ile
        595                 600                 605

Gly Glu Val Leu Arg Gly Leu Ala Leu Gly Thr Glu Ser Gly Leu Phe
610                 615                 620

Ser Pro Cys Tyr Leu Ser Leu Arg Phe Asp Leu Thr Arg Asp Lys Leu
625                 630                 635                 640

Leu Ser Met Ala Pro Gln Glu Ala Thr Leu Asp Gln Ala Ala Val Ser
                645                 650                 655

```
Asn Ala Val Asp Gly Phe Leu Gly Arg Leu Ser Leu Glu Arg Glu Asp
                660                 665                 670

Arg Asp Ala Trp His Leu Pro Ala Tyr Lys Cys Val Asp Arg Leu Asp
        675                 680                 685

Lys Val Leu Met Ile Ile Pro Leu Ile Asn Val Thr Phe Ile Ile Ser
    690                 695                 700

Ser Asp Arg Glu Val Arg Gly Ser Ala Leu Tyr Glu Ala Ser Thr Thr
705                 710                 715                 720

Tyr Leu Ser Ser Ser Leu Phe Leu Ser Pro Val Ile Met Asn Lys Cys
                725                 730                 735

Ser Gln Gly Ala Val Ala Gly Glu Pro Arg Gln Ile Pro Lys Ile Gln
            740                 745                 750

Asn Phe Thr Arg Thr Gln Lys Ser Cys Ile Phe Cys Gly Phe Ala Leu
        755                 760                 765

Leu Ser Tyr Asp Glu Lys Glu Gly Leu Glu Thr Thr Thr Tyr Ile Thr
    770                 775                 780

Ser Gln Glu Val Gln Asn Ser Ile Leu Ser Ser Asn Tyr Phe Asp Phe
785                 790                 795                 800

Asp Asn Leu His Val His Tyr Leu Leu Leu Thr Thr Asn Gly Thr Val
                805                 810                 815

Met Glu Ile Ala Gly Leu Tyr Glu Glu Arg Ala Ser Gly Ser Gly Tyr
            820                 825                 830

Ile Pro Glu Ala Pro Arg Asp Gly Gln Ala Tyr Val Arg Lys Asp Gly
        835                 840                 845

Glu Trp Val Leu Leu Ser Thr Phe Leu Gly Ser Gly Ser Gly Ser Gly
    850                 855                 860

Leu Val Pro Arg Gly Ser Gly Ala Gly Gly His His His His His His
865                 870                 875                 880

His
```

```
<210> SEQ ID NO 12
<211> LENGTH: 899
<212> TYPE: PRT
<213> ORGANISM: Artificial Sequence
<220> FEATURE:
<223> OTHER INFORMATION: Synthetic polypeptide

<400> SEQUENCE: 12
```

```
Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Gly Ser Gly Ser Ala Ser
```

```
              130                 135                 140
Ser Gly Ala Ser Ala Ser Gly Ser Ser Asn Gly Ser Gly Ser Gly Ser
145                 150                 155                 160

Gly Ser Asn Ser Ser Ala Ser Ser Gly Ala Ser Ser Gly Gly Ala Ser
                165                 170                 175

Gly Gly Ser Gly Gly Ser Gly Ala Ala Ser Leu Ser Glu Val Lys Leu
            180                 185                 190

His Leu Asp Ile Glu Gly His Ala Ser His Tyr Thr Ile Pro Trp Thr
            195                 200                 205

Glu Leu Met Ala Lys Val Pro Gly Leu Ser Pro Glu Ala Leu Trp Arg
        210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
                245                 250                 255

Val Asp Ile Pro Ala Val Ser Glu Gly Ser Met Gln Val Asp Ala Ser
            260                 265                 270

Lys Val His Pro Gly Val Ile Ser Gly Leu Asn Ser Pro Ala Cys Met
        275                 280                 285

Leu Ser Ala Pro Leu Glu Lys Gln Leu Phe Tyr Tyr Ile Gly Thr Met
290                 295                 300

Leu Pro Asn Thr Arg Pro His Ser Tyr Val Phe Tyr Gln Leu Arg Cys
305                 310                 315                 320

His Leu Ser Tyr Val Ala Leu Ser Ile Asn Gly Asp Lys Phe Gln Tyr
                325                 330                 335

Thr Gly Ala Met Thr Ser Lys Phe Leu Met Gly Thr Tyr Lys Arg Val
            340                 345                 350

Thr Glu Lys Gly Asp Glu His Val Leu Ser Leu Val Phe Gly Lys Thr
        355                 360                 365

Lys Asp Leu Pro Asp Leu Arg Gly Pro Phe Ser Tyr Pro Ser Leu Thr
370                 375                 380

Ser Ala Gln Ser Gly Asp Tyr Ser Leu Val Ile Val Thr Thr Phe Val
385                 390                 395                 400

His Tyr Ala Asn Phe His Asn Tyr Phe Val Pro Asn Leu Lys Asp Met
                405                 410                 415

Phe Ser Arg Ala Val Thr Met Thr Ala Ala Ser Tyr Ala Arg Tyr Val
            420                 425                 430

Leu Gln Lys Leu Val Leu Leu Glu Met Lys Gly Gly Cys Arg Glu Pro
        435                 440                 445

Glu Leu Asp Thr Glu Thr Leu Thr Thr Met Phe Glu Val Ser Val Ala
450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
                485                 490                 495

Asp Ile Ile Gly Ile Cys Tyr Gly Ala Thr Val Lys Gly Met Gln Ser
            500                 505                 510

Tyr Gly Leu Glu Arg Leu Ala Ala Met Leu Met Ala Thr Val Lys Met
        515                 520                 525

Glu Glu Leu Gly His Leu Thr Thr Glu Lys Gln Glu Tyr Ala Leu Arg
530                 535                 540

Leu Ala Thr Val Gly Tyr Pro Lys Ala Gly Val Tyr Ser Gly Leu Ile
545                 550                 555                 560
```

Gly Gly Ala Thr Ser Val Leu Leu Ser Ala Tyr Asn Arg His Pro Leu
                565                 570                 575
Phe Gln Pro Leu His Thr Val Met Arg Glu Thr Leu Phe Ile Gly Ser
            580                 585                 590
His Val Val Leu Arg Glu Leu Arg Leu Asn Val Thr Thr Gln Gly Pro
        595                 600                 605
Asn Leu Ala Leu Tyr Gln Leu Leu Ser Thr Ala Leu Cys Ser Ala Leu
    610                 615                 620
Glu Ile Gly Glu Val Leu Arg Gly Leu Ala Leu Gly Thr Glu Ser Gly
625                 630                 635                 640
Leu Phe Ser Pro Cys Tyr Leu Ser Leu Arg Phe Asp Leu Thr Arg Asp
                645                 650                 655
Lys Leu Leu Ser Met Ala Pro Gln Glu Ala Thr Leu Asp Gln Ala Ala
            660                 665                 670
Val Ser Asn Ala Val Asp Gly Phe Leu Gly Arg Leu Ser Leu Glu Arg
        675                 680                 685
Glu Asp Arg Asp Ala Trp His Leu Pro Ala Tyr Lys Cys Val Asp Arg
    690                 695                 700
Leu Asp Lys Val Leu Met Ile Ile Pro Leu Ile Asn Val Thr Phe Ile
705                 710                 715                 720
Ile Ser Ser Asp Arg Glu Val Arg Gly Ser Ala Leu Tyr Glu Ala Ser
                725                 730                 735
Thr Thr Tyr Leu Ser Ser Ser Leu Phe Leu Ser Pro Val Ile Met Asn
            740                 745                 750
Lys Cys Ser Gln Gly Ala Val Ala Gly Glu Pro Arg Gln Ile Pro Lys
        755                 760                 765
Ile Gln Asn Phe Thr Arg Thr Gln Lys Ser Cys Ile Phe Cys Gly Phe
    770                 775                 780
Ala Leu Leu Ser Tyr Asp Glu Lys Glu Gly Leu Glu Thr Thr Thr Tyr
785                 790                 795                 800
Ile Thr Ser Gln Glu Val Gln Asn Ser Ile Leu Ser Ser Asn Tyr Phe
                805                 810                 815
Asp Phe Asp Asn Leu His Val His Tyr Leu Leu Leu Thr Thr Asn Gly
            820                 825                 830
Thr Val Met Glu Ile Ala Gly Leu Tyr Glu Glu Arg Ala Ser Gly Ser
        835                 840                 845
Gly Tyr Ile Pro Glu Ala Pro Arg Asp Gly Gln Ala Tyr Val Arg Lys
    850                 855                 860
Asp Gly Glu Trp Val Leu Leu Ser Thr Phe Leu Gly Ser Gly Ser Gly
865                 870                 875                 880
Ser Gly Leu Val Pro Arg Gly Ser Gly Ala Gly Gly His His
                885                 890                 895
His His His

<210> SEQ ID NO 13
<211> LENGTH: 1021
<212> TYPE: PRT
<213> ORGANISM: Artificial Sequence
<220> FEATURE:
<223> OTHER INFORMATION: Synthetic polypeptide

<400> SEQUENCE: 13

Met Arg Ala Val Gly Val Phe Leu Ala Ile Cys Leu Val Thr Ile Phe
1               5                   10                  15

-continued

Val Leu Pro Thr Trp Gly Asn Trp Ala Tyr Pro Cys Cys His Val Thr
          20                  25                  30

Gln Leu Arg Ala Gln His Leu Leu Ala Leu Glu Asn Ile Ser Asp Ile
          35                  40                  45

Tyr Leu Val Ser Asn Gln Thr Cys Asp Gly Phe Ser Leu Ala Ser Leu
50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
              85                  90                  95

Ser Ser Ala Leu Thr Gly His Leu Arg Glu Leu Leu Thr Thr Leu Glu
          100                 105                 110

Thr Leu Tyr Gly Ser Phe Ser Val Glu Asp Leu Phe Gly Ala Asn Leu
          115                 120                 125

Asn Arg Tyr Ala Trp His Arg Gly Gly Gly Ser Gly Ser Gly Ser
          130                 135                 140

Asn Ser Ser Ala Ser Ser Gly Ala Ser Ser Gly Gly Ala Ser Gly Gly
145                 150                 155                 160

Ser Gly Gly Ser Gly Ala Ala Ser Leu Ser Glu Val Lys Leu His Leu
                  165                 170                 175

Asp Ile Glu Gly His Ala Ser His Tyr Thr Ile Pro Trp Thr Glu Leu
              180                 185                 190

Met Ala Lys Val Pro Gly Leu Ser Pro Glu Ala Leu Trp Arg Glu Ala
          195                 200                 205

Asn Val Thr Glu Asp Leu Ala Ser Met Leu Asn Arg Tyr Lys Leu Ile
210                 215                 220

Tyr Lys Thr Ser Gly Thr Leu Gly Ile Ala Leu Ala Glu Pro Val Asp
225                 230                 235                 240

Ile Pro Ala Val Ser Glu Gly Ser Met Gln Val Asp Ala Ser Lys Val
              245                 250                 255

His Pro Gly Val Ile Ser Gly Leu Asn Ser Pro Ala Cys Met Leu Ser
          260                 265                 270

Ala Pro Leu Glu Lys Gln Leu Phe Tyr Tyr Ile Gly Thr Met Leu Pro
          275                 280                 285

Asn Thr Arg Pro His Ser Tyr Val Phe Tyr Gln Leu Arg Cys His Leu
290                 295                 300

Ser Tyr Val Ala Leu Ser Ile Asn Gly Asp Lys Phe Gln Tyr Thr Gly
305                 310                 315                 320

Ala Met Thr Ser Lys Phe Leu Met Gly Thr Tyr Lys Arg Val Thr Glu
              325                 330                 335

Lys Gly Asp Glu His Val Leu Ser Leu Val Phe Gly Lys Thr Lys Asp
          340                 345                 350

Leu Pro Asp Leu Arg Gly Pro Phe Ser Tyr Pro Ser Leu Thr Ser Ala
          355                 360                 365

Gln Ser Gly Asp Tyr Ser Leu Val Ile Val Thr Thr Phe Val His Tyr
370                 375                 380

Ala Asn Phe His Asn Tyr Phe Val Pro Asn Leu Lys Asp Met Phe Ser
385                 390                 395                 400

Arg Ala Val Thr Met Thr Ala Ala Ser Tyr Ala Arg Tyr Val Leu Gln
              405                 410                 415

Lys Leu Val Leu Leu Glu Met Lys Gly Gly Cys Arg Glu Pro Glu Leu
          420                 425                 430

Asp Thr Glu Thr Leu Thr Thr Met Phe Glu Val Ser Val Ala Phe Phe

```
            435                 440                 445
Lys Val Gly His Ala Val Gly Glu Thr Gly Asn Gly Cys Val Asp Leu
    450                 455                 460

Arg Trp Leu Ala Lys Ser Phe Phe Glu Leu Thr Val Leu Lys Asp Ile
465                 470                 475                 480

Ile Gly Ile Cys Tyr Gly Ala Thr Val Lys Gly Met Gln Ser Tyr Gly
                    485                 490                 495

Leu Glu Arg Leu Ala Ala Met Leu Met Ala Thr Val Lys Met Glu Glu
                500                 505                 510

Leu Gly His Leu Thr Thr Glu Lys Gln Glu Tyr Ala Leu Arg Leu Ala
            515                 520                 525

Thr Val Gly Tyr Pro Lys Ala Gly Val Tyr Ser Gly Leu Ile Gly Gly
        530                 535                 540

Ala Thr Ser Val Leu Leu Ser Ala Tyr Asn Arg His Pro Leu Phe Gln
545                 550                 555                 560

Pro Leu His Thr Val Met Arg Glu Thr Leu Phe Ile Gly Ser His Val
                    565                 570                 575

Val Leu Arg Glu Leu Arg Leu Asn Val Thr Thr Gln Gly Pro Asn Leu
                580                 585                 590

Ala Leu Tyr Gln Leu Leu Ser Thr Ala Leu Cys Ser Ala Leu Glu Ile
            595                 600                 605

Gly Glu Val Leu Arg Gly Leu Ala Leu Gly Thr Glu Ser Gly Leu Phe
        610                 615                 620

Ser Pro Cys Tyr Leu Ser Leu Arg Phe Asp Leu Thr Arg Asp Lys Leu
625                 630                 635                 640

Leu Ser Met Ala Pro Gln Glu Ala Thr Leu Asp Gln Ala Ala Val Ser
                    645                 650                 655

Asn Ala Val Asp Gly Phe Leu Gly Arg Leu Ser Leu Glu Arg Glu Asp
                660                 665                 670

Arg Asp Ala Trp His Leu Pro Ala Tyr Lys Cys Val Asp Arg Leu Asp
            675                 680                 685

Lys Val Leu Met Ile Ile Pro Leu Ile Asn Val Thr Phe Ile Ile Ser
        690                 695                 700

Ser Asp Arg Glu Val Arg Gly Ser Ala Leu Tyr Glu Ala Ser Thr Thr
705                 710                 715                 720

Tyr Leu Ser Ser Ser Leu Phe Leu Ser Pro Val Ile Met Asn Lys Cys
                    725                 730                 735

Ser Gln Gly Ala Val Ala Gly Glu Pro Arg Gln Ile Pro Lys Ile Gln
                740                 745                 750

Asn Phe Thr Arg Thr Gln Lys Ser Cys Ile Phe Cys Gly Phe Ala Leu
            755                 760                 765

Leu Ser Tyr Asp Glu Lys Glu Gly Leu Glu Thr Thr Thr Tyr Ile Thr
        770                 775                 780

Ser Gln Glu Val Gln Asn Ser Ile Leu Ser Ser Asn Tyr Phe Asp Phe
785                 790                 795                 800

Asp Asn Leu His Val His Tyr Leu Leu Leu Thr Thr Asn Gly Thr Val
                    805                 810                 815

Met Glu Ile Ala Gly Leu Tyr Glu Glu Arg Ala Ser Gly Gly Gly Ser
                820                 825                 830

Gly Gly Gly Ser Gly Gly Gly Ser Gly Gly Gly Ser Gly Gly Gly Ser
            835                 840                 845

Glu Ser Gln Val Arg Gln Gln Phe Ser Lys Asp Ile Glu Lys Leu Leu
        850                 855                 860
```

```
Asn Glu Gln Val Asn Lys Glu Met Gln Ser Ser Asn Leu Tyr Met Ser
865                 870                 875                 880

Met Ser Ser Trp Ser Tyr Thr His Ser Leu Asp Gly Ala Gly Leu Phe
            885                 890                 895

Leu Phe Asp His Ala Ala Glu Glu Tyr Glu His Ala Lys Lys Leu Ile
        900                 905                 910

Ile Phe Leu Asn Glu Asn Asn Val Pro Val Gln Leu Thr Ser Ile Ser
        915                 920                 925

Ala Pro Glu His Lys Phe Glu Gly Leu Thr Gln Ile Phe Gln Lys Ala
930                 935                 940

Tyr Glu His Glu Gln His Ile Ser Glu Ser Ile Asn Asn Ile Val Asp
945                 950                 955                 960

His Ala Ile Lys Cys Lys Asp His Ala Thr Phe Asn Phe Leu Gln Trp
                965                 970                 975

Tyr Val Ala Glu Gln His Glu Glu Val Leu Phe Lys Asp Ile Leu
            980                 985                 990

Asp Lys Ile Glu Leu Ile Gly Asn  Glu Asn His Gly Leu  Tyr Leu Ala
            995                 1000                1005

Asp Gln  Tyr Val Lys Gly Ile  Ala Lys Ser Arg Lys  Ser
    1010                1015                1020

<210> SEQ ID NO 14
<211> LENGTH: 1039
<212> TYPE: PRT
<213> ORGANISM: Artificial Sequence
<220> FEATURE:
<223> OTHER INFORMATION: Synthetic polypeptide

<400> SEQUENCE: 14

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Ala Ser
    130                 135                 140

Ser Gly Ala Ser Ala Ser Gly Ser Ser Asn Gly Ser Gly Ser Gly Ser
145                 150                 155                 160

Gly Ser Asn Ser Ser Ala Ser Ser Gly Ala Ser Ser Gly Gly Ala Ser
                165                 170                 175

Gly Gly Ser Gly Gly Ser Gly Ala Ala Ser Leu Ser Glu Val Lys Leu
            180                 185                 190

His Leu Asp Ile Glu Gly His Ala Ser His Tyr Thr Ile Pro Trp Thr
        195                 200                 205
```

```
Glu Leu Met Ala Lys Val Pro Gly Leu Ser Pro Glu Ala Leu Trp Arg
    210                 215                 220
Glu Ala Asn Val Thr Glu Asp Leu Ala Ser Met Leu Asn Arg Tyr Lys
225                 230                 235                 240
Leu Ile Tyr Lys Thr Ser Gly Thr Leu Gly Ile Ala Leu Ala Glu Pro
                245                 250                 255
Val Asp Ile Pro Ala Val Ser Glu Gly Ser Met Gln Val Asp Ala Ser
            260                 265                 270
Lys Val His Pro Gly Val Ile Ser Gly Leu Asn Ser Pro Ala Cys Met
        275                 280                 285
Leu Ser Ala Pro Leu Glu Lys Gln Leu Phe Tyr Tyr Ile Gly Thr Met
    290                 295                 300
Leu Pro Asn Thr Arg Pro His Ser Tyr Val Phe Tyr Gln Leu Arg Cys
305                 310                 315                 320
His Leu Ser Tyr Val Ala Leu Ser Ile Asn Gly Asp Lys Phe Gln Tyr
                325                 330                 335
Thr Gly Ala Met Thr Ser Lys Phe Leu Met Gly Thr Tyr Lys Arg Val
            340                 345                 350
Thr Glu Lys Gly Asp Glu His Val Leu Ser Leu Val Phe Gly Lys Thr
        355                 360                 365
Lys Asp Leu Pro Asp Leu Arg Gly Pro Phe Ser Tyr Pro Ser Leu Thr
    370                 375                 380
Ser Ala Gln Ser Gly Asp Tyr Ser Leu Val Ile Val Thr Thr Phe Val
385                 390                 395                 400
His Tyr Ala Asn Phe His Asn Tyr Phe Val Pro Asn Leu Lys Asp Met
                405                 410                 415
Phe Ser Arg Ala Val Thr Met Thr Ala Ala Ser Tyr Ala Arg Tyr Val
            420                 425                 430
Leu Gln Lys Leu Val Leu Leu Glu Met Lys Gly Gly Cys Arg Glu Pro
        435                 440                 445
Glu Leu Asp Thr Glu Thr Leu Thr Thr Met Phe Glu Val Ser Val Ala
    450                 455                 460
Phe Phe Lys Val Gly His Ala Val Gly Glu Thr Gly Asn Gly Cys Val
465                 470                 475                 480
Asp Leu Arg Trp Leu Ala Lys Ser Phe Phe Glu Leu Thr Val Leu Lys
                485                 490                 495
Asp Ile Ile Gly Ile Cys Tyr Gly Ala Thr Val Lys Gly Met Gln Ser
            500                 505                 510
Tyr Gly Leu Glu Arg Leu Ala Ala Met Leu Met Ala Thr Val Lys Met
        515                 520                 525
Glu Glu Leu Gly His Leu Thr Thr Glu Lys Gln Glu Tyr Ala Leu Arg
    530                 535                 540
Leu Ala Thr Val Gly Tyr Pro Lys Ala Gly Val Tyr Ser Gly Leu Ile
545                 550                 555                 560
Gly Gly Ala Thr Ser Val Leu Leu Ser Ala Tyr Asn Arg His Pro Leu
                565                 570                 575
Phe Gln Pro Leu His Thr Val Met Arg Glu Thr Leu Phe Ile Gly Ser
            580                 585                 590
His Val Val Leu Arg Glu Leu Arg Leu Asn Val Thr Thr Gln Gly Pro
        595                 600                 605
Asn Leu Ala Leu Tyr Gln Leu Leu Ser Thr Ala Leu Cys Ser Ala Leu
    610                 615                 620
```

Glu Ile Gly Glu Val Leu Arg Gly Leu Ala Leu Gly Thr Glu Ser Gly
625                 630                 635                 640

Leu Phe Ser Pro Cys Tyr Leu Ser Leu Arg Phe Asp Leu Thr Arg Asp
            645                 650                 655

Lys Leu Leu Ser Met Ala Pro Gln Glu Ala Thr Leu Asp Gln Ala Ala
            660                 665                 670

Val Ser Asn Ala Val Asp Gly Phe Leu Gly Arg Leu Ser Leu Glu Arg
            675                 680                 685

Glu Asp Arg Asp Ala Trp His Leu Pro Ala Tyr Lys Cys Val Asp Arg
690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
            725                 730                 735

Thr Thr Tyr Leu Ser Ser Ser Leu Phe Leu Ser Pro Val Ile Met Asn
            740                 745                 750

Lys Cys Ser Gln Gly Ala Val Ala Gly Glu Pro Arg Gln Ile Pro Lys
            755                 760                 765

Ile Gln Asn Phe Thr Arg Thr Gln Lys Ser Cys Ile Phe Cys Gly Phe
770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
            805                 810                 815

Asp Phe Asp Asn Leu His Val His Tyr Leu Leu Leu Thr Thr Asn Gly
            820                 825                 830

Thr Val Met Glu Ile Ala Gly Leu Tyr Glu Glu Arg Ala Ser Gly Gly
            835                 840                 845

Gly Ser Gly Gly Gly Ser Gly Gly Gly Ser Gly Gly Gly Ser Gly Gly
            850                 855                 860

Gly Ser Glu Ser Gln Val Arg Gln Gln Phe Ser Lys Asp Ile Glu Lys
865                 870                 875                 880

Leu Leu Asn Glu Gln Val Asn Lys Glu Met Gln Ser Ser Asn Leu Tyr
            885                 890                 895

Met Ser Met Ser Ser Trp Ser Tyr Thr His Ser Leu Asp Gly Ala Gly
            900                 905                 910

Leu Phe Leu Phe Asp His Ala Ala Glu Glu Tyr Glu His Ala Lys Lys
            915                 920                 925

Leu Ile Ile Phe Leu Asn Glu Asn Asn Val Pro Val Gln Leu Thr Ser
930                 935                 940

Ile Ser Ala Pro Glu His Lys Phe Glu Gly Leu Thr Gln Ile Phe Gln
945                 950                 955                 960

Lys Ala Tyr Glu His Glu Gln His Ile Ser Glu Ser Ile Asn Asn Ile
            965                 970                 975

Val Asp His Ala Ile Lys Cys Lys Asp His Ala Thr Phe Asn Phe Leu
            980                 985                 990

Gln Trp Tyr Val Ala Glu Gln His Glu Glu Glu Val Leu Phe Lys Asp
            995                 1000                1005

Ile Leu Asp Lys Ile Glu Leu Ile Gly Asn Glu Asn His Gly Leu
            1010                1015                1020

Tyr Leu Ala Asp Gln Tyr Val Lys Gly Ile Ala Lys Ser Arg Lys
            1025                1030                1035

Ser

<210> SEQ ID NO 15
<211> LENGTH: 838
<212> TYPE: PRT
<213> ORGANISM: Artificial Sequence
<220> FEATURE:
<223> OTHER INFORMATION: Synthetic polypeptide

<400> SEQUENCE: 15

```
Met Glu Thr Asp Thr Leu Leu Leu Trp Val Leu Leu Leu Trp Val Pro
1               5                   10                  15

Gly Ser Thr Gly Asn Trp Ala Tyr Pro Cys Cys His Val Thr Gln Leu
            20                  25                  30

Arg Ala Gln His Leu Leu Ala Leu Glu Asn Ile Ser Asp Ile Tyr Leu
        35                  40                  45

Val Ser Asn Gln Thr Cys Asp Gly Phe Ser Leu Ala Ser Leu Asn Ser
    50                  55                  60

Pro Lys Asn Gly Ser Asn Gln Leu Val Ile Ser Arg Cys Ala Asn Gly
65                  70                  75                  80

Leu Asn Val Val Ser Phe Phe Ile Ser Ile Leu Lys Arg Ser Ser Ser
                85                  90                  95

Ala Leu Thr Gly His Leu Arg Glu Leu Leu Thr Thr Leu Glu Thr Leu
            100                 105                 110

Tyr Gly Ser Phe Ser Val Glu Asp Leu Phe Gly Ala Asn Leu Asn Arg
        115                 120                 125

Tyr Ala Trp His Arg Gly Gly Gly Gly Gly Ser Gly Gly Gly Gly
    130                 135                 140

Ser Gly Gly Gly Gly Ser Gly Ala Ala Ser Leu Ser Glu Val Lys Leu
145                 150                 155                 160

His Leu Asp Ile Glu Gly His Ala Ser His Tyr Thr Ile Pro Trp Thr
                165                 170                 175

Glu Leu Met Ala Lys Val Pro Gly Leu Ser Pro Glu Ala Leu Trp Arg
            180                 185                 190

Glu Ala Asn Val Thr Glu Asp Leu Ala Ser Met Leu Asn Arg Tyr Lys
        195                 200                 205

Leu Ile Tyr Lys Thr Ser Gly Thr Leu Gly Ile Ala Leu Ala Glu Pro
    210                 215                 220

Val Asp Ile Pro Ala Val Ser Glu Gly Ser Met Gln Val Asp Ala Ser
225                 230                 235                 240

Lys Val His Pro Gly Val Ile Ser Gly Leu Asn Ser Pro Ala Cys Met
                245                 250                 255

Leu Ser Ala Pro Leu Glu Lys Gln Leu Phe Tyr Tyr Ile Gly Thr Met
            260                 265                 270

Leu Pro Asn Thr Arg Pro His Ser Tyr Val Phe Tyr Gln Leu Arg Cys
        275                 280                 285

His Leu Ser Tyr Val Ala Leu Ser Ile Asn Gly Asp Lys Phe Gln Tyr
    290                 295                 300

Thr Gly Ala Met Thr Ser Lys Phe Leu Met Gly Thr Tyr Lys Arg Val
305                 310                 315                 320

Thr Glu Lys Gly Asp Glu His Val Leu Ser Leu Val Phe Gly Lys Thr
                325                 330                 335

Lys Asp Leu Pro Asp Leu Arg Gly Pro Phe Ser Tyr Pro Ser Leu Thr
            340                 345                 350

Ser Ala Gln Ser Gly Asp Tyr Ser Leu Val Ile Val Thr Thr Phe Val
        355                 360                 365
```

```
His Tyr Ala Asn Phe His Asn Tyr Phe Val Pro Asn Leu Lys Asp Met
    370                 375                 380

Phe Ser Arg Ala Val Thr Met Thr Ala Ala Ser Tyr Ala Arg Tyr Val
385                 390                 395                 400

Leu Gln Lys Leu Val Leu Leu Glu Met Lys Gly Gly Cys Arg Glu Pro
                405                 410                 415

Glu Leu Asp Thr Glu Thr Leu Thr Thr Met Phe Glu Val Ser Val Ala
            420                 425                 430

Phe Phe Lys Val Gly His Ala Val Gly Glu Thr Gly Asn Gly Cys Val
        435                 440                 445

Asp Leu Arg Trp Leu Ala Lys Ser Phe Phe Glu Leu Thr Val Leu Lys
    450                 455                 460

Asp Ile Ile Gly Ile Cys Tyr Gly Ala Thr Val Lys Gly Met Gln Ser
465                 470                 475                 480

Tyr Gly Leu Glu Arg Leu Ala Ala Met Leu Met Ala Thr Val Lys Met
                485                 490                 495

Glu Glu Leu Gly His Leu Thr Thr Glu Lys Gln Glu Tyr Ala Leu Arg
            500                 505                 510

Leu Ala Thr Val Gly Tyr Pro Lys Ala Gly Val Tyr Ser Gly Leu Ile
        515                 520                 525

Gly Gly Ala Thr Ser Val Leu Leu Ser Ala Tyr Asn Arg His Pro Leu
530                 535                 540

Phe Gln Pro Leu His Thr Val Met Arg Glu Thr Leu Phe Ile Gly Ser
545                 550                 555                 560

His Val Val Leu Arg Glu Leu Arg Leu Asn Val Thr Thr Gln Gly Pro
                565                 570                 575

Asn Leu Ala Leu Tyr Gln Leu Leu Ser Thr Ala Leu Cys Ser Ala Leu
            580                 585                 590

Glu Ile Gly Glu Val Leu Arg Gly Leu Ala Leu Gly Thr Glu Ser Gly
        595                 600                 605

Leu Phe Ser Pro Cys Tyr Leu Ser Leu Arg Phe Asp Leu Thr Arg Asp
    610                 615                 620

Lys Leu Leu Ser Met Ala Pro Gln Glu Ala Thr Leu Asp Gln Ala Ala
625                 630                 635                 640

Val Ser Asn Ala Val Asp Gly Phe Leu Gly Arg Leu Ser Leu Glu Arg
                645                 650                 655

Glu Asp Arg Asp Ala Trp His Leu Pro Ala Tyr Lys Cys Val Asp Arg
            660                 665                 670

Leu Asp Lys Val Leu Met Ile Ile Pro Leu Ile Asn Val Thr Phe Ile
        675                 680                 685

Ile Ser Ser Asp Arg Glu Val Arg Gly Ser Ala Leu Tyr Glu Ala Ser
    690                 695                 700

Thr Thr Tyr Leu Ser Ser Ser Leu Phe Leu Ser Pro Val Ile Met Asn
705                 710                 715                 720

Lys Cys Ser Gln Gly Ala Val Ala Gly Glu Pro Arg Gln Ile Pro Lys
                725                 730                 735

Ile Gln Asn Phe Thr Arg Thr Gln Lys Ser Cys Ile Phe Cys Gly Phe
            740                 745                 750

Ala Leu Leu Ser Tyr Asp Glu Lys Glu Gly Leu Glu Thr Thr Thr Tyr
        755                 760                 765

Ile Thr Ser Gln Glu Val Gln Asn Ser Ile Leu Ser Ser Asn Tyr Phe
    770                 775                 780
```

```
Asp Phe Asp Asn Leu His Val His Tyr Leu Leu Thr Thr Asn Gly
785                 790                 795                 800

Thr Val Met Glu Ile Ala Gly Leu Tyr Glu Glu Arg Ala Ser Gly Ser
            805                 810                 815

Gly Ser Gly Ser Gly Leu Val Pro Arg Gly Ser Gly Ala Gly Gly Gly
        820                 825                 830

His His His His His His
        835

<210> SEQ ID NO 16
<211> LENGTH: 867
<212> TYPE: PRT
<213> ORGANISM: Artificial Sequence
<220> FEATURE:
<223> OTHER INFORMATION: Synthetic polypeptide

<400> SEQUENCE: 16

Met Glu Thr Asp Thr Leu Leu Leu Trp Val Leu Leu Leu Trp Val Pro
1               5                   10                  15

Gly Ser Thr Gly Asn Trp Ala Tyr Pro Cys Cys His Val Thr Gln Leu
            20                  25                  30

Arg Ala Gln His Leu Leu Ala Leu Glu Asn Ile Ser Asp Ile Tyr Leu
        35                  40                  45

Val Ser Asn Gln Thr Cys Asp Gly Phe Ser Leu Ala Ser Leu Asn Ser
50                  55                  60

Pro Lys Asn Gly Ser Asn Gln Leu Val Ile Ser Arg Cys Ala Asn Gly
65                  70                  75                  80

Leu Asn Val Val Ser Phe Phe Ile Ser Ile Leu Lys Arg Ser Ser Ser
                85                  90                  95

Ala Leu Thr Gly His Leu Arg Glu Leu Leu Thr Thr Leu Glu Thr Leu
            100                 105                 110

Tyr Gly Ser Phe Ser Val Glu Asp Leu Phe Gly Ala Asn Leu Asn Arg
        115                 120                 125

Tyr Ala Trp His Arg Gly Gly Gly Gly Gly Ser Gly Gly Gly Gly
    130                 135                 140

Ser Gly Gly Gly Gly Ser Gly Ala Ala Ser Leu Ser Glu Val Lys Leu
145                 150                 155                 160

His Leu Asp Ile Glu Gly His Ala Ser His Tyr Thr Ile Pro Trp Thr
                165                 170                 175

Glu Leu Met Ala Lys Val Pro Gly Leu Ser Pro Glu Ala Leu Trp Arg
            180                 185                 190

Glu Ala Asn Val Thr Glu Asp Leu Ala Ser Met Leu Asn Arg Tyr Lys
        195                 200                 205

Leu Ile Tyr Lys Thr Ser Gly Thr Leu Gly Ile Ala Leu Ala Glu Pro
    210                 215                 220

Val Asp Ile Pro Ala Val Ser Glu Gly Ser Met Gln Val Asp Ala Ser
225                 230                 235                 240

Lys Val His Pro Gly Val Ile Ser Gly Leu Asn Ser Pro Ala Cys Met
                245                 250                 255

Leu Ser Ala Pro Leu Glu Lys Gln Leu Phe Tyr Tyr Ile Gly Thr Met
            260                 265                 270

Leu Pro Asn Thr Arg Pro His Ser Tyr Val Phe Tyr Gln Leu Arg Cys
        275                 280                 285

His Leu Ser Tyr Val Ala Leu Ser Ile Asn Gly Asp Lys Phe Gln Tyr
    290                 295                 300
```

-continued

Thr Gly Ala Met Thr Ser Lys Phe Leu Met Gly Tyr Lys Arg Val
305                 310                 315                 320

Thr Glu Lys Gly Asp Glu His Val Leu Ser Leu Val Phe Gly Lys Thr
            325                 330                 335

Lys Asp Leu Pro Asp Leu Arg Gly Pro Phe Ser Tyr Pro Ser Leu Thr
            340                 345                 350

Ser Ala Gln Ser Gly Asp Tyr Ser Leu Val Ile Val Thr Thr Phe Val
            355                 360                 365

His Tyr Ala Asn Phe His Asn Tyr Phe Val Pro Asn Leu Lys Asp Met
370                 375                 380

Phe Ser Arg Ala Val Thr Met Thr Ala Ala Ser Tyr Ala Arg Tyr Val
385                 390                 395                 400

Leu Gln Lys Leu Val Leu Leu Glu Met Lys Gly Gly Cys Arg Glu Pro
                405                 410                 415

Glu Leu Asp Thr Glu Thr Leu Thr Thr Met Phe Glu Val Ser Val Ala
            420                 425                 430

Phe Phe Lys Val Gly His Ala Val Gly Glu Thr Gly Asn Gly Cys Val
            435                 440                 445

Asp Leu Arg Trp Leu Ala Lys Ser Phe Phe Glu Leu Thr Val Leu Lys
450                 455                 460

Asp Ile Ile Gly Ile Cys Tyr Gly Ala Thr Val Lys Gly Met Gln Ser
465                 470                 475                 480

Tyr Gly Leu Glu Arg Leu Ala Ala Met Leu Met Ala Thr Val Lys Met
                485                 490                 495

Glu Glu Leu Gly His Leu Thr Thr Glu Lys Gln Glu Tyr Ala Leu Arg
            500                 505                 510

Leu Ala Thr Val Gly Tyr Pro Lys Ala Gly Val Tyr Ser Gly Leu Ile
            515                 520                 525

Gly Gly Ala Thr Ser Val Leu Leu Ser Ala Tyr Asn Arg His Pro Leu
            530                 535                 540

Phe Gln Pro Leu His Thr Val Met Arg Glu Thr Leu Phe Ile Gly Ser
545                 550                 555                 560

His Val Val Leu Arg Glu Leu Arg Leu Asn Val Thr Thr Gln Gly Pro
                565                 570                 575

Asn Leu Ala Leu Tyr Gln Leu Leu Ser Thr Ala Leu Cys Ser Ala Leu
            580                 585                 590

Glu Ile Gly Glu Val Leu Arg Gly Leu Ala Leu Gly Thr Glu Ser Gly
            595                 600                 605

Leu Phe Ser Pro Cys Tyr Leu Ser Leu Arg Phe Asp Leu Thr Arg Asp
            610                 615                 620

Lys Leu Leu Ser Met Ala Pro Gln Glu Ala Thr Leu Asp Gln Ala Ala
625                 630                 635                 640

Val Ser Asn Ala Val Asp Gly Phe Leu Gly Arg Leu Ser Leu Glu Arg
                645                 650                 655

Glu Asp Arg Asp Ala Trp His Leu Pro Ala Tyr Lys Cys Val Asp Arg
            660                 665                 670

Leu Asp Lys Val Leu Met Ile Ile Pro Leu Ile Asn Val Thr Phe Ile
            675                 680                 685

Ile Ser Ser Asp Arg Glu Val Arg Gly Ser Ala Leu Tyr Glu Ala Ser
            690                 695                 700

Thr Thr Tyr Leu Ser Ser Ser Leu Phe Leu Ser Pro Val Ile Met Asn
705                 710                 715                 720

Lys Cys Ser Gln Gly Ala Val Ala Gly Glu Pro Arg Gln Ile Pro Lys

```
                    725                 730                 735
Ile Gln Asn Phe Thr Arg Thr Gln Lys Ser Cys Ile Phe Cys Gly Phe
                740                 745                 750

Ala Leu Leu Ser Tyr Asp Glu Lys Glu Gly Leu Glu Thr Thr Thr Tyr
            755                 760                 765

Ile Thr Ser Gln Glu Val Gln Asn Ser Ile Leu Ser Ser Asn Tyr Phe
        770                 775                 780

Asp Phe Asp Asn Leu His Val His Tyr Leu Leu Leu Thr Thr Asn Gly
785                 790                 795                 800

Thr Val Met Glu Ile Ala Gly Leu Tyr Glu Glu Arg Ala Ser Gly Ser
                805                 810                 815

Gly Tyr Ile Pro Glu Ala Pro Arg Asp Gly Gln Ala Tyr Val Arg Lys
                820                 825                 830

Asp Gly Glu Trp Val Leu Leu Ser Thr Phe Leu Gly Ser Gly Ser Gly
            835                 840                 845

Ser Gly Leu Val Pro Arg Gly Ser Gly Ala Gly Gly His His His
        850                 855                 860

His His His
865

<210> SEQ ID NO 17
<211> LENGTH: 1019
<212> TYPE: PRT
<213> ORGANISM: Artificial Sequence
<220> FEATURE:
<223> OTHER INFORMATION: Synthetic polypeptide

<400> SEQUENCE: 17

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
                20                  25                  30

Gln Leu Arg Ala Gln His Leu Leu Ala Leu Glu Asn Ile Ser Asp Ile
            35                  40                  45

Tyr Leu Val Ser Asn Gln Thr Cys Asp Gly Phe Ser Leu Ala Ser Leu
        50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Ala Ser
        130                 135                 140

Ala Glu Ala Ala Ala Lys Glu Ala Ala Lys Ala Gly Gly Ser Gly
145                 150                 155                 160

Gly Ser Gly Ala Ala Ser Leu Ser Glu Val Lys Leu His Leu Asp Ile
                165                 170                 175

Glu Gly His Ala Ser His Tyr Thr Ile Pro Trp Thr Glu Leu Met Ala
            180                 185                 190

Lys Val Pro Gly Leu Ser Pro Glu Ala Leu Trp Arg Glu Ala Asn Val
        195                 200                 205

Thr Glu Asp Leu Ala Ser Met Leu Asn Arg Tyr Lys Leu Ile Tyr Lys
```

```
              210                 215                 220
Thr Ser Gly Thr Leu Gly Ile Ala Leu Ala Glu Pro Val Asp Ile Pro
225                 230                 235                 240

Ala Val Ser Glu Gly Ser Met Gln Val Asp Ala Ser Lys Val His Pro
                245                 250                 255

Gly Val Ile Ser Gly Leu Asn Ser Pro Ala Cys Met Leu Ser Ala Pro
                260                 265                 270

Leu Glu Lys Gln Leu Phe Tyr Tyr Ile Gly Thr Met Leu Pro Asn Thr
                275                 280                 285

Arg Pro His Ser Tyr Val Phe Tyr Gln Leu Arg Cys His Leu Ser Tyr
                290                 295                 300

Val Ala Leu Ser Ile Asn Gly Asp Lys Phe Gln Tyr Thr Gly Ala Met
305                 310                 315                 320

Thr Ser Lys Phe Leu Met Gly Thr Tyr Lys Arg Val Thr Glu Lys Gly
                325                 330                 335

Asp Glu His Val Leu Ser Leu Val Phe Gly Lys Thr Lys Asp Leu Pro
                340                 345                 350

Asp Leu Arg Gly Pro Phe Ser Tyr Pro Ser Leu Thr Ser Ala Gln Ser
                355                 360                 365

Gly Asp Tyr Ser Leu Val Ile Val Thr Thr Phe Val His Tyr Ala Asn
                370                 375                 380

Phe His Asn Tyr Phe Val Pro Asn Leu Lys Asp Met Phe Ser Arg Ala
385                 390                 395                 400

Val Thr Met Thr Ala Ala Ser Tyr Ala Arg Tyr Val Leu Gln Lys Leu
                405                 410                 415

Val Leu Leu Glu Met Lys Gly Gly Cys Arg Glu Pro Glu Leu Asp Thr
                420                 425                 430

Glu Thr Leu Thr Thr Met Phe Glu Val Ser Val Ala Phe Phe Lys Val
                435                 440                 445

Gly His Ala Val Gly Glu Thr Gly Asn Gly Cys Val Asp Leu Arg Trp
                450                 455                 460

Leu Ala Lys Ser Phe Phe Glu Leu Thr Val Leu Lys Asp Ile Ile Gly
465                 470                 475                 480

Ile Cys Tyr Gly Ala Thr Val Lys Gly Met Gln Ser Tyr Gly Leu Glu
                485                 490                 495

Arg Leu Ala Ala Met Leu Met Ala Thr Val Lys Met Glu Glu Leu Gly
                500                 505                 510

His Leu Thr Thr Glu Lys Gln Glu Tyr Ala Leu Arg Leu Ala Thr Val
                515                 520                 525

Gly Tyr Pro Lys Ala Gly Val Tyr Ser Gly Leu Ile Gly Gly Ala Thr
                530                 535                 540

Ser Val Leu Leu Ser Ala Tyr Asn Arg His Pro Leu Phe Gln Pro Leu
545                 550                 555                 560

His Thr Val Met Arg Glu Thr Leu Phe Ile Gly Ser His Val Val Leu
                565                 570                 575

Arg Glu Leu Arg Leu Asn Val Thr Thr Gln Gly Pro Asn Leu Ala Leu
                580                 585                 590

Tyr Gln Leu Leu Ser Thr Ala Leu Cys Ser Ala Leu Glu Ile Gly Glu
                595                 600                 605

Val Leu Arg Gly Leu Ala Leu Gly Thr Glu Ser Gly Leu Phe Ser Pro
                610                 615                 620

Cys Tyr Leu Ser Leu Arg Phe Asp Leu Thr Arg Asp Lys Leu Leu Ser
625                 630                 635                 640
```

Met Ala Pro Gln Glu Ala Thr Leu Asp Gln Ala Ala Val Ser Asn Ala
                645                 650                 655

Val Asp Gly Phe Leu Gly Arg Leu Ser Leu Glu Arg Glu Asp Arg Asp
            660                 665                 670

Ala Trp His Leu Pro Ala Tyr Lys Cys Val Asp Arg Leu Asp Lys Val
        675                 680                 685

Leu Met Ile Ile Pro Leu Ile Asn Val Thr Phe Ile Ile Ser Ser Asp
    690                 695                 700

Arg Glu Val Arg Gly Ser Ala Leu Tyr Glu Ala Ser Thr Thr Tyr Leu
705                 710                 715                 720

Ser Ser Ser Leu Phe Leu Ser Pro Val Ile Met Asn Lys Cys Ser Gln
                725                 730                 735

Gly Ala Val Ala Gly Glu Pro Arg Gln Ile Pro Lys Ile Gln Asn Phe
            740                 745                 750

Thr Arg Thr Gln Lys Ser Cys Ile Phe Cys Gly Phe Ala Leu Leu Ser
        755                 760                 765

Tyr Asp Glu Lys Glu Gly Leu Glu Thr Thr Thr Tyr Ile Thr Ser Gln
    770                 775                 780

Glu Val Gln Asn Ser Ile Leu Ser Ser Asn Tyr Phe Asp Phe Asp Asn
785                 790                 795                 800

Leu His Val His Tyr Leu Leu Leu Thr Thr Asn Gly Thr Val Met Glu
                805                 810                 815

Ile Ala Gly Leu Tyr Glu Glu Arg Ala Ser Gly Gly Ser Gly Gly
            820                 825                 830

Gly Ser Gly Gly Gly Ser Gly Gly Ser Gly Gly Gly Ser Glu Ser
        835                 840                 845

Gln Val Arg Gln Gln Phe Ser Lys Asp Ile Glu Lys Leu Leu Asn Glu
    850                 855                 860

Gln Val Asn Lys Glu Met Gln Ser Ser Asn Leu Tyr Met Ser Met Ser
865                 870                 875                 880

Ser Trp Ser Tyr Thr His Ser Leu Asp Gly Ala Gly Leu Phe Leu Phe
                885                 890                 895

Asp His Ala Ala Glu Glu Tyr Glu His Ala Lys Lys Leu Ile Ile Phe
            900                 905                 910

Leu Asn Glu Asn Asn Val Pro Val Gln Leu Thr Ser Ile Ser Ala Pro
        915                 920                 925

Glu His Lys Phe Glu Gly Leu Thr Gln Ile Phe Gln Lys Ala Tyr Glu
    930                 935                 940

His Glu Gln His Ile Ser Glu Ser Ile Asn Asn Ile Val Asp His Ala
945                 950                 955                 960

Ile Lys Cys Lys Asp His Ala Thr Phe Asn Phe Leu Gln Trp Tyr Val
                965                 970                 975

Ala Glu Gln His Glu Glu Val Leu Phe Lys Asp Ile Leu Asp Lys
            980                 985                 990

Ile Glu Leu Ile Gly Asn Glu Asn  His Gly Leu Tyr Leu  Ala Asp Gln
        995                 1000                1005

Tyr Val  Lys Gly Ile Ala Lys  Ser Arg Lys Ser
     1010                1015

<210> SEQ ID NO 18
<211> LENGTH: 1025
<212> TYPE: PRT
<213> ORGANISM: Artificial Sequence
<220> FEATURE:

<223> OTHER INFORMATION: Synthetic polypeptide

<400> SEQUENCE: 18

```
Met Arg Ala Val Gly Val Phe Leu Ala Ile Cys Leu Val Thr Ile Phe
1               5                   10                  15
Val Leu Pro Thr Trp Gly Asn Trp Ala Tyr Pro Cys Cys His Val Thr
            20                  25                  30
Gln Leu Arg Ala Gln His Leu Leu Ala Leu Glu Asn Ile Ser Asp Ile
        35                  40                  45
Tyr Leu Val Ser Asn Gln Thr Cys Asp Gly Phe Ser Leu Ala Ser Leu
    50                  55                  60
Asn Ser Pro Lys Asn Gly Ser Asn Gln Leu Val Ile Ser Arg Cys Ala
65                  70                  75                  80
Asn Gly Leu Asn Val Val Ser Phe Phe Ile Ser Ile Leu Lys Arg Ser
                85                  90                  95
Ser Ser Ala Leu Thr Gly His Leu Arg Glu Leu Leu Thr Thr Leu Glu
            100                 105                 110
Thr Leu Tyr Gly Ser Phe Ser Val Glu Asp Leu Phe Gly Ala Asn Leu
        115                 120                 125
Asn Arg Tyr Ala Trp His Arg Gly Gly Gly Ser Gly Ser Ala Ser
    130                 135                 140
Ala Glu Ala Ala Ala Lys Glu Ala Ala Ala Lys Glu Ala Ala Ala Lys
145                 150                 155                 160
Ala Ser Gly Gly Ser Gly Gly Ser Gly Ala Ala Ser Leu Ser Glu Val
                165                 170                 175
Lys Leu His Leu Asp Ile Glu Gly His Ala Ser His Tyr Thr Ile Pro
            180                 185                 190
Trp Thr Glu Leu Met Ala Lys Val Pro Gly Leu Ser Pro Glu Ala Leu
        195                 200                 205
Trp Arg Glu Ala Asn Val Thr Glu Asp Leu Ala Ser Met Leu Asn Arg
    210                 215                 220
Tyr Lys Leu Ile Tyr Lys Thr Ser Gly Thr Leu Gly Ile Ala Leu Ala
225                 230                 235                 240
Glu Pro Val Asp Ile Pro Ala Val Ser Glu Gly Ser Met Gln Val Asp
                245                 250                 255
Ala Ser Lys Val His Pro Gly Val Ile Ser Gly Leu Asn Ser Pro Ala
            260                 265                 270
Cys Met Leu Ser Ala Pro Leu Glu Lys Gln Leu Phe Tyr Tyr Ile Gly
        275                 280                 285
Thr Met Leu Pro Asn Thr Arg Pro His Ser Tyr Val Phe Tyr Gln Leu
    290                 295                 300
Arg Cys His Leu Ser Tyr Val Ala Leu Ser Ile Asn Gly Asp Lys Phe
305                 310                 315                 320
Gln Tyr Thr Gly Ala Met Thr Ser Lys Phe Leu Met Gly Thr Tyr Lys
                325                 330                 335
Arg Val Thr Glu Lys Gly Asp Glu His Val Leu Ser Leu Val Phe Gly
            340                 345                 350
Lys Thr Lys Asp Leu Pro Asp Leu Arg Gly Pro Phe Ser Tyr Pro Ser
        355                 360                 365
Leu Thr Ser Ala Gln Ser Gly Asp Tyr Ser Leu Val Ile Val Thr Thr
    370                 375                 380
Phe Val His Tyr Ala Asn Phe His Asn Tyr Phe Val Pro Asn Leu Lys
385                 390                 395                 400
```

```
Asp Met Phe Ser Arg Ala Val Thr Met Thr Ala Ala Ser Tyr Ala Arg
                405                 410                 415
Tyr Val Leu Gln Lys Leu Val Leu Leu Glu Met Lys Gly Gly Cys Arg
            420                 425                 430
Glu Pro Glu Leu Asp Thr Glu Thr Leu Thr Thr Met Phe Glu Val Ser
        435                 440                 445
Val Ala Phe Phe Lys Val Gly His Ala Val Gly Glu Thr Gly Asn Gly
    450                 455                 460
Cys Val Asp Leu Arg Trp Leu Ala Lys Ser Phe Phe Glu Leu Thr Val
465                 470                 475                 480
Leu Lys Asp Ile Ile Gly Ile Cys Tyr Gly Ala Thr Val Lys Gly Met
                485                 490                 495
Gln Ser Tyr Gly Leu Glu Arg Leu Ala Ala Met Leu Met Ala Thr Val
            500                 505                 510
Lys Met Glu Glu Leu Gly His Leu Thr Thr Glu Lys Gln Glu Tyr Ala
        515                 520                 525
Leu Arg Leu Ala Thr Val Gly Tyr Pro Lys Ala Gly Val Tyr Ser Gly
    530                 535                 540
Leu Ile Gly Gly Ala Thr Ser Val Leu Leu Ser Ala Tyr Asn Arg His
545                 550                 555                 560
Pro Leu Phe Gln Pro Leu His Thr Val Met Arg Glu Thr Leu Phe Ile
                565                 570                 575
Gly Ser His Val Val Leu Arg Glu Leu Arg Leu Asn Val Thr Thr Gln
            580                 585                 590
Gly Pro Asn Leu Ala Leu Tyr Gln Leu Leu Ser Thr Ala Leu Cys Ser
        595                 600                 605
Ala Leu Glu Ile Gly Glu Val Leu Arg Gly Leu Ala Leu Gly Thr Glu
    610                 615                 620
Ser Gly Leu Phe Ser Pro Cys Tyr Leu Ser Leu Arg Phe Asp Leu Thr
625                 630                 635                 640
Arg Asp Lys Leu Leu Ser Met Ala Pro Gln Glu Ala Thr Leu Asp Gln
                645                 650                 655
Ala Ala Val Ser Asn Ala Val Asp Gly Phe Leu Gly Arg Leu Ser Leu
            660                 665                 670
Glu Arg Glu Asp Arg Asp Ala Trp His Leu Pro Ala Tyr Lys Cys Val
        675                 680                 685
Asp Arg Leu Asp Lys Val Leu Met Ile Ile Pro Leu Ile Asn Val Thr
    690                 695                 700
Phe Ile Ile Ser Ser Asp Arg Glu Val Arg Gly Ser Ala Leu Tyr Glu
705                 710                 715                 720
Ala Ser Thr Thr Tyr Leu Ser Ser Ser Leu Phe Leu Ser Pro Val Ile
                725                 730                 735
Met Asn Lys Cys Ser Gln Gly Ala Val Ala Gly Glu Pro Arg Gln Ile
            740                 745                 750
Pro Lys Ile Gln Asn Phe Thr Arg Thr Gln Lys Ser Cys Ile Phe Cys
        755                 760                 765
Gly Phe Ala Leu Leu Ser Tyr Asp Glu Lys Glu Gly Leu Glu Thr Thr
    770                 775                 780
Thr Tyr Ile Thr Ser Gln Glu Val Gln Asn Ser Ile Leu Ser Ser Asn
785                 790                 795                 800
Tyr Phe Asp Phe Asp Asn Leu His Val His Tyr Leu Leu Leu Thr Thr
                805                 810                 815
Asn Gly Thr Val Met Glu Ile Ala Gly Leu Tyr Glu Glu Arg Ala Ser
```

```
                    820                 825                 830
Gly Gly Gly Ser Gly Gly Gly Ser Gly Gly Gly Ser Gly Gly Gly Ser
                835                 840                 845

Gly Gly Gly Ser Glu Ser Gln Val Arg Gln Gln Phe Ser Lys Asp Ile
    850                 855                 860

Glu Lys Leu Leu Asn Glu Gln Val Asn Lys Glu Met Gln Ser Ser Asn
865                 870                 875                 880

Leu Tyr Met Ser Met Ser Ser Trp Ser Tyr Thr His Ser Leu Asp Gly
                885                 890                 895

Ala Gly Leu Phe Leu Phe Asp His Ala Ala Glu Glu Tyr Glu His Ala
            900                 905                 910

Lys Lys Leu Ile Ile Phe Leu Asn Glu Asn Asn Val Pro Val Gln Leu
        915                 920                 925

Thr Ser Ile Ser Ala Pro Glu His Lys Phe Glu Gly Leu Thr Gln Ile
    930                 935                 940

Phe Gln Lys Ala Tyr Glu His Glu Gln His Ile Ser Glu Ser Ile Asn
945                 950                 955                 960

Asn Ile Val Asp His Ala Ile Lys Cys Lys Asp His Ala Thr Phe Asn
                965                 970                 975

Phe Leu Gln Trp Tyr Val Ala Glu Gln His Glu Glu Val Leu Phe
            980                 985                 990

Lys Asp Ile Leu Asp Lys Ile Glu  Leu Ile Gly Asn Glu  Asn His Gly
        995                 1000                1005

Leu Tyr  Leu Ala Asp Gln Tyr  Val Lys Gly Ile Ala  Lys Ser Arg
    1010                1015                1020

Lys Ser
    1025

<210> SEQ ID NO 19
<211> LENGTH: 1065
<212> TYPE: PRT
<213> ORGANISM: Artificial Sequence
<220> FEATURE:
<223> OTHER INFORMATION: Synthetic polypeptide

<400> SEQUENCE: 19

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Ala Ser
    130                 135                 140

Ser Gly Ala Ser Ala Ser Gly Ser Ser Asn Gly Ser Gly Ser Gly Ser
```

```
            145                 150                 155                 160
        Gly Ser Asn Ser Ser Ala Ser Ser Gly Ala Ser Ser Gly Gly Ala Ser
                        165                 170                 175
        Gly Gly Ser Gly Gly Ser Gly Ala Ala Ser Leu Ser Glu Val Lys Leu
                        180                 185                 190
        His Leu Asp Ile Glu Gly His Ala Ser His Tyr Thr Ile Pro Trp Thr
                        195                 200                 205
        Glu Leu Met Ala Lys Val Pro Gly Leu Ser Pro Glu Ala Leu Trp Arg
                        210                 215                 220
        Glu Ala Asn Val Thr Glu Asp Leu Ala Ser Met Leu Asn Arg Tyr Lys
        225                 230                 235                 240
        Leu Ile Tyr Lys Thr Ser Gly Thr Leu Gly Ile Ala Leu Ala Glu Pro
                        245                 250                 255
        Val Asp Ile Pro Ala Val Ser Glu Gly Ser Met Gln Val Asp Ala Ser
                        260                 265                 270
        Lys Val His Pro Gly Val Ile Ser Gly Leu Asn Ser Pro Ala Cys Met
                        275                 280                 285
        Leu Ser Ala Pro Leu Glu Lys Gln Leu Phe Tyr Ile Gly Thr Met
        290                 295                 300
        Leu Pro Asn Thr Arg Pro His Ser Tyr Val Phe Tyr Gln Leu Arg Cys
        305                 310                 315                 320
        His Leu Ser Tyr Val Ala Leu Ser Ile Asn Gly Asp Lys Phe Gln Tyr
                        325                 330                 335
        Thr Gly Ala Met Thr Ser Lys Phe Leu Met Gly Thr Tyr Lys Arg Val
                        340                 345                 350
        Thr Glu Lys Gly Asp Glu His Val Leu Ser Leu Val Phe Gly Lys Thr
                        355                 360                 365
        Lys Asp Leu Pro Asp Leu Arg Gly Pro Phe Ser Tyr Pro Ser Leu Thr
                        370                 375                 380
        Ser Ala Gln Ser Gly Asp Tyr Ser Leu Val Ile Val Thr Thr Phe Val
        385                 390                 395                 400
        His Tyr Ala Asn Phe His Asn Tyr Phe Val Pro Asn Leu Lys Asp Met
                        405                 410                 415
        Phe Ser Arg Ala Val Thr Met Thr Ala Ala Ser Tyr Ala Arg Tyr Val
                        420                 425                 430
        Leu Gln Lys Leu Val Leu Leu Glu Met Lys Gly Gly Cys Arg Glu Pro
                        435                 440                 445
        Glu Leu Asp Thr Glu Thr Leu Thr Thr Met Phe Glu Val Ser Val Ala
                        450                 455                 460
        Phe Phe Lys Val Gly His Ala Val Gly Glu Thr Gly Asn Gly Cys Val
        465                 470                 475                 480
        Asp Leu Arg Trp Leu Ala Lys Ser Phe Phe Glu Leu Thr Val Leu Lys
                        485                 490                 495
        Asp Ile Ile Gly Ile Cys Tyr Gly Ala Thr Val Lys Gly Met Gln Ser
                        500                 505                 510
        Tyr Gly Leu Glu Arg Leu Ala Ala Met Leu Met Ala Thr Val Lys Met
                        515                 520                 525
        Glu Glu Leu Gly His Leu Thr Thr Glu Lys Gln Glu Tyr Ala Leu Arg
                        530                 535                 540
        Leu Ala Thr Val Gly Tyr Pro Lys Ala Gly Val Tyr Ser Gly Leu Ile
        545                 550                 555                 560
        Gly Gly Ala Thr Ser Val Leu Leu Ser Ala Tyr Asn Arg His Pro Leu
                        565                 570                 575
```

```
Phe Gln Pro Leu His Thr Val Met Arg Glu Thr Leu Phe Ile Gly Ser
            580                 585                 590

His Val Val Leu Arg Glu Leu Arg Leu Asn Val Thr Thr Gln Gly Pro
            595                 600                 605

Asn Leu Ala Leu Tyr Gln Leu Leu Ser Thr Ala Leu Cys Ser Ala Leu
            610                 615                 620

Glu Ile Gly Glu Val Leu Arg Gly Leu Ala Leu Gly Thr Ser Gly
625                 630                 635                 640

Leu Phe Ser Pro Cys Tyr Leu Ser Leu Arg Phe Asp Leu Thr Arg Asp
                645                 650                 655

Lys Leu Leu Ser Met Ala Pro Gln Glu Ala Thr Leu Asp Gln Ala Ala
                660                 665                 670

Val Ser Asn Ala Val Asp Gly Phe Leu Gly Arg Leu Ser Leu Glu Arg
                675                 680                 685

Glu Asp Arg Asp Ala Trp His Leu Pro Ala Tyr Lys Cys Val Asp Arg
                690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
                725                 730                 735

Thr Thr Tyr Leu Ser Ser Ser Leu Phe Leu Ser Pro Val Ile Met Asn
                740                 745                 750

Lys Cys Ser Gln Gly Ala Val Ala Gly Glu Pro Arg Gln Ile Pro Lys
                755                 760                 765

Ile Gln Asn Phe Thr Arg Thr Gln Lys Ser Cys Ile Phe Cys Gly Phe
                770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
                805                 810                 815

Asp Phe Asp Asn Leu His Val His Tyr Leu Leu Leu Thr Thr Asn Gly
                820                 825                 830

Thr Val Met Glu Ile Ala Gly Leu Tyr Glu Glu Arg Ala Ser Gly Gly
                835                 840                 845

Gly Ser Gly Ser Ala Ser Ser Gly Ala Ser Ala Ser Gly Ser Ser Gly
                850                 855                 860

Ser Gly Ser Gly Ser Gly Ser Ser Ala Ser Ser Gly Ala Ser Ser
865                 870                 875                 880

Gly Gly Ala Ser Gly Gly Ser Gly Ser Gly Glu Ser Gln Val
                885                 890                 895

Arg Gln Gln Phe Ser Lys Asp Ile Glu Lys Leu Leu Asn Glu Gln Val
                900                 905                 910

Asn Lys Glu Met Gln Ser Ser Asn Leu Tyr Met Ser Met Ser Ser Trp
                915                 920                 925

Ser Tyr Thr His Ser Leu Asp Gly Ala Gly Leu Phe Leu Phe Asp His
                930                 935                 940

Ala Ala Glu Glu Tyr Glu His Ala Lys Lys Leu Ile Ile Phe Leu Asn
945                 950                 955                 960

Glu Asn Asn Val Pro Val Gln Leu Thr Ser Ile Ser Ala Pro Glu His
                965                 970                 975

Lys Phe Glu Gly Leu Thr Gln Ile Phe Gln Lys Ala Tyr Glu His Glu
                980                 985                 990
```

```
Gln His Ile Ser Glu Ser Ile Asn  Asn Ile Val Asp His  Ala Ile Lys
         995                 1000                 1005

Cys Lys Asp His Ala Thr Phe  Asn Phe Leu Gln Trp  Tyr Val Ala
    1010                1015                 1020

Glu Gln His Glu Glu Glu Val  Leu Phe Lys Asp Ile  Leu Asp Lys
    1025                1030                 1035

Ile Glu Leu Ile Gly Asn Glu  Asn His Gly Leu Tyr  Leu Ala Asp
    1040                1045                 1050

Gln Tyr Val Lys Gly Ile Ala  Lys Ser Arg Lys Ser
    1055                1060                 1065
```

<210> SEQ ID NO 20
<211> LENGTH: 1065
<212> TYPE: PRT
<213> ORGANISM: Artificial Sequence
<220> FEATURE:
<223> OTHER INFORMATION: Synthetic polypeptide

<400> SEQUENCE: 20

```
Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Ala Ser
    130                 135                 140

Ser Gly Ala Ser Ala Ser Gly Ser Ser Asn Gly Ser Gly Ser Gly Ser
145                 150                 155                 160

Gly Ser Asn Ser Ser Ala Ser Ser Gly Ala Ser Ser Gly Gly Ala Ser
                165                 170                 175

Gly Gly Ser Gly Gly Ser Gly Ala Ala Ser Leu Ser Glu Val Lys Leu
            180                 185                 190

His Leu Asp Ile Glu Gly His Ala Ser His Tyr Thr Ile Pro Trp Thr
        195                 200                 205

Glu Leu Met Ala Lys Val Pro Gly Leu Ser Pro Glu Ala Leu Trp Arg
    210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
                245                 250                 255

Val Asp Ile Pro Ala Val Ser Glu Gly Ser Met Gln Val Asp Ala Ser
            260                 265                 270

Lys Val His Pro Gly Val Ile Ser Gly Leu Asn Ser Pro Ala Cys Met
        275                 280                 285
```

-continued

```
Leu Ser Ala Pro Leu Glu Lys Gln Leu Phe Tyr Tyr Ile Gly Thr Met
290                 295                 300
Leu Pro Asn Thr Arg Pro His Ser Tyr Val Phe Tyr Gln Leu Arg Cys
305                 310                 315                 320
His Leu Ser Tyr Val Ala Leu Ser Ile Asn Gly Asp Lys Phe Gln Tyr
            325                 330                 335
Thr Gly Ala Met Thr Ser Lys Phe Leu Met Gly Thr Tyr Lys Arg Val
            340                 345                 350
Thr Glu Lys Gly Asp Glu His Val Leu Ser Leu Val Phe Gly Lys Thr
        355                 360                 365
Lys Asp Leu Pro Asp Leu Arg Gly Pro Phe Ser Tyr Pro Ser Leu Thr
370                 375                 380
Ser Ala Gln Ser Gly Asp Tyr Ser Leu Val Ile Val Thr Thr Phe Val
385                 390                 395                 400
His Tyr Ala Asn Phe His Asn Tyr Phe Val Pro Asn Leu Lys Asp Met
                405                 410                 415
Phe Ser Arg Ala Val Thr Met Thr Ala Ala Ser Tyr Ala Arg Tyr Val
            420                 425                 430
Leu Gln Lys Leu Val Leu Leu Glu Met Lys Gly Gly Cys Arg Glu Pro
        435                 440                 445
Glu Leu Asp Thr Glu Thr Leu Thr Thr Met Phe Glu Val Ser Val Ala
450                 455                 460
Phe Phe Lys Val Gly His Ala Val Gly Glu Thr Gly Asn Gly Cys Val
465                 470                 475                 480
Asp Leu Arg Trp Leu Ala Lys Ser Phe Phe Glu Leu Thr Val Leu Lys
                485                 490                 495
Asp Ile Ile Gly Ile Cys Tyr Gly Ala Thr Val Lys Gly Met Gln Ser
            500                 505                 510
Tyr Gly Leu Glu Arg Leu Ala Ala Met Leu Met Ala Thr Val Lys Met
        515                 520                 525
Glu Glu Leu Gly His Leu Thr Thr Glu Lys Gln Glu Tyr Ala Leu Arg
530                 535                 540
Leu Ala Thr Val Gly Tyr Pro Lys Ala Gly Val Tyr Ser Gly Leu Ile
545                 550                 555                 560
Gly Gly Ala Thr Ser Val Leu Leu Ser Ala Tyr Asn Arg His Pro Leu
                565                 570                 575
Phe Gln Pro Leu His Thr Val Met Arg Glu Thr Leu Phe Ile Gly Ser
            580                 585                 590
His Val Val Leu Arg Glu Leu Arg Leu Asn Val Thr Thr Gln Gly Pro
        595                 600                 605
Asn Leu Ala Leu Tyr Gln Leu Leu Ser Thr Ala Leu Cys Ser Ala Leu
610                 615                 620
Glu Ile Gly Glu Val Leu Arg Gly Leu Ala Leu Gly Thr Glu Ser Gly
625                 630                 635                 640
Leu Phe Ser Pro Cys Tyr Leu Ser Leu Arg Phe Asp Leu Thr Arg Asp
                645                 650                 655
Lys Leu Leu Ser Met Ala Pro Gln Glu Ala Thr Leu Asp Gln Ala Ala
            660                 665                 670
Val Ser Asn Ala Val Asp Gly Phe Leu Gly Arg Leu Ser Leu Glu Arg
        675                 680                 685
Glu Asp Arg Asp Ala Trp His Leu Pro Ala Tyr Lys Cys Val Asp Arg
690                 695                 700
Leu Asp Lys Val Leu Met Ile Ile Pro Leu Ile Asn Val Thr Phe Ile
```

```
            705                 710                 715                 720
    Ile Ser Ser Asp Arg Glu Val Arg Gly Ser Ala Leu Tyr Glu Ala Ser
                    725                 730                 735

Thr Thr Tyr Leu Ser Ser Leu Phe Leu Ser Pro Val Ile Met Asn
                740                 745                 750

Lys Cys Ser Gln Gly Ala Val Ala Gly Glu Pro Arg Gln Ile Pro Lys
                    755                 760                 765

Ile Gln Asn Phe Thr Arg Thr Gln Lys Ser Cys Ile Phe Cys Gly Phe
        770                 775                 780

Ala Leu Leu Ser Tyr Asp Glu Lys Glu Gly Leu Glu Thr Thr Thr Tyr
    785                 790                 795                 800

Ile Thr Ser Gln Glu Val Gln Asn Ser Ile Leu Ser Ser Asn Tyr Phe
                    805                 810                 815

Asp Phe Asp Asn Leu His Val His Tyr Leu Leu Leu Thr Thr Asn Gly
                820                 825                 830

Thr Val Met Glu Ile Ala Gly Leu Tyr Glu Glu Arg Ala Ser Gly Gly
                835                 840                 845

Gly Ser Gly Ser Ala Ser Ser Gly Ala Ser Ala Ser Gly Ser Ser Cys
    850                 855                 860

Ser Gly Ser Gly Ser Gly Ser Ser Ser Ala Ser Ser Gly Ala Ser Ser
    865                 870                 875                 880

Gly Gly Ala Ser Gly Gly Ser Gly Gly Ser Gly Glu Ser Gln Val
                    885                 890                 895

Arg Gln Gln Phe Ser Lys Asp Ile Glu Lys Leu Leu Asn Glu Gln Val
                900                 905                 910

Asn Lys Glu Met Gln Ser Ser Asn Leu Tyr Met Ser Met Ser Ser Trp
                915                 920                 925

Ser Tyr Thr His Ser Leu Asp Gly Ala Gly Leu Phe Leu Phe Asp His
                930                 935                 940

Ala Ala Glu Glu Tyr Glu His Ala Lys Lys Leu Ile Ile Phe Leu Asn
    945                 950                 955                 960

Glu Asn Asn Val Pro Val Gln Leu Thr Ser Ile Ser Ala Pro Glu His
                    965                 970                 975

Lys Phe Glu Gly Leu Thr Gln Ile Phe Gln Lys Ala Tyr Glu His Glu
                980                 985                 990

Gln His Ile Ser Glu Ser Ile Asn Asn Ile Val Asp His Ala Ile Lys
                    995                 1000                1005

Ser Lys Asp His Ala Thr Phe Asn Phe Leu Gln Trp Tyr Val Ala
            1010                1015                1020

Glu Gln His Glu Glu Val Leu Phe Lys Asp Ile Leu Asp Lys
            1025                1030                1035

Ile Glu Leu Ile Gly Asn Glu Asn His Gly Leu Tyr Leu Ala Asp
            1040                1045                1050

Gln Tyr Val Lys Gly Ile Ala Lys Ser Arg Lys Ser
            1055                1060                1065

<210> SEQ ID NO 21
<211> LENGTH: 1366
<212> TYPE: PRT
<213> ORGANISM: Artificial Sequence
<220> FEATURE:
<223> OTHER INFORMATION: Synthetic polypeptide

<400> SEQUENCE: 21

Met Arg Ala Val Gly Val Phe Leu Ala Ile Cys Leu Val Thr Ile Phe
```

-continued

```
1               5                   10                  15
Val Leu Pro Thr Trp Gly Asn Trp Ala Tyr Pro Cys Cys His Val Thr
                20                  25                  30
Gln Leu Arg Ala Gln His Leu Leu Ala Leu Glu Asn Ile Ser Asp Ile
                35                  40                  45
Tyr Leu Val Ser Asn Gln Thr Cys Asp Gly Phe Ser Leu Ala Ser Leu
        50                  55                  60
Asn Ser Pro Lys Asn Gly Ser Asn Gln Leu Val Ile Ser Arg Cys Ala
65                  70                  75                  80
Asn Gly Leu Asn Val Val Ser Phe Phe Ile Ser Ile Leu Lys Arg Ser
                85                  90                  95
Ser Ser Ala Leu Thr Gly His Leu Arg Glu Leu Leu Thr Thr Leu Glu
                100                 105                 110
Thr Leu Tyr Gly Ser Phe Ser Val Glu Asp Leu Phe Gly Ala Asn Leu
                115                 120                 125
Asn Arg Tyr Ala Trp His Arg Gly Gly Gly Ser Gly Ser Ala Ser
                130                 135                 140
Ser Gly Ala Ser Ala Ser Gly Ser Ser Asn Gly Ser Gly Ser Gly Ser
145                 150                 155                 160
Gly Ser Asn Ser Ser Ala Ser Ser Gly Ala Ser Ser Gly Gly Ala Ser
                165                 170                 175
Gly Gly Ser Gly Gly Ser Gly Ala Ala Ser Leu Ser Glu Val Lys Leu
                180                 185                 190
His Leu Asp Ile Glu Gly His Ala Ser His Tyr Thr Ile Pro Trp Thr
                195                 200                 205
Glu Leu Met Ala Lys Val Pro Gly Leu Ser Pro Glu Ala Leu Trp Arg
                210                 215                 220
Glu Ala Asn Val Thr Glu Asp Leu Ala Ser Met Leu Asn Arg Tyr Lys
225                 230                 235                 240
Leu Ile Tyr Lys Thr Ser Gly Thr Leu Gly Ile Ala Leu Ala Glu Pro
                245                 250                 255
Val Asp Ile Pro Ala Val Ser Glu Gly Ser Met Gln Val Asp Ala Ser
                260                 265                 270
Lys Val His Pro Gly Val Ile Ser Gly Leu Asn Ser Pro Ala Cys Met
                275                 280                 285
Leu Ser Ala Pro Leu Glu Lys Gln Leu Phe Tyr Tyr Ile Gly Thr Met
                290                 295                 300
Leu Pro Asn Thr Arg Pro His Ser Tyr Val Phe Tyr Gln Leu Arg Cys
305                 310                 315                 320
His Leu Ser Tyr Val Ala Leu Ser Ile Asn Gly Asp Lys Phe Gln Tyr
                325                 330                 335
Thr Gly Ala Met Thr Ser Lys Phe Leu Met Gly Thr Tyr Lys Arg Val
                340                 345                 350
Thr Glu Lys Gly Asp Glu His Val Leu Ser Leu Val Phe Gly Lys Thr
                355                 360                 365
Lys Asp Leu Pro Asp Leu Arg Gly Pro Phe Ser Tyr Pro Ser Leu Thr
                370                 375                 380
Ser Ala Gln Ser Gly Asp Tyr Ser Leu Val Ile Val Thr Thr Phe Val
385                 390                 395                 400
His Tyr Ala Asn Phe His Asn Tyr Phe Val Pro Asn Leu Lys Asp Met
                405                 410                 415
Phe Ser Arg Ala Val Thr Met Thr Ala Ala Ser Tyr Ala Arg Tyr Val
                420                 425                 430
```

```
Leu Gln Lys Leu Val Leu Glu Met Lys Gly Gly Cys Arg Glu Pro
        435                 440                 445

Glu Leu Asp Thr Glu Thr Leu Thr Thr Met Phe Glu Val Ser Val Ala
        450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
                485                 490                 495

Asp Ile Ile Gly Ile Cys Tyr Gly Ala Thr Val Lys Gly Met Gln Ser
                500                 505                 510

Tyr Gly Leu Glu Arg Leu Ala Ala Met Leu Met Ala Thr Val Lys Met
        515                 520                 525

Glu Glu Leu Gly His Leu Thr Thr Glu Lys Gln Glu Tyr Ala Leu Arg
        530                 535                 540

Leu Ala Thr Val Gly Tyr Pro Lys Ala Gly Val Tyr Ser Gly Leu Ile
545                 550                 555                 560

Gly Gly Ala Thr Ser Val Leu Leu Ser Ala Tyr Asn Arg His Pro Leu
                565                 570                 575

Phe Gln Pro Leu His Thr Val Met Arg Glu Thr Leu Phe Ile Gly Ser
            580                 585                 590

His Val Val Leu Arg Glu Leu Arg Leu Asn Val Thr Thr Gln Gly Pro
            595                 600                 605

Asn Leu Ala Leu Tyr Gln Leu Leu Ser Thr Ala Leu Cys Ser Ala Leu
            610                 615                 620

Glu Ile Gly Glu Val Leu Arg Gly Leu Ala Leu Gly Thr Glu Ser Gly
625                 630                 635                 640

Leu Phe Ser Pro Cys Tyr Leu Ser Leu Arg Phe Asp Leu Thr Arg Asp
                645                 650                 655

Lys Leu Leu Ser Met Ala Pro Gln Glu Ala Thr Leu Asp Gln Ala Ala
                660                 665                 670

Val Ser Asn Ala Val Asp Gly Phe Leu Gly Arg Leu Ser Leu Glu Arg
        675                 680                 685

Glu Asp Arg Asp Ala Trp His Leu Pro Ala Tyr Lys Cys Val Asp Arg
        690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
                725                 730                 735

Thr Thr Tyr Leu Ser Ser Ser Leu Phe Leu Ser Pro Val Ile Met Asn
                740                 745                 750

Lys Cys Ser Gln Gly Ala Val Ala Gly Glu Pro Arg Gln Ile Pro Lys
        755                 760                 765

Ile Gln Asn Phe Thr Arg Thr Gln Lys Ser Cys Ile Phe Cys Gly Phe
        770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
                805                 810                 815

Asp Phe Asp Asn Leu His Val His Tyr Leu Leu Leu Thr Thr Asn Gly
                820                 825                 830

Thr Val Met Glu Ile Ala Gly Leu Tyr Glu Glu Arg Ala Ser Gly Gly
        835                 840                 845
```

-continued

```
Gly Ser Gly Ser Ala Ser Ser Gly Ala Ser Ala Ser Gly Ser Ser Gly
850                 855                 860

Ser Gly Ser Gly Ser Gly Ser Ser Ala Ser Ser Gly Asp Ser Lys
865                 870                 875                 880

Gly Ser Ser Gln Lys Gly Ser Arg Leu Leu Leu Leu Val Val Ser
            885                 890                 895

Asn Leu Leu Leu Pro Gln Gly Val Leu Ala Tyr Phe Leu Pro Pro Arg
            900                 905                 910

Val Arg Gly Gly Arg Val Ala Ala Ala Ile Thr Trp Val Pro
        915                 920                 925

Lys Pro Asn Val Glu Val Trp Pro Val Asp Pro Pro Pro Val Asn
930                 935                 940

Phe Asn Lys Thr Ala Glu Gln Glu Tyr Gly Asp Lys Glu Val Lys Leu
945                 950                 955                 960

Pro His Trp Thr Pro Thr Leu His Thr Phe Gln Val Pro Gln Asn Tyr
                965                 970                 975

Thr Lys Ala Asn Cys Thr Tyr Cys Asn Thr Arg Glu Tyr Thr Phe Ser
            980                 985                 990

Tyr Lys Gly Cys Cys Phe Tyr Phe  Thr Lys Lys Lys His  Thr Trp Asn
            995                 1000                1005

Gly Cys  Phe Gln Ala Cys Ala  Glu Leu Tyr Pro Cys  Thr Tyr Phe
    1010                1015                1020

Tyr Gly  Pro Thr Pro Asp Ile  Leu Pro Val Val Thr  Arg Asn Leu
    1025                1030                1035

Asn Ala  Ile Glu Ser Leu Trp  Val Gly Val Tyr Arg  Val Gly Glu
    1040                1045                1050

Gly Asn  Trp Thr Ser Leu Asp  Gly Gly Thr Phe Lys  Val Tyr Gln
    1055                1060                1065

Ile Phe  Gly Ser His Cys Thr  Tyr Val Ser Lys Phe  Ser Thr Val
    1070                1075                1080

Pro Val  Ser His His Glu Cys  Ser Phe Leu Lys Pro  Cys Leu Cys
    1085                1090                1095

Val Ser  Gln Arg Ser Asn Ser  Gly Gly Ser Gly Ser  Ala Ser Ser
    1100                1105                1110

Gly Ala  Ser Ala Ser Gly Ser  Ser Gly Ser Gly Ser  Gly Ser Gly
    1115                1120                1125

Ser Ser  Ser Ala Ser Ser Gly  Ala Ser Ser Gly Gly  Ala Ser Gly
    1130                1135                1140

Gly Ser  Gly Gly Ser Gly Gly  Gly Ser Gly Ser Ala  Ser Ser Gly
    1145                1150                1155

Ala Ser  Ala Ser Gly Ser Ser  Gly Ser Gly Ser Gly  Ser Gly Ser
    1160                1165                1170

Ser Ser  Ala Ser Ser Gly Ala  Ser Ser Gly Gly Ala  Ser Gly Gly
    1175                1180                1185

Ser Gly  Gly Ser Gly Glu Ser  Gln Val Arg Gln Gln  Phe Ser Lys
    1190                1195                1200

Asp Ile  Glu Lys Leu Leu Asn  Glu Gln Val Asn Lys  Glu Met Gln
    1205                1210                1215

Ser Ser  Asn Leu Tyr Met Ser  Met Ser Ser Trp Ser  Tyr Thr His
    1220                1225                1230

Ser Leu  Asp Gly Ala Gly Leu  Phe Leu Phe Asp His  Ala Ala Glu
    1235                1240                1245

Glu Tyr  Glu His Ala Lys Lys  Leu Ile Ile Phe Leu  Asn Glu Asn
```

```
                1250                1255                1260

Asn Val Pro Val Gln Leu Thr Ser Ile Ser Ala Pro Glu His Lys
        1265                1270                1275

Phe Glu Gly Leu Thr Gln Ile Phe Gln Lys Ala Tyr Glu His Glu
    1280                1285                1290

Gln His Ile Ser Glu Ser Ile Asn Asn Ile Val Asp His Ala Ile
        1295                1300                1305

Lys Cys Lys Asp His Ala Thr Phe Asn Phe Leu Gln Trp Tyr Val
    1310                1315                1320

Ala Glu Gln His Glu Glu Val Leu Phe Lys Asp Ile Leu Asp
    1325                1330                1335

Lys Ile Glu Leu Ile Gly Asn Glu Asn His Gly Leu Tyr Leu Ala
    1340                1345                1350

Asp Gln Tyr Val Lys Gly Ile Ala Lys Ser Arg Lys Ser
    1355                1360                1365

<210> SEQ ID NO 22
<211> LENGTH: 1065
<212> TYPE: PRT
<213> ORGANISM: Artificial Sequence
<220> FEATURE:
<223> OTHER INFORMATION: Synthetic polypeptide

<400> SEQUENCE: 22

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Ala Ser
    130                 135                 140

Ser Gly Ala Ser Ala Ser Gly Ser Ser Asn Gly Ser Gly Ser Gly Ser
145                 150                 155                 160

Gly Ser Asn Ser Ser Ala Ser Ser Gly Ala Ser Ser Gly Gly Ala Ser
                165                 170                 175

Gly Gly Ser Gly Gly Ser Gly Ala Ala Ser Leu Ser Glu Val Lys Leu
            180                 185                 190

His Leu Asp Ile Glu Gly His Ala Ser His Tyr Thr Ile Pro Trp Thr
        195                 200                 205

Glu Leu Met Ala Lys Val Pro Gly Leu Ser Pro Glu Ala Leu Trp Arg
    210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
```

```
            245                 250                 255
Val Asp Ile Pro Ala Val Ser Glu Gly Ser Met Gln Val Asp Ala Ser
            260                 265                 270

Lys Val His Pro Gly Val Ile Ser Gly Leu Asn Ser Pro Ala Cys Met
            275                 280                 285

Leu Ser Ala Pro Leu Glu Lys Gln Leu Phe Tyr Tyr Ile Gly Thr Met
            290                 295                 300

Leu Pro Asn Thr Arg Pro His Ser Tyr Val Phe Tyr Gln Leu Arg Ala
305                 310                 315                 320

His Leu Ser Tyr Val Ala Leu Ser Ile Asn Gly Asp Lys Phe Gln Tyr
            325                 330                 335

Thr Gly Ala Met Thr Ser Lys Phe Leu Met Gly Thr Tyr Lys Arg Val
            340                 345                 350

Thr Glu Lys Gly Asp Glu His Val Leu Ser Leu Val Phe Gly Lys Thr
            355                 360                 365

Lys Asp Leu Pro Asp Leu Arg Gly Pro Phe Ser Tyr Pro Ser Leu Thr
            370                 375                 380

Ser Ala Gln Ser Gly Asp Tyr Ser Leu Val Ile Val Thr Thr Phe Val
385                 390                 395                 400

His Tyr Ala Asn Phe His Asn Tyr Phe Val Pro Asn Leu Lys Asp Met
                    405                 410                 415

Phe Ser Arg Ala Val Thr Met Thr Ala Ala Ser Tyr Ala Arg Tyr Val
            420                 425                 430

Leu Gln Lys Leu Val Leu Leu Glu Met Lys Gly Gly Cys Arg Glu Pro
            435                 440                 445

Glu Leu Asp Thr Glu Thr Leu Thr Thr Met Phe Glu Val Ser Val Ala
            450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
                    485                 490                 495

Asp Ile Ile Gly Ile Cys Tyr Gly Ala Thr Val Lys Gly Met Gln Ser
            500                 505                 510

Tyr Gly Leu Glu Arg Leu Ala Ala Met Leu Met Ala Thr Val Lys Met
            515                 520                 525

Glu Glu Leu Gly His Leu Thr Thr Glu Lys Gln Glu Tyr Ala Leu Arg
            530                 535                 540

Leu Ala Thr Val Gly Tyr Pro Lys Ala Gly Val Tyr Ser Gly Leu Ile
545                 550                 555                 560

Gly Gly Ala Thr Ser Val Leu Leu Ser Ala Tyr Asn Arg His Pro Leu
                    565                 570                 575

Phe Gln Pro Leu His Thr Val Met Arg Glu Thr Leu Phe Ile Gly Ser
            580                 585                 590

His Val Val Leu Arg Glu Leu Arg Leu Asn Val Thr Thr Gln Gly Pro
            595                 600                 605

Asn Leu Ala Leu Tyr Gln Leu Leu Ser Thr Ala Leu Cys Ser Ala Leu
            610                 615                 620

Glu Ile Gly Glu Val Leu Arg Gly Leu Ala Leu Gly Thr Glu Ser Gly
625                 630                 635                 640

Leu Phe Ser Pro Cys Tyr Leu Ser Leu Arg Phe Asp Leu Thr Arg Asp
                    645                 650                 655

Lys Leu Leu Ser Met Ala Pro Gln Glu Ala Thr Leu Asp Gln Ala Ala
            660                 665                 670
```

Val Ser Asn Ala Val Asp Gly Phe Leu Gly Arg Leu Ser Leu Glu Arg
            675                 680                 685

Glu Asp Arg Asp Ala Trp His Leu Pro Ala Tyr Lys Cys Val Asp Arg
690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
            725                 730                 735

Thr Thr Tyr Leu Ser Ser Ser Leu Phe Leu Ser Pro Val Ile Met Asn
            740                 745                 750

Lys Cys Ser Gln Gly Ala Val Ala Gly Glu Pro Arg Gln Ile Pro Lys
            755                 760                 765

Ile Gln Asn Phe Thr Arg Thr Gln Lys Ser Cys Ile Phe Cys Gly Phe
            770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
            805                 810                 815

Asp Phe Asp Asn Leu His Val His Tyr Leu Leu Leu Thr Thr Asn Gly
            820                 825                 830

Thr Val Met Glu Ile Ala Gly Leu Tyr Glu Glu Arg Ala Ser Gly Gly
            835                 840                 845

Gly Ser Gly Ser Ala Ser Ser Gly Ala Ser Ala Ser Gly Ser Ser Gly
            850                 855                 860

Ser Gly Ser Gly Ser Gly Ser Ser Ala Ser Gly Ala Ser Ser
865                 870                 875                 880

Gly Gly Ala Ser Gly Gly Ser Gly Gly Ser Gly Glu Ser Gln Val
            885                 890                 895

Arg Gln Gln Phe Ser Lys Asp Ile Glu Lys Leu Leu Asn Glu Gln Val
            900                 905                 910

Asn Lys Glu Met Gln Ser Ser Asn Leu Tyr Met Ser Met Ser Ser Trp
            915                 920                 925

Ser Tyr Thr His Ser Leu Asp Gly Ala Gly Leu Phe Leu Phe Asp His
            930                 935                 940

Ala Ala Glu Glu Tyr Glu His Ala Lys Lys Leu Ile Ile Phe Leu Asn
945                 950                 955                 960

Glu Asn Asn Val Pro Val Gln Leu Thr Ser Ile Ser Ala Pro Glu His
            965                 970                 975

Lys Phe Glu Gly Leu Thr Gln Ile Phe Gln Lys Ala Tyr Glu His Glu
            980                 985                 990

Gln His Ile Ser Glu Ser Ile Asn Asn Ile Val Asp His Ala Ile Lys
            995                 1000                1005

Cys Lys Asp His Ala Thr Phe Asn Phe Leu Gln Trp Tyr Val Ala
   1010                1015                1020

Glu Gln His Glu Glu Glu Val Leu Phe Lys Asp Ile Leu Asp Lys
   1025                1030                1035

Ile Glu Leu Ile Gly Asn Glu Asn His Gly Leu Tyr Leu Ala Asp
   1040                1045                1050

Gln Tyr Val Lys Gly Ile Ala Lys Ser Arg Lys Ser
   1055                1060                1065

<210> SEQ ID NO 23
<211> LENGTH: 1065

```
<212> TYPE: PRT
<213> ORGANISM: Artificial Sequence
<220> FEATURE:
<223> OTHER INFORMATION: Synthetic polypeptide

<400> SEQUENCE: 23

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
            85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Ala Ser
    130                 135                 140

Ser Gly Ala Ser Ala Ser Gly Ser Ser Asn Gly Ser Gly Ser Gly Ser
145                 150                 155                 160

Gly Ser Asn Ser Ser Ala Ser Ser Gly Ala Ser Ser Gly Gly Ala Ser
            165                 170                 175

Gly Gly Ser Gly Gly Ser Gly Ala Ala Ser Leu Ser Glu Val Lys Leu
        180                 185                 190

His Leu Asp Ile Glu Gly His Ala Ser His Tyr Thr Ile Pro Trp Thr
    195                 200                 205

Glu Leu Met Ala Lys Val Pro Gly Leu Ser Pro Glu Ala Leu Trp Arg
210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
            245                 250                 255

Val Asp Ile Pro Ala Val Ser Glu Gly Ser Met Gln Val Asp Ala Ser
        260                 265                 270

Lys Val His Pro Gly Val Ile Ser Gly Leu Asn Ser Pro Ala Cys Met
    275                 280                 285

Leu Ser Ala Pro Leu Glu Lys Gln Leu Phe Tyr Tyr Ile Gly Thr Met
290                 295                 300

Leu Pro Asn Thr Arg Pro His Ser Tyr Val Phe Tyr Gln Leu Arg Ala
305                 310                 315                 320

His Leu Ser Tyr Val Ala Leu Ser Ile Asn Gly Asp Lys Phe Gln Tyr
            325                 330                 335

Thr Gly Ala Met Thr Ser Lys Phe Leu Met Gly Thr Tyr Lys Arg Val
        340                 345                 350

Thr Glu Lys Gly Asp Glu His Val Leu Ser Leu Val Phe Gly Lys Thr
    355                 360                 365

Lys Asp Leu Pro Asp Leu Arg Gly Pro Phe Ser Tyr Pro Ser Leu Thr
370                 375                 380
```

```
Ser Ala Gln Ser Gly Asp Tyr Ser Leu Val Ile Val Thr Phe Val
385                 390                 395                 400

His Tyr Ala Asn Phe His Asn Tyr Phe Val Pro Asn Leu Lys Asp Met
                405                 410                 415

Phe Ser Arg Ala Val Thr Met Thr Ala Ala Ser Tyr Ala Arg Tyr Val
            420                 425                 430

Leu Gln Lys Leu Val Leu Leu Glu Met Lys Gly Gly Cys Arg Glu Pro
        435                 440                 445

Glu Leu Asp Thr Glu Thr Leu Thr Thr Met Phe Glu Val Ser Val Ala
    450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
                485                 490                 495

Asp Ile Ile Gly Ile Cys Tyr Gly Ala Thr Val Lys Gly Met Gln Ser
                500                 505                 510

Tyr Gly Leu Glu Arg Leu Ala Ala Met Leu Met Ala Thr Val Lys Met
        515                 520                 525

Glu Glu Leu Gly His Leu Thr Thr Glu Lys Gln Glu Tyr Ala Leu Arg
    530                 535                 540

Leu Ala Thr Val Gly Tyr Pro Lys Ala Gly Val Tyr Ser Gly Leu Ile
545                 550                 555                 560

Gly Gly Ala Thr Ser Val Leu Ser Ala Tyr Asn Arg His Pro Leu
                565                 570                 575

Phe Gln Pro Leu His Thr Val Met Arg Glu Thr Leu Phe Ile Gly Ser
            580                 585                 590

His Val Val Leu Arg Glu Leu Arg Leu Asn Val Thr Thr Gln Gly Pro
        595                 600                 605

Asn Leu Ala Leu Tyr Gln Leu Leu Ser Thr Ala Leu Cys Ser Ala Leu
    610                 615                 620

Glu Ile Gly Glu Val Leu Arg Gly Leu Ala Leu Gly Thr Glu Ser Gly
625                 630                 635                 640

Leu Phe Ser Pro Cys Tyr Leu Ser Leu Arg Phe Asp Leu Thr Arg Asp
                645                 650                 655

Lys Leu Leu Ser Met Ala Pro Gln Glu Ala Thr Leu Asp Gln Ala Ala
                660                 665                 670

Val Ser Asn Ala Val Asp Gly Phe Leu Gly Arg Leu Ser Leu Glu Arg
        675                 680                 685

Glu Asp Arg Asp Ala Trp His Leu Pro Ala Tyr Lys Cys Val Asp Arg
    690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
                725                 730                 735

Thr Thr Tyr Leu Ser Ser Ser Leu Phe Leu Ser Pro Val Ile Met Asn
            740                 745                 750

Lys Cys Ser Gln Gly Ala Val Ala Gly Glu Pro Arg Gln Ile Pro Lys
        755                 760                 765

Ile Gln Asn Phe Thr Arg Thr Gln Lys Ser Cys Ile Phe Cys Gly Phe
    770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
```

```
                    805                 810                 815
Asp Phe Asp Asn Leu His Val His Tyr Leu Leu Thr Thr Asn Gly
                820                 825                 830

Thr Val Met Glu Ile Ala Gly Leu Tyr Glu Glu Arg Ala Ser Gly Gly
            835                 840                 845

Gly Ser Gly Ser Ala Ser Ser Gly Ala Ser Ala Ser Gly Ser Ser Cys
        850                 855                 860

Ser Gly Ser Gly Ser Gly Ser Ser Ala Ser Ser Gly Ala Ser Ser
865                 870                 875                 880

Gly Gly Ala Ser Gly Gly Ser Gly Gly Ser Gly Glu Ser Gln Val
                885                 890                 895

Arg Gln Gln Phe Ser Lys Asp Ile Glu Lys Leu Leu Asn Glu Gln Val
                900                 905                 910

Asn Lys Glu Met Gln Ser Ser Asn Leu Tyr Met Ser Met Ser Ser Trp
                915                 920                 925

Ser Tyr Thr His Ser Leu Asp Gly Ala Gly Leu Phe Leu Phe Asp His
            930                 935                 940

Ala Ala Glu Glu Tyr Glu His Ala Lys Lys Leu Ile Ile Phe Leu Asn
945                 950                 955                 960

Glu Asn Asn Val Pro Val Gln Leu Thr Ser Ile Ser Ala Pro Glu His
                965                 970                 975

Lys Phe Glu Gly Leu Thr Gln Ile Phe Gln Lys Ala Tyr Glu His Glu
            980                 985                 990

Gln His Ile Ser Glu Ser Ile Asn Asn Ile Val Asp His Ala Ile Lys
                995                 1000                1005

Ser Lys Asp His Ala Thr Phe Asn Phe Leu Gln Trp Tyr Val Ala
            1010                1015                1020

Glu Gln His Glu Glu Val Leu Phe Lys Asp Ile Leu Asp Lys
        1025                1030                1035

Ile Glu Leu Ile Gly Asn Glu Asn His Gly Leu Tyr Leu Ala Asp
    1040                1045                1050

Gln Tyr Val Lys Gly Ile Ala Lys Ser Arg Lys Ser
    1055                1060                1065

<210> SEQ ID NO 24
<211> LENGTH: 648
<212> TYPE: PRT
<213> ORGANISM: Artificial Sequence
<220> FEATURE:
<223> OTHER INFORMATION: Synthetic polypeptide

<400> SEQUENCE: 24

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Glu Ala
            20                  25                  30

Ala Leu Leu Val Cys Gln Tyr Thr Ile Gln Ser Leu Ile His Leu Thr
        35                  40                  45

Gly Glu Asp Pro Gly Phe Phe Asn Val Glu Ile Pro Glu Phe Pro Phe
    50                  55                  60

Tyr Pro Thr Cys Asn Val Cys Thr Ala Asp Val Asn Val Thr Ile Asn
65                  70                  75                  80

Phe Asp Val Gly Gly Lys Lys His Gln Leu Asp Leu Asp Phe Gly Gln
            85                  90                  95

Leu Thr Pro His Thr Lys Ala Val Tyr Gln Pro Arg Gly Ala Phe Gly
```

```
                100             105             110
Gly Ser Glu Asn Ala Thr Asn Leu Phe Leu Glu Leu Leu Gly Ala
        115                 120             125

Gly Glu Leu Ala Leu Thr Met Arg Ser Lys Leu Pro Ile Asn Val
130                     135             140

Thr Thr Gly Glu Glu Gln Gln Val Ser Leu Glu Ser Val Asp Val Tyr
145                 150             155             160

Phe Gln Asp Val Phe Gly Thr Met Trp Cys His His Ala Glu Met Gln
                165             170             175

Asn Pro Val Tyr Leu Ile Pro Glu Thr Val Pro Tyr Ile Lys Trp Asp
            180             185             190

Asn Cys Asn Ser Thr Asn Ile Thr Ala Val Val Arg Ala Gln Gly Leu
        195             200             205

Asp Val Thr Leu Pro Leu Ser Leu Pro Thr Ser Ala Gln Asp Ser Asn
    210             215             220

Phe Ser Val Lys Thr Glu Met Leu Gly Asn Glu Ile Asp Ile Glu Cys
225             230             235             240

Ile Met Glu Asp Gly Glu Ile Ser Gln Val Leu Pro Gly Asp Asn Lys
                245             250             255

Phe Asn Ile Thr Cys Ser Gly Tyr Glu Ser His Val Pro Ser Gly Gly
            260             265             270

Ile Leu Thr Ser Thr Ser Pro Val Ala Thr Pro Ile Pro Gly Thr Gly
        275             280             285

Tyr Ala Tyr Ser Leu Arg Leu Thr Pro Arg Pro Val Ser Arg Phe Leu
    290             295             300

Gly Asn Asn Ser Ile Leu Tyr Val Phe Tyr Ser Gly Asn Gly Pro Lys
305             310             315             320

Ala Ser Gly Gly Asp Tyr Cys Ile Gln Ser Asn Ile Val Phe Ser Asp
                325             330             335

Glu Ile Pro Ala Ser Gln Asp Met Pro Thr Asn Thr Thr Asp Ile Thr
            340             345             350

Tyr Val Gly Asp Asn Ala Thr Tyr Ser Val Pro Met Val Thr Ser Glu
        355             360             365

Asp Ala Asn Ser Pro Asn Val Thr Val Thr Ala Phe Trp Ala Trp Pro
    370             375             380

Asn Asn Thr Glu Thr Asp Phe Lys Cys Lys Trp Thr Leu Thr Ser Gly
385             390             395             400

Thr Pro Ser Gly Cys Glu Asn Ile Ser Gly Ala Phe Ala Ser Asn Arg
                405             410             415

Thr Phe Asp Ile Thr Val Ser Gly Leu Gly Thr Ala Pro Lys Thr Leu
            420             425             430

Ile Ile Thr Arg Thr Ala Thr Asn Ala Thr Thr Thr His Lys Val
        435             440             445

Ile Phe Ser Lys Ala Pro Glu Gly Ser Thr Gln Cys Asn Val Asn Pro
    450             455             460

Val Gln Ile Pro Lys Asp Trp Ile Thr Met His Arg Ser Cys Arg Asn
465             470             475             480

Ser Met Arg Gln Gln Ile Gln Met Glu Val Gly Ala Ser Leu Gln Tyr
                485             490             495

Leu Ala Met Gly Ala His Phe Ser Lys Asp Val Val Asn Arg Pro Gly
            500             505             510

Phe Ala Gln Leu Phe Phe Asp Ala Ala Ser Glu Glu Arg Glu His Ala
        515             520             525
```

```
Met Lys Leu Ile Glu Tyr Leu Leu Met Arg Gly Glu Leu Thr Asn Asp
            530                 535                 540

Val Ser Ser Leu Leu Gln Val Arg Pro Pro Thr Arg Ser Ser Trp Lys
545                 550                 555                 560

Gly Gly Val Glu Ala Leu Glu His Ala Leu Ser Met Glu Ser Asp Val
                565                 570                 575

Thr Lys Ser Ile Arg Asn Val Ile Lys Ala Cys Glu Asp Asp Ser Glu
            580                 585                 590

Phe Asn Asp Tyr His Leu Val Asp Tyr Leu Thr Gly Asp Phe Leu Glu
        595                 600                 605

Glu Gln Tyr Lys Gly Gln Arg Asp Leu Ala Gly Lys Ala Ser Thr Leu
    610                 615                 620

Lys Lys Leu Met Asp Arg His Glu Ala Leu Gly Glu Phe Ile Phe Asp
625                 630                 635                 640

Lys Lys Leu Leu Gly Ile Asp Val
                645

<210> SEQ ID NO 25
<211> LENGTH: 1039
<212> TYPE: PRT
<213> ORGANISM: Artificial Sequence
<220> FEATURE:
<223> OTHER INFORMATION: Synthetic polypeptide

<400> SEQUENCE: 25

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Ala Ser
    130                 135                 140

Ser Gly Ala Ser Ala Gly Ser Ser Asn Gly Ser Gly Ser Gly Ser
145                 150                 155                 160

Gly Ser Asn Ser Ser Ala Ser Ser Gly Ala Ser Ser Gly Gly Ala Ser
                165                 170                 175

Gly Gly Ser Gly Gly Ser Gly Ala Ala Ser Leu Ser Glu Val Lys Leu
            180                 185                 190

His Leu Asp Ile Glu Gly His Ala Ser His Tyr Thr Ile Pro Trp Thr
        195                 200                 205

Glu Leu Met Ala Lys Val Pro Gly Leu Ser Pro Glu Ala Leu Trp Arg
    210                 215                 220

Glu Ala Asn Val Thr Glu Asp Leu Ala Ser Met Leu Asn Arg Tyr Lys
225                 230                 235                 240
```

```
Leu Ile Tyr Lys Thr Ser Gly Thr Leu Gly Ile Ala Leu Ala Glu Pro
            245                 250                 255

Val Asp Ile Pro Ala Val Ser Glu Gly Ser Met Gln Val Asp Ala Ser
            260                 265                 270

Lys Val His Pro Gly Val Ile Ser Gly Leu Asn Ser Pro Ala Cys Met
            275                 280                 285

Leu Ser Ala Pro Leu Glu Lys Gln Leu Phe Tyr Tyr Ile Gly Thr Met
            290                 295                 300

Leu Pro Asn Thr Arg Pro His Ser Tyr Val Phe Tyr Gln Leu Arg Cys
305                 310                 315                 320

His Leu Ser Tyr Val Ala Leu Ser Ile Asn Gly Asp Lys Phe Gln Tyr
            325                 330                 335

Thr Gly Ala Met Thr Ser Lys Phe Leu Met Gly Thr Tyr Lys Arg Val
            340                 345                 350

Thr Glu Lys Gly Asp Glu His Val Leu Ser Leu Val Phe Gly Lys Thr
            355                 360                 365

Lys Asp Leu Pro Asp Leu Arg Gly Pro Phe Ser Tyr Pro Ser Leu Thr
            370                 375                 380

Ser Ala Gln Ser Gly Asp Tyr Ser Leu Val Ile Val Thr Thr Phe Val
385                 390                 395                 400

His Tyr Ala Asn Phe His Asn Tyr Phe Val Pro Asn Leu Lys Asp Met
            405                 410                 415

Phe Ser Arg Ala Val Thr Met Thr Ala Ala Ser Tyr Ala Arg Tyr Val
            420                 425                 430

Leu Gln Lys Leu Val Leu Leu Glu Met Lys Gly Gly Cys Arg Glu Pro
            435                 440                 445

Glu Leu Asp Thr Glu Thr Leu Thr Thr Met Phe Glu Val Ser Val Ala
            450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
            485                 490                 495

Asp Ile Ile Gly Ile Cys Tyr Gly Ala Thr Val Lys Gly Met Gln Ser
            500                 505                 510

Tyr Gly Leu Glu Arg Leu Ala Ala Met Leu Met Ala Thr Val Lys Met
            515                 520                 525

Glu Glu Leu Gly His Leu Thr Thr Glu Lys Gln Glu Tyr Ala Leu Arg
            530                 535                 540

Leu Ala Thr Val Gly Tyr Pro Lys Ala Gly Val Tyr Ser Gly Leu Ile
545                 550                 555                 560

Gly Gly Ala Thr Ser Val Leu Leu Ser Ala Tyr Asn Arg His Pro Leu
            565                 570                 575

Phe Gln Pro Leu His Thr Val Met Arg Glu Thr Leu Phe Ile Gly Ser
            580                 585                 590

His Val Val Leu Arg Glu Leu Arg Leu Asn Val Thr Thr Gln Gly Pro
            595                 600                 605

Asn Leu Ala Leu Tyr Gln Leu Leu Ser Thr Ala Leu Cys Ser Ala Leu
            610                 615                 620

Glu Ile Gly Glu Val Leu Arg Gly Leu Ala Leu Gly Thr Glu Ser Gly
625                 630                 635                 640

Leu Phe Ser Pro Cys Tyr Leu Ser Leu Arg Phe Asp Leu Thr Arg Asp
            645                 650                 655
```

-continued

Lys Leu Leu Ser Met Ala Pro Gln Glu Ala Thr Leu Asp Gln Ala Ala
                660                 665                 670

Val Ser Asn Ala Val Asp Gly Phe Leu Gly Arg Leu Ser Leu Glu Arg
            675                 680                 685

Glu Asp Arg Asp Ala Trp His Leu Pro Ala Tyr Lys Cys Val Asp Arg
        690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
                725                 730                 735

Thr Thr Tyr Leu Ser Ser Ser Leu Phe Leu Ser Pro Val Ile Met Asn
            740                 745                 750

Lys Cys Ser Gln Gly Ala Val Ala Gly Glu Pro Arg Gln Ile Pro Lys
        755                 760                 765

Ile Gln Asn Phe Thr Arg Thr Gln Lys Ser Cys Ile Phe Cys Gly Phe
        770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
                805                 810                 815

Asp Phe Asp Asn Leu His Val His Tyr Leu Leu Leu Thr Thr Asn Gly
            820                 825                 830

Thr Val Met Glu Ile Ala Gly Leu Tyr Glu Glu Arg Ala Ser Gly Ser
        835                 840                 845

Thr Gln Cys Asn Val Asn Pro Val Gln Ile Pro Lys Asp Trp Ile Thr
        850                 855                 860

Met His Arg Ser Cys Arg Asn Ser Met Arg Gln Gln Ile Gln Met Glu
865                 870                 875                 880

Val Gly Ala Ser Leu Gln Tyr Leu Ala Met Gly Ala His Phe Ser Lys
                885                 890                 895

Asp Val Val Asn Arg Pro Gly Phe Ala Gln Leu Phe Phe Asp Ala Ala
            900                 905                 910

Ser Glu Glu Arg Glu His Ala Met Lys Leu Ile Glu Tyr Leu Leu Met
        915                 920                 925

Arg Gly Glu Leu Thr Asn Asp Val Ser Ser Leu Leu Gln Val Arg Pro
        930                 935                 940

Pro Thr Arg Ser Ser Trp Lys Gly Gly Val Glu Ala Leu Glu His Ala
945                 950                 955                 960

Leu Ser Met Glu Ser Asp Val Thr Lys Ser Ile Arg Asn Val Ile Lys
                965                 970                 975

Ala Cys Glu Asp Asp Ser Glu Phe Asn Asp Tyr His Leu Val Asp Tyr
            980                 985                 990

Leu Thr Gly Asp Phe Leu Glu Glu Gln Tyr Lys Gly Gln Arg Asp Leu
        995                 1000                1005

Ala Gly Lys Ala Ser Thr Leu Lys Lys Leu Met Asp Arg His Glu
        1010                1015                1020

Ala Leu Gly Glu Phe Ile Phe Asp Lys Lys Leu Leu Gly Ile Asp
        1025                1030                1035

Val

<210> SEQ ID NO 26
<211> LENGTH: 669
<212> TYPE: PRT
<213> ORGANISM: Artificial Sequence
<220> FEATURE:
<223> OTHER INFORMATION: Synthetic polypeptide

<400> SEQUENCE: 26

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Glu Ala
            20                  25                  30

Ala Leu Leu Val Cys Gln Tyr Thr Ile Gln Ser Leu Ile His Leu Thr
        35                  40                  45

Gly Glu Asp Pro Gly Phe Phe Asn Val Glu Ile Pro Glu Phe Pro Phe
50                  55                  60

Tyr Pro Thr Cys Asn Val Cys Thr Ala Asp Val Asn Val Thr Ile Asn
65                  70                  75                  80

Phe Asp Val Gly Gly Lys Lys His Gln Leu Asp Leu Asp Phe Gly Gln
                85                  90                  95

Leu Thr Pro His Thr Lys Ala Val Tyr Gln Pro Arg Gly Ala Phe Gly
            100                 105                 110

Gly Ser Glu Asn Ala Thr Asn Leu Phe Leu Leu Glu Leu Leu Gly Ala
        115                 120                 125

Gly Glu Leu Ala Leu Thr Met Arg Ser Lys Lys Leu Pro Ile Asn Val
130                 135                 140

Thr Thr Gly Glu Glu Gln Gln Val Ser Leu Glu Ser Val Asp Val Tyr
145                 150                 155                 160

Phe Gln Asp Val Phe Gly Thr Met Trp Cys His His Ala Glu Met Gln
                165                 170                 175

Asn Pro Val Tyr Leu Ile Pro Glu Thr Val Pro Tyr Ile Lys Trp Asp
            180                 185                 190

Asn Cys Asn Ser Thr Asn Ile Thr Ala Val Val Arg Ala Gln Gly Leu
        195                 200                 205

Asp Val Thr Leu Pro Leu Ser Leu Pro Thr Ser Ala Gln Asp Ser Asn
210                 215                 220

Phe Ser Val Lys Thr Glu Met Leu Gly Asn Glu Ile Asp Ile Glu Cys
225                 230                 235                 240

Ile Met Glu Asp Gly Glu Ile Ser Gln Val Leu Pro Gly Asp Asn Lys
                245                 250                 255

Phe Asn Ile Thr Cys Ser Gly Tyr Glu Ser His Val Pro Ser Gly Gly
            260                 265                 270

Ile Leu Thr Ser Thr Ser Pro Val Ala Thr Pro Ile Pro Gly Thr Gly
        275                 280                 285

Tyr Ala Tyr Ser Leu Arg Leu Thr Pro Arg Pro Val Ser Arg Phe Leu
290                 295                 300

Gly Asn Asn Ser Ile Leu Tyr Val Phe Tyr Ser Gly Asn Gly Pro Lys
305                 310                 315                 320

Ala Ser Gly Gly Asp Tyr Cys Ile Gln Ser Asn Ile Val Phe Ser Asp
                325                 330                 335

Glu Ile Pro Ala Ser Gln Asp Met Pro Thr Asn Thr Thr Asp Ile Thr
            340                 345                 350

Tyr Val Gly Asp Asn Ala Thr Tyr Ser Val Pro Met Val Thr Ser Glu
        355                 360                 365

Asp Ala Asn Ser Pro Asn Val Thr Val Thr Ala Phe Trp Ala Trp Pro
370                 375                 380

Asn Asn Thr Glu Thr Asp Phe Lys Cys Lys Trp Thr Leu Thr Ser Gly
385                 390                 395                 400
```

```
Thr Pro Ser Gly Cys Glu Asn Ile Ser Gly Ala Phe Ala Ser Asn Arg
            405                 410                 415

Thr Phe Asp Ile Thr Val Ser Gly Leu Gly Thr Ala Pro Lys Thr Leu
            420                 425                 430

Ile Ile Thr Arg Thr Ala Thr Asn Ala Thr Thr Thr His Lys Val
            435                 440                 445

Ile Phe Ser Lys Ala Pro Glu Gly Ser Ala Thr Cys Tyr Asn Asp
450                 455                 460

Val Ala Leu Asp Cys Gly Ile Thr Ser Asn Ser Leu Ala Leu Pro Arg
465                 470                 475                 480

Cys Asn Ala Val Tyr Gly Glu Tyr Gly Ser His Gly Asn Val Ala Thr
            485                 490                 495

Glu Leu Gln Ala Tyr Ala Lys Leu His Leu Glu Arg Ser Tyr Asp Tyr
            500                 505                 510

Leu Leu Ser Ala Ala Tyr Phe Asn Asn Tyr Gln Thr Asn Arg Ala Gly
            515                 520                 525

Phe Ser Lys Leu Phe Lys Lys Leu Ser Asp Glu Ala Trp Ser Lys Thr
530                 535                 540

Ile Asp Ile Ile Lys His Val Thr Lys Arg Gly Asp Lys Met Asn Phe
545                 550                 555                 560

Asp Gln His Ser Thr Met Lys Thr Glu Arg Lys Asn Tyr Thr Ala Glu
            565                 570                 575

Asn His Glu Leu Glu Ala Leu Ala Lys Ala Leu Asp Thr Gln Lys Glu
            580                 585                 590

Leu Ala Glu Arg Ala Phe Tyr Ile His Arg Glu Ala Thr Arg Asn Ser
            595                 600                 605

Gln His Leu His Asp Pro Glu Ile Ala Gln Tyr Leu Glu Glu Glu Phe
            610                 615                 620

Ile Glu Asp His Ala Glu Lys Ile Arg Thr Leu Ala Gly His Thr Ser
625                 630                 635                 640

Asp Leu Lys Lys Phe Ile Thr Ala Asn Asn Gly His Asp Leu Ser Leu
            645                 650                 655

Ala Leu Tyr Val Phe Asp Glu Tyr Leu Gln Lys Thr Val
            660                 665

<210> SEQ ID NO 27
<211> LENGTH: 1060
<212> TYPE: PRT
<213> ORGANISM: Artificial Sequence
<220> FEATURE:
<223> OTHER INFORMATION: Synthetic polypeptide

<400> SEQUENCE: 27

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Ala Leu Glu Asn Ile Ser Asp Ile
            35                  40                  45

Tyr Leu Val Ser Asn Gln Thr Cys Asp Gly Phe Ser Leu Ala Ser Leu
        50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
            85                  90                  95
```

```
Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Ala Ser
    130                 135                 140

Ser Gly Ala Ser Ala Ser Gly Ser Ser Asn Gly Ser Gly Ser Gly Ser
145                 150                 155                 160

Gly Ser Asn Ser Ser Ala Ser Ser Gly Ala Ser Ser Gly Gly Ala Ser
            165                 170                 175

Gly Gly Ser Gly Gly Ser Gly Ala Ala Ser Leu Ser Glu Val Lys Leu
            180                 185                 190

His Leu Asp Ile Glu Gly His Ala Ser His Tyr Thr Ile Pro Trp Thr
            195                 200                 205

Glu Leu Met Ala Lys Val Pro Gly Leu Ser Pro Glu Ala Leu Trp Arg
        210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
                245                 250                 255

Val Asp Ile Pro Ala Val Ser Glu Gly Ser Met Gln Val Asp Ala Ser
            260                 265                 270

Lys Val His Pro Gly Val Ile Ser Gly Leu Asn Ser Pro Ala Cys Met
            275                 280                 285

Leu Ser Ala Pro Leu Glu Lys Gln Leu Phe Tyr Tyr Ile Gly Thr Met
        290                 295                 300

Leu Pro Asn Thr Arg Pro His Ser Tyr Val Phe Tyr Gln Leu Arg Cys
305                 310                 315                 320

His Leu Ser Tyr Val Ala Leu Ser Ile Asn Gly Asp Lys Phe Gln Tyr
                325                 330                 335

Thr Gly Ala Met Thr Ser Lys Phe Leu Met Gly Thr Tyr Lys Arg Val
            340                 345                 350

Thr Glu Lys Gly Asp Glu His Val Leu Ser Leu Val Phe Gly Lys Thr
        355                 360                 365

Lys Asp Leu Pro Asp Leu Arg Gly Pro Phe Ser Tyr Pro Ser Leu Thr
370                 375                 380

Ser Ala Gln Ser Gly Asp Tyr Ser Leu Val Ile Val Thr Thr Phe Val
385                 390                 395                 400

His Tyr Ala Asn Phe His Asn Tyr Phe Val Pro Asn Leu Lys Asp Met
                405                 410                 415

Phe Ser Arg Ala Val Thr Met Thr Ala Ala Ser Tyr Ala Arg Tyr Val
            420                 425                 430

Leu Gln Lys Leu Val Leu Leu Glu Met Lys Gly Gly Cys Arg Glu Pro
        435                 440                 445

Glu Leu Asp Thr Glu Thr Leu Thr Thr Met Phe Glu Val Ser Val Ala
        450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
                485                 490                 495

Asp Ile Ile Gly Ile Cys Tyr Gly Ala Thr Val Lys Gly Met Gln Ser
            500                 505                 510
```

-continued

Tyr Gly Leu Glu Arg Leu Ala Ala Met Leu Met Ala Thr Val Lys Met
    515                 520                 525

Glu Glu Leu Gly His Leu Thr Thr Glu Lys Gln Glu Tyr Ala Leu Arg
530                 535                 540

Leu Ala Thr Val Gly Tyr Pro Lys Ala Gly Val Tyr Ser Gly Leu Ile
545                 550                 555                 560

Gly Gly Ala Thr Ser Val Leu Leu Ser Ala Tyr Asn Arg His Pro Leu
                565                 570                 575

Phe Gln Pro Leu His Thr Val Met Arg Glu Thr Leu Phe Ile Gly Ser
            580                 585                 590

His Val Val Leu Arg Glu Leu Arg Leu Asn Val Thr Thr Gln Gly Pro
        595                 600                 605

Asn Leu Ala Leu Tyr Gln Leu Leu Ser Thr Ala Leu Cys Ser Ala Leu
    610                 615                 620

Glu Ile Gly Glu Val Leu Arg Gly Leu Ala Leu Gly Thr Glu Ser Gly
625                 630                 635                 640

Leu Phe Ser Pro Cys Tyr Leu Ser Leu Arg Phe Asp Leu Thr Arg Asp
                645                 650                 655

Lys Leu Leu Ser Met Ala Pro Gln Glu Ala Thr Leu Asp Gln Ala Ala
            660                 665                 670

Val Ser Asn Ala Val Asp Gly Phe Leu Gly Arg Leu Ser Leu Glu Arg
        675                 680                 685

Glu Asp Arg Asp Ala Trp His Leu Pro Ala Tyr Lys Cys Val Asp Arg
    690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
                725                 730                 735

Thr Thr Tyr Leu Ser Ser Ser Leu Phe Leu Ser Pro Val Ile Met Asn
            740                 745                 750

Lys Cys Ser Gln Gly Ala Val Ala Gly Glu Pro Arg Gln Ile Pro Lys
        755                 760                 765

Ile Gln Asn Phe Thr Arg Thr Gln Lys Ser Cys Ile Phe Cys Gly Phe
    770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
                805                 810                 815

Asp Phe Asp Asn Leu His Val His Tyr Leu Leu Leu Thr Thr Asn Gly
            820                 825                 830

Thr Val Met Glu Ile Ala Gly Leu Tyr Glu Glu Arg Ala Ser Gly Ser
        835                 840                 845

Ala Asp Thr Cys Tyr Asn Asp Val Ala Leu Asp Cys Gly Ile Thr Ser
    850                 855                 860

Asn Ser Leu Ala Leu Pro Arg Cys Asn Ala Val Tyr Gly Glu Tyr Gly
865                 870                 875                 880

Ser His Gly Asn Val Ala Thr Glu Leu Gln Ala Tyr Ala Lys Leu His
                885                 890                 895

Leu Glu Arg Ser Tyr Asp Tyr Leu Leu Ser Ala Ala Tyr Phe Asn Asn
            900                 905                 910

Tyr Gln Thr Asn Arg Ala Gly Phe Ser Lys Leu Phe Lys Lys Leu Ser
        915                 920                 925

Asp Glu Ala Trp Ser Lys Thr Ile Asp Ile Ile Lys His Val Thr Lys

```
Arg Gly Asp Lys Met Asn Phe Asp Gln His Ser Thr Met Lys Thr Glu
945                 950                 955                 960

Arg Lys Asn Tyr Thr Ala Glu Asn His Glu Leu Glu Ala Leu Ala Lys
            965                 970                 975

Ala Leu Asp Thr Gln Lys Glu Leu Ala Glu Arg Ala Phe Tyr Ile His
                980                 985                 990

Arg Glu Ala Thr Arg Asn Ser Gln His Leu His Asp Pro Glu Ile Ala
            995                 1000                1005

Gln Tyr Leu Glu Glu Glu Phe Ile Glu Asp His Ala Glu Lys Ile
    1010                1015                1020

Arg Thr Leu Ala Gly His Thr Ser Asp Leu Lys Lys Phe Ile Thr
    1025                1030                1035

Ala Asn Asn Gly His Asp Leu Ser Leu Ala Leu Tyr Val Phe Asp
    1040                1045                1050

Glu Tyr Leu Gln Lys Thr Val
    1055                1060

<210> SEQ ID NO 28
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 28

Gly Gly Gly Gly Ser Gly Gly Gly Gly Ser Gly Gly Gly Gly Ser Gly
1               5                   10                  15

<210> SEQ ID NO 29
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 29

Gly Gly Ser Gly Ser Gly Ser Asn Ser Ser Ala Ser Ser Gly Ala Ser
1               5                   10                  15

Ser Gly Gly Ala Ser Gly Gly Ser Gly Gly Ser Gly
            20                  25

<210> SEQ ID NO 30
<211> LENGTH: 46
<212> TYPE: PRT
<213> ORGANISM: Artificial Sequence
<220> FEATURE:
<223> OTHER INFORMATION: Synthetic polypeptide

<400> SEQUENCE: 30

Gly Gly Ser Gly Ser Ala Ser Ser Gly Ala Ser Ala Ser Gly Ser Ser
1               5                   10                  15

Asn Gly Ser Gly Ser Gly Ser Gly Ser Asn Ser Ser Ala Ser Ser Gly
            20                  25                  30

Ala Ser Ser Gly Gly Ala Ser Gly Gly Ser Gly Gly Ser Gly
        35                  40                  45

<210> SEQ ID NO 31
<211> LENGTH: 26
<212> TYPE: PRT
<213> ORGANISM: Artificial Sequence
```

```
<220> FEATURE:
<223> OTHER INFORMATION: Synthetic polypeptide

<400> SEQUENCE: 31

Gly Gly Ser Gly Ser Ala Ser Ala Glu Ala Ala Ala Lys Glu Ala Ala
1               5                   10                  15

Ala Lys Ala Gly Gly Ser Gly Gly Ser Gly
            20                  25

<210> SEQ ID NO 32
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 32

Gly Gly Ser Gly Ser Ala Ser Ala Glu Ala Ala Ala Lys Glu Ala Ala
1               5                   10                  15

Ala Lys Glu Ala Ala Ala Lys Ala Ser Gly Gly Ser Gly Gly Ser Gly
            20                  25                  30

<210> SEQ ID NO 33
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 33

Ser Gly Gly Gly Ser Gly Ser Ala Ser Ser Gly Ala Ser Ala Ser Gly
1               5                   10                  15

Ser Ser Cys Ser Gly Ser Gly Ser Gly Ser Ser Ser Ala Ser Ser Gly
            20                  25                  30

Ala Ser Ser Gly Gly Ala Ser Gly Gly Ser Gly Gly Ser Gly
            35                  40                  45

<210> SEQ ID NO 34
<211> LENGTH: 228
<212> TYPE: PRT
<213> ORGANISM: Epstein Barr Virus

<400> SEQUENCE: 34

Asp Ser Lys Gly Ser Ser Gln Lys Gly Ser Arg Leu Leu Leu Leu Leu
1               5                   10                  15

Val Val Ser Asn Leu Leu Leu Pro Gln Gly Val Leu Ala Tyr Phe Leu
            20                  25                  30

Pro Pro Arg Val Arg Gly Gly Gly Arg Val Ala Ala Ala Ala Ile Thr
            35                  40                  45

Trp Val Pro Lys Pro Asn Val Glu Val Trp Pro Val Asp Pro Pro Pro
        50                  55                  60

Pro Val Asn Phe Asn Lys Thr Ala Glu Gln Glu Tyr Gly Asp Lys Glu
65                  70                  75                  80

Val Lys Leu Pro His Trp Thr Pro Thr Leu His Thr Phe Gln Val Pro
                85                  90                  95

Gln Asn Tyr Thr Lys Ala Asn Cys Thr Tyr Cys Asn Thr Arg Glu Tyr
            100                 105                 110

Thr Phe Ser Tyr Lys Gly Cys Cys Phe Tyr Phe Thr Lys Lys Lys His
            115                 120                 125

Thr Trp Asn Gly Cys Phe Gln Ala Cys Ala Glu Leu Tyr Pro Cys Thr
```

```
                130                 135                 140
Tyr Phe Tyr Gly Pro Thr Pro Asp Ile Leu Pro Val Val Thr Arg Asn
145                 150                 155                 160

Leu Asn Ala Ile Glu Ser Leu Trp Val Gly Val Tyr Arg Val Gly Glu
                165                 170                 175

Gly Asn Trp Thr Ser Leu Asp Gly Gly Thr Phe Lys Val Tyr Gln Ile
                180                 185                 190

Phe Gly Ser His Cys Thr Tyr Val Ser Lys Phe Ser Thr Val Pro Val
                195                 200                 205

Ser His His Glu Cys Ser Phe Leu Lys Pro Cys Leu Cys Val Ser Gln
                210                 215                 220

Arg Ser Asn Ser
225

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
tgactgtgaa cgttcgagat ga                                          22

<210> SEQ ID NO 36
<211> LENGTH: 115
<212> TYPE: PRT
<213> ORGANISM: Epstein Barr Virus

<400> SEQUENCE: 36

Asn Trp Ala Tyr Pro Cys Cys His Val Thr Gln Leu Arg Ala Gln His
1               5                   10                  15

Leu Leu Ala Leu Glu Asn Ile Ser Asp Ile Tyr Leu Val Ser Asn Gln
                20                  25                  30

Thr Cys Asp Gly Phe Ser Leu Ala Ser Leu Asn Ser Pro Lys Asn Gly
                35                  40                  45

Ser Asn Gln Leu Val Ile Ser Arg Cys Ala Asn Gly Leu Asn Val Val
            50                  55                  60

Ser Phe Phe Ile Ser Ile Leu Lys Arg Ser Ser Ser Ala Leu Thr Gly
65                  70                  75                  80

His Leu Arg Glu Leu Leu Thr Thr Leu Glu Thr Leu Tyr Gly Ser Phe
                85                  90                  95

Ser Val Glu Asp Leu Phe Gly Ala Asn Leu Asn Arg Tyr Ala Trp His
                100                 105                 110

Arg Gly Gly
        115

<210> SEQ ID NO 37
<211> LENGTH: 662
<212> TYPE: PRT
<213> ORGANISM: Epstein Barr Virus

<400> SEQUENCE: 37

Ala Ala Ser Leu Ser Glu Val Lys Leu His Leu Asp Ile Glu Gly His
1               5                   10                  15

Ala Ser His Tyr Thr Ile Pro Trp Thr Glu Leu Met Ala Lys Val Pro
                20                  25                  30

Gly Leu Ser Pro Glu Ala Leu Trp Arg Glu Ala Asn Val Thr Glu Asp
```

```
                35                  40                  45
Leu Ala Ser Met Leu Asn Arg Tyr Lys Leu Ile Tyr Lys Thr Ser Gly
 50                  55                  60

Thr Leu Gly Ile Ala Leu Ala Glu Pro Val Asp Ile Pro Ala Val Ser
 65                  70                  75                  80

Glu Gly Ser Met Gln Val Asp Ala Ser Lys Val His Pro Gly Val Ile
                 85                  90                  95

Ser Gly Leu Asn Ser Pro Ala Cys Met Leu Ser Ala Pro Leu Glu Lys
                100                 105                 110

Gln Leu Phe Tyr Tyr Ile Gly Thr Met Leu Pro Asn Thr Arg Pro His
            115                 120                 125

Ser Tyr Val Phe Tyr Gln Leu Arg Cys His Leu Ser Tyr Val Ala Leu
        130                 135                 140

Ser Ile Asn Gly Asp Lys Phe Gln Tyr Thr Gly Ala Met Thr Ser Lys
145                 150                 155                 160

Phe Leu Met Gly Thr Tyr Lys Arg Val Thr Glu Lys Gly Asp Glu His
                165                 170                 175

Val Leu Ser Leu Val Phe Gly Lys Thr Lys Asp Leu Pro Asp Leu Arg
            180                 185                 190

Gly Pro Phe Ser Tyr Pro Ser Leu Thr Ser Ala Gln Ser Gly Asp Tyr
        195                 200                 205

Ser Leu Val Ile Val Thr Thr Phe Val His Tyr Ala Asn Phe His Asn
210                 215                 220

Tyr Phe Val Pro Asn Leu Lys Asp Met Phe Ser Arg Ala Val Thr Met
225                 230                 235                 240

Thr Ala Ala Ser Tyr Ala Arg Tyr Val Leu Gln Lys Leu Val Leu Leu
                245                 250                 255

Glu Met Lys Gly Gly Cys Arg Glu Pro Glu Leu Asp Thr Glu Thr Leu
            260                 265                 270

Thr Thr Met Phe Glu Val Ser Val Ala Phe Lys Val Gly His Ala
        275                 280                 285

Val Gly Glu Thr Gly Asn Gly Cys Val Asp Leu Arg Trp Leu Ala Lys
290                 295                 300

Ser Phe Phe Glu Leu Thr Val Leu Lys Asp Ile Ile Gly Ile Cys Tyr
305                 310                 315                 320

Gly Ala Thr Val Lys Gly Met Gln Ser Tyr Gly Leu Glu Arg Leu Ala
                325                 330                 335

Ala Met Leu Met Ala Thr Val Lys Met Glu Glu Leu Gly His Leu Thr
            340                 345                 350

Thr Glu Lys Gln Glu Tyr Ala Leu Arg Leu Ala Thr Val Gly Tyr Pro
        355                 360                 365

Lys Ala Gly Val Tyr Ser Gly Leu Ile Gly Gly Ala Thr Ser Val Leu
370                 375                 380

Leu Ser Ala Tyr Asn Arg His Pro Leu Phe Gln Pro Leu His Thr Val
385                 390                 395                 400

Met Arg Glu Thr Leu Phe Ile Gly Ser His Val Val Leu Arg Glu Leu
                405                 410                 415

Arg Leu Asn Val Thr Thr Gln Gly Pro Asn Leu Ala Leu Tyr Gln Leu
            420                 425                 430

Leu Ser Thr Ala Leu Cys Ser Ala Leu Glu Ile Gly Glu Val Leu Arg
        435                 440                 445

Gly Leu Ala Leu Gly Thr Glu Ser Gly Leu Phe Ser Pro Cys Tyr Leu
450                 455                 460
```

Ser Leu Arg Phe Asp Leu Thr Arg Asp Lys Leu Leu Ser Met Ala Pro
465                 470                 475                 480

Gln Glu Ala Thr Leu Asp Gln Ala Ala Val Ser Asn Ala Val Asp Gly
            485                 490                 495

Phe Leu Gly Arg Leu Ser Leu Glu Arg Glu Asp Arg Asp Ala Trp His
        500                 505                 510

Leu Pro Ala Tyr Lys Cys Val Asp Arg Leu Asp Lys Val Leu Met Ile
    515                 520                 525

Ile Pro Leu Ile Asn Val Thr Phe Ile Ile Ser Ser Asp Arg Glu Val
530                 535                 540

Arg Gly Ser Ala Leu Tyr Glu Ala Ser Thr Thr Tyr Leu Ser Ser Ser
545                 550                 555                 560

Leu Phe Leu Ser Pro Val Ile Met Asn Lys Cys Ser Gln Gly Ala Val
                565                 570                 575

Ala Gly Glu Pro Arg Gln Ile Pro Lys Ile Gln Asn Phe Thr Arg Thr
            580                 585                 590

Gln Lys Ser Cys Ile Phe Cys Gly Phe Ala Leu Leu Ser Tyr Asp Glu
        595                 600                 605

Lys Glu Gly Leu Glu Thr Thr Thr Tyr Ile Thr Ser Gln Glu Val Gln
    610                 615                 620

Asn Ser Ile Leu Ser Ser Asn Tyr Phe Asp Phe Asp Asn Leu His Val
625                 630                 635                 640

His Tyr Leu Leu Leu Thr Thr Asn Gly Thr Val Met Glu Ile Ala Gly
                645                 650                 655

Leu Tyr Glu Glu Arg Ala
            660

<210> SEQ ID NO 38
<211> LENGTH: 425
<212> TYPE: PRT
<213> ORGANISM: Epstein Barr Virus

<400> SEQUENCE: 38

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln

```
                165                 170                 175
Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
            195                 200                 205

Glu Cys Ile Met Glu Asp Glu Ile Ser Gln Val Leu Pro Gly Asp
        210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
        290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
        370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr His
                405                 410                 415

Lys Val Ile Phe Ser Lys Ala Pro Glu
            420                 425

<210> SEQ ID NO 39
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 39

Cys Leu Val Pro Arg Gly Ser Leu Glu His His His His His
1               5                   10                  15

<210> SEQ ID NO 40
<211> LENGTH: 154
<212> TYPE: PRT
<213> ORGANISM: Aquifex aeolicus

<400> SEQUENCE: 40

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Cys Ile Val Arg His Gly Gly Arg Glu Glu Asp Ile
        35                  40                  45
```

```
Thr Leu Val Arg Val Pro Gly Ser Trp Glu Ile Pro Val Ala Ala Gly
         50                  55                  60

Glu Leu Ala Arg Lys Glu Asp Ile Asp Ala Val Ile Ala Ile Gly Val
 65                  70                  75                  80

Leu Ile Arg Gly Ala Thr Pro His Phe Asp Tyr Ile Ala Ser Glu Val
                 85                  90                  95

Ser Lys Gly Leu Ala Asn Leu Ser Leu Glu Leu Arg Lys Pro Ile Thr
            100                 105                 110

Phe Gly Val Ile Thr Ala Asp Thr Leu Glu Gln Ala Ile Glu Arg Ala
            115                 120                 125

Gly Thr Lys His Gly Asn Lys Gly Trp Glu Ala Ala Leu Ser Ala Ile
130                 135                 140

Glu Met Ala Asn Leu Phe Lys Ser Leu Arg
145                 150

<210> SEQ ID NO 41
<211> LENGTH: 156
<212> TYPE: PRT
<213> ORGANISM: Escherichia coli

<400> SEQUENCE: 41

Met Asn Ile Ile Glu Ala Asn Val Ala Thr Pro Asp Ala Arg Val Ala
 1               5                  10                  15

Ile Thr Ile Ala Arg Phe Asn Asn Phe Ile Asn Asp Ser Leu Leu Glu
                20                  25                  30

Gly Ala Ile Asp Ala Leu Lys Arg Ile Gly Gln Val Lys Asp Glu Asn
             35                  40                  45

Ile Thr Val Val Trp Val Pro Gly Ala Tyr Glu Leu Pro Leu Ala Ala
 50                  55                  60

Gly Ala Leu Ala Lys Thr Gly Lys Tyr Asp Ala Val Ile Ala Leu Gly
 65                  70                  75                  80

Thr Val Ile Arg Gly Gly Thr Ala His Phe Glu Tyr Val Ala Gly Gly
                 85                  90                  95

Ala Ser Asn Gly Leu Ala His Val Ala Gln Asp Ser Glu Ile Pro Val
            100                 105                 110

Ala Phe Gly Val Leu Thr Thr Glu Ser Ile Glu Gln Ala Ile Glu Arg
            115                 120                 125

Ala Gly Thr Lys Ala Gly Asn Lys Gly Ala Glu Ala Ala Leu Thr Ala
130                 135                 140

Leu Glu Met Ile Asn Val Leu Lys Ala Ile Lys Ala
145                 150                 155

<210> SEQ ID NO 42

<400> SEQUENCE: 42

000

<210> SEQ ID NO 43

<400> SEQUENCE: 43

000

<210> SEQ ID NO 44

<400> SEQUENCE: 44
```

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

-continued

<210> SEQ ID NO 56
<400> SEQUENCE: 56
000

<210> SEQ ID NO 57
<400> SEQUENCE: 57
000

<210> SEQ ID NO 58
<400> SEQUENCE: 58
000

<210> SEQ ID NO 59
<400> SEQUENCE: 59
000

<210> SEQ ID NO 60
<400> SEQUENCE: 60
000

<210> SEQ ID NO 61
<400> SEQUENCE: 61
000

<210> SEQ ID NO 62
<400> SEQUENCE: 62
000

<210> SEQ ID NO 63
<400> SEQUENCE: 63
000

<210> SEQ ID NO 64
<400> SEQUENCE: 64
000

<210> SEQ ID NO 65
<400> SEQUENCE: 65
000

<210> SEQ ID NO 66
<400> SEQUENCE: 66
000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

```
<210> SEQ ID NO 101
<400> SEQUENCE: 101
000

<210> SEQ ID NO 102
<400> SEQUENCE: 102
000

<210> SEQ ID NO 103
<400> SEQUENCE: 103
000

<210> SEQ ID NO 104
<400> SEQUENCE: 104
000

<210> SEQ ID NO 105
<400> SEQUENCE: 105
000

<210> SEQ ID NO 106
<400> SEQUENCE: 106
000

<210> SEQ ID NO 107
<400> SEQUENCE: 107
000

<210> SEQ ID NO 108
<400> SEQUENCE: 108
000

<210> SEQ ID NO 109
<400> SEQUENCE: 109
000

<210> SEQ ID NO 110
<400> SEQUENCE: 110
000

<210> SEQ ID NO 111
<400> SEQUENCE: 111
000

<210> SEQ ID NO 112
```

```
<400> SEQUENCE: 112
000

<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
000

<210> SEQ ID NO 123
<400> SEQUENCE: 123
```

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

```
<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 201

Glu Ser Gln Val Arg Gln Gln Phe Ser Lys Asp Ile Glu Lys Leu Leu
1               5                   10                  15
```

```
Asn Glu Gln Val Asn Lys Glu Met Gln Ser Ser Asn Leu Tyr Met Cys
                20                  25                  30

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
                100                 105                 110

His Ala Ile Lys Ser Lys Asp His Ala Thr Phe Asn Phe Leu Gln Trp
                115                 120                 125

Tyr Val Ala Glu Gln His Glu Glu Val Leu Phe Lys Asp Ile Leu
            130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 202
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 202

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
                20                  25                  30

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Cys Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
                100                 105                 110

His Ala Ile Lys Ser Lys Asp His Ala Thr Phe Asn Phe Leu Gln Trp
                115                 120                 125

Tyr Val Ala Glu Gln His Glu Glu Val Leu Phe Lys Asp Ile Leu
            130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 203
<211> LENGTH: 173
<212> TYPE: PRT
<213> ORGANISM: Artificial Sequence
```

<220> FEATURE:
<223> OTHER INFORMATION: Synthetic polypeptide

<400> SEQUENCE: 203

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
                20                  25                  30

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
        50                  55                  60

Ile Phe Leu Asn Glu Asn Asn Val Pro Val Gln Leu Thr Ser Ile Ser
65                  70                  75                  80

Cys Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
                100                 105                 110

His Ala Ile Lys Ser Lys Asp His Ala Thr Phe Asn Phe Leu Gln Trp
            115                 120                 125

Tyr Val Ala Glu Gln His Glu Glu Val Leu Phe Lys Asp Ile Leu
        130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 204
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 204

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
                20                  25                  30

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
        50                  55                  60

Ile Phe Leu Asn Glu Asn Asn Val Pro Val Gln Leu Thr Ser Ile Ser
65                  70                  75                  80

Ala Pro Glu His Cys Phe Glu Gly Leu Thr Gln Ile Phe Gln Lys Ala
                85                  90                  95

Tyr Glu His Glu Gln His Ile Ser Glu Ser Ile Asn Asn Ile Val Asp
                100                 105                 110

His Ala Ile Lys Ser Lys Asp His Ala Thr Phe Asn Phe Leu Gln Trp
            115                 120                 125

Tyr Val Ala Glu Gln His Glu Glu Val Leu Phe Lys Asp Ile Leu
        130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser

-continued

```
                165                 170

<210> SEQ ID NO 205
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 205

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30

Met Ser Ser Trp Ser Tyr Thr His Ser Leu Asp Gly Ala Gly Leu Phe
        35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Cys Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 206
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 206

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30

Met Ser Ser Trp Ser Tyr Thr His Ser Leu Asp Gly Ala Gly Leu Phe
        35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Cys Lys Asp His Ala Thr Phe Asn Phe Leu Gln Trp
        115                 120                 125
```

```
Tyr Val Ala Glu Gln His Glu Glu Val Leu Phe Lys Asp Ile Leu
            130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 207
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 207

Glu Ser Gln Val Arg Gln Gln Phe Ser Lys Asp Ile Glu Lys Leu Leu
1               5                   10                  15

Asn Cys Gln Val Asn Lys Glu Met Gln Ser Ser Asn Leu Tyr Met Ser
                20                  25                  30

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
        50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
                100                 105                 110

His Ala Ile Lys Ser Lys Asp His Ala Thr Phe Asn Phe Leu Gln Trp
            115                 120                 125

Tyr Val Ala Glu Gln His Glu Glu Val Leu Phe Lys Asp Ile Leu
        130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 208
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 208

Glu Ser Gln Val Arg Gln Gln Phe Ser Lys Asp Ile Glu Lys Leu Leu
1               5                   10                  15

Asn Glu Gln Val Asn Lys Glu Met Asn Ser Ser Asn Leu Tyr Met Ser
                20                  25                  30

Met Ser Ser Trp Cys Tyr Thr His Ser Leu Asp Gly Ala Gly Leu Phe
            35                  40                  45

Leu Phe Asp His Ala Ala Glu Glu Tyr Glu His Ala Lys Lys Leu Ile
        50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95
```

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 209
<211> LENGTH: 166
<212> TYPE: PRT
<213> ORGANISM: Helicobacter pylori

<400> SEQUENCE: 209

Leu Ser Lys Asp Ile Ile Lys Leu Leu Asn Glu Gln Val Asn Lys Glu
1               5                   10                  15

Met Asn Ser Ser Asn Leu Tyr Met Ser Met Ser Ser Trp Cys Tyr Thr
            20                  25                  30

His Ser Leu Asp Gly Ala Gly Leu Phe Leu Phe Asp His Ala Ala Glu
        35                  40                  45

Glu Tyr Glu His Ala Lys Lys Leu Ile Ile Phe Leu Asn Glu Asn Asn
    50                  55                  60

Val Pro Val Gln Leu Thr Ser Ile Ser Ala Pro Glu His Lys Phe Glu
65                  70                  75                  80

Gly Leu Thr Gln Ile Phe Gln Lys Ala Tyr Glu His Glu Gln His Ile
                85                  90                  95

Ser Glu Ser Ile Asn Asn Ile Val Asp His Ala Ile Lys Ser Lys Asp
            100                 105                 110

His Ala Thr Phe Asn Phe Leu Gln Trp Tyr Val Ala Glu Gln His Glu
        115                 120                 125

Glu Val Leu Phe Lys Asp Ile Leu Asp Lys Ile Glu Leu Ile Gly
    130                 135                 140

Asn Glu Asn His Gly Leu Tyr Leu Ala Asp Gln Tyr Val Lys Gly Ile
145                 150                 155                 160

Ala Lys Ser Arg Lys Ser
                165

<210> SEQ ID NO 210
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 210
tgactgtgaa cgttcgagat ga                                         22

<210> SEQ ID NO 211
<211> LENGTH: 191
<212> TYPE: PRT
<213> ORGANISM: Trichoplusia ni

<400> SEQUENCE: 211

Thr Gln Cys Asn Val Asn Pro Val Gln Ile Pro Lys Asp Trp Ile Thr
1               5                   10                  15

```
Met His Arg Ser Cys Arg Asn Ser Met Arg Gln Gln Ile Gln Met Glu
             20                  25                  30

Val Gly Ala Ser Leu Gln Tyr Leu Ala Met Gly Ala His Phe Ser Lys
         35                  40                  45

Asp Val Val Asn Arg Pro Gly Phe Ala Gln Leu Phe Phe Asp Ala Ala
     50                  55                  60

Ser Glu Glu Arg Glu His Ala Met Lys Leu Ile Glu Tyr Leu Leu Met
 65                  70                  75                  80

Arg Gly Glu Leu Thr Asn Asp Val Ser Ser Leu Leu Gln Val Arg Pro
                 85                  90                  95

Pro Thr Arg Ser Ser Trp Lys Gly Gly Val Glu Ala Leu Glu His Ala
            100                 105                 110

Leu Ser Met Glu Ser Asp Val Thr Lys Ser Ile Arg Asn Val Ile Lys
        115                 120                 125

Ala Cys Glu Asp Asp Ser Glu Phe Asn Asp Tyr His Leu Val Asp Tyr
130                 135                 140

Leu Thr Gly Asp Phe Leu Glu Glu Gln Tyr Lys Gly Gln Arg Asp Leu
145                 150                 155                 160

Ala Gly Lys Ala Ser Thr Leu Lys Lys Leu Met Asp Arg His Glu Ala
                165                 170                 175

Leu Gly Glu Phe Ile Phe Asp Lys Lys Leu Leu Gly Ile Asp Val
            180                 185                 190

<210> SEQ ID NO 212
<211> LENGTH: 212
<212> TYPE: PRT
<213> ORGANISM: Trichoplusia ni

<400> SEQUENCE: 212

Ala Asp Thr Cys Tyr Asn Asp Val Ala Leu Asp Cys Gly Ile Thr Ser
1                5                  10                  15

Asn Ser Leu Ala Leu Pro Arg Cys Asn Ala Val Tyr Gly Glu Tyr Gly
             20                  25                  30

Ser His Gly Asn Val Ala Thr Glu Leu Gln Ala Tyr Ala Lys Leu His
         35                  40                  45

Leu Glu Arg Ser Tyr Asp Tyr Leu Leu Ser Ala Ala Tyr Phe Asn Asn
     50                  55                  60

Tyr Gln Thr Asn Arg Ala Gly Phe Ser Lys Leu Phe Lys Lys Leu Ser
 65                  70                  75                  80

Asp Glu Ala Trp Ser Lys Thr Ile Asp Ile Ile Lys His Val Thr Lys
                 85                  90                  95

Arg Gly Asp Lys Met Asn Phe Asp Gln His Ser Thr Met Lys Thr Glu
            100                 105                 110

Arg Lys Asn Tyr Thr Ala Glu Asn His Glu Leu Glu Ala Leu Ala Lys
        115                 120                 125

Ala Leu Asp Thr Gln Lys Glu Leu Ala Glu Arg Ala Phe Tyr Ile His
    130                 135                 140

Arg Glu Ala Thr Arg Asn Ser Gln His Leu His Asp Pro Glu Ile Ala
145                 150                 155                 160

Gln Tyr Leu Glu Glu Glu Phe Ile Glu Asp His Ala Glu Lys Ile Arg
                165                 170                 175

Thr Leu Ala Gly His Thr Ser Asp Leu Lys Lys Phe Ile Thr Ala Asn
            180                 185                 190

Asn Gly His Asp Leu Ser Leu Ala Leu Tyr Val Phe Asp Glu Tyr Leu
```

Gln Lys Thr Val
       210

<210> SEQ ID NO 213
<211> LENGTH: 174
<212> TYPE: PRT
<213> ORGANISM: Pyrococcus furiosus

<400> SEQUENCE: 213

Met Leu Ser Glu Arg Met Leu Lys Ala Leu Asn Asp Gln Leu Asn Arg
1               5                   10                  15

Glu Leu Tyr Ser Ala Tyr Leu Tyr Phe Ala Met Ala Ala Tyr Phe Glu
            20                  25                  30

Asp Leu Gly Leu Glu Gly Phe Ala Asn Trp Met Lys Ala Gln Ala Glu
        35                  40                  45

Glu Glu Ile Gly His Ala Leu Arg Phe Tyr Asn Tyr Ile Tyr Asp Arg
    50                  55                  60

Asn Gly Arg Val Glu Leu Asp Glu Ile Pro Lys Pro Pro Lys Glu Trp
65                  70                  75                  80

Glu Ser Pro Leu Lys Ala Phe Glu Ala Ala Tyr Glu His Glu Lys Phe
                85                  90                  95

Ile Ser Lys Ser Ile Tyr Glu Leu Ala Ala Leu Ala Glu Glu Glu Lys
            100                 105                 110

Asp Tyr Ser Thr Arg Ala Phe Leu Glu Trp Phe Ile Asn Glu Gln Val
        115                 120                 125

Glu Glu Glu Ala Ser Val Lys Lys Ile Leu Asp Lys Leu Lys Phe Ala
    130                 135                 140

Lys Asp Ser Pro Gln Ile Leu Phe Met Leu Asp Lys Glu Leu Ser Ala
145                 150                 155                 160

Arg Ala Pro Lys Leu Pro Gly Leu Leu Met Gln Gly Gly Glu
                165                 170

<210> SEQ ID NO 214
<211> LENGTH: 183
<212> TYPE: PRT
<213> ORGANISM: Homo sapeins

<400> SEQUENCE: 214

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Gln
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys

```
                130                 135                 140
Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Gln Glu Ser
            180
```

<210> SEQ ID NO 215
<211> LENGTH: 204
<212> TYPE: PRT
<213> ORGANISM: Homo sapeins

<400> SEQUENCE: 215

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ser Ser
                20                  25                  30

Gln Ile Arg Gln Asn Tyr Ser Thr Asp Val Glu Ala Ala Val Asn Ser
            35                  40                  45

Leu Val Asn Leu Tyr Leu Gln Ala Ser Tyr Thr Tyr Leu Ser Leu Gly
    50                  55                  60

Phe Tyr Phe Asp Arg Asp Asp Val Ala Leu Glu Gly Val Ser His Phe
65                  70                  75                  80

Phe Arg Glu Leu Ala Glu Glu Lys Arg Glu Gly Tyr Glu Arg Leu Leu
                85                  90                  95

Lys Met Gln Asn Gln Arg Gly Gly Arg Ala Leu Phe Gln Asp Ile Lys
            100                 105                 110

Lys Pro Ala Glu Asp Glu Trp Gly Lys Thr Pro Asp Ala Met Lys Ala
    115                 120                 125

Ala Met Ala Leu Glu Lys Lys Leu Asn Gln Ala Leu Leu Asp Leu His
130                 135                 140

Ala Leu Gly Ser Ala Arg Thr Asp Pro His Leu Cys Asp Phe Leu Glu
145                 150                 155                 160

Thr His Phe Leu Asp Glu Glu Val Lys Leu Ile Lys Lys Met Gly Asp
                165                 170                 175

His Leu Thr Asn Leu His Arg Leu Gly Gly Pro Glu Ala Gly Leu Gly
            180                 185                 190

Glu Tyr Leu Phe Glu Arg Leu Thr Leu Lys His Asp
    195                 200
```

<210> SEQ ID NO 216
<211> LENGTH: 154
<212> TYPE: PRT
<213> ORGANISM: Aquifex aeolicus

<400> SEQUENCE: 216

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
                20                  25                  30

Gly Ala Ile Asp Cys Ile Val Arg His Gly Gly Arg Glu Glu Asp Ile
            35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
```

```
                65                  70                  75                  80
Leu Ile Arg Gly Ala Thr Pro His Phe Asp Tyr Ile Ala Ser Glu Val
                    85                  90                  95

Ser Lys Gly Leu Ala Asn Leu Ser Leu Glu Leu Arg Lys Pro Ile Thr
                100                 105                 110

Phe Gly Val Ile Thr Ala Asp Thr Leu Glu Gln Ala Ile Glu Arg Ala
                115                 120                 125

Gly Thr Lys His Gly Asn Lys Gly Trp Glu Ala Ala Leu Ser Ala Ile
        130                 135                 140

Glu Met Ala Asn Leu Phe Lys Ser Leu Arg
145                 150
```

<210> SEQ ID NO 217
<211> LENGTH: 8
<212> TYPE: PRT
<213> ORGANISM: Unknown
<220> FEATURE:
<223> OTHER INFORMATION: Bullfrog linker sequence

<400> SEQUENCE: 217

```
Glu Ser Gln Val Arg Gln Gln Phe
1               5
```

<210> SEQ ID NO 218
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 218

```
Cys Leu Val Pro Arg Gly Ser Leu Glu His His His His His
1               5                   10                  15
```

<210> SEQ ID NO 219
<211> LENGTH: 156
<212> TYPE: PRT
<213> ORGANISM: Escherichia coli

<400> SEQUENCE: 219

```
Met Asn Ile Ile Glu Ala Asn Val Ala Thr Pro Asp Ala Arg Val Ala
1               5                   10                  15

Ile Thr Ile Ala Arg Phe Asn Asn Phe Ile Asn Asp Ser Leu Leu Glu
                20                  25                  30

Gly Ala Ile Asp Ala Leu Lys Arg Ile Gly Gln Val Lys Asp Glu Asn
            35                  40                  45

Ile Thr Val Val Trp Val Pro Gly Ala Tyr Glu Leu Pro Leu Ala Ala
        50                  55                  60

Gly Ala Leu Ala Lys Thr Gly Lys Tyr Asp Ala Val Ile Ala Leu Gly
65                  70                  75                  80

Thr Val Ile Arg Gly Gly Thr Ala His Phe Glu Tyr Val Ala Gly Gly
                    85                  90                  95

Ala Ser Asn Gly Leu Ala His Val Ala Gln Asp Ser Glu Ile Pro Val
                100                 105                 110

Ala Phe Gly Val Leu Thr Thr Glu Ser Ile Glu Gln Ala Ile Glu Arg
                115                 120                 125

Ala Gly Thr Lys Ala Gly Asn Lys Gly Ala Glu Ala Ala Leu Thr Ala
        130                 135                 140

Leu Glu Met Ile Asn Val Leu Lys Ala Ile Lys Ala
145                 150
```

145            150            155

<210> SEQ ID NO 220
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 220

Gly Gly Gly Gly Ser Gly Gly Gly Ser Gly Gly Gly Gly Ser Gly
1               5                   10                  15

<210> SEQ ID NO 221
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 221

Gly Gly Ser Gly Ser Gly Ser Asn Ser Ser Ala Ser Ser Gly Ala Ser
1               5                   10                  15

Ser Gly Gly Ala Ser Gly Gly Ser Gly Gly Ser Gly
            20                  25

<210> SEQ ID NO 222
<211> LENGTH: 46
<212> TYPE: PRT
<213> ORGANISM: Artificial Sequence
<220> FEATURE:
<223> OTHER INFORMATION: Synthetic polypeptide

<400> SEQUENCE: 222

Gly Gly Ser Gly Ser Ala Ser Ser Gly Ala Ser Ala Ser Gly Ser Ser
1               5                   10                  15

Asn Gly Ser Gly Ser Gly Ser Gly Ser Asn Ser Ser Ala Ser Ser Gly
            20                  25                  30

Ala Ser Ser Gly Gly Ala Ser Gly Gly Ser Gly Gly Ser Gly
        35                  40                  45

<210> SEQ ID NO 223
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 223

Gly Gly Ser Gly Ser Ala Ser Ala Glu Ala Ala Ala Lys Glu Ala Ala
1               5                   10                  15

Ala Lys Ala Gly Gly Ser Gly Gly Ser Gly
            20                  25

<210> SEQ ID NO 224
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 224

Gly Gly Ser Gly Ser Ala Ser Ala Glu Ala Ala Ala Lys Glu Ala Ala
1               5                   10                  15

```
Ala Lys Glu Ala Ala Lys Ala Ser Gly Gly Ser Gly Gly Ser Gly
        20                  25                  30
```

<210> SEQ ID NO 225
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 225

```
Ser Gly Gly Gly Ser Gly Ser Ala Ser Ser Gly Ala Ser Ala Ser Gly
1               5                   10                  15

Ser Ser Cys Ser Gly Ser Gly Ser Gly Ser Ser Ala Ser Ser Gly
            20                  25                  30

Ala Ser Ser Gly Gly Ala Ser Gly Gly Ser Gly Gly Ser Gly
            35                  40                  45
```

<210> SEQ ID NO 226
<211> LENGTH: 1086
<212> TYPE: PRT
<213> ORGANISM: Artificial Sequence
<220> FEATURE:
<223> OTHER INFORMATION: Synthetic polypeptide

<400> SEQUENCE: 226

```
Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
                20                  25                  30

Gln Leu Arg Ala Gln His Leu Leu Ala Leu Glu Asn Ile Ser Asp Ile
            35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Ala Ser
    130                 135                 140

Ser Gly Ala Ser Ala Ser Gly Ser Asn Gly Ser Gly Ser Gly Ser
145                 150                 155                 160

Gly Ser Asn Ser Ser Ala Ser Ser Gly Ala Ser Ser Gly Ala Ser
                165                 170                 175

Gly Gly Ser Gly Gly Ser Gly Ala Ala Ser Leu Ser Glu Val Lys Leu
            180                 185                 190

His Leu Asp Ile Glu Gly His Ala Ser His Tyr Thr Ile Pro Trp Thr
        195                 200                 205

Glu Leu Met Ala Lys Val Pro Gly Leu Ser Pro Glu Ala Leu Trp Arg
    210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
                245                 250                 255
```

```
Val Asp Ile Pro Ala Val Ser Glu Gly Ser Met Gln Val Asp Ala Ser
            260                 265                 270

Lys Val His Pro Gly Val Ile Ser Gly Leu Asn Ser Pro Ala Cys Met
            275                 280                 285

Leu Ser Ala Pro Leu Glu Lys Gln Leu Phe Tyr Tyr Ile Gly Thr Met
            290                 295                 300

Leu Pro Asn Thr Arg Pro His Ser Tyr Val Phe Tyr Gln Leu Arg Ala
305                 310                 315                 320

His Leu Ser Tyr Val Ala Leu Ser Ile Asn Gly Asp Lys Phe Gln Tyr
                325                 330                 335

Thr Gly Ala Met Thr Ser Lys Phe Leu Met Gly Thr Tyr Lys Arg Val
            340                 345                 350

Thr Glu Lys Gly Asp Glu His Val Leu Ser Leu Val Phe Gly Lys Thr
            355                 360                 365

Lys Asp Leu Pro Asp Leu Arg Gly Pro Phe Ser Tyr Pro Ser Leu Thr
370                 375                 380

Ser Ala Gln Ser Gly Asp Tyr Ser Leu Val Ile Val Thr Thr Phe Val
385                 390                 395                 400

His Tyr Ala Asn Phe His Asn Tyr Phe Val Pro Asn Leu Lys Asp Met
                405                 410                 415

Phe Ser Arg Ala Val Thr Met Thr Ala Ala Ser Tyr Ala Arg Tyr Val
            420                 425                 430

Leu Gln Lys Leu Val Leu Leu Glu Met Lys Gly Gly Cys Arg Glu Pro
            435                 440                 445

Glu Leu Asp Thr Glu Thr Leu Thr Thr Met Phe Glu Val Ser Val Ala
            450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
                485                 490                 495

Asp Ile Ile Gly Ile Cys Tyr Gly Ala Thr Val Lys Gly Met Gln Ser
            500                 505                 510

Tyr Gly Leu Glu Arg Leu Ala Ala Met Leu Met Ala Thr Val Lys Met
            515                 520                 525

Glu Glu Leu Gly His Leu Thr Thr Glu Lys Gln Glu Tyr Ala Leu Arg
            530                 535                 540

Leu Ala Thr Val Gly Tyr Pro Lys Ala Gly Val Tyr Ser Gly Leu Ile
545                 550                 555                 560

Gly Gly Ala Thr Ser Val Leu Leu Ser Ala Tyr Asn Arg His Pro Leu
                565                 570                 575

Phe Gln Pro Leu His Thr Val Met Arg Glu Thr Leu Phe Ile Gly Ser
            580                 585                 590

His Val Val Leu Arg Glu Leu Arg Leu Asn Val Thr Thr Gln Gly Pro
            595                 600                 605

Asn Leu Ala Leu Tyr Gln Leu Leu Ser Thr Ala Leu Cys Ser Ala Leu
            610                 615                 620

Glu Ile Gly Glu Val Leu Arg Gly Leu Ala Leu Gly Thr Glu Ser Gly
625                 630                 635                 640

Leu Phe Ser Pro Cys Tyr Leu Ser Leu Arg Phe Asp Leu Thr Arg Asp
                645                 650                 655

Lys Leu Leu Ser Met Ala Pro Gln Glu Ala Thr Leu Asp Gln Ala Ala
            660                 665                 670
```

```
Val Ser Asn Ala Val Asp Gly Phe Leu Gly Arg Leu Ser Leu Glu Arg
        675                 680                 685

Glu Asp Arg Asp Ala Trp His Leu Pro Ala Tyr Lys Cys Val Asp Arg
690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
                725                 730                 735

Thr Thr Tyr Leu Ser Ser Ser Leu Phe Leu Ser Pro Val Ile Met Asn
            740                 745                 750

Lys Cys Ser Gln Gly Ala Val Ala Gly Glu Pro Arg Gln Ile Pro Lys
            755                 760                 765

Ile Gln Asn Phe Thr Arg Thr Gln Lys Ser Cys Ile Phe Cys Gly Phe
        770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
                805                 810                 815

Asp Phe Asp Asn Leu His Val His Tyr Leu Leu Leu Thr Thr Asn Gly
            820                 825                 830

Thr Val Met Glu Ile Ala Gly Leu Tyr Glu Glu Arg Ala Ser Gly Gly
        835                 840                 845

Gly Ser Gly Ser Ala Ser Ser Gly Ala Ser Ala Ser Gly Ser Ser Gly
    850                 855                 860

Ser Gly Ser Gly Ser Gly Ser Ser Ser Ala Ser Ser Gly Leu Ala Tyr
865                 870                 875                 880

Phe Leu Pro Pro Arg Val Arg Gly Gly Gly Arg Val Ala Ala Ala Ala
                885                 890                 895

Ile Thr Trp Val Pro Lys Pro Asn Val Glu Val Trp Pro Val Asp Pro
            900                 905                 910

Pro Pro Pro Val Asn Phe Asn Lys Thr Ala Glu Gln Glu Tyr Gly Asp
        915                 920                 925

Lys Glu Val Lys Leu Pro His Trp Thr Pro Thr Leu His Thr Phe Gln
930                 935                 940

Val Pro Gln Asn Tyr Thr Lys Ala Asn Cys Thr Tyr Cys Asn Thr Arg
945                 950                 955                 960

Glu Tyr Thr Phe Ser Tyr Lys Gly Cys Cys Phe Tyr Phe Thr Lys Lys
                965                 970                 975

Lys His Thr Trp Asn Gly Cys Phe Gln Ala Cys Ala Glu Leu Tyr Pro
            980                 985                 990

Cys Thr Tyr Phe Tyr Gly Pro Thr Pro Asp Ile Leu Pro Val Val Thr
        995                 1000                1005

Arg Asn Leu Asn Ala Ile Glu Ser Leu Trp Val Gly Val Tyr Arg
    1010                1015                1020

Val Gly Glu Gly Asn Trp Thr Ser Leu Asp Gly Gly Thr Phe Lys
    1025                1030                1035

Val Tyr Gln Ile Phe Gly Ser His Cys Thr Tyr Val Ser Lys Phe
    1040                1045                1050

Ser Thr Val Pro Val Ser His His Glu Cys Ser Phe Leu Lys Pro
    1055                1060                1065

Cys Leu Cys Val Ser Gln Arg Ser Asn Ser Gly Ser His His His
    1070                1075                1080

His His His
```

1085

<210> SEQ ID NO 227
<211> LENGTH: 1339
<212> TYPE: PRT
<213> ORGANISM: Artificial Sequence
<220> FEATURE:
<223> OTHER INFORMATION: Synthetic polypeptide

<400> SEQUENCE: 227

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Ala Ser
    130                 135                 140

Ser Gly Ala Ser Ala Ser Gly Ser Ser Asn Gly Ser Gly Ser Gly Ser
145                 150                 155                 160

Gly Ser Asn Ser Ser Ala Ser Ser Gly Ala Ser Ser Gly Gly Ala Ser
                165                 170                 175

Gly Gly Ser Gly Gly Ser Gly Ala Ala Ser Leu Ser Glu Val Lys Leu
            180                 185                 190

His Leu Asp Ile Glu Gly His Ala Ser His Tyr Thr Ile Pro Trp Thr
        195                 200                 205

Glu Leu Met Ala Lys Val Pro Gly Leu Ser Pro Glu Ala Leu Trp Arg
    210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
                245                 250                 255

Val Asp Ile Pro Ala Val Ser Glu Gly Ser Met Gln Val Asp Ala Ser
            260                 265                 270

Lys Val His Pro Gly Val Ile Ser Gly Leu Asn Ser Pro Ala Cys Met
        275                 280                 285

Leu Ser Ala Pro Leu Glu Lys Gln Leu Phe Tyr Tyr Ile Gly Thr Met
    290                 295                 300

Leu Pro Asn Thr Arg Pro His Ser Tyr Val Phe Tyr Gln Leu Arg Ala
305                 310                 315                 320

His Leu Ser Tyr Val Ala Leu Ser Ile Asn Gly Asp Lys Phe Gln Tyr
                325                 330                 335

Thr Gly Ala Met Thr Ser Lys Phe Leu Met Gly Thr Tyr Lys Arg Val
            340                 345                 350

Thr Glu Lys Gly Asp Glu His Val Leu Ser Leu Val Phe Gly Lys Thr

```
                355                 360                 365
Lys Asp Leu Pro Asp Leu Arg Gly Pro Phe Ser Tyr Pro Ser Leu Thr
    370                 375                 380
Ser Ala Gln Ser Gly Asp Tyr Ser Leu Val Ile Val Thr Thr Phe Val
385                 390                 395                 400
His Tyr Ala Asn Phe His Asn Tyr Phe Val Pro Asn Leu Lys Asp Met
                405                 410                 415
Phe Ser Arg Ala Val Thr Met Thr Ala Ala Ser Tyr Ala Arg Tyr Val
            420                 425                 430
Leu Gln Lys Leu Val Leu Leu Glu Met Lys Gly Gly Cys Arg Glu Pro
        435                 440                 445
Glu Leu Asp Thr Glu Thr Leu Thr Thr Met Phe Glu Val Ser Val Ala
    450                 455                 460
Phe Phe Lys Val Gly His Ala Val Gly Glu Thr Gly Asn Gly Cys Val
465                 470                 475                 480
Asp Leu Arg Trp Leu Ala Lys Ser Phe Phe Glu Leu Thr Val Leu Lys
                485                 490                 495
Asp Ile Ile Gly Ile Cys Tyr Gly Ala Thr Val Lys Gly Met Gln Ser
            500                 505                 510
Tyr Gly Leu Glu Arg Leu Ala Ala Met Leu Met Ala Thr Val Lys Met
        515                 520                 525
Glu Glu Leu Gly His Leu Thr Thr Glu Lys Gln Glu Tyr Ala Leu Arg
    530                 535                 540
Leu Ala Thr Val Gly Tyr Pro Lys Ala Gly Val Tyr Ser Gly Leu Ile
545                 550                 555                 560
Gly Gly Ala Thr Ser Val Leu Ser Ala Tyr Asn Arg His Pro Leu
                565                 570                 575
Phe Gln Pro Leu His Thr Val Met Arg Glu Thr Leu Phe Ile Gly Ser
            580                 585                 590
His Val Val Leu Arg Glu Leu Arg Leu Asn Val Thr Thr Gln Gly Pro
        595                 600                 605
Asn Leu Ala Leu Tyr Gln Leu Leu Ser Thr Ala Leu Cys Ser Ala Leu
    610                 615                 620
Glu Ile Gly Glu Val Leu Arg Gly Leu Ala Leu Gly Thr Glu Ser Gly
625                 630                 635                 640
Leu Phe Ser Pro Cys Tyr Leu Ser Leu Arg Phe Asp Leu Thr Arg Asp
                645                 650                 655
Lys Leu Leu Ser Met Ala Pro Gln Glu Ala Thr Leu Asp Gln Ala Ala
            660                 665                 670
Val Ser Asn Ala Val Asp Gly Phe Leu Gly Arg Leu Ser Leu Glu Arg
        675                 680                 685
Glu Asp Arg Asp Ala Trp His Leu Pro Ala Tyr Lys Cys Val Asp Arg
    690                 695                 700
Leu Asp Lys Val Leu Met Ile Ile Pro Leu Ile Asn Val Thr Phe Ile
705                 710                 715                 720
Ile Ser Ser Asp Arg Glu Val Arg Gly Ser Ala Leu Tyr Glu Ala Ser
                725                 730                 735
Thr Thr Tyr Leu Ser Ser Ser Leu Phe Leu Ser Pro Val Ile Met Asn
            740                 745                 750
Lys Cys Ser Gln Gly Ala Val Ala Gly Glu Pro Arg Gln Ile Pro Lys
        755                 760                 765
Ile Gln Asn Phe Thr Arg Thr Gln Lys Ser Cys Ile Phe Cys Gly Phe
    770                 775                 780
```

```
Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
            805                 810                 815

Asp Phe Asp Asn Leu His Val His Tyr Leu Leu Leu Thr Thr Asn Gly
        820                 825                 830

Thr Val Met Glu Ile Ala Gly Leu Tyr Glu Glu Arg Ala Ser Gly Gly
            835                 840                 845

Gly Ser Gly Ser Ala Ser Ser Gly Ala Ser Ala Ser Gly Ser Ser Gly
        850                 855                 860

Ser Gly Ser Gly Ser Gly Ser Ser Ala Ser Ser Gly Ser Leu Ala Tyr
865                 870                 875                 880

Phe Leu Pro Pro Arg Val Arg Gly Gly Gly Arg Val Ala Ala Ala Ala
            885                 890                 895

Ile Thr Trp Val Pro Lys Pro Asn Val Glu Val Trp Pro Val Asp Pro
            900                 905                 910

Pro Pro Pro Val Asn Phe Asn Lys Thr Ala Glu Gln Glu Tyr Gly Asp
        915                 920                 925

Lys Glu Val Lys Leu Pro His Trp Thr Pro Thr Leu His Thr Phe Gln
930                 935                 940

Val Pro Gln Asn Tyr Thr Lys Ala Asn Cys Thr Tyr Cys Asn Thr Arg
945                 950                 955                 960

Glu Tyr Thr Phe Ser Tyr Lys Gly Cys Cys Phe Tyr Phe Thr Lys Lys
            965                 970                 975

Lys His Thr Trp Asn Gly Cys Phe Gln Ala Cys Ala Glu Leu Tyr Pro
        980                 985                 990

Cys Thr Tyr Phe Tyr Gly Pro Thr Pro Asp Ile Leu Pro Val Val Thr
        995                 1000                1005

Arg Asn Leu Asn Ala Ile Glu Ser Leu Trp Val Gly Val Tyr Arg
    1010                1015                1020

Val Gly Glu Gly Asn Trp Thr Ser Leu Asp Gly Gly Thr Phe Lys
    1025                1030                1035

Val Tyr Gln Ile Phe Gly Ser His Cys Thr Tyr Val Ser Lys Phe
    1040                1045                1050

Ser Thr Val Pro Val Ser His His Glu Cys Ser Phe Leu Lys Pro
    1055                1060                1065

Cys Leu Cys Val Ser Gln Arg Ser Asn Ser Gly Gly Ser Gly Ser
    1070                1075                1080

Ala Ser Ser Gly Ala Ser Ala Ser Gly Ser Ser Gly Ser Gly Ser
    1085                1090                1095

Gly Ser Gly Ser Ser Ser Ala Ser Ser Gly Ala Ser Ser Gly Gly
    1100                1105                1110

Ala Ser Gly Gly Ser Gly Gly Ser Gly Gly Gly Ser Gly Ser Ala
    1115                1120                1125

Ser Ser Gly Ala Ser Ala Ser Gly Ser Ser Gly Ser Gly Ser Gly
    1130                1135                1140

Ser Gly Ser Ser Ser Ala Ser Ser Gly Ala Ser Ser Gly Gly Ala
    1145                1150                1155

Ser Gly Gly Ser Gly Gly Ser Gly Glu Ser Gln Val Arg Gln Gln
    1160                1165                1170

Phe Ser Lys Asp Ile Glu Lys Leu Leu Asn Glu Gln Val Asn Lys
    1175                1180                1185
```

```
Glu Met Gln Ser Ser Asn Leu Tyr Met Ser Met Ser Ser Trp Ser
    1190                1195                1200

Tyr Thr His Ser Leu Asp Gly Ala Gly Leu Phe Leu Phe Asp His
    1205                1210                1215

Ala Ala Glu Glu Tyr Glu His Ala Lys Lys Leu Ile Ile Phe Leu
    1220                1225                1230

Asn Glu Asn Asn Val Pro Val Gln Leu Thr Ser Ile Ser Ala Pro
    1235                1240                1245

Glu His Lys Phe Glu Gly Leu Thr Gln Ile Phe Gln Lys Ala Tyr
    1250                1255                1260

Glu His Glu Gln His Ile Ser Glu Ser Ile Asn Asn Ile Val Asp
    1265                1270                1275

His Ala Ile Lys Cys Lys Asp His Ala Thr Phe Asn Phe Leu Gln
    1280                1285                1290

Trp Tyr Val Ala Glu Gln His Glu Glu Glu Val Leu Phe Lys Asp
    1295                1300                1305

Ile Leu Asp Lys Ile Glu Leu Ile Gly Asn Glu Asn His Gly Leu
    1310                1315                1320

Tyr Leu Ala Asp Gln Tyr Val Lys Gly Ile Ala Lys Ser Arg Lys
    1325                1330                1335

Ser

<210> SEQ ID NO 228
<211> LENGTH: 1295
<212> TYPE: PRT
<213> ORGANISM: Artificial Sequence
<220> FEATURE:
<223> OTHER INFORMATION: Synthetic polypeptide

<400> SEQUENCE: 228

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
                20                  25                  30

Gln Leu Arg Ala Gln His Leu Leu Ala Leu Glu Asn Ile Ser Asp Ile
            35                  40                  45

Tyr Leu Val Ser Asn Gln Thr Cys Asp Gly Phe Ser Leu Ala Ser Leu
        50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly Gly Ser Gly Ser Ala Ser
    130                 135                 140

Ser Gly Ala Ser Ala Ser Gly Ser Asn Gly Ser Gly Ser Gly Ser
145                 150                 155                 160

Gly Ser Asn Ser Ser Ala Ser Ser Gly Ala Ser Ser Gly Ala Ser
                165                 170                 175

Gly Gly Ser Gly Gly Ser Gly Ala Ala Ser Leu Ser Glu Val Lys Leu
            180                 185                 190

His Leu Asp Ile Glu Gly His Ala Ser His Tyr Thr Ile Pro Trp Thr
```

```
            195                 200                 205
Glu Leu Met Ala Lys Val Pro Gly Leu Ser Pro Glu Ala Leu Trp Arg
210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
                245                 250                 255

Val Asp Ile Pro Ala Val Ser Glu Gly Ser Met Gln Val Asp Ala Ser
                260                 265                 270

Lys Val His Pro Gly Val Ile Ser Gly Leu Asn Ser Pro Ala Cys Met
                275                 280                 285

Leu Ser Ala Pro Leu Glu Lys Gln Leu Phe Tyr Tyr Ile Gly Thr Met
                290                 295                 300

Leu Pro Asn Thr Arg Pro His Ser Tyr Val Phe Tyr Gln Leu Arg Ala
305                 310                 315                 320

His Leu Ser Tyr Val Ala Leu Ser Ile Asn Gly Asp Lys Phe Gln Tyr
                325                 330                 335

Thr Gly Ala Met Thr Ser Lys Phe Leu Met Gly Thr Tyr Lys Arg Val
                340                 345                 350

Thr Glu Lys Gly Asp Glu His Val Leu Ser Leu Val Phe Gly Lys Thr
                355                 360                 365

Lys Asp Leu Pro Asp Leu Arg Gly Pro Phe Ser Tyr Pro Ser Leu Thr
370                 375                 380

Ser Ala Gln Ser Gly Asp Tyr Ser Leu Val Ile Val Thr Thr Phe Val
385                 390                 395                 400

His Tyr Ala Asn Phe His Asn Tyr Phe Val Pro Asn Leu Lys Asp Met
                405                 410                 415

Phe Ser Arg Ala Val Thr Met Thr Ala Ala Ser Tyr Ala Arg Tyr Val
                420                 425                 430

Leu Gln Lys Leu Val Leu Leu Glu Met Lys Gly Gly Cys Arg Glu Pro
                435                 440                 445

Glu Leu Asp Thr Glu Thr Leu Thr Thr Met Phe Glu Val Ser Val Ala
450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
                485                 490                 495

Asp Ile Ile Gly Ile Cys Tyr Gly Ala Thr Val Lys Gly Met Gln Ser
                500                 505                 510

Tyr Gly Leu Glu Arg Leu Ala Ala Met Leu Met Ala Thr Val Lys Met
                515                 520                 525

Glu Glu Leu Gly His Leu Thr Thr Glu Lys Gln Glu Tyr Ala Leu Arg
                530                 535                 540

Leu Ala Thr Val Gly Tyr Pro Lys Ala Gly Val Tyr Ser Gly Leu Ile
545                 550                 555                 560

Gly Gly Ala Thr Ser Val Leu Leu Ser Ala Tyr Asn Arg His Pro Leu
                565                 570                 575

Phe Gln Pro Leu His Thr Val Met Arg Glu Thr Leu Phe Ile Gly Ser
                580                 585                 590

His Val Val Leu Arg Glu Leu Arg Leu Asn Val Thr Thr Gln Gly Pro
                595                 600                 605

Asn Leu Ala Leu Tyr Gln Leu Leu Ser Thr Ala Leu Cys Ser Ala Leu
                610                 615                 620
```

-continued

Glu Ile Gly Glu Val Leu Arg Gly Leu Ala Leu Gly Thr Glu Ser Gly
625                 630                 635                 640

Leu Phe Ser Pro Cys Tyr Leu Ser Leu Arg Phe Asp Leu Thr Arg Asp
            645                 650                 655

Lys Leu Leu Ser Met Ala Pro Gln Glu Ala Thr Leu Asp Gln Ala Ala
        660                 665                 670

Val Ser Asn Ala Val Asp Gly Phe Leu Gly Arg Leu Ser Leu Glu Arg
    675                 680                 685

Glu Asp Arg Asp Ala Trp His Leu Pro Ala Tyr Lys Cys Val Asp Arg
690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
            725                 730                 735

Thr Thr Tyr Leu Ser Ser Ser Leu Phe Leu Ser Pro Val Ile Met Asn
        740                 745                 750

Lys Cys Ser Gln Gly Ala Val Ala Gly Glu Pro Arg Gln Ile Pro Lys
    755                 760                 765

Ile Gln Asn Phe Thr Arg Thr Gln Lys Ser Cys Ile Phe Cys Gly Phe
770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
            805                 810                 815

Asp Phe Asp Asn Leu His Val His Tyr Leu Leu Leu Thr Thr Asn Gly
        820                 825                 830

Thr Val Met Glu Ile Ala Gly Leu Tyr Glu Glu Arg Ala Ser Gly Gly
    835                 840                 845

Gly Ser Gly Ser Ala Ser Ser Gly Ala Ser Ala Ser Gly Ser Ser Gly
850                 855                 860

Ser Gly Ser Gly Ser Gly Ser Ser Ala Ser Ser Gly Leu Ala Tyr
865                 870                 875                 880

Phe Leu Pro Pro Arg Val Arg Gly Gly Arg Val Ala Ala Ala
            885                 890                 895

Ile Thr Trp Val Pro Lys Pro Asn Val Glu Val Trp Pro Val Asp Pro
        900                 905                 910

Pro Pro Pro Val Asn Phe Asn Lys Thr Ala Glu Gln Glu Tyr Gly Asp
    915                 920                 925

Lys Glu Val Lys Leu Pro His Trp Thr Pro Thr Leu His Thr Phe Gln
930                 935                 940

Val Pro Gln Asn Tyr Thr Lys Ala Asn Cys Thr Tyr Cys Asn Thr Arg
945                 950                 955                 960

Glu Tyr Thr Phe Ser Tyr Lys Gly Cys Cys Phe Tyr Phe Thr Lys Lys
            965                 970                 975

Lys His Thr Trp Asn Gly Cys Phe Gln Ala Cys Ala Glu Leu Tyr Pro
        980                 985                 990

Cys Thr Tyr Phe Tyr Gly Pro Thr Pro Asp Ile Leu Pro Val Val Thr
    995                 1000                1005

Arg Asn Leu Asn Ala Ile Glu Ser Leu Trp Val Gly Val Tyr Arg
    1010                1015                1020

Val Gly Glu Gly Asn Trp Ser Leu Asp Gly Gly Thr Phe Lys
    1025                1030                1035

```
Val Tyr Gln Ile Phe Gly Ser His Cys Thr Tyr Val Ser Lys Phe
    1040                1045                1050

Ser Thr Val Pro Val Ser His His Glu Cys Ser Phe Leu Lys Pro
    1055                1060                1065

Cys Leu Cys Val Ser Gln Arg Ser Asn Ser Gly Gly Ser Gly Ser
    1070                1075                1080

Ala Ser Ser Gly Ala Ser Ala Ser Gly Ser Ser Gly Ser Gly Ser
    1085                1090                1095

Gly Ser Gly Ser Ser Ser Ala Ser Ser Gly Ala Ser Ser Gly Gly
    1100                1105                1110

Ala Ser Gly Gly Ser Gly Gly Ser Gly Glu Ser Gln Val Arg Gln
    1115                1120                1125

Gln Phe Ser Lys Asp Ile Glu Lys Leu Leu Asn Glu Gln Val Asn
    1130                1135                1140

Lys Glu Met Gln Ser Ser Asn Leu Tyr Met Ser Met Ser Ser Trp
    1145                1150                1155

Ser Tyr Thr His Ser Leu Asp Gly Ala Gly Leu Phe Leu Phe Asp
    1160                1165                1170

His Ala Ala Glu Glu Tyr Glu His Ala Lys Lys Leu Ile Ile Phe
    1175                1180                1185

Leu Asn Glu Asn Asn Val Pro Val Gln Leu Thr Ser Ile Ser Ala
    1190                1195                1200

Pro Glu His Lys Phe Glu Gly Leu Thr Gln Ile Phe Gln Lys Ala
    1205                1210                1215

Tyr Glu His Glu Gln His Ile Ser Glu Ser Ile Asn Asn Ile Val
    1220                1225                1230

Asp His Ala Ile Lys Cys Lys Asp His Ala Thr Phe Asn Phe Leu
    1235                1240                1245

Gln Trp Tyr Val Ala Glu Gln His Glu Glu Val Leu Phe Lys
    1250                1255                1260

Asp Ile Leu Asp Lys Ile Glu Leu Ile Gly Asn Glu Asn His Gly
    1265                1270                1275

Leu Tyr Leu Ala Asp Gln Tyr Val Lys Gly Ile Ala Lys Ser Arg
    1280                1285                1290

Lys Ser
    1295

<210> SEQ ID NO 229
<211> LENGTH: 1263
<212> TYPE: PRT
<213> ORGANISM: Artificial Sequence
<220> FEATURE:
<223> OTHER INFORMATION: Synthetic polypeptide

<400> SEQUENCE: 229

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
                20                  25                  30

Gln Leu Arg Ala Gln His Leu Leu Ala Leu Glu Asn Ile Ser Asp Ile
            35                  40                  45

Tyr Leu Val Ser Asn Gln Thr Cys Asp Gly Phe Ser Leu Ala Ser Leu
        50                  55                  60

Asn Ser Pro Lys Asn Gly Ser Asn Gln Leu Val Ile Ser Arg Cys Ala
65                  70                  75                  80
```

```
Asn Gly Leu Asn Val Ser Phe Phe Ile Ser Ile Leu Lys Arg Ser
             85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
            115                 120                 125

Asn Arg Tyr Ala Trp His Arg Gly Gly Gly Ser Gly Ser Ala Ser
            130                 135                 140

Ser Gly Ala Ser Ala Ser Gly Ser Ser Asn Gly Ser Ser Gly Ser
145                 150                 155                 160

Gly Ser Asn Ser Ser Ala Ser Ser Gly Ala Ser Ser Gly Gly Ala Ser
                165                 170                 175

Gly Gly Ser Gly Gly Ser Gly Ala Ala Ser Leu Ser Glu Val Lys Leu
            180                 185                 190

His Leu Asp Ile Glu Gly His Ala Ser His Tyr Thr Ile Pro Trp Thr
            195                 200                 205

Glu Leu Met Ala Lys Val Pro Gly Leu Ser Pro Glu Ala Leu Trp Arg
            210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
                245                 250                 255

Val Asp Ile Pro Ala Val Ser Glu Gly Ser Met Gln Val Asp Ala Ser
            260                 265                 270

Lys Val His Pro Gly Val Ile Ser Gly Leu Asn Ser Pro Ala Cys Met
            275                 280                 285

Leu Ser Ala Pro Leu Glu Lys Gln Leu Phe Tyr Tyr Ile Gly Thr Met
290                 295                 300

Leu Pro Asn Thr Arg Pro His Ser Tyr Val Phe Tyr Gln Leu Arg Ala
305                 310                 315                 320

His Leu Ser Tyr Val Ala Leu Ser Ile Asn Gly Asp Lys Phe Gln Tyr
                325                 330                 335

Thr Gly Ala Met Thr Ser Lys Phe Leu Met Gly Thr Tyr Lys Arg Val
            340                 345                 350

Thr Glu Lys Gly Asp Glu His Val Leu Ser Leu Val Phe Gly Lys Thr
            355                 360                 365

Lys Asp Leu Pro Asp Leu Arg Gly Pro Phe Ser Tyr Pro Ser Leu Thr
370                 375                 380

Ser Ala Gln Ser Gly Asp Tyr Ser Leu Val Ile Val Thr Thr Phe Val
385                 390                 395                 400

His Tyr Ala Asn Phe His Asn Tyr Phe Val Pro Asn Leu Lys Asp Met
                405                 410                 415

Phe Ser Arg Ala Val Thr Met Thr Ala Ala Ser Tyr Ala Arg Tyr Val
            420                 425                 430

Leu Gln Lys Leu Val Leu Leu Glu Met Lys Gly Gly Cys Arg Glu Pro
            435                 440                 445

Glu Leu Asp Thr Glu Thr Leu Thr Thr Met Phe Glu Val Ser Val Ala
            450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
                485                 490                 495

Asp Ile Ile Gly Ile Cys Tyr Gly Ala Thr Val Lys Gly Met Gln Ser
```

```
            500                 505                 510
Tyr Gly Leu Glu Arg Leu Ala Ala Met Leu Met Ala Thr Val Lys Met
            515                 520                 525
Glu Glu Leu Gly His Leu Thr Thr Glu Lys Gln Glu Tyr Ala Leu Arg
            530                 535                 540
Leu Ala Thr Val Gly Tyr Pro Lys Ala Gly Val Tyr Ser Gly Leu Ile
545                 550                 555                 560
Gly Gly Ala Thr Ser Val Leu Leu Ser Ala Tyr Asn Arg His Pro Leu
                565                 570                 575
Phe Gln Pro Leu His Thr Val Met Arg Glu Thr Leu Phe Ile Gly Ser
            580                 585                 590
His Val Val Leu Arg Glu Leu Arg Leu Asn Val Thr Thr Gln Gly Pro
            595                 600                 605
Asn Leu Ala Leu Tyr Gln Leu Leu Ser Thr Ala Leu Cys Ser Ala Leu
            610                 615                 620
Glu Ile Gly Glu Val Leu Arg Gly Leu Ala Leu Gly Thr Glu Ser Gly
625                 630                 635                 640
Leu Phe Ser Pro Cys Tyr Leu Ser Leu Arg Phe Asp Leu Thr Arg Asp
                645                 650                 655
Lys Leu Leu Ser Met Ala Pro Gln Glu Ala Thr Leu Asp Gln Ala Ala
            660                 665                 670
Val Ser Asn Ala Val Asp Gly Phe Leu Gly Arg Leu Ser Leu Glu Arg
            675                 680                 685
Glu Asp Arg Asp Ala Trp His Leu Pro Ala Tyr Lys Cys Val Asp Arg
            690                 695                 700
Leu Asp Lys Val Leu Met Ile Ile Pro Leu Ile Asn Val Thr Phe Ile
705                 710                 715                 720
Ile Ser Ser Asp Arg Glu Val Arg Gly Ser Ala Leu Tyr Glu Ala Ser
                725                 730                 735
Thr Thr Tyr Leu Ser Ser Ser Leu Phe Leu Ser Pro Val Ile Met Asn
            740                 745                 750
Lys Cys Ser Gln Gly Ala Val Ala Gly Glu Pro Arg Gln Ile Pro Lys
            755                 760                 765
Ile Gln Asn Phe Thr Arg Thr Gln Lys Ser Cys Ile Phe Cys Gly Phe
            770                 775                 780
Ala Leu Leu Ser Tyr Asp Glu Lys Glu Gly Leu Glu Thr Thr Thr Tyr
785                 790                 795                 800
Ile Thr Ser Gln Glu Val Gln Asn Ser Ile Leu Ser Ser Asn Tyr Phe
                805                 810                 815
Asp Phe Asp Asn Leu His Val His Tyr Leu Leu Leu Thr Thr Asn Gly
            820                 825                 830
Thr Val Met Glu Ile Ala Gly Leu Tyr Glu Glu Arg Ala Ser Gly Gly
            835                 840                 845
Gly Ser Gly Ser Ala Ser Ser Gly Ala Ser Ala Ser Gly Ser Ser Gly
            850                 855                 860
Ser Gly Ser Gly Ser Gly Ser Ser Ala Ser Ser Gly Leu Ala Tyr
865                 870                 875                 880
Phe Leu Pro Pro Arg Val Arg Gly Gly Arg Val Ala Ala Ala
                885                 890                 895
Ile Thr Trp Val Pro Lys Pro Asn Val Glu Val Trp Pro Val Asp Pro
            900                 905                 910
Pro Pro Pro Val Asn Phe Asn Lys Thr Ala Glu Gln Glu Tyr Gly Asp
            915                 920                 925
```

```
Lys Glu Val Lys Leu Pro His Trp Thr Pro Thr Leu His Thr Phe Gln
        930                 935                 940

Val Pro Gln Asn Tyr Thr Lys Ala Asn Cys Thr Tyr Cys Asn Thr Arg
945                 950                 955                 960

Glu Tyr Thr Phe Ser Tyr Lys Gly Cys Cys Phe Tyr Phe Thr Lys Lys
                965                 970                 975

Lys His Thr Trp Asn Gly Cys Phe Gln Ala Cys Ala Glu Leu Tyr Pro
            980                 985                 990

Cys Thr Tyr Phe Tyr Gly Pro Thr Pro Asp Ile Leu Pro Val Val Thr
        995                 1000                1005

Arg Asn Leu Asn Ala Ile Glu Ser Leu Trp Val Gly Val Tyr Arg
    1010                1015                1020

Val Gly Glu Gly Asn Trp Thr Ser Leu Asp Gly Gly Thr Phe Lys
    1025                1030                1035

Val Tyr Gln Ile Phe Gly Ser His Cys Thr Tyr Val Ser Lys Phe
    1040                1045                1050

Ser Thr Val Pro Val Ser His His Glu Cys Ser Phe Leu Lys Pro
    1055                1060                1065

Cys Leu Cys Val Ser Gln Arg Ser Asn Ser Glu Pro Glu Pro Glu
    1070                1075                1080

Pro Glu Pro Glu Pro Gly Gly Glu Ser Gln Val Arg Gln Gln Phe
    1085                1090                1095

Ser Lys Asp Ile Glu Lys Leu Leu Asn Glu Gln Val Asn Lys Glu
    1100                1105                1110

Met Gln Ser Ser Asn Leu Tyr Met Ser Met Ser Ser Trp Ser Tyr
    1115                1120                1125

Thr His Ser Leu Asp Gly Ala Gly Leu Phe Leu Phe Asp His Ala
    1130                1135                1140

Ala Glu Glu Tyr Glu His Ala Lys Lys Leu Ile Ile Phe Leu Asn
    1145                1150                1155

Glu Asn Asn Val Pro Val Gln Leu Thr Ser Ile Ser Ala Pro Glu
    1160                1165                1170

His Lys Phe Glu Gly Leu Thr Gln Ile Phe Gln Lys Ala Tyr Glu
    1175                1180                1185

His Glu Gln His Ile Ser Glu Ser Ile Asn Asn Ile Val Asp His
    1190                1195                1200

Ala Ile Lys Cys Lys Asp His Ala Thr Phe Asn Phe Leu Gln Trp
    1205                1210                1215

Tyr Val Ala Glu Gln His Glu Glu Val Leu Phe Lys Asp Ile
    1220                1225                1230

Leu Asp Lys Ile Glu Leu Ile Gly Asn Glu Asn His Gly Leu Tyr
    1235                1240                1245

Leu Ala Asp Gln Tyr Val Lys Gly Ile Ala Lys Ser Arg Lys Ser
    1250                1255                1260

<210> SEQ ID NO 230
<211> LENGTH: 1255
<212> TYPE: PRT
<213> ORGANISM: Artificial Sequence
<220> FEATURE:
<223> OTHER INFORMATION: Synthetic polypeptide

<400> SEQUENCE: 230

Met Arg Ala Val Gly Val Phe Leu Ala Ile Cys Leu Val Thr Ile Phe
1               5                   10                  15
```

```
Val Leu Pro Thr Trp Gly Asn Trp Ala Tyr Pro Cys Cys His Val Thr
         20                  25                  30

Gln Leu Arg Ala Gln His Leu Ala Leu Glu Asn Ile Ser Asp Ile
         35                  40                  45

Tyr Leu Val Ser Asn Gln Thr Cys Asp Gly Phe Ser Leu Ala Ser Leu
 50                  55                  60

Asn Ser Pro Lys Asn Gly Ser Asn Gln Leu Val Ile Ser Arg Cys Ala
 65                  70                  75                  80

Asn Gly Leu Asn Val Val Ser Phe Phe Ile Ser Ile Leu Lys Arg Ser
             85                  90                  95

Ser Ser Ala Leu Thr Gly His Leu Arg Glu Leu Leu Thr Thr Leu Glu
             100                 105                 110

Thr Leu Tyr Gly Ser Phe Ser Val Glu Asp Leu Phe Gly Ala Asn Leu
             115                 120                 125

Asn Arg Tyr Ala Trp His Arg Gly Gly Gly Ser Gly Ser Ala Ser
 130                 135                 140

Ser Gly Ala Ser Ala Ser Gly Ser Ser Asn Gly Ser Gly Ser Gly Ser
145                 150                 155                 160

Gly Ser Asn Ser Ser Ala Ser Ser Gly Ala Ser Ser Gly Ala Ser
             165                 170                 175

Gly Gly Ser Gly Gly Ser Gly Ala Ala Ser Leu Ser Glu Val Lys Leu
             180                 185                 190

His Leu Asp Ile Glu Gly His Ala Ser His Tyr Thr Ile Pro Trp Thr
             195                 200                 205

Glu Leu Met Ala Lys Val Pro Gly Leu Ser Pro Glu Ala Leu Trp Arg
             210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
             245                 250                 255

Val Asp Ile Pro Ala Val Ser Glu Gly Ser Met Gln Val Asp Ala Ser
             260                 265                 270

Lys Val His Pro Gly Val Ile Ser Gly Leu Asn Ser Pro Ala Cys Met
             275                 280                 285

Leu Ser Ala Pro Leu Glu Lys Gln Leu Phe Tyr Tyr Ile Gly Thr Met
 290                 295                 300

Leu Pro Asn Thr Arg Pro His Ser Tyr Val Phe Tyr Gln Leu Arg Ala
305                 310                 315                 320

His Leu Ser Tyr Val Ala Leu Ser Ile Asn Gly Asp Lys Phe Gln Tyr
             325                 330                 335

Thr Gly Ala Met Thr Ser Lys Phe Leu Met Gly Thr Tyr Lys Arg Val
             340                 345                 350

Thr Glu Lys Gly Asp Glu His Val Leu Ser Leu Val Phe Gly Lys Thr
             355                 360                 365

Lys Asp Leu Pro Asp Leu Arg Gly Pro Phe Ser Tyr Pro Ser Leu Thr
 370                 375                 380

Ser Ala Gln Ser Gly Asp Tyr Ser Leu Val Ile Val Thr Thr Phe Val
385                 390                 395                 400

His Tyr Ala Asn Phe His Asn Tyr Phe Val Pro Asn Leu Lys Asp Met
             405                 410                 415

Phe Ser Arg Ala Val Thr Met Thr Ala Ala Ser Tyr Ala Arg Tyr Val
             420                 425                 430
```

```
Leu Gln Lys Leu Val Leu Leu Glu Met Lys Gly Gly Cys Arg Glu Pro
            435                 440                 445

Glu Leu Asp Thr Glu Thr Leu Thr Thr Met Phe Glu Val Ser Val Ala
        450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
                485                 490                 495

Asp Ile Ile Gly Ile Cys Tyr Gly Ala Thr Val Lys Gly Met Gln Ser
            500                 505                 510

Tyr Gly Leu Glu Arg Leu Ala Ala Met Leu Met Ala Thr Val Lys Met
        515                 520                 525

Glu Glu Leu Gly His Leu Thr Thr Glu Lys Gln Glu Tyr Ala Leu Arg
        530                 535                 540

Leu Ala Thr Val Gly Tyr Pro Lys Ala Gly Val Tyr Ser Gly Leu Ile
545                 550                 555                 560

Gly Gly Ala Thr Ser Val Leu Leu Ser Ala Tyr Asn Arg His Pro Leu
                565                 570                 575

Phe Gln Pro Leu His Thr Val Met Arg Glu Thr Leu Phe Ile Gly Ser
            580                 585                 590

His Val Val Leu Arg Glu Leu Arg Leu Asn Val Thr Thr Gln Gly Pro
        595                 600                 605

Asn Leu Ala Leu Tyr Gln Leu Leu Ser Thr Ala Leu Cys Ser Ala Leu
        610                 615                 620

Glu Ile Gly Glu Val Leu Arg Gly Leu Ala Leu Gly Thr Glu Ser Gly
625                 630                 635                 640

Leu Phe Ser Pro Cys Tyr Leu Ser Leu Arg Phe Asp Leu Thr Arg Asp
                645                 650                 655

Lys Leu Leu Ser Met Ala Pro Gln Glu Ala Thr Leu Asp Gln Ala Ala
            660                 665                 670

Val Ser Asn Ala Val Asp Gly Phe Leu Gly Arg Leu Ser Leu Glu Arg
        675                 680                 685

Glu Asp Arg Asp Ala Trp His Leu Pro Ala Tyr Lys Cys Val Asp Arg
        690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
                725                 730                 735

Thr Thr Tyr Leu Ser Ser Ser Leu Phe Leu Ser Pro Val Ile Met Asn
            740                 745                 750

Lys Cys Ser Gln Gly Ala Val Ala Gly Glu Pro Arg Gln Ile Pro Lys
        755                 760                 765

Ile Gln Asn Phe Thr Arg Thr Gln Lys Ser Cys Ile Phe Cys Gly Phe
        770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
                805                 810                 815

Asp Phe Asp Asn Leu His Val His Tyr Leu Leu Leu Thr Thr Asn Gly
            820                 825                 830

Thr Val Met Glu Ile Ala Gly Leu Tyr Glu Glu Arg Ala Ser Gly Gly
        835                 840                 845

Gly Ser Gly Ser Ala Ser Ser Gly Ala Ser Ala Ser Gly Ser Ser Gly
```

```
             850             855             860
Ser Gly Ser Gly Ser Gly Ser Ser Ala Ser Ser Gly Leu Ala Tyr
            865             870             875             880
Phe Leu Pro Pro Arg Val Arg Gly Gly Arg Val Ala Ala Ala
                    885             890             895
Ile Thr Trp Val Pro Lys Pro Asn Val Glu Val Trp Pro Val Asp Pro
                900             905             910
Pro Pro Pro Val Asn Phe Asn Lys Thr Ala Glu Gln Glu Tyr Gly Asp
            915             920             925
Lys Glu Val Lys Leu Pro His Trp Thr Pro Thr Leu His Thr Phe Gln
            930             935             940
Val Pro Gln Asn Tyr Thr Lys Ala Asn Cys Thr Tyr Cys Asn Thr Arg
945             950             955             960
Glu Tyr Thr Phe Ser Tyr Lys Gly Cys Cys Phe Tyr Phe Thr Lys Lys
                965             970             975
Lys His Thr Trp Asn Gly Cys Phe Gln Ala Cys Ala Glu Leu Tyr Pro
            980             985             990
Cys Thr Tyr Phe Tyr Gly Pro Thr Pro Asp Ile Leu Pro Val Val Thr
            995             1000            1005
Arg Asn Leu Asn Ala Ile Glu Ser Leu Trp Val Gly Val Tyr Arg
    1010            1015            1020
Val Gly Glu Gly Asn Trp Thr Ser Leu Asp Gly Gly Thr Phe Lys
    1025            1030            1035
Val Tyr Gln Ile Phe Gly Ser His Cys Thr Tyr Val Ser Lys Phe
    1040            1045            1050
Ser Thr Val Pro Val Ser His His Glu Cys Ser Phe Leu Lys Pro
    1055            1060            1065
Cys Leu Cys Val Ser Gln Arg Ser Asn Ser Gly Gly Ser Gly Glu
    1070            1075            1080
Ser Gln Val Arg Gln Gln Phe Ser Lys Asp Ile Glu Lys Leu Leu
    1085            1090            1095
Asn Glu Gln Val Asn Lys Glu Met Gln Ser Ser Asn Leu Tyr Met
    1100            1105            1110
Ser Met Ser Ser Trp Ser Tyr Thr His Ser Leu Asp Gly Ala Gly
    1115            1120            1125
Leu Phe Leu Phe Asp His Ala Ala Glu Glu Tyr Glu His Ala Lys
    1130            1135            1140
Lys Leu Ile Ile Phe Leu Asn Glu Asn Asn Val Pro Val Gln Leu
    1145            1150            1155
Thr Ser Ile Ser Ala Pro Glu His Lys Phe Glu Gly Leu Thr Gln
    1160            1165            1170
Ile Phe Gln Lys Ala Tyr Glu His Glu Gln His Ile Ser Glu Ser
    1175            1180            1185
Ile Asn Asn Ile Val Asp His Ala Ile Lys Cys Lys Asp His Ala
    1190            1195            1200
Thr Phe Asn Phe Leu Gln Trp Tyr Val Ala Glu Gln His Glu Glu
    1205            1210            1215
Glu Val Leu Phe Lys Asp Ile Leu Asp Lys Ile Glu Leu Ile Gly
    1220            1225            1230
Asn Glu Asn His Gly Leu Tyr Leu Ala Asp Gln Tyr Val Lys Gly
    1235            1240            1245
Ile Ala Lys Ser Arg Lys Ser
    1250            1255
```

```
<210> SEQ ID NO 231
<211> LENGTH: 1329
<212> TYPE: PRT
<213> ORGANISM: Artificial Sequence
<220> FEATURE:
<223> OTHER INFORMATION: Synthetic polypeptide

<400> SEQUENCE: 231
```

| | | | | | | | | | | | | | | | |
|---|---|---|---|---|---|---|---|---|---|---|---|---|---|---|---|
| Met | Asp | Ser | Lys | Gly | Ser | Ser | Gln | Lys | Gly | Ser | Arg | Leu | Leu | Leu | Leu |
| 1 | | | | 5 | | | | | 10 | | | | | 15 | |
| Leu | Val | Val | Ser | Asn | Leu | Leu | Pro | Gln | Gly | Val | Leu | Ala | Asn | Trp | |
| | | | 20 | | | | | 25 | | | | | 30 | | |
| Ala | Tyr | Pro | Cys | Cys | His | Val | Thr | Gln | Leu | Arg | Ala | Gln | His | Leu | Leu |
| | | | 35 | | | | | 40 | | | | | 45 | | |
| Ala | Leu | Glu | Asn | Ile | Ser | Asp | Ile | Tyr | Leu | Val | Ser | Asn | Gln | Thr | Cys |
| | 50 | | | | | 55 | | | | | 60 | | | | |
| Asp | Ala | Phe | Ser | Leu | Ala | Ser | Leu | Asn | Ser | Pro | Lys | Gln | Gly | Ser | Asn |
| 65 | | | | | 70 | | | | | 75 | | | | | 80 |
| Gln | Leu | Val | Ile | Ser | Arg | Cys | Ala | Asn | Gly | Leu | Asn | Val | Val | Ser | Phe |
| | | | | 85 | | | | | 90 | | | | | 95 | |
| Phe | Ile | Ser | Ile | Leu | Lys | Arg | Ser | Ser | Ala | Leu | Thr | Gly | His | Leu | |
| | | | 100 | | | | | 105 | | | | | 110 | | |
| Arg | Glu | Leu | Leu | Thr | Thr | Leu | Glu | Thr | Leu | Tyr | Gly | Ser | Phe | Ser | Val |
| | | | 115 | | | | | 120 | | | | | 125 | | |
| Glu | Asp | Leu | Phe | Gly | Ala | Gln | Leu | Asn | Arg | Tyr | Ala | Trp | His | Arg | Gly |
| | 130 | | | | | 135 | | | | | 140 | | | | |
| Gly | Gly | Gly | Ser | Gly | Ser | Ala | Ser | Ser | Gly | Ala | Ser | Ala | Ser | Gly | Ser |
| 145 | | | | | 150 | | | | | 155 | | | | | 160 |
| Ser | Gly | Gly | Ser | Gly | Ser | Gly | Ser | Gly | Ser | Ser | Ala | Ser | Ser | | |
| | | | | 165 | | | | | 170 | | | | | 175 | |
| Gly | Ala | Ser | Ser | Gly | Gly | Ala | Ser | Gly | Gly | Ser | Gly | Ser | Gly | Ala | |
| | | | 180 | | | | | 185 | | | | | 190 | | |
| Ala | Ser | Leu | Ser | Glu | Val | Lys | Leu | His | Leu | Asp | Ile | Glu | Gly | His | Ala |
| | | | 195 | | | | | 200 | | | | | 205 | | |
| Ser | His | Tyr | Thr | Ile | Pro | Trp | Thr | Glu | Leu | Leu | Ala | Lys | Val | Pro | Gly |
| | 210 | | | | | 215 | | | | | 220 | | | | |
| Leu | Ser | Pro | Glu | Ala | Leu | Trp | Arg | Glu | Ala | Asn | Val | Thr | Glu | Asp | Leu |
| 225 | | | | | 230 | | | | | 235 | | | | | 240 |
| Ala | Ser | Met | Leu | Asn | Arg | Tyr | Lys | Leu | Ile | Tyr | Lys | Thr | Ser | Gly | Thr |
| | | | | 245 | | | | | 250 | | | | | 255 | |
| Leu | Gly | Ile | Ala | Leu | Ala | Glu | Pro | Val | Asp | Ile | Pro | Ala | Val | Ser | Glu |
| | | | 260 | | | | | 265 | | | | | 270 | | |
| Gly | Ser | Met | Gln | Val | Asp | Ala | Ser | Lys | Val | His | Pro | Gly | Val | Ile | Ser |
| | | | 275 | | | | | 280 | | | | | 285 | | |
| Gly | Leu | Asn | Ser | Pro | Ala | Cys | Met | Leu | Ser | Ala | Pro | Leu | Glu | Lys | Gln |
| | 290 | | | | | 295 | | | | | 300 | | | | |
| Leu | Phe | Tyr | Tyr | Ile | Gly | Thr | Met | Leu | Pro | Asn | Thr | Arg | Pro | His | Ser |
| 305 | | | | | 310 | | | | | 315 | | | | | 320 |
| Tyr | Val | Phe | Tyr | Gln | Leu | Arg | Cys | His | Leu | Ser | Tyr | Val | Ala | Leu | Ser |
| | | | | 325 | | | | | 330 | | | | | 335 | |
| Ile | Asn | Gly | Asp | Lys | Phe | Gln | Tyr | Thr | Gly | Ala | Met | Thr | Ser | Lys | Phe |
| | | | 340 | | | | | 345 | | | | | 350 | | |
| Leu | Met | Gly | Thr | Tyr | Lys | Arg | Val | Thr | Glu | Lys | Gly | Asp | Glu | His | Val |
| | | | 355 | | | | | 360 | | | | | 365 | | |

```
Leu Ser Leu Val Phe Gly Lys Thr Lys Asp Leu Pro Asp Leu Arg Gly
        370                 375                 380

Pro Phe Ser Tyr Pro Ser Leu Thr Ser Ala Gln Ser Gly Glu Tyr Ser
385                 390                 395                 400

Leu Val Ile Val Thr Thr Phe Val His Tyr Ala Asn Phe His Asn Tyr
                405                 410                 415

Phe Val Pro Asn Leu Lys Asp Met Phe Ser Arg Ala Val Thr Met Thr
            420                 425                 430

Ala Ala Ser Tyr Ala Arg Tyr Val Leu Gln Lys Leu Val Leu Leu Glu
        435                 440                 445

Met Lys Gly Gly Cys Arg Glu Pro Glu Leu Glu Thr Glu Thr Leu Thr
    450                 455                 460

Thr Met Phe Glu Val Ser Val Ala Phe Phe Lys Val Gly His Ala Val
465                 470                 475                 480

Gly Glu Thr Gly Asn Gly Cys Val Asp Leu Arg Trp Leu Ala Lys Ser
                485                 490                 495

Phe Phe Glu Leu Thr Val Leu Lys Asp Ile Ile Gly Ile Cys Tyr Gly
            500                 505                 510

Ala Thr Val Lys Gly Met Gln Ser Tyr Gly Leu Glu Arg Leu Ala Ala
        515                 520                 525

Ile Leu Met Ala Thr Val Lys Met Glu Glu Leu Gly His Leu Thr Thr
    530                 535                 540

Glu Lys Gln Glu Tyr Ala Leu Arg Leu Ala Thr Val Gly Tyr Pro Lys
545                 550                 555                 560

Ala Gly Val Tyr Ser Gly Leu Ile Gly Gly Ala Thr Ser Val Leu Leu
                565                 570                 575

Ser Ala Tyr Asn Arg His Pro Leu Phe Gln Pro Leu His Thr Val Met
            580                 585                 590

Arg Glu Thr Leu Phe Ile Gly Ser His Val Val Leu Arg Glu Leu Arg
        595                 600                 605

Leu Asn Val Thr Thr Gln Gly Pro Asn Leu Ala Leu Tyr Gln Leu Leu
    610                 615                 620

Ser Thr Ala Leu Cys Ser Ala Leu Glu Ile Gly Glu Val Leu Arg Gly
625                 630                 635                 640

Leu Ala Leu Gly Thr Glu Ser Gly Leu Phe Ser Pro Cys Tyr Leu Ser
                645                 650                 655

Leu Arg Phe Asp Leu Thr Arg Asp Lys Leu Leu Ser Ile Ala Pro Gln
            660                 665                 670

Glu Ala Thr Leu Asp Gln Ala Ala Val Ser Gln Ala Val Asp Gly Phe
        675                 680                 685

Leu Gly Arg Leu Ser Leu Glu Arg Glu Asp Arg Asp Ala Trp His Leu
    690                 695                 700

Pro Ala Tyr Lys Cys Val Asp Arg Leu Asp Lys Val Leu Met Ile Ile
705                 710                 715                 720

Pro Leu Ile Asn Val Thr Phe Ile Ile Ser Asp Arg Glu Val Arg
                725                 730                 735

Gly Ser Ala Leu Tyr Glu Ala Ser Thr Thr Tyr Leu Ser Ser Ser Leu
            740                 745                 750

Phe Leu Ser Pro Val Ile Leu Asn Lys Cys Ser Gln Gly Ala Val Ala
        755                 760                 765

Gly Glu Pro Arg Gln Ile Pro Lys Ile Gln Asn Phe Thr Arg Thr Gln
    770                 775                 780
```

```
Lys Ser Cys Ile Phe Cys Gly Phe Ala Leu Leu Ser Tyr Asp Glu Lys
785                 790                 795                 800

Glu Gly Leu Glu Thr Thr Thr Tyr Ile Thr Ser Gln Glu Val Gln Asn
            805                 810                 815

Ser Ile Leu Ser Ser Asn Tyr Phe Asp Phe Asp Asn Leu His Val His
            820                 825                 830

Tyr Leu Leu Leu Thr Thr Asn Gly Thr Val Met Glu Ile Ala Gly Leu
            835                 840                 845

Tyr Glu Glu Arg Ala Ser Gly Gly Ser Gly Ser Ala Ser Ser Gly
        850                 855                 860

Ala Ser Ala Ser Gly Ser Ser Gly Ser Gly Ser Gly Ser Gly Ser Ser
865                 870                 875                 880

Ser Ala Ser Ser Gly Ala Ile Thr Trp Val Pro Lys Pro Asn Val Glu
                885                 890                 895

Val Trp Pro Val Asp Pro Pro Pro Val Asn Phe Asn Lys Thr Ala
                900                 905                 910

Glu Gln Glu Tyr Gly Asp Lys Glu Val Lys Leu Pro His Trp Thr Pro
            915                 920                 925

Thr Leu His Thr Phe Gln Val Pro Gln Asn Tyr Thr Lys Ala Asn Cys
        930                 935                 940

Thr Tyr Cys Asn Thr Arg Glu Tyr Thr Phe Ser Tyr Lys Gly Cys Cys
945                 950                 955                 960

Phe Tyr Phe Thr Lys Lys His Thr Trp Gln Gly Cys Phe Gln Ala
                965                 970                 975

Cys Ala Glu Leu Tyr Pro Cys Thr Tyr Phe Tyr Gly Pro Thr Pro Asp
            980                 985                 990

Ile Leu Pro Val Val Thr Arg Ser Leu Gln Ala Ile Glu Ser Leu Trp
            995                 1000                1005

Val Gly Val Tyr Arg Val Gly Glu Gly Asn Trp Thr Ser Leu Asp
    1010                1015                1020

Gly Gly Thr Phe Lys Val Tyr Gln Ile Phe Gly Ser His Cys Thr
    1025                1030                1035

Tyr Val Ser Lys Phe Ser Thr Val Pro Val Ser His His Glu Cys
    1040                1045                1050

Ser Phe Leu Lys Pro Cys Leu Cys Val Ser Gln Arg Ser Asn Ser
    1055                1060                1065

Gly Gly Ser Gly Ser Ala Ser Ser Gly Ala Ser Ala Ser Gly Ser
    1070                1075                1080

Ser Gly Ser Gly Ser Gly Ser Gly Ser Ser Ala Ser Ser Gly
    1085                1090                1095

Ala Ser Ser Gly Gly Ala Ser Gly Gly Ser Gly Gly Ser Gly Gly
    1100                1105                1110

Gly Ser Gly Ser Ala Ser Ser Gly Ala Ser Ala Ser Gly Ser Ser
    1115                1120                1125

Gly Ser Gly Ser Gly Ser Gly Ser Ser Ser Ala Ser Ser Gly Ala
    1130                1135                1140

Ser Ser Gly Gly Ala Ser Gly Ser Gly Gly Ser Gly Glu Ser
    1145                1150                1155

Gln Val Arg Ser Gln Phe Ser Lys Asp Ile Glu Lys Leu Leu Asn
    1160                1165                1170

Glu Gln Val Asn Lys Glu Met Gln Ser Ser Asn Leu Tyr Met Ser
    1175                1180                1185

Met Ser Ser Trp Ser Tyr Thr His Ser Leu Asp Gly Ala Gly Leu
```

```
                    1190                1195                1200
Phe Leu Phe Asp His Ala Ala Glu Glu Tyr Glu His Ala Lys Lys
            1205                1210                1215
Leu Ile Ile Phe Leu Asn Glu Asn Asn Val Pro Val Gln Leu Thr
            1220                1225                1230
Ser Ile Ser Ala Pro Glu His Lys Phe Glu Gly Leu Thr Gln Ile
            1235                1240                1245
Phe Gln Lys Ala Tyr Glu His Glu Gln His Ile Ser Glu Ser Ile
            1250                1255                1260
Asn Gln Ile Val Asp His Ala Ile Lys Cys Lys Asp His Ala Thr
            1265                1270                1275
Phe Asn Phe Leu Gln Trp Tyr Val Ala Glu Gln His Glu Glu Glu
            1280                1285                1290
Val Leu Phe Lys Asp Ile Leu Asp Lys Ile Glu Leu Ile Gly Gln
            1295                1300                1305
Glu Asn His Gly Leu Tyr Leu Ala Asp Gln Tyr Val Lys Gly Ile
            1310                1315                1320
Ala Lys Ser Arg Lys Ser
            1325

<210> SEQ ID NO 232
<211> LENGTH: 1066
<212> TYPE: PRT
<213> ORGANISM: Artificial Sequence
<220> FEATURE:
<223> OTHER INFORMATION: Synthetic polypeptide

<400> SEQUENCE: 232

Met Arg Ala Val Gly Val Phe Leu Ala Ile Cys Leu Val Thr Ile Phe
1               5                   10                  15
Val Leu Pro Thr Trp Gly Asn Trp Ala Tyr Pro Cys Cys His Val Thr
                20                  25                  30
Gln Leu Arg Ala Gln His Leu Leu Ala Leu Glu Asn Ile Ser Asp Ile
            35                  40                  45
Tyr Leu Val Ser Asn Gln Thr Cys Asp Gly Phe Ser Leu Ala Ser Leu
        50                  55                  60
Asn Ser Pro Lys Asn Gly Ser Asn Gln Leu Val Ile Ser Arg Cys Ala
65                  70                  75                  80
Asn Gly Leu Asn Val Val Ser Phe Phe Ile Ser Ile Leu Lys Arg Ser
                85                  90                  95
Ser Ser Ala Leu Thr Gly His Leu Arg Glu Leu Leu Thr Thr Leu Glu
            100                 105                 110
Thr Leu Tyr Gly Ser Phe Ser Val Glu Asp Leu Phe Gly Ala Asn Leu
        115                 120                 125
Asn Arg Tyr Ala Trp His Arg Gly Gly Gly Ser Gly Ser Ala Ser
    130                 135                 140
Ser Gly Ala Ser Ala Ser Gly Ser Ser Asn Gly Ser Gly Ser Gly Ser
145                 150                 155                 160
Gly Ser Asn Ser Ser Ala Ser Ser Gly Ala Ser Ser Gly Gly Ala Ser
                165                 170                 175
Gly Gly Ser Gly Gly Ser Gly Ala Ala Ser Leu Ser Glu Val Lys Leu
            180                 185                 190
His Leu Asp Ile Glu Gly His Ala Ser His Tyr Thr Ile Pro Trp Thr
        195                 200                 205
Glu Leu Met Ala Lys Val Pro Gly Leu Ser Pro Glu Ala Leu Trp Arg
```

```
                 210                 215                 220

Glu Ala Asn Val Thr Glu Asp Leu Ala Ser Met Leu Asn Arg Tyr Lys
225                 230                 235                 240

Leu Ile Tyr Lys Thr Ser Gly Thr Leu Gly Ile Ala Leu Ala Glu Pro
                245                 250                 255

Val Asp Ile Pro Ala Val Ser Glu Gly Ser Met Gln Val Asp Ala Ser
                260                 265                 270

Lys Val His Pro Gly Val Ile Ser Gly Leu Asn Ser Pro Ala Cys Met
                275                 280                 285

Leu Ser Ala Pro Leu Glu Lys Gln Leu Phe Tyr Tyr Ile Gly Thr Met
                290                 295                 300

Leu Pro Asn Thr Arg Pro His Ser Tyr Val Phe Tyr Gln Leu Arg Ala
305                 310                 315                 320

His Leu Ser Tyr Val Ala Leu Ser Ile Asn Gly Asp Lys Phe Gln Tyr
                325                 330                 335

Thr Gly Ala Met Thr Ser Lys Phe Leu Met Gly Thr Tyr Lys Arg Val
                340                 345                 350

Thr Glu Lys Gly Asp Glu His Val Leu Ser Leu Val Phe Gly Lys Thr
                355                 360                 365

Lys Asp Leu Pro Asp Leu Arg Gly Pro Phe Ser Tyr Pro Ser Leu Thr
                370                 375                 380

Ser Ala Gln Ser Gly Asp Tyr Ser Leu Val Ile Val Thr Thr Phe Val
385                 390                 395                 400

His Tyr Ala Asn Phe His Asn Tyr Phe Val Pro Asn Leu Lys Asp Met
                405                 410                 415

Phe Ser Arg Ala Val Thr Met Thr Ala Ala Ser Tyr Ala Arg Tyr Val
                420                 425                 430

Leu Gln Lys Leu Val Leu Leu Glu Met Lys Gly Gly Cys Arg Glu Pro
                435                 440                 445

Glu Leu Asp Thr Glu Thr Leu Thr Thr Met Phe Glu Val Ser Val Ala
                450                 455                 460

Phe Phe Lys Val Gly His Ala Val Gly Glu Thr Gly Asn Gly Cys Val
465                 470                 475                 480

Asp Leu Arg Trp Leu Ala Lys Ser Phe Phe Glu Leu Thr Val Leu Lys
                485                 490                 495

Asp Ile Ile Gly Ile Cys Tyr Gly Ala Thr Val Lys Gly Met Gln Ser
                500                 505                 510

Tyr Gly Leu Glu Arg Leu Ala Ala Met Leu Met Ala Thr Val Lys Met
                515                 520                 525

Glu Glu Leu Gly His Leu Thr Thr Glu Lys Gln Glu Tyr Ala Leu Arg
530                 535                 540

Leu Ala Thr Val Gly Tyr Pro Lys Ala Gly Val Tyr Ser Gly Leu Ile
545                 550                 555                 560

Gly Gly Ala Thr Ser Val Leu Leu Ser Ala Tyr Asn Arg His Pro Leu
                565                 570                 575

Phe Gln Pro Leu His Thr Val Met Arg Glu Thr Leu Phe Ile Gly Ser
                580                 585                 590

His Val Val Leu Arg Glu Leu Arg Leu Asn Val Thr Thr Gln Gly Pro
                595                 600                 605

Asn Leu Ala Leu Tyr Gln Leu Leu Ser Thr Ala Leu Cys Ser Ala Leu
                610                 615                 620

Glu Ile Gly Glu Val Leu Arg Gly Leu Ala Leu Gly Thr Glu Ser Gly
625                 630                 635                 640
```

```
Leu Phe Ser Pro Cys Tyr Leu Ser Leu Arg Phe Asp Leu Thr Arg Asp
                645                 650                 655

Lys Leu Leu Ser Met Ala Pro Gln Glu Ala Thr Leu Asp Gln Ala Ala
            660                 665                 670

Val Ser Asn Ala Val Asp Gly Phe Leu Gly Arg Leu Ser Leu Glu Arg
        675                 680                 685

Glu Asp Arg Asp Ala Trp His Leu Pro Ala Tyr Lys Cys Val Asp Arg
    690                 695                 700

Leu Asp Lys Val Leu Met Ile Ile Pro Leu Ile Asn Val Thr Phe Ile
705                 710                 715                 720

Ile Ser Ser Asp Arg Glu Val Arg Gly Ser Ala Leu Tyr Glu Ala Ser
                725                 730                 735

Thr Thr Tyr Leu Ser Ser Ser Leu Phe Leu Ser Pro Val Ile Met Asn
            740                 745                 750

Lys Cys Ser Gln Gly Ala Val Ala Gly Glu Pro Arg Gln Ile Pro Lys
        755                 760                 765

Ile Gln Asn Phe Thr Arg Thr Gln Lys Ser Cys Ile Phe Cys Gly Phe
    770                 775                 780

Ala Leu Leu Ser Tyr Asp Glu Lys Glu Gly Leu Glu Thr Thr Thr Tyr
785                 790                 795                 800

Ile Thr Ser Gln Glu Val Gln Asn Ser Ile Leu Ser Ser Asn Tyr Phe
                805                 810                 815

Asp Phe Asp Asn Leu His Val His Tyr Leu Leu Leu Thr Thr Asn Gly
            820                 825                 830

Thr Val Met Glu Ile Ala Gly Leu Tyr Glu Glu Arg Ala Ser Gly Glu
        835                 840                 845

Pro Glu Pro Glu Pro Glu Pro Glu Pro Glu Pro Glu Pro Glu Pro Glu
    850                 855                 860

Pro Glu Pro Glu Pro Glu Pro Glu Pro Glu Pro Glu Pro Glu Pro Glu
865                 870                 875                 880

Pro Glu Pro Glu Pro Glu Pro Glu Pro Glu Pro Glu Pro Glu Ser Gln
                885                 890                 895

Val Arg Gln Gln Phe Ser Lys Asp Ile Glu Lys Leu Leu Asn Glu Gln
            900                 905                 910

Val Asn Lys Glu Met Gln Ser Ser Asn Leu Tyr Met Ser Met Ser Ser
        915                 920                 925

Trp Ser Tyr Thr His Ser Leu Asp Gly Ala Gly Leu Phe Leu Phe Asp
    930                 935                 940

His Ala Ala Glu Glu Tyr Glu His Ala Lys Lys Leu Ile Ile Phe Leu
945                 950                 955                 960

Asn Glu Asn Asn Val Pro Val Gln Leu Thr Ser Ile Ser Ala Pro Glu
                965                 970                 975

His Lys Phe Glu Gly Leu Thr Gln Ile Phe Gln Lys Ala Tyr Glu His
            980                 985                 990

Glu Gln His Ile Ser Glu Ser Ile Asn Asn Ile Val Asp His Ala Ile
        995                1000                1005

Lys Cys Lys Asp His Ala Thr Phe Asn Phe Leu Gln Trp Tyr Val
    1010                1015                1020

Ala Glu Gln His Glu Glu Glu Val Leu Phe Lys Asp Ile Leu Asp
    1025                1030                1035

Lys Ile Glu Leu Ile Gly Asn Glu Asn His Gly Leu Tyr Leu Ala
    1040                1045                1050
```

Asp Gln Tyr Val Lys Gly Ile Ala Lys Ser Arg Lys Ser
        1055                1060                1065

<210> SEQ ID NO 233
<211> LENGTH: 46
<212> TYPE: PRT
<213> ORGANISM: Artificial Sequence
<220> FEATURE:
<223> OTHER INFORMATION: Synthetic polypeptide

<400> SEQUENCE: 233

Gly Gly Ser Gly Ser Ala Ser Ser Gly Ala Ser Ala Ser Gly Ser Ser
1               5                   10                  15

Gly Gly Ser Gly Ser Gly Ser Gly Ser Ser Ala Ser Ser Gly
            20                  25                  30

Ala Ser Ser Gly Gly Ala Ser Gly Gly Ser Gly Gly Ser Gly
        35                  40                  45

<210> SEQ ID NO 234
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 234

Ser Gly Gly Gly Ser Gly Ser Ala Ser Ser Gly Ala Ser Ala Ser Gly
1               5                   10                  15

Ser Ser Gly Ser Gly Ser Gly Ser Ser Ser Ala Ser Ser Gly
            20                  25                  30

<210> SEQ ID NO 235
<211> LENGTH: 88
<212> TYPE: PRT
<213> ORGANISM: Artificial Sequence
<220> FEATURE:
<223> OTHER INFORMATION: Synthetic polypeptide

<400> SEQUENCE: 235

Gly Gly Ser Gly Ser Ala Ser Ser Gly Ala Ser Ala Ser Gly Ser Ser
1               5                   10                  15

Gly Ser Gly Ser Gly Ser Gly Ser Ser Ser Ala Ser Ser Gly Ala Ser
            20                  25                  30

Ser Gly Gly Ala Ser Gly Gly Ser Gly Gly Ser Gly Gly Ser Gly
        35                  40                  45

Ser Ala Ser Ser Gly Ala Ser Ala Ser Gly Ser Ser Gly Ser Gly Ser
    50                  55                  60

Gly Ser Gly Ser Ser Ser Ala Ser Ser Gly Ala Ser Ser Gly Gly Ala
65                  70                  75                  80

Ser Gly Gly Ser Gly Gly Ser Gly
                85

<210> SEQ ID NO 236
<211> LENGTH: 44
<212> TYPE: PRT
<213> ORGANISM: Artificial Sequence
<220> FEATURE:
<223> OTHER INFORMATION: Synthetic polypeptide

<400> SEQUENCE: 236

Gly Gly Ser Gly Ser Ala Ser Ser Gly Ala Ser Ala Ser Gly Ser Ser
1               5                   10                  15

Gly Ser Gly Ser Gly Ser Ser Ala Ser Ser Gly Ala Ser
            20                  25                  30

Ser Gly Gly Ala Ser Gly Gly Ser Gly Gly Ser Gly
        35                  40

<210> SEQ ID NO 237
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 237

Glu Pro Glu Pro Glu Pro Glu Pro Glu Pro Gly Gly
1               5                   10

<210> SEQ ID NO 238
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 238

Ser Gly Glu Pro Glu Pro Glu Pro Glu Pro Glu Pro Glu Pro Glu Pro
1               5                   10                  15

Glu Pro Glu Pro Glu Pro Glu Pro Glu Pro Glu Pro Glu Pro Glu Pro
            20                  25                  30

Glu Pro Glu Pro Glu Pro Glu Pro Glu Pro Glu Pro Glu Pro Glu Pro
        35                  40                  45

<210> SEQ ID NO 239
<211> LENGTH: 201
<212> TYPE: PRT
<213> ORGANISM: Artificial Sequence
<220> FEATURE:
<223> OTHER INFORMATION: Synthetic polypeptide

<400> SEQUENCE: 239

Leu Ala Tyr Phe Leu Pro Pro Arg Val Arg Gly Gly Gly Arg Val Ala
1               5                   10                  15

Ala Ala Ala Ile Thr Trp Val Pro Lys Pro Asn Val Glu Val Trp Pro
            20                  25                  30

Val Asp Pro Pro Pro Val Asn Phe Asn Lys Thr Ala Glu Gln Glu
        35                  40                  45

Tyr Gly Asp Lys Glu Val Lys Leu Pro His Trp Thr Pro Thr Leu His
50                  55                  60

Thr Phe Gln Val Pro Gln Asn Tyr Thr Lys Ala Asn Cys Thr Tyr Cys
65                  70                  75                  80

Asn Thr Arg Glu Tyr Thr Phe Ser Tyr Lys Gly Cys Cys Phe Tyr Phe
                85                  90                  95

Thr Lys Lys Lys His Thr Trp Asn Gly Cys Phe Gln Ala Cys Ala Glu
            100                 105                 110

Leu Tyr Pro Cys Thr Tyr Phe Tyr Gly Pro Thr Pro Asp Ile Leu Pro
        115                 120                 125

Val Val Thr Arg Asn Leu Asn Ala Ile Glu Ser Leu Trp Val Gly Val
        130                 135                 140

Tyr Arg Val Gly Glu Gly Asn Trp Thr Ser Leu Asp Gly Gly Thr Phe
145                 150                 155                 160

Lys Val Tyr Gln Ile Phe Gly Ser His Cys Thr Tyr Val Ser Lys Phe

```
                165                 170                 175
Ser Thr Val Pro Val Ser His His Glu Cys Ser Phe Leu Lys Pro Cys
            180                 185                 190

Leu Cys Val Ser Gln Arg Ser Asn Ser
        195                 200

<210> SEQ ID NO 240
<211> LENGTH: 183
<212> TYPE: PRT
<213> ORGANISM: Artificial Sequence
<220> FEATURE:
<223> OTHER INFORMATION: Synthetic polypeptide

<400> SEQUENCE: 240

Ala Ile Thr Trp Val Pro Lys Pro Asn Val Glu Val Trp Pro Val Asp
1               5                   10                  15

Pro Pro Pro Val Asn Phe Asn Lys Thr Ala Glu Gln Glu Tyr Gly
            20                  25                  30

Asp Lys Glu Val Lys Leu Pro His Trp Thr Pro Thr Leu His Thr Phe
        35                  40                  45

Gln Val Pro Gln Asn Tyr Thr Lys Ala Asn Cys Thr Tyr Cys Asn Thr
    50                  55                  60

Arg Glu Tyr Thr Phe Ser Tyr Lys Gly Cys Cys Phe Tyr Phe Thr Lys
65                  70                  75                  80

Lys Lys His Thr Trp Gln Gly Cys Phe Gln Ala Cys Ala Glu Leu Tyr
                85                  90                  95

Pro Cys Thr Tyr Phe Tyr Gly Pro Thr Pro Asp Ile Leu Pro Val Val
            100                 105                 110

Thr Arg Ser Leu Gln Ala Ile Glu Ser Leu Trp Val Gly Val Tyr Arg
        115                 120                 125

Val Gly Glu Gly Asn Trp Thr Ser Leu Asp Gly Gly Thr Phe Lys Val
    130                 135                 140

Tyr Gln Ile Phe Gly Ser His Cys Thr Tyr Val Ser Lys Phe Ser Thr
145                 150                 155                 160

Val Pro Val Ser His His Glu Cys Ser Phe Leu Lys Pro Cys Leu Cys
                165                 170                 175

Val Ser Gln Arg Ser Asn Ser
            180

<210> SEQ ID NO 241
<211> LENGTH: 1329
<212> TYPE: PRT
<213> ORGANISM: Artificial Sequence
<220> FEATURE:
<223> OTHER INFORMATION: Synthetic polypeptide

<400> SEQUENCE: 241

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Asn Trp
            20                  25                  30

Ala Tyr Pro Cys Cys His Val Thr Gln Leu Arg Ala Gln His Leu Leu
        35                  40                  45

Ala Leu Glu Asn Ile Ser Asp Ile Tyr Leu Val Ser Asn Gln Thr Cys
    50                  55                  60

Asp Ala Phe Ser Leu Ala Ser Leu Asn Ser Pro Lys Gln Gly Ser Asn
65                  70                  75                  80
```

```
Gln Leu Val Ile Ser Arg Cys Ala Asn Gly Leu Asn Val Val Ser Phe
             85                  90                  95
Phe Ile Ser Ile Leu Lys Arg Ser Ser Ala Leu Thr Gly His Leu
        100                 105                 110
Arg Glu Leu Leu Thr Thr Leu Glu Thr Leu Tyr Gly Ser Phe Ser Val
        115                 120                 125
Glu Asp Leu Phe Gly Ala Gln Leu Asn Arg Tyr Ala Trp His Arg Gly
130                 135                 140
Gly Gly Gly Ser Gly Ser Ala Ser Ser Gly Ala Ser Ala Ser Gly Ser
145                 150                 155                 160
Ser Gly Ser Gly Ser Gly Ser Gly Ser Ser Ala Ser Ser
                165                 170                 175
Gly Ala Ser Ser Gly Ala Ser Gly Gly Ser Gly Gly Ser Gly Ala
                180                 185                 190
Ala Ser Leu Ser Glu Val Lys Leu His Leu Asp Ile Glu Gly His Ala
            195                 200                 205
Ser His Tyr Thr Ile Pro Trp Thr Glu Leu Leu Ala Lys Val Pro Gly
        210                 215                 220
Leu Ser Pro Glu Ala Leu Trp Arg Glu Ala Asn Val Thr Glu Asp Leu
225                 230                 235                 240
Ala Ser Met Leu Asn Arg Tyr Lys Leu Ile Tyr Lys Thr Ser Gly Thr
                245                 250                 255
Leu Gly Ile Ala Leu Ala Glu Pro Val Asp Ile Pro Ala Val Ser Glu
                260                 265                 270
Gly Ser Met Gln Val Asp Ala Ser Lys Val His Pro Gly Val Ile Ser
            275                 280                 285
Gly Leu Asn Ser Pro Ala Cys Met Leu Ser Ala Pro Leu Glu Lys Gln
        290                 295                 300
Leu Phe Tyr Tyr Ile Gly Thr Met Leu Pro Asn Thr Arg Pro His Ser
305                 310                 315                 320
Tyr Val Phe Tyr Gln Leu Arg Cys His Leu Ser Tyr Val Ala Leu Ser
                325                 330                 335
Ile Asn Gly Asp Lys Phe Gln Tyr Thr Gly Ala Met Thr Ser Lys Phe
            340                 345                 350
Leu Met Gly Thr Tyr Lys Arg Val Thr Glu Lys Gly Asp Glu His Val
        355                 360                 365
Leu Ser Leu Val Phe Gly Lys Thr Lys Asp Leu Pro Asp Leu Arg Gly
370                 375                 380
Pro Phe Ser Tyr Pro Ser Leu Thr Ser Ala Gln Ser Gly Glu Tyr Ser
385                 390                 395                 400
Leu Val Ile Val Thr Thr Phe Val His Tyr Ala Asn Phe His Asn Tyr
                405                 410                 415
Phe Val Pro Asn Leu Lys Asp Met Phe Ser Arg Ala Val Thr Met Thr
            420                 425                 430
Ala Ala Ser Tyr Ala Arg Tyr Val Leu Gln Lys Leu Val Leu Leu Glu
        435                 440                 445
Met Lys Gly Gly Cys Arg Glu Pro Glu Leu Glu Thr Glu Thr Leu Thr
450                 455                 460
Thr Met Phe Glu Val Ser Val Ala Phe Phe Lys Val Gly His Ala Val
465                 470                 475                 480
Gly Glu Thr Gly Asn Gly Cys Val Asp Leu Arg Trp Leu Ala Lys Ser
                485                 490                 495
Phe Phe Glu Leu Thr Val Leu Lys Asp Ile Ile Gly Ile Cys Tyr Gly
```

```
                500             505             510
Ala Thr Val Lys Gly Met Gln Ser Tyr Gly Leu Glu Arg Leu Ala Ala
            515             520             525
Ile Leu Met Ala Thr Val Lys Met Glu Glu Leu Gly His Leu Thr Thr
            530             535             540
Glu Lys Gln Glu Tyr Ala Leu Arg Leu Ala Thr Val Gly Tyr Pro Lys
545             550             555             560
Ala Gly Val Tyr Ser Gly Leu Ile Gly Ala Thr Ser Val Leu Leu
            565             570             575
Ser Ala Tyr Asn Arg His Pro Leu Phe Gln Pro Leu His Thr Val Met
            580             585             590
Arg Glu Thr Leu Phe Ile Gly Ser His Val Val Leu Arg Glu Leu Arg
            595             600             605
Leu Asn Val Thr Thr Gln Gly Pro Asn Leu Ala Leu Tyr Gln Leu Leu
            610             615             620
Ser Thr Ala Leu Cys Ser Ala Leu Glu Ile Gly Glu Val Leu Arg Gly
625             630             635             640
Leu Ala Leu Gly Thr Glu Ser Gly Leu Phe Ser Pro Cys Tyr Leu Ser
            645             650             655
Leu Arg Phe Asp Leu Thr Arg Asp Lys Leu Leu Ser Ile Ala Pro Gln
            660             665             670
Glu Ala Thr Leu Asp Gln Ala Ala Val Ser Gln Ala Val Asp Gly Phe
            675             680             685
Leu Gly Arg Leu Ser Leu Glu Arg Glu Asp Arg Asp Ala Trp His Leu
            690             695             700
Pro Ala Tyr Lys Cys Val Asp Arg Leu Asp Lys Val Leu Met Ile Ile
705             710             715             720
Pro Leu Ile Asn Val Thr Phe Ile Ile Ser Ser Asp Arg Glu Val Arg
            725             730             735
Gly Ser Ala Leu Tyr Glu Ala Ser Thr Thr Tyr Leu Ser Ser Ser Leu
            740             745             750
Phe Leu Ser Pro Val Ile Met Asn Lys Cys Ser Gln Gly Ala Val Ala
            755             760             765
Gly Glu Pro Arg Gln Ile Pro Lys Ile Gln Asn Phe Thr Arg Thr Gln
            770             775             780
Lys Ser Cys Ile Phe Cys Gly Phe Ala Leu Leu Ser Tyr Asp Glu Lys
785             790             795             800
Glu Gly Leu Glu Thr Thr Thr Tyr Ile Thr Ser Gln Glu Val Gln Asn
            805             810             815
Ser Ile Leu Ser Ser Asn Tyr Phe Asp Phe Asp Asn Leu His Val His
            820             825             830
Tyr Leu Leu Leu Thr Thr Asn Gly Thr Val Met Glu Ile Ala Gly Leu
            835             840             845
Tyr Glu Glu Arg Ala Ser Gly Gly Ser Gly Ser Ala Ser Ser Gly
            850             855             860
Ala Ser Ala Ser Gly Ser Ser Gly Ser Gly Ser Gly Ser Ser
865             870             875             880
Ser Ala Ser Ser Gly Ala Ile Thr Trp Val Pro Lys Pro Asn Val Glu
            885             890             895
Val Trp Pro Val Asp Pro Pro Pro Val Asn Phe Asn Lys Thr Ala
            900             905             910
Glu Gln Glu Tyr Gly Asp Lys Glu Val Lys Leu Pro His Trp Thr Pro
            915             920             925
```

```
Thr Leu His Thr Phe Gln Val Pro Gln Asn Tyr Thr Lys Ala Asn Cys
    930                 935                 940

Thr Tyr Cys Asn Thr Arg Glu Tyr Thr Phe Ser Tyr Lys Gly Cys Cys
945                 950                 955                 960

Phe Tyr Phe Thr Lys Lys Lys His Thr Trp Gln Gly Cys Phe Gln Ala
                965                 970                 975

Cys Ala Glu Leu Tyr Pro Cys Thr Tyr Phe Tyr Gly Pro Thr Pro Asp
                980                 985                 990

Ile Leu Pro Val Val Thr Arg Asn Leu Asn Ala Ile Glu Ser Leu Trp
        995                 1000                1005

Val Gly Val Tyr Arg Val Gly Glu Gly Asn Trp Thr Ser Leu Asp
    1010                1015                1020

Gly Gly Thr Phe Lys Val Tyr Gln Ile Phe Gly Ser His Cys Thr
    1025                1030                1035

Tyr Val Ser Lys Phe Ser Thr Val Pro Val Ser His His Glu Cys
    1040                1045                1050

Ser Phe Leu Lys Pro Cys Leu Cys Val Ser Gln Arg Ser Asn Ser
    1055                1060                1065

Gly Gly Ser Gly Ser Ala Ser Ser Gly Ala Ser Ala Ser Gly Ser
    1070                1075                1080

Ser Gly Ser Gly Ser Gly Gly Ser Ser Ser Ala Ser Ser Gly
    1085                1090                1095

Ala Ser Ser Gly Gly Ala Ser Gly Gly Ser Gly Gly Ser Gly Gly
    1100                1105                1110

Gly Ser Gly Ser Ala Ser Ser Gly Ala Ser Ala Ser Gly Ser Ser
    1115                1120                1125

Gly Ser Gly Ser Gly Ser Gly Ser Ser Ser Ala Ser Ser Gly Ala
    1130                1135                1140

Ser Ser Gly Gly Ala Ser Gly Gly Ser Gly Gly Ser Gly Glu Ser
    1145                1150                1155

Gln Val Arg Ser Gln Phe Ser Lys Asp Ile Glu Lys Leu Leu Asn
    1160                1165                1170

Glu Gln Val Asn Lys Glu Met Gln Ser Ser Asn Leu Tyr Met Ser
    1175                1180                1185

Met Ser Ser Trp Ser Tyr Thr His Ser Leu Asp Gly Ala Gly Leu
    1190                1195                1200

Phe Leu Phe Asp His Ala Ala Glu Glu Tyr Glu His Ala Lys Lys
    1205                1210                1215

Leu Ile Ile Phe Leu Asn Glu Asn Asn Val Pro Val Gln Leu Thr
    1220                1225                1230

Ser Ile Ser Ala Pro Glu His Lys Phe Glu Gly Leu Thr Gln Ile
    1235                1240                1245

Phe Gln Lys Ala Tyr Glu His Glu Gln His Ile Ser Glu Ser Ile
    1250                1255                1260

Asn Gln Ile Val Asp His Ala Ile Lys Cys Lys Asp His Ala Thr
    1265                1270                1275

Phe Asn Phe Leu Gln Trp Tyr Val Ala Glu Gln His Glu Glu Glu
    1280                1285                1290

Val Leu Phe Lys Asp Ile Leu Asp Lys Ile Glu Leu Ile Gly Gln
    1295                1300                1305

Glu Asn His Gly Leu Tyr Leu Ala Asp Gln Tyr Val Lys Gly Ile
    1310                1315                1320
```

Ala Lys Ser Arg Lys Ser
        1325

<210> SEQ ID NO 242
<211> LENGTH: 1329
<212> TYPE: PRT
<213> ORGANISM: Artificial Sequence
<220> FEATURE:
<223> OTHER INFORMATION: Synthetic polypeptide

<400> SEQUENCE: 242

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Asn Trp
            20                  25                  30

Ala Tyr Pro Cys Cys His Val Thr Gln Leu Arg Ala Gln His Leu Leu
            35                  40                  45

Ala Leu Glu Asn Ile Ser Asp Ile Tyr Leu Val Ser Asn Gln Thr Cys
        50                  55                  60

Asp Ala Phe Ser Leu Ala Ser Leu Asn Ser Pro Lys Gln Gly Ser Asn
65                  70                  75                  80

Gln Leu Val Ile Ser Arg Cys Ala Asn Gly Leu Asn Val Val Ser Phe
                85                  90                  95

Phe Ile Ser Ile Leu Lys Arg Ser Ser Ser Ala Leu Thr Gly His Leu
            100                 105                 110

Arg Glu Leu Leu Thr Thr Leu Glu Thr Leu Tyr Gly Ser Phe Ser Val
            115                 120                 125

Glu Asp Leu Phe Gly Ala Gln Leu Asn Arg Tyr Ala Trp His Arg Gly
130                 135                 140

Gly Gly Gly Ser Gly Ser Ala Ser Ser Gly Ala Ser Ala Ser Gly Ser
145                 150                 155                 160

Ser Gly Gly Ser Gly Ser Gly Ser Gly Ser Ser Ala Ser Ser
                165                 170                 175

Gly Ala Ser Ser Gly Gly Ala Ser Gly Gly Ser Gly Gly Ser Gly Ala
            180                 185                 190

Ala Ser Leu Ser Glu Val Lys Leu His Leu Asp Ile Glu Gly His Ala
            195                 200                 205

Ser His Tyr Thr Ile Pro Trp Thr Glu Leu Leu Ala Lys Val Pro Gly
        210                 215                 220

Leu Ser Pro Glu Ala Leu Trp Arg Glu Ala Asn Val Thr Glu Asp Leu
225                 230                 235                 240

Ala Ser Met Leu Asn Arg Tyr Lys Leu Ile Tyr Lys Thr Ser Gly Thr
                245                 250                 255

Leu Gly Ile Ala Leu Ala Glu Pro Val Asp Ile Pro Ala Val Ser Glu
            260                 265                 270

Gly Ser Met Gln Val Asp Ala Ser Lys Val His Pro Gly Val Ile Ser
            275                 280                 285

Gly Leu Asn Ser Pro Ala Cys Met Leu Ser Ala Pro Leu Glu Lys Gln
        290                 295                 300

Leu Phe Tyr Tyr Ile Gly Thr Met Leu Pro Asn Thr Arg Pro His Ser
305                 310                 315                 320

Tyr Val Phe Tyr Gln Leu Arg Cys His Leu Ser Tyr Val Ala Leu Ser
                325                 330                 335

Ile Asn Gly Asp Lys Phe Gln Tyr Thr Gly Ala Met Thr Ser Lys Phe
            340                 345                 350

```
Leu Met Gly Thr Tyr Lys Arg Val Thr Glu Lys Gly Asp Glu His Val
            355                 360                 365

Leu Ser Leu Val Phe Gly Lys Thr Lys Asp Leu Pro Asp Leu Arg Gly
        370                 375                 380

Pro Phe Ser Tyr Pro Ser Leu Thr Ser Ala Gln Ser Gly Glu Tyr Ser
385                 390                 395                 400

Leu Val Ile Val Thr Thr Phe Val His Tyr Ala Asn Phe His Asn Tyr
                405                 410                 415

Phe Val Pro Asn Leu Lys Asp Met Phe Ser Arg Ala Val Thr Met Thr
                420                 425                 430

Ala Ala Ser Tyr Ala Arg Tyr Val Leu Gln Lys Leu Val Leu Leu Glu
            435                 440                 445

Met Lys Gly Gly Cys Arg Glu Pro Glu Leu Glu Thr Glu Thr Leu Thr
        450                 455                 460

Thr Met Phe Glu Val Ser Val Ala Phe Phe Lys Val Gly His Ala Val
465                 470                 475                 480

Gly Glu Thr Gly Asn Gly Cys Val Asp Leu Arg Trp Leu Ala Lys Ser
                485                 490                 495

Phe Phe Glu Leu Thr Val Leu Lys Asp Ile Ile Gly Ile Cys Tyr Gly
                500                 505                 510

Ala Thr Val Lys Gly Met Gln Ser Tyr Gly Leu Glu Arg Leu Ala Ala
            515                 520                 525

Met Leu Met Ala Thr Val Lys Met Glu Glu Leu Gly His Leu Thr Thr
        530                 535                 540

Glu Lys Gln Glu Tyr Ala Leu Arg Leu Ala Thr Val Gly Tyr Pro Lys
545                 550                 555                 560

Ala Gly Val Tyr Ser Gly Leu Ile Gly Gly Ala Thr Ser Val Leu Leu
                565                 570                 575

Ser Ala Tyr Asn Arg His Pro Leu Phe Gln Pro Leu His Thr Val Met
                580                 585                 590

Arg Glu Thr Leu Phe Ile Gly Ser His Val Val Leu Arg Glu Leu Arg
            595                 600                 605

Leu Asn Val Thr Thr Gln Gly Pro Asn Leu Ala Leu Tyr Gln Leu Leu
        610                 615                 620

Ser Thr Ala Leu Cys Ser Ala Leu Glu Ile Gly Glu Val Leu Arg Gly
625                 630                 635                 640

Leu Ala Leu Gly Thr Glu Ser Gly Leu Phe Ser Pro Cys Tyr Leu Ser
                645                 650                 655

Leu Arg Phe Asp Leu Thr Arg Asp Lys Leu Leu Ser Met Ala Pro Gln
                660                 665                 670

Glu Ala Thr Leu Asp Gln Ala Ala Val Ser Asn Ala Val Asp Gly Phe
            675                 680                 685

Leu Gly Arg Leu Ser Leu Glu Arg Glu Asp Arg Asp Ala Trp His Leu
        690                 695                 700

Pro Ala Tyr Lys Cys Val Asp Arg Leu Asp Lys Val Leu Met Ile Ile
705                 710                 715                 720

Pro Leu Ile Asn Val Thr Phe Ile Ile Ser Ser Asp Arg Glu Val Arg
                725                 730                 735

Gly Ser Ala Leu Tyr Glu Ala Ser Thr Thr Tyr Leu Ser Ser Ser Leu
                740                 745                 750

Phe Leu Ser Pro Val Ile Met Asn Lys Cys Ser Gln Gly Ala Val Ala
            755                 760                 765
```

```
Gly Glu Pro Arg Gln Ile Pro Lys Ile Gln Asn Phe Thr Arg Thr Gln
        770                 775                 780

Lys Ser Cys Ile Phe Cys Gly Phe Ala Leu Leu Ser Tyr Asp Glu Lys
785                 790                 795                 800

Glu Gly Leu Glu Thr Thr Thr Tyr Ile Thr Ser Gln Glu Val Gln Asn
                    805                 810                 815

Ser Ile Leu Ser Ser Asn Tyr Phe Asp Phe Asp Asn Leu His Val His
                820                 825                 830

Tyr Leu Leu Leu Thr Thr Asn Gly Thr Val Met Glu Ile Ala Gly Leu
            835                 840                 845

Tyr Glu Glu Arg Ala Ser Gly Gly Ser Gly Ser Ala Ser Ser Gly
850                 855                 860

Ala Ser Ala Ser Gly Ser Ser Gly Ser Gly Ser Gly Ser Ser
865                 870                 875                 880

Ser Ala Ser Ser Gly Ala Ile Thr Trp Val Pro Lys Pro Asn Val Glu
                885                 890                 895

Val Trp Pro Val Asp Pro Pro Pro Val Asn Phe Asn Lys Thr Ala
        900                 905                 910

Glu Gln Glu Tyr Gly Asp Lys Glu Val Lys Leu Pro His Trp Thr Pro
            915                 920                 925

Thr Leu His Thr Phe Gln Val Pro Gln Asn Tyr Thr Lys Ala Asn Cys
930                 935                 940

Thr Tyr Cys Asn Thr Arg Glu Tyr Thr Phe Ser Tyr Lys Gly Cys Cys
945                 950                 955                 960

Phe Tyr Phe Thr Lys Lys Lys His Thr Trp Asn Gly Cys Phe Gln Ala
                965                 970                 975

Cys Ala Glu Leu Tyr Pro Cys Thr Tyr Phe Tyr Gly Pro Thr Pro Asp
            980                 985                 990

Ile Leu Pro Val Val Thr Arg Asn Leu Asn Ala Ile Glu Ser Leu Trp
        995                 1000                1005

Val Gly Val Tyr Arg Val Gly Glu Gly Asn Trp Thr Ser Leu Asp
    1010                1015                1020

Gly Gly Thr Phe Lys Val Tyr Gln Ile Phe Gly Ser His Cys Thr
    1025                1030                1035

Tyr Val Ser Lys Phe Ser Thr Val Pro Val Ser His His Glu Cys
    1040                1045                1050

Ser Phe Leu Lys Pro Cys Leu Cys Val Ser Gln Arg Ser Asn Ser
    1055                1060                1065

Gly Gly Ser Gly Ser Ala Ser Gly Ala Ser Ala Ser Gly Ser
    1070                1075                1080

Ser Gly Ser Gly Ser Gly Ser Gly Ser Ser Ser Ala Ser Ser Gly
    1085                1090                1095

Ala Ser Ser Gly Gly Ala Ser Gly Gly Ser Gly Gly Ser Gly Gly
    1100                1105                1110

Gly Ser Gly Ser Ala Ser Ser Gly Ala Ser Ala Ser Gly Ser Ser
    1115                1120                1125

Gly Ser Gly Ser Gly Ser Gly Ser Ser Ser Ala Ser Ser Gly Ala
    1130                1135                1140

Ser Ser Gly Gly Ala Ser Gly Gly Ser Gly Gly Ser Gly Glu Ser
    1145                1150                1155

Gln Val Arg Ser Gln Phe Ser Lys Asp Ile Glu Lys Leu Leu Asn
    1160                1165                1170
```

Glu Gln Val Asn Lys Glu Met Gln Ser Ser Asn Leu Tyr Met Ser
    1175                1180                1185

Met Ser Ser Trp Ser Tyr Thr His Ser Leu Asp Gly Ala Gly Leu
    1190                1195                1200

Phe Leu Phe Asp His Ala Ala Glu Glu Tyr Glu His Ala Lys Lys
    1205                1210                1215

Leu Ile Ile Phe Leu Asn Glu Asn Asn Val Pro Val Gln Leu Thr
    1220                1225                1230

Ser Ile Ser Ala Pro Glu His Lys Phe Glu Gly Leu Thr Gln Ile
    1235                1240                1245

Phe Gln Lys Ala Tyr Glu His Glu Gln His Ile Ser Glu Ser Ile
    1250                1255                1260

Asn Gln Ile Val Asp His Ala Ile Lys Cys Lys Asp His Ala Thr
    1265                1270                1275

Phe Asn Phe Leu Gln Trp Tyr Val Ala Glu Gln His Glu Glu Glu
    1280                1285                1290

Val Leu Phe Lys Asp Ile Leu Asp Lys Ile Glu Leu Ile Gly Gln
    1295                1300                1305

Glu Asn His Gly Leu Tyr Leu Ala Asp Gln Tyr Val Lys Gly Ile
    1310                1315                1320

Ala Lys Ser Arg Lys Ser
    1325

<210> SEQ ID NO 243
<211> LENGTH: 6
<212> TYPE: PRT
<213> ORGANISM: Artificial Sequence
<220> FEATURE:
<223> OTHER INFORMATION: 6xHis tag

<400> SEQUENCE: 243

His His His His His His
1               5

<210> SEQ ID NO 244
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 244

Gly Gly Gly Ser
1

<210> SEQ ID NO 245
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 245

Gly Gly Gly Ser Gly Gly Gly Ser
1               5

<210> SEQ ID NO 246
<211> LENGTH: 20
<212> TYPE: PRT
<213> ORGANISM: Artificial Sequence
<220> FEATURE:
<223> OTHER INFORMATION: Synthetic polypeptide

```
<400> SEQUENCE: 246

Gly Gly Gly Ser Gly Gly Gly Ser Gly Gly Gly Ser Gly Gly Gly Ser
1               5                   10                  15

Gly Gly Gly Ser
            20

<210> SEQ ID NO 247
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 247
tccatgacgt tcctgacgtt                                              20
```

ANTIGENIC EPSTEIN BARR VIRUS POLYPEPTIDES

This application is a continuation of International Application No. PCT/US2019/025419, filed Apr. 2, 2019, which claims the benefit of priority of U.S. Provisional Patent Application No. 62/652,201, filed Apr. 3, 2018, the entire contents of which are incorporated herein by reference.

This invention was created in the performance of a Cooperative Research and Development Agreement with the National Institutes of Health, an Agency of the Department of Health and Human Services (Medical Virology Section, Laboratory of Infectious Diseases, at the National Institute of Allergy and Infectious Diseases). The Government of the United States has certain rights in this invention.

The instant application contains a Sequence Listing which has been submitted electronically in ASCII format and is hereby incorporated by reference in its entirety. Said ASCII copy, created on Sep. 30, 2020, is named 2020-09-30_01121-0032-00US SL ST25.txt and is 377,852 bytes in size.

Even with many successes in the field of vaccinology, new breakthroughs are needed to protect humans against many life-threatening infectious diseases. Many currently licensed vaccines rely on decade-old technologies to produce live-attenuated or inactivated killed pathogens, which carry inherent safety concerns and in many cases, stimulate only short-lived, weak immune responses that require the administration of multiple doses. While advances in genetic and biochemical engineering have made it possible to develop therapeutic agents to challenging disease targets, these applications to the field of vaccinology have not been fully realized. Recombinant protein technologies now allow the design of optimal antigens. Additionally, nanoparticles have increasingly demonstrated the potential for optimal antigen presentation and targeted drug delivery. Nanoparticles with multiple attached antigens have been shown to have increased binding avidity afforded by the multivalent display of their molecular cargos, and an ability to cross biological barriers more efficiently due to their nanoscopic size. *Helicobacter pylori* (*H. pylori*) ferritin nanoparticles fused to influenza virus haemagglutinin (HA) protein has allowed improved antigen stability and increased immunogenicity in mouse influenza models (see Kanekiyo et al., Nature 499:102-106 (2013)). This fusion protein self-assembled into an octahedrally-symmetric nanoparticle and presented 8 trimeric HA spikes to give a robust immune response in various pre-clinical models when used with an adjuvant.

Epstein Barr virus (EBV) infects about 95% of the adult population worldwide and has been known to be associated with two B-cell lymphomas, Burkitt's and Hodgkin's lymphomas. The virus can also infect epithelial cells and is associated with nasopharyngeal cancer. Furthermore, EBV causes most cases of infectious mononucleosis in developed countries, affecting mainly children and young adults. Infectious mononucleosis can result in a long recovery period of up to one month. There are currently no approved vaccines on the market, so there is a strong need for a preventive vaccine.

Here, a set of new polypeptides, nanoparticles, compositions, methods, and uses involving EBV polypeptides is presented. Novel EBV single-chain gL and gH (sometimes depicted as gL/gH or gH/gL) polypeptides were generated, as were antigenic polypeptides comprising these novel EBV polypeptides and ferritin. Antigenic polypeptides and nanoparticles comprising the single-chain gL and gH polypeptides can comprise a relatively long linker between the gL and gH sequences, which was observed to provide an increase in immunogenicity. Antigenic ferritin polypeptides and nanoparticles comprising EBV gp220 polypeptides were also generated. Furthermore, self-adjuvanting antigenic polypeptides comprising the described EBV polypeptides and ferritin were developed wherein immune-stimulatory moieties, such as adjuvants, were directly, chemically attached to the antigenic polypeptide. The direct conjugation of an immune-stimulatory moiety to the antigenic polypeptide allows for targeted co-delivery of the immune-stimulatory moiety and EBV polypeptide in a single macromolecular entity, which can greatly decrease the potential for systemic toxicity that is feared with traditional vaccines that comprise antigens and immune-stimulatory molecules such as adjuvants as separate molecules. The co-delivery of immune-stimulatory moieties together with EBV polypeptides in a macromolecular entity and their multivalent presentation may also reduce the overall dose needed to elicit protection, reducing manufacturing burdens and costs.

SUMMARY

It is an object of this disclosure to provide compositions, kits, methods, and uses that can provide one or more of the advantages discussed above, or at least provide the public with a useful choice. Accordingly, the following embodiments are disclosed herein.

Embodiment 1 is an antigenic EBV polypeptide comprising an Epstein Barr Virus (EBV) gL polypeptide and an EBV gH polypeptide, wherein a linker having a length of at least 15 amino acids separates the EBV gL polypeptide and the EBV gH polypeptide.

Embodiment 2 is an antigenic EBV polypeptide comprising an Epstein Barr Virus (EBV) gL polypeptide, an EBV gH polypeptide, and an EBV gp42 polypeptide, wherein a linker having a length of at least 15 amino acids separates the EBV gL polypeptide and the EBV gH polypeptide.

Embodiment 3 is the antigenic EBV polypeptide of embodiment 1 or embodiment 2, further comprising a ferritin.

Embodiment 4 is an antigenic EBV polypeptide comprising an EBV polypeptide and a ferritin protein, wherein the ferritin protein comprises a mutation replacing a surface-exposed amino acid with a cysteine.

Embodiment 5 is the antigenic EBV polypeptide of embodiment 4, wherein the EBV polypeptide comprises an EBV gL polypeptide, an EBV gH polypeptide, or an EBV gp220 polypeptide.

Embodiment 6 is the antigenic EBV polypeptide of embodiment 5, wherein the EBV polypeptide comprises a gL polypeptide and the polypeptide further comprises an EBV gH polypeptide.

Embodiment 7 is the antigenic EBV polypeptide of any one of embodiments 1 or 3-6, wherein the polypeptide further comprises an EBV gp42 polypeptide.

Embodiment 8 is a composition comprising a first antigenic EBV polypeptide and a second antigenic EBV polypeptide, wherein the first antigenic EBV polypeptide comprises a ferritin heavy chain and a first EBV polypeptide, the second antigenic EBV polypeptide comprises a ferritin light chain and a second EBV polypeptide, and the first and second EBV polypeptides are different.

Embodiment 9 is the composition of embodiment 8, wherein the first EBV polypeptide or the second EBV polypeptide comprises a gp220 polypeptide.

Embodiment 10 is the composition of any one of embodiments 8 to 9, wherein (i) the first antigenic EBV polypeptide comprises one or both of a gL polypeptide and a gH polypeptide and the second antigenic EBV polypeptide comprises a gp220 polypeptide, or (ii) the first antigenic EBV polypeptide comprises a gp220 polypeptide and the second antigenic EBV polypeptide comprises one or both of a gL polypeptide and a gH polypeptide.

Embodiment 11 is the composition of any one of embodiments 8 to 10, wherein the first antigenic EBV polypeptide comprises a gL polypeptide and a gH polypeptide; or the second antigenic EBV polypeptide comprises a gL polypeptide and an EBV gH polypeptide.

Embodiment 12 is the composition of embodiment 10 or 11, wherein the antigenic EBV polypeptide comprising a gL polypeptide and/or a gH polypeptide further comprises a gp42 polypeptide.

Embodiment 13 is the antigenic EBV polypeptide or composition of any one of embodiments 1-12, comprising a gH and gL polypeptide, wherein the gH polypeptide is C-terminal to the gL polypeptide, optionally comprising a gp42 polypeptide, wherein the gp42 polypeptide is C-terminal to the gH polypeptide.

Embodiment 14 is the antigenic EBV polypeptide or composition of any one of embodiments 1-13, comprising a gp42 polypeptide, wherein the gp42 polypeptide comprises an amino acid sequence with at least 80%, 85%, 90%, 95%, 97%, 98%, 99%, or 100% identity to SEQ ID NO: 239 or 240.

Embodiment 15 is the antigenic EBV polypeptide or composition of any one of embodiments 1-14, comprising an EBV gH polypeptide and an EBV gp42 polypeptide, wherein a linker having a length of at least 15 amino acids separates the EBV gH polypeptide and the EBV gp42 polypeptide. optionally wherein the linker has a length of 15 to 60 amino acids, 20 to 60 amino acids, 30 to 60 amino acids, 40 to 60 amino acids, 30 to 50 amino acids, or 40 to 50 amino acids, further optionally wherein the linker comprises an amino acid sequence with at least 80%, 85%, 90%, 95%, 97%, 98%, 99%, or 100% identity to SEQ ID NO: 234.

Embodiment 16 is the antigenic EBV polypeptide or composition of any one of the preceding embodiments, comprising a linker, wherein the linker has a length of at least 15 amino acids, optionally wherein the linker separates a first EBV polypeptide and a second EBV polypeptide.

Embodiment 17 is the antigenic EBV polypeptide or composition of embodiment 16, wherein the linker has a length of 15 to 60 amino acids, 20 to 60 amino acids, 30 to 60 amino acids, 40 to 60 amino acids, 30 to 50 amino acids, or 40 to 50 amino acids.

Embodiment 18 is the antigenic EBV polypeptide or composition of any one of the preceding embodiments, wherein the EBV polypeptide comprises an amino acid sequence with at least 80%, 85%, 90%, 95%, 97%, 98%, 99%, or 100% identity to SEQ ID NO: 36.

Embodiment 19 is the antigenic EBV polypeptide or composition of any one of the preceding embodiments, wherein the EBV polypeptide comprises an amino acid sequence with at least 80%, 85%, 90%, 95%, 97%, 98%, 99%, or 100% identity to SEQ ID NO: 37.

Embodiment 20 is the antigenic EBV polypeptide or composition of any one of the preceding embodiments, wherein the polypeptide comprises a linker comprising an amino acid sequence with at least 80%, 85%, 90%, 95%, 97%, 98%, 99%, or 100% identity to SEQ ID NO: 30, optionally wherein the linker separates a First EBV polypeptide and a second EBV polypeptide.

Embodiment 21 is the antigenic EBV polypeptide or composition of any one of the preceding embodiments, wherein the EBV polypeptide comprises an amino acid sequence with at least 80%, 85%, 90%, 95%, 97%, 98%, 99%, or 100% identity to SEQ ID NO: 38.

Embodiment 22 is the antigenic EBV polypeptide or composition of any one of embodiments 3-21, further comprising a further linker that separates the EBV polypeptide and the ferritin.

Embodiment 23 is the antigenic EBV polypeptide or composition of any one of embodiments 3-22, comprising an EBV gp42 polypeptide located N-terminal to the ferritin and C-terminal to the gH polypeptide, wherein a linker separates the EBV gp42 polypeptide and the ferritin, optionally wherein the linker has a length of at least 15 amino acids or has a length of 15 to 60 amino acids, 20 to 60 amino acids, 30 to 60 amino acids, 40 to 60 amino acids, 30 to 50 amino acids, or 40 to 50 amino acids, further optionally wherein the linker comprises an amino acid sequence with at least 80%, 85%, 90%, 95%, 97%, 98%, 99%, or 100% identity to any one of SEQ ID NOs: 233, 234, 235, 236, 237, or 238.

Embodiment 24 is the antigenic EBV polypeptide or composition of embodiment 22 or 23, wherein the linker comprises a cysteine.

Embodiment 25 is the antigenic EBV polypeptide or composition of any one of embodiments 22-24, wherein the linker comprises an amino acid sequence with at least 80%, 85%, 90%, 95%, 97%, 98%, 99%, or 100% identity to SEQ ID NO: 33.

Embodiment 26 is the antigenic EBV polypeptide or composition of embodiments 24-25, wherein the cysteine is conjugated to an immune-stimulatory moiety, optionally wherein the immune-stimulatory moiety is an agonist of TLR2, TLR7/8, TLR9, or STING.

Embodiment 27 is the antigenic EBV polypeptide or composition of any one of embodiments 3-26, wherein the ferritin comprises one or more of E12C, S26C, S72C, A75C, K79C, S100C, and S111C mutations of *H. pylori* ferritin or one or more corresponding mutations in a non-*H. pylori* ferritin as determined by pairwise or structural alignment.

Embodiment 28 is the antigenic EBV polypeptide or composition of any one of embodiments 3-27, wherein the ferritin comprises a mutation replacing a surface-exposed asparagine with a non-asparagine amino acid, optionally wherein the asparagine is at position 19 of *H. pylori* ferritin, or an analogous position in a non-*H. pylori* ferritin as determined by pairwise or structural alignment.

Embodiment 29 is the antigenic EBV polypeptide or composition of any one of embodiments 3-28, wherein the ferritin comprises a mutation replacing an internal cysteine with a non-cysteine amino acid, optionally wherein the internal cysteine is at position 31 of *H. pylori* ferritin, or a position that corresponds to position 31 of *H. pylori* ferritin as determined by pair-wise or structural alignment.

Embodiment 30 is the antigenic EBV polypeptide or composition of any one of embodiments 3-29, wherein the ferritin comprises an amino acid sequence with 80%, 85%, 90%, 95%, 98%, or 99% identity to any one of SEQ ID NOs 201-207 or 211-215.

Embodiment 31 is the antigenic EBV polypeptide or composition of any one of embodiments 1-31, wherein the antigenic EBV polypeptide comprises a sequence with at least 80%, 85%, 90%, 95%, 98%, or 99% identity to amino acids 23-1078 of SEQ ID NO: 226.

Embodiment 32 is the antigenic EBV polypeptide or composition of any one of embodiments 1-31, wherein the antigenic EBV polypeptide comprises a sequence with at least 80%, 85%, 90%, 95%, 98%, or 99% identity to any one of SEQ ID NOs: 226-231 or 241-242, optionally lacking the leader sequence.

Embodiment 33 is a ferritin particle comprising the antigenic EBV polypeptide or the first and second polypeptides of any one of embodiments 3-32.

Embodiment 34 is a composition comprising the antigenic EBV polypeptide(s) or ferritin particle of any one of the preceding embodiments and a pharmaceutically acceptable carrier.

Embodiment 35 is the composition of embodiment 34, wherein the ferritin particle comprises an EBV gL polypeptide and an EBV gH polypeptide, and the composition further comprises a second fern tin particle comprising a gp220 polypeptide.

Embodiment 36 is the antigenic EBV polypeptide, ferritin particle, or composition of any one of the preceding embodiments for use in a method of eliciting an immune response to influenza or in protecting a subject against infection with EBV.

Embodiment 37 is a method of eliciting an immune response to EBV or protecting a subject against infection with EBV comprising administering any one or more antigenic EBV polypeptide, ferritin particle, or composition of any one of the preceding embodiments s to a subject.

Embodiment 38 is the antigenic EBV polypeptide, ferritin particle, composition, or method of any one of embodiments 36-37, wherein the subject is human.

Embodiment 39 is a nucleic acid encoding the antigenic EBV polypeptide of any one of embodiments 1-32, optionally wherein the nucleic acid is an mRNA.

Additional objects and advantages will be set forth in the description which follows, and/or will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate certain embodiments and together with the description, serve to explain the principles described herein.

BRIEF DESCRIPTION OF THE DRAWINGS

FIG. 1B also presents the UV absorbance trace of fractions from a size exclusion column (Superose® 6) purification.

FIGS. 2A-2E shows purification and characterization of single-chain gL/gH-ferritin nanoparticles (SEQ ID NO: 14). A UV absorbance trace of Superose® 6 purification fractions is shown (FIG. 2A), as well as Coomassie (FIG. 2B) and Western blot (FIG. 2C) analysis of selected fractions from the purification (L indicates molecular weight ladder; the positions of the 150 and 250 kDa bands are indicated at right in FIG. 2B). Dynamic light scattering (FIG. 2D) and electron microscopy (FIG. 2E) analyses of the single-chain nanoparticles are also presented.

FIG. 8A shows a structure of part of a ferritin comprising a mutation replacing a surface-exposed amino acid with a cysteine, in which the location of the cysteine is indicated.

11C, D) ferritin nanoparticles, indicating that conjugation of SM7/8a to these nanoparticles did not disrupt nanoparticle structure.

Figure 12A:
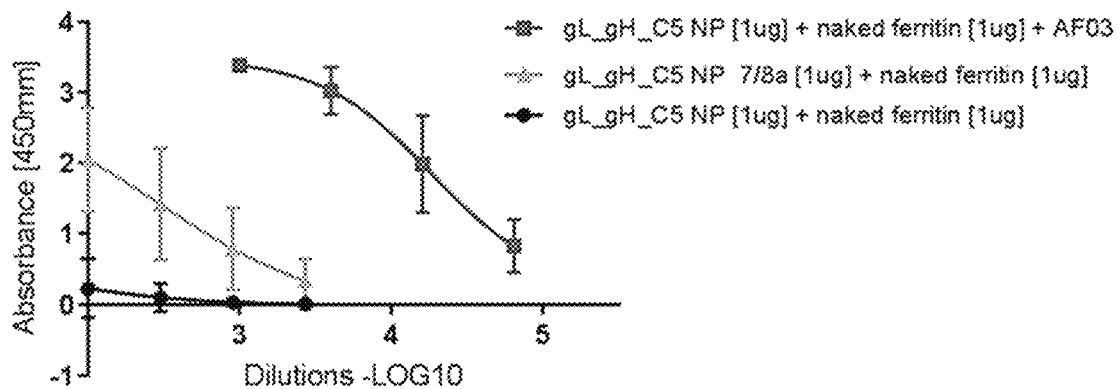
Figure 12B:
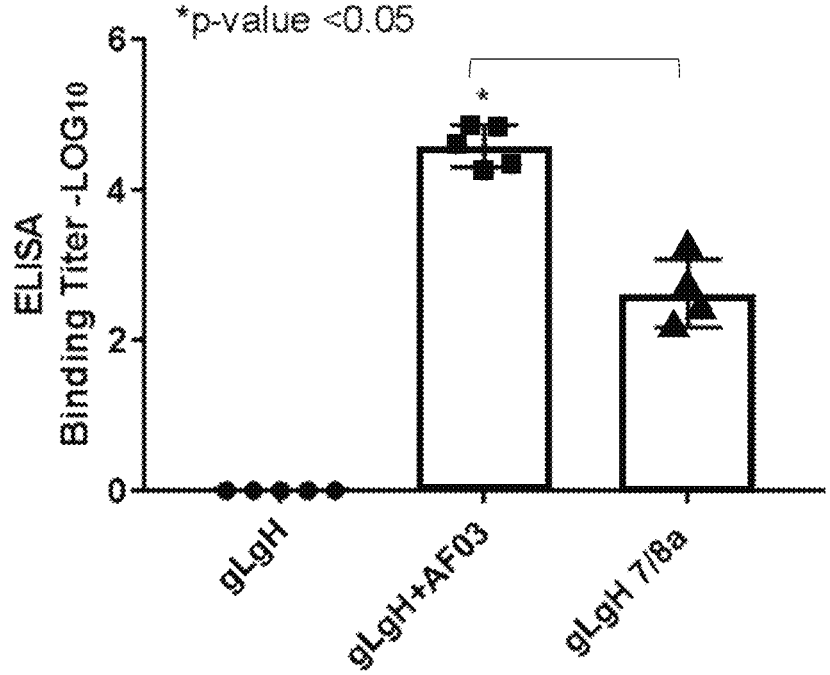

FIGS. 12A-12B show antibody responses in mice after treatment with ferritin nanoparticles comprising single-chain gL/gH either without conjugated SM7/8a or other adjuvant, with AF03 adjuvant as a separate molecule, or with conjugated SM7/8a. ELISA results are shown as individual dilutions (FIG. 12A) and binding titers (FIG. 12B).

Figure 13A:
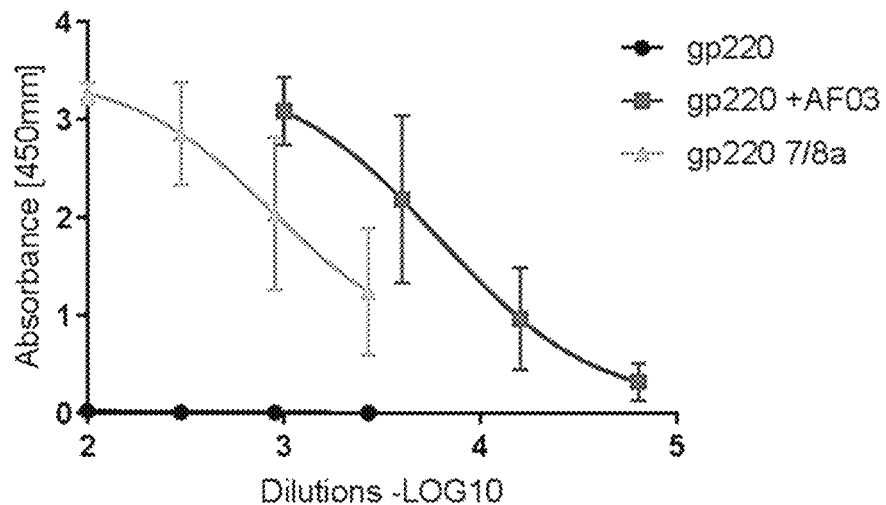
Figure 13B:
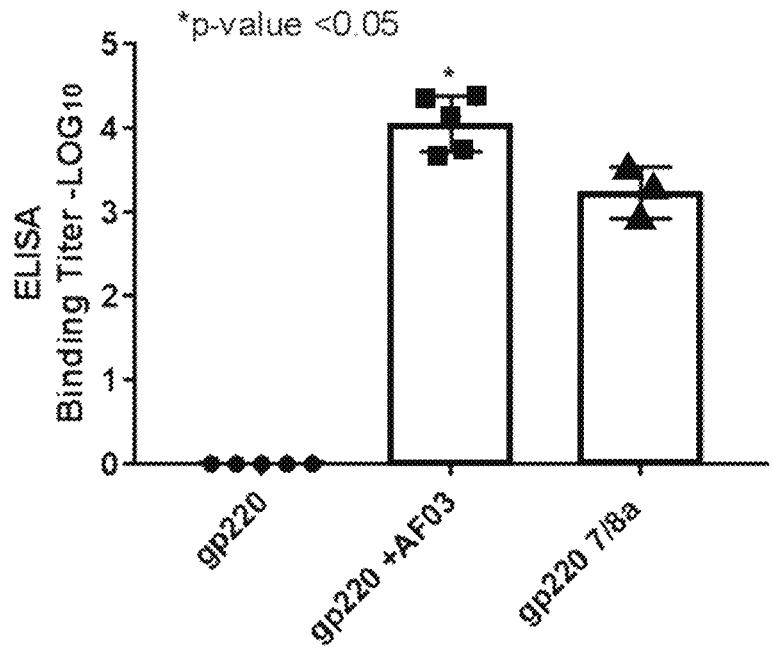
Figure 14A:
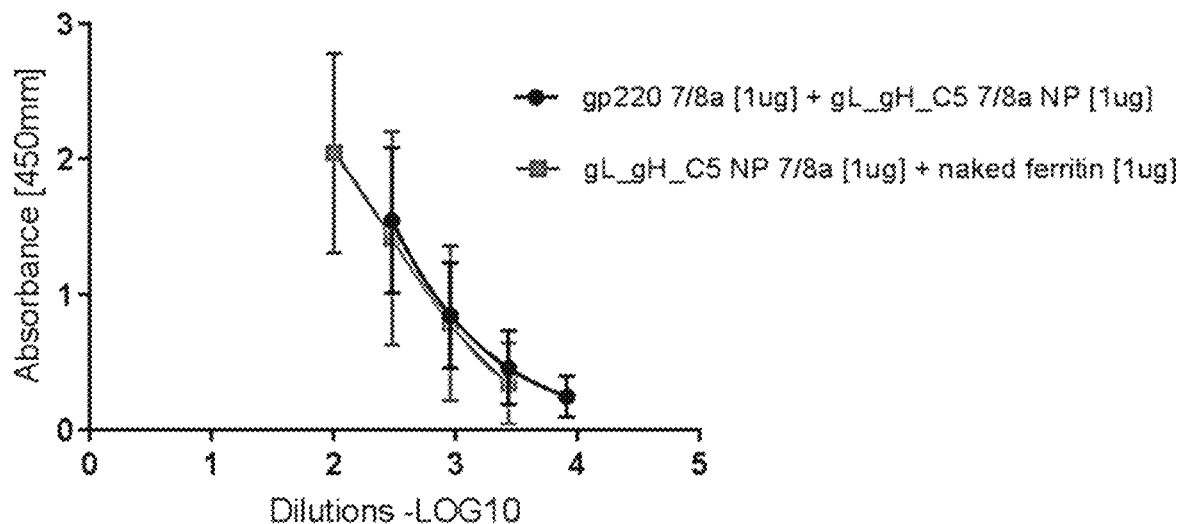
Figure 14B:
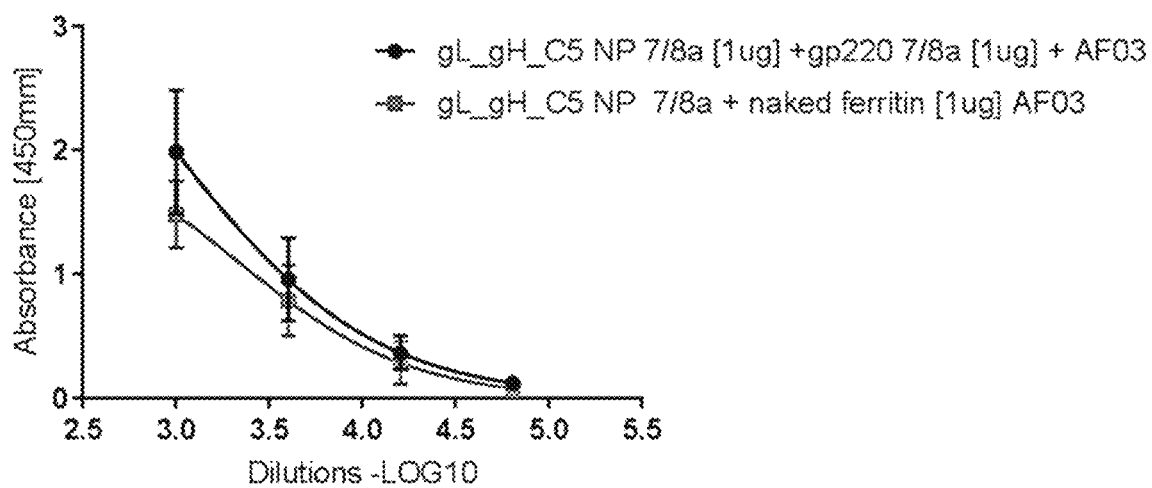
Figure 15A:
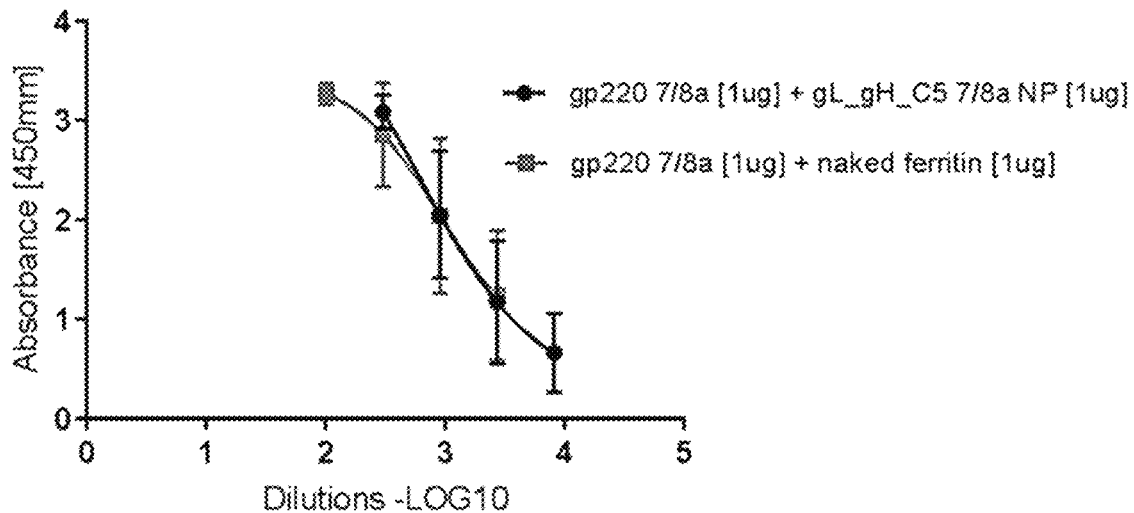
Figure 15B:
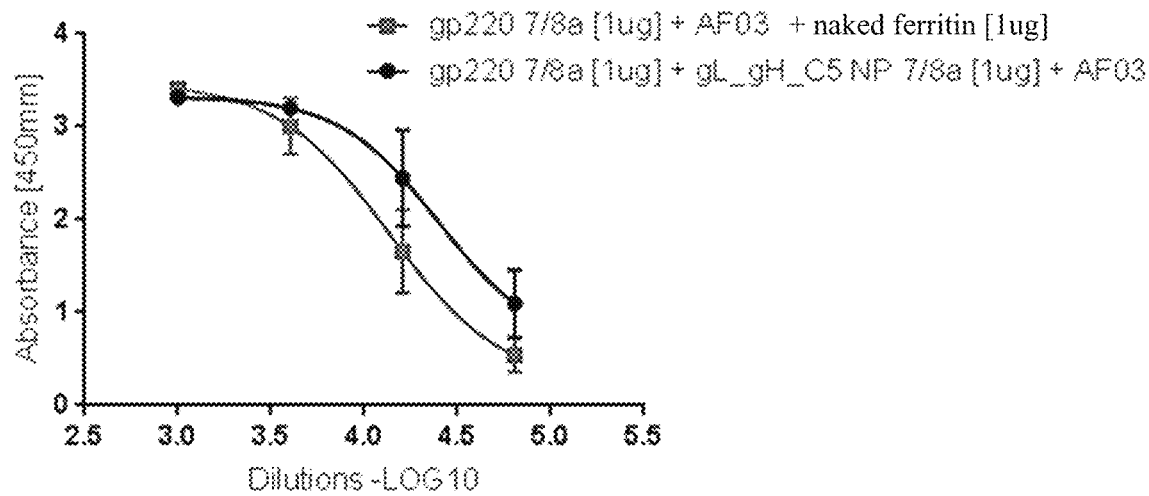
Figures 29A, 29B:
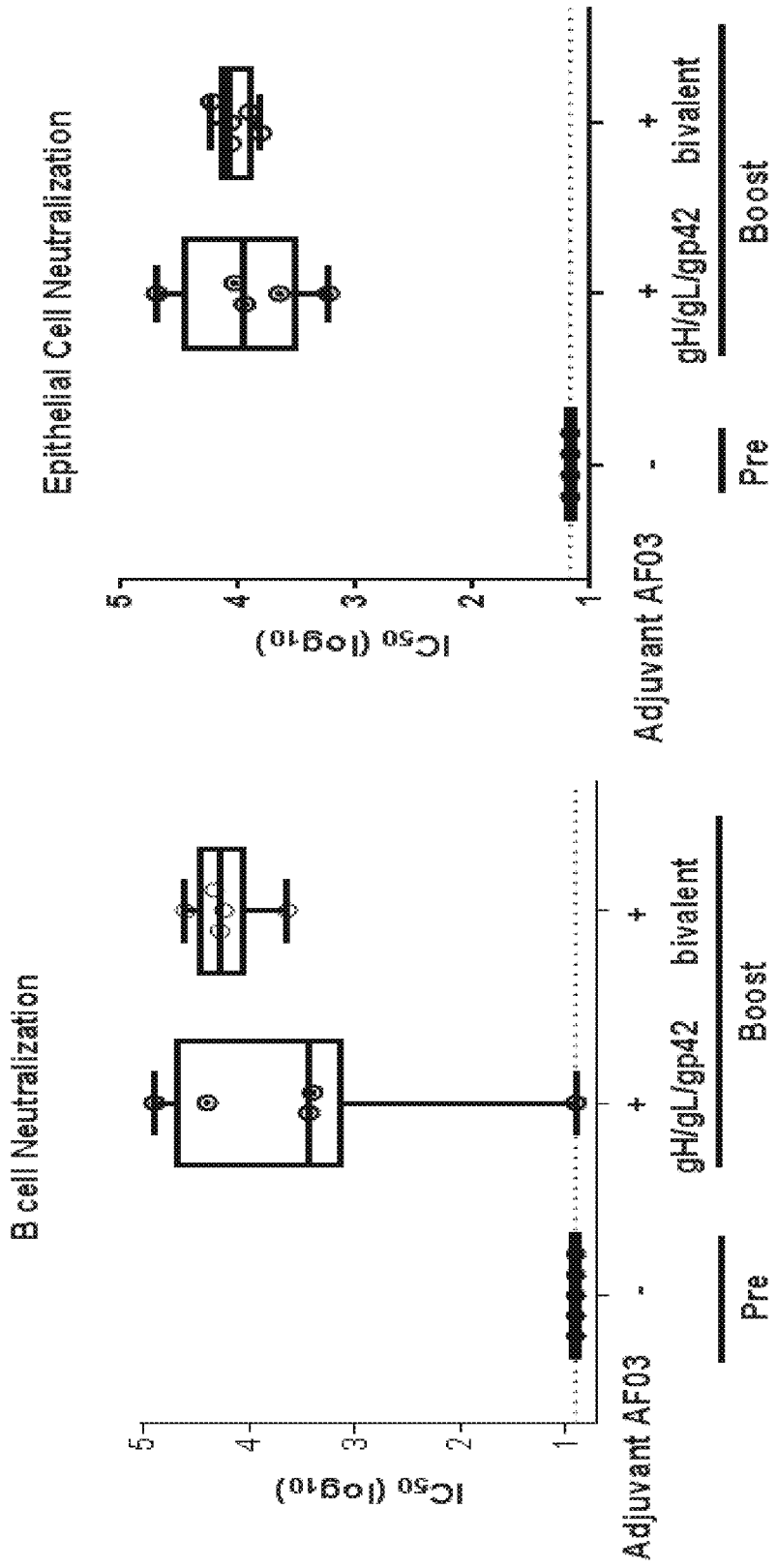

FIGS. 13A-13B show antibody responses in mice after treatment with nanoparticles comprising gp220 either alone, with AF03 adjuvant as a separate molecule, or with conjugated SM7/8a. ELISA results are shown as individual dilutions (FIG. 13A) and binding titers (FIG. 13B).

FIGS. 14A-14B show anti-gL/gH antibody responses in mice after treatment with gp220 nanoparticles conjugated to SM7/8a and single-chain gL/gH ferritin nanoparticles conjugated to SM7/8a compared to treatment with single-chain gL/gH ferritin nanoparticles conjugated to SM7/8a and naked ferritin, as measured by ELISA. Results are shown for experiments without (FIG. 14A) or with (FIG. 14B) admixed AF03.

FIGS. 15A-15B show anti-gp220 antibody responses in mice after treatment with gp220 nanoparticles conjugated to SM7/8a and single-chain gL/gH nanoparticles conjugated to SM7/8a compared to treatment with gp220 nanoparticles conjugated to SM7/8a and naked ferritin, as measured by ELISA. Results are shown for experiments without (FIG. 15A) or with (FIG. 15B) admixed AF03.

FIG. 16 shows anti-gL/gH antibody responses in mice after treatment with single-chain gL/gH nanoparticles (gL/gH_C5; SEQ ID NO: 19) and naked ferritin, with or without either or both of admixed AF03 adjuvant and/or SM7/8a conjugated to the single-chain gL/gH nanoparticles, as measured by ELISA endpoint titer.

FIG. 17 shows anti-gp220 antibody responses in mice after treatment with gp220 nanoparticles and naked ferritin, with or without either or both of admixed AF03 adjuvant and/or SM7/8a conjugated to the gp220 nanoparticles.

FIG. 18 shows anti-gL/gH antibody responses in mice after treatment with bivalent compositions comprising gp220 nanoparticles and single-chain gL/gH nanoparticles. As indicated in the legend, some nanoparticles were conjugated to SM7/8a, and some nanoparticles were admixed with AF03. The order of symbols from top to bottom in the key matches the order of symbols from left to right in the graph.

FIG. 19 shows anti-gp220 antibody responses in mice after treatment with bivalent compositions comprising single-chain gL/gH nanoparticles and gp220 nanoparticles and/or naked ferritin. As indicated in the legend, some nanoparticles were conjugated to SM7/8a, and some nanoparticles were admixed with AF03. The order of symbols from top to bottom in the key matches the order of symbols from left to right in the graph.

FIGS. 20A-20D show antibody responses in mice after treatment with gL_gH_C7 nanoparticle (SEQ ID NO: 20) with or without admixed AF03 adjuvant and/or conjugation to SM7/8a (FIG. 20A, 20C, or 20D) or CpG oligodeoxynucleotide (FIG. 20B). Shown are endpoint titer from prime bleed measured by ELISA (FIG. 20A), ELISA results at individual dilutions from booster bleed (FIG. 20B), and endpoint titers measured by ELISA from booster bleed (FIG. 20C) and terminal bleed (FIG. 20D).

FIG. 21 shows antibody responses in mice after treatment with the gL_gH_C5 nanoparticle (SEQ ID NO: 19) with or without admixed AF03 adjuvant and/or conjugation to SM7/8a as endpoint titers measured by ELISA from the prime, boost, and terminal bleeds.

FIG. 22 shows antibody responses in mice after treatment with a gp220 nanoparticle with or without admixed AF03 adjuvant and/or conjugation to SM7/8a as endpoint titers measured by ELISA from the prime, boost, and terminal bleeds.

FIG. 23A shows the light and heavy chains of *T. ni* ferritin with or without fusion to either gp220 or gL/gH, visualized by Coomassie staining (FIG. 23A). The 20, 25, 75, 100, and 150 kDa markers in the rightmost lane of FIG. 23A are labeled. FIG. 23B provides an illustration of the constructs comprising light and heavy chains of *T. ni* ferritin with or without fusion to either gp220 or gL/gH.

FIGS. 24A-24D demonstrate ion exchange (Q column) chromatographic and size-exclusion chromatographic (SEC) purification of gp220-*T. ni* ferritin. Shown are absorbance traces from the Q column at pH 7 (FIG. 24A) and SEC Superose® 6, 16/600 (FIG. 24B); Coomassie staining of fractions from Q column at pH 7 (FIG. 24C) (lanes from left are input ("In"), flow-through ("FT"), mol. wt. ladder (sizes labeled at left in kD), and selected fractions); and Coomassie staining of fractions from SEC Superose® 6, 16/600 (FIG. 24D) (lanes from left are mol. wt. ladder (sizes labeled at left in kD) and selected fractions). FIG. 24E shows an illustration of the constructs.

FIGS. 25A-25D demonstrate ion exchange (Q column) chromatographic and size-exclusion chromatographic (SEC) purification of gL/gH (Light)/gp220 (Heavy)—*T. ni* ferritin. Shown are absorbance traces from the Q column at pH 7 (FIG. 25A) and SEC Superose® 6, 16/600 (FIG. 25B); Coomassie staining of fractions from Q column at pH 7 (FIG. 25C) (lanes from left are input ("In"), flow-through ("FT"), mol. wt. ladder (sizes labeled at left in kD), and selected fractions); and Coomassie staining of fractions from SEC Superose® 6, 16/600 (FIG. 25D) (lanes from left are mol. wt ladder (sizes labeled at left in kD) and selected fractions). FIG. 25E shows an illustration of the constructs.

FIGS. 26A-26H show gp220-*T. ni* ferritin or gL/gH (light chain)/gp220 (heavy chain)—*T. ni* ferritin constructs visualized by Coomassie staining Coomassie (FIG. 26A and FIG. 26E), illustrated diagrammatically (FIG. 26B and FIG. 26F), characterized by dynamic light scattering (DLS) (FIG. 26D and FIG. 26H), and visualized in electron micrographs (FIG. 26C and FIG. 26G). FIGS. 26A-26D present data with gp220 fused to both the light and the heavy chain (diagram in FIG. 26B). FIGS. 26E-26H present data with gp220 fused to the heavy chain and gL/gH fused to the light chain (diagram in FIG. 26F).

FIGS. 27A-FIG. 27C show naked *T. ni* ferritin particles (i.e., not fused to a non-ferritin polypeptide) visualized by Coomassie staining (FIG. 27A), visualized in electron micrographs (FIG. 27B), and characterized by DLS (FIG. 27C).

FIG. 28A shows a SDS denaturing Coomassie-stained gel (at left) with a purified gH/gL/gp42 NP construct (SEQ ID NO: 227), which was expressed in 293 expi cells, and (at right) the size exclusion chromatography (SEC) peak of the gH/gL/gp42 NP. Units of the horizontal axis of the SEC chromatogram are mL. FIG. 28B shows the gH/gL/gp42 NP purified from the CHO pools to have a dynamic light scattering radius of around 26.2 nm.

FIG. 29A-B show an assessment of the immune response elicited by a monovalent gH/gL/gp42 nanoparticle composition in combination with a naked ferritin nanoparticle or a bivalent composition (gH/gL/gp42 nanoparticle in combination with a gp220). FIG. 29A shows B cell neutralization. FIG. 29B shows epithelial cell neutralization.

Figure 30A:
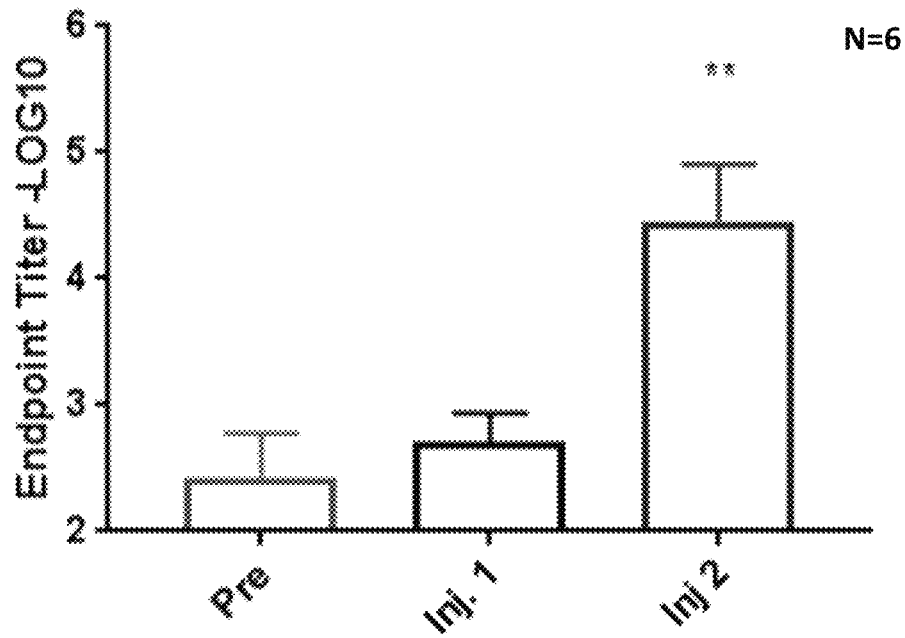
Figure 30B:
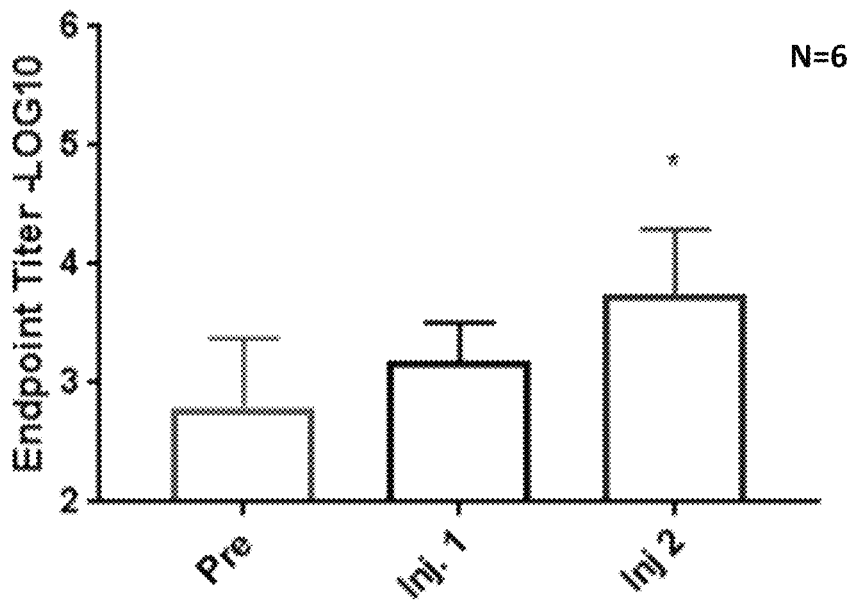
Figure 30E:
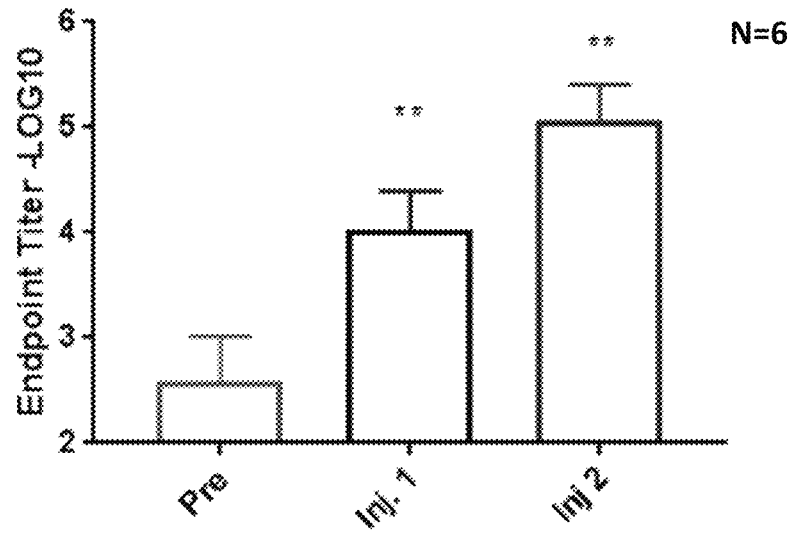
Figure 30F:
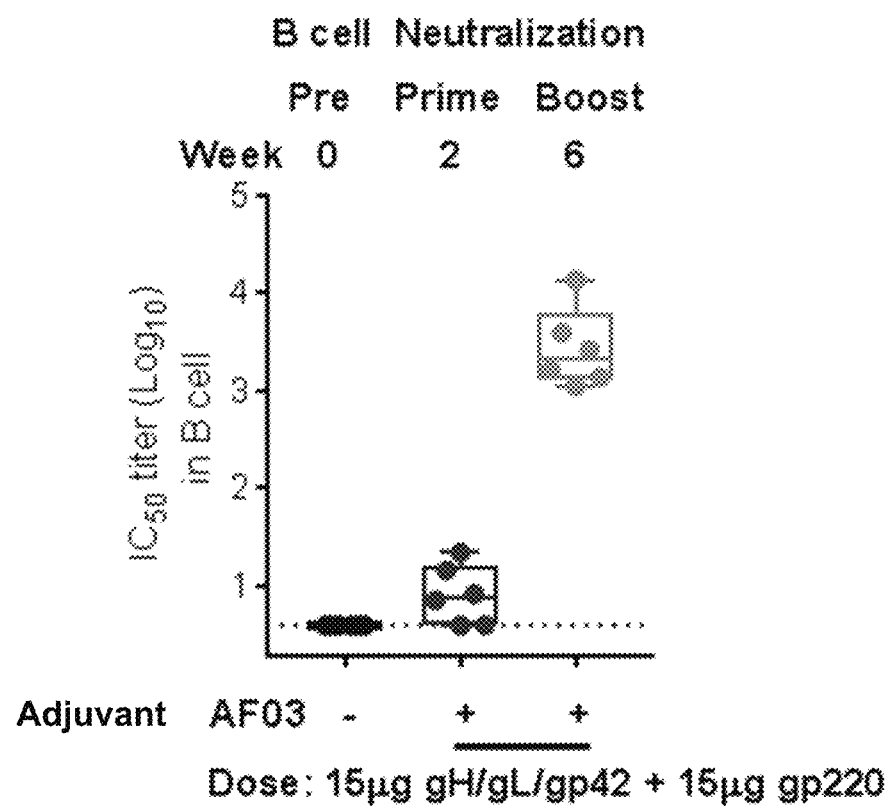
Figure 30G:
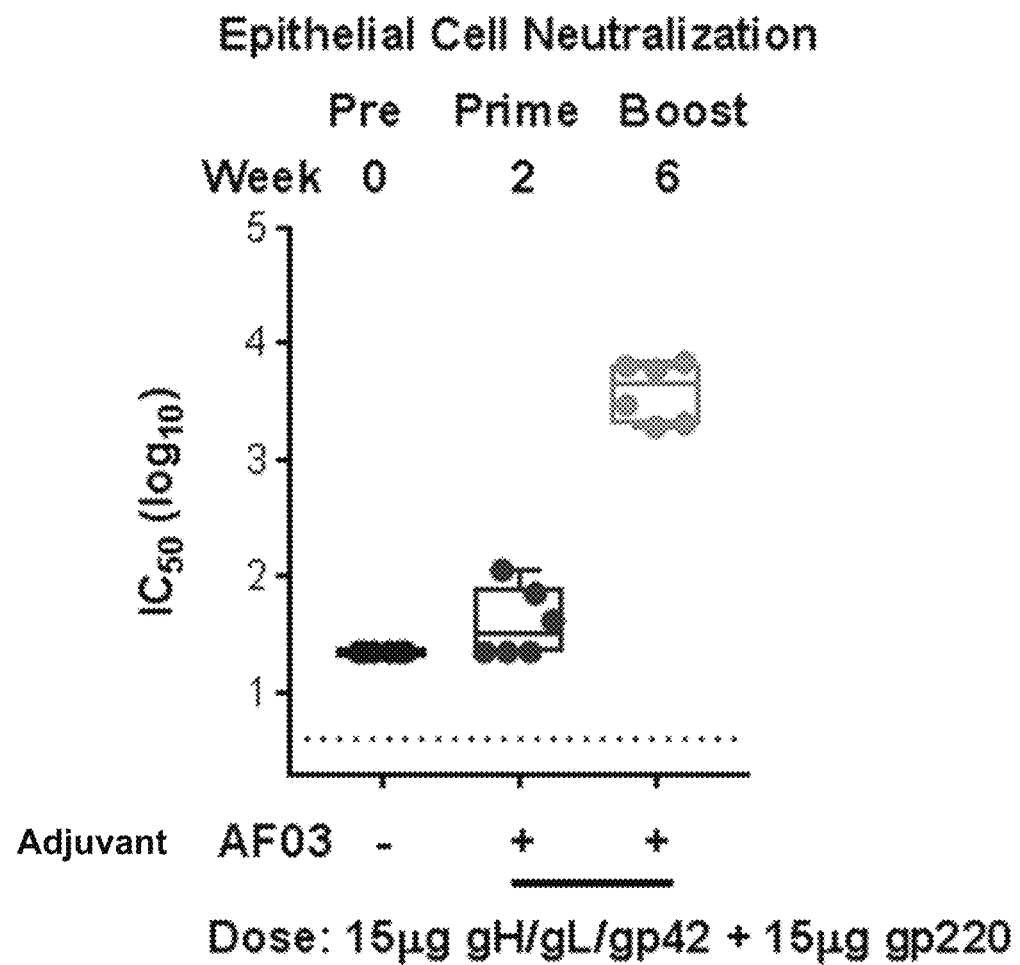

FIGS. 30A-E show endpoint binding titers against the indicated antigens. FIGS. 30F-G show an EBV viral neutralizing assay (in B cells and epithelial cells, respectively) of sera from ferrets vaccinated as indicated. Prime=Inj. 1 and Boost=Inj. 2.

Figure 31A:
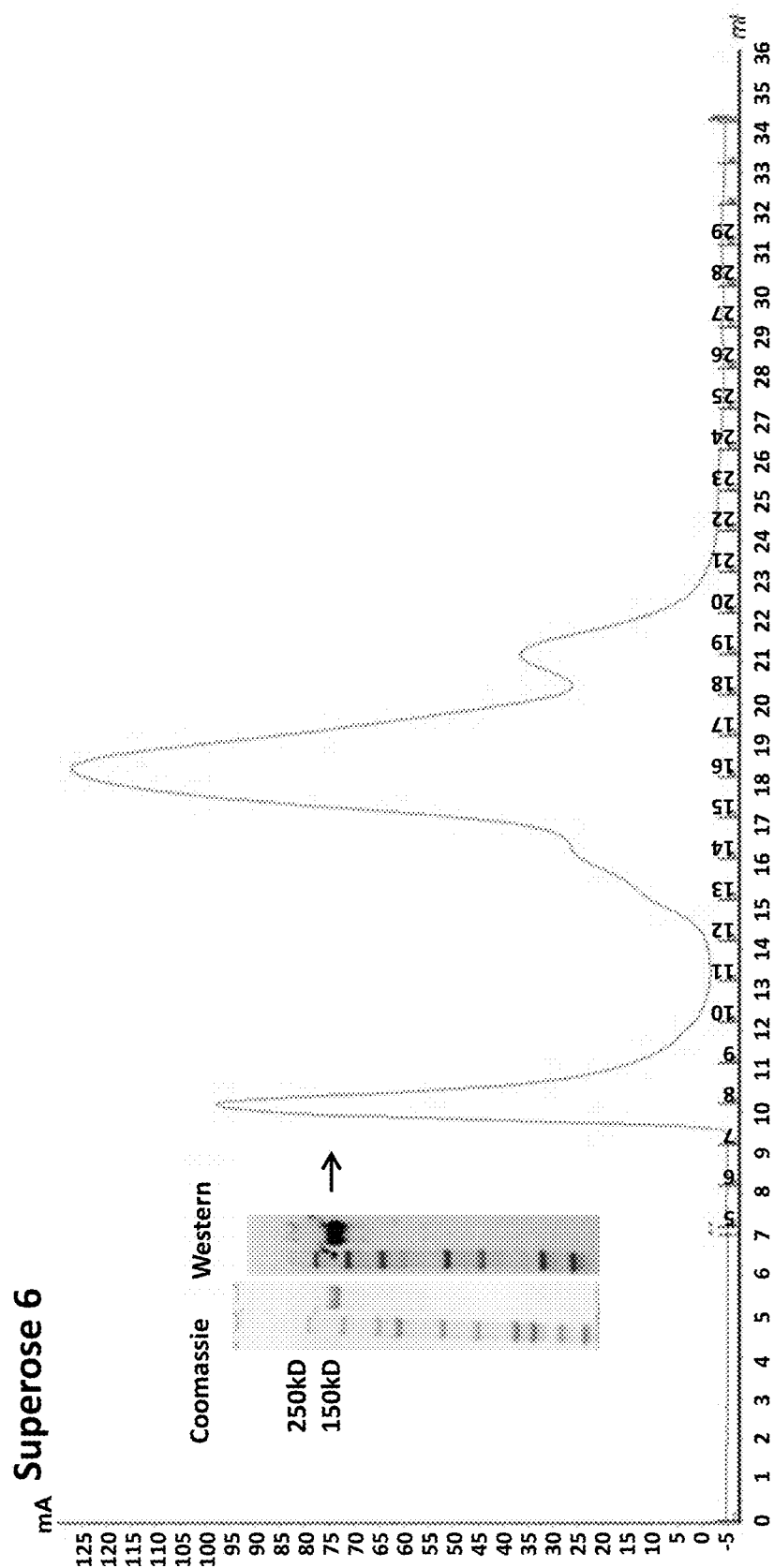
Figure 31B:
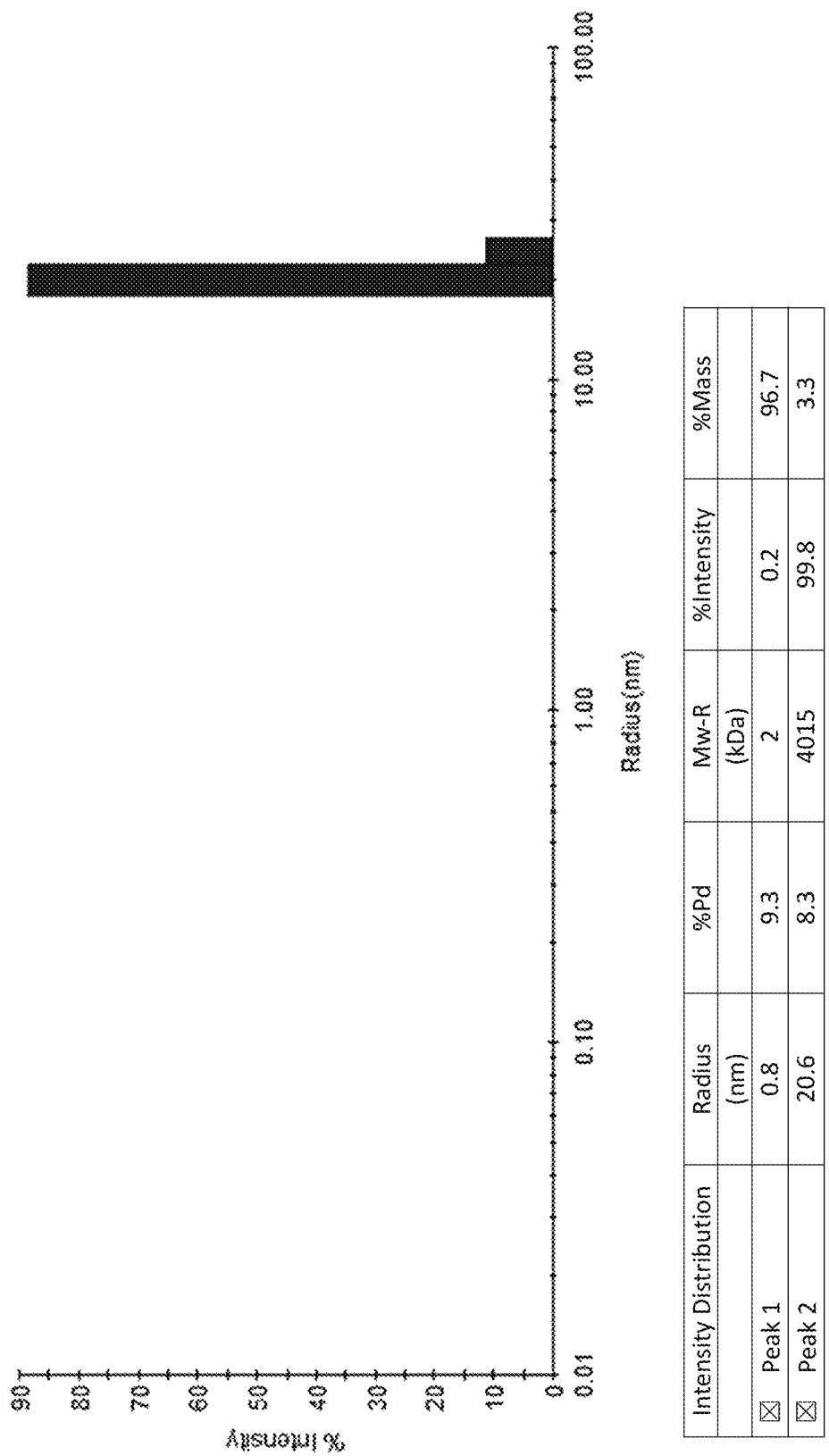

FIGS. 31A-B: FIG. 31A shows purification of gH/gL/gp42_NP_C12 (SEQ ID NO: 228) using Superose 6 size exclusion chromatography. The arrow depicts the fractions collected from the peak with a denaturing coomassie gel analysis and a western blot analysis using anti-ferritin antibodies. FIG. 31B is a dynamic light scattering analysis of the sample in FIG. 31A, which shows the particle size radius of 20.6 nm.

Figure 32A:
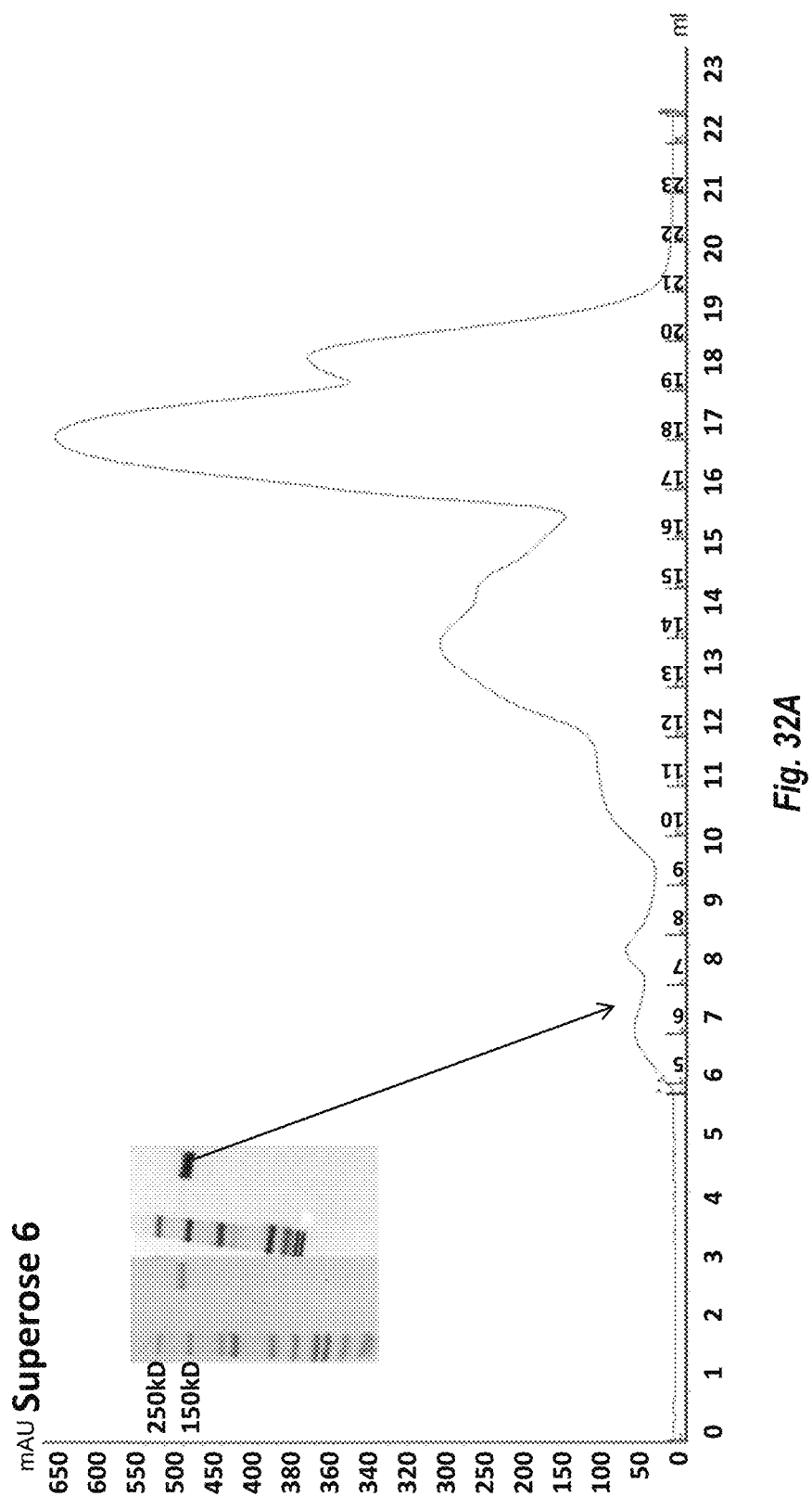
Figure 32B:
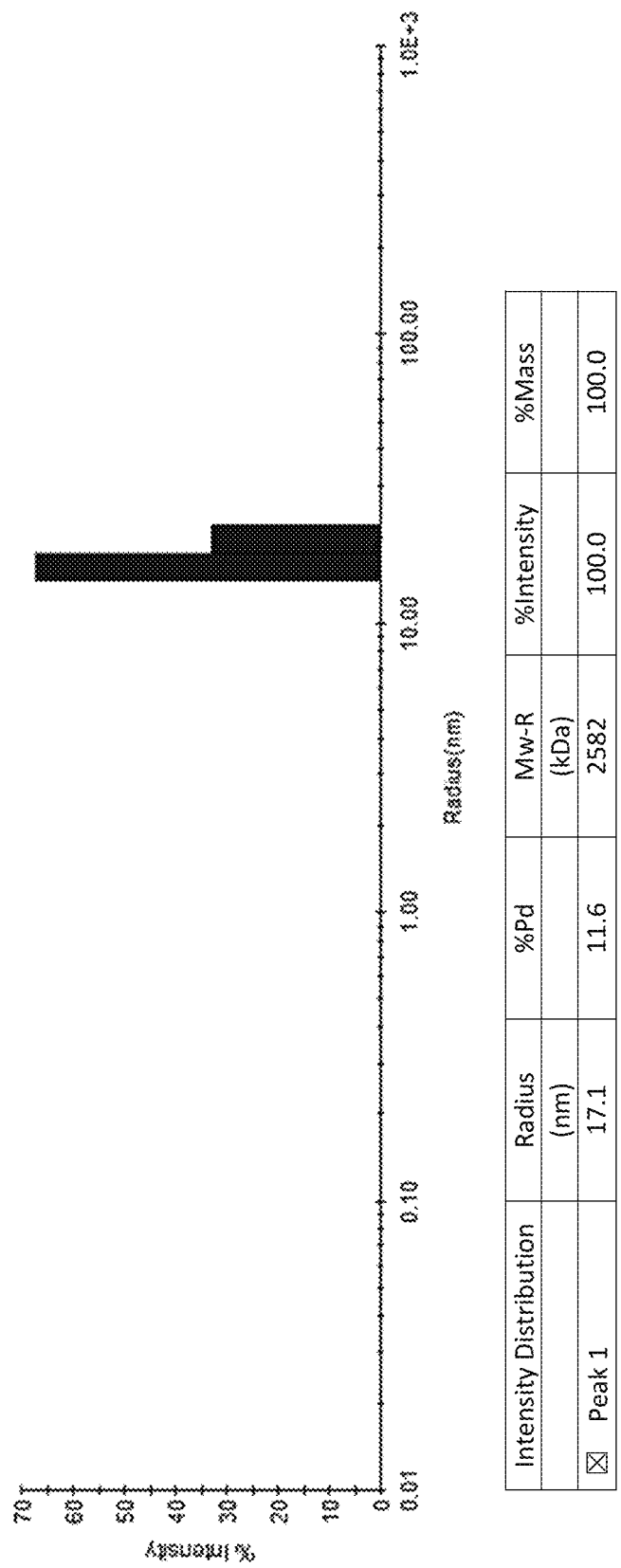

FIGS. 32A-B: FIG. 32A shows purification of gH/gL/gp42_NP_C13 (SEQ ID NO: 229) using the Superose 6 size exclusion chromatography. The arrow depicts the fractions collected from the peak with a denaturing coomassie gel analysis and a western blot analysis using anti-ferritin antibodies. FIG. 32B is a dynamic light scattering analysis of the sample in FIG. 32A, which shows the particle size radius of 17.1 nm.

Figure 33A:
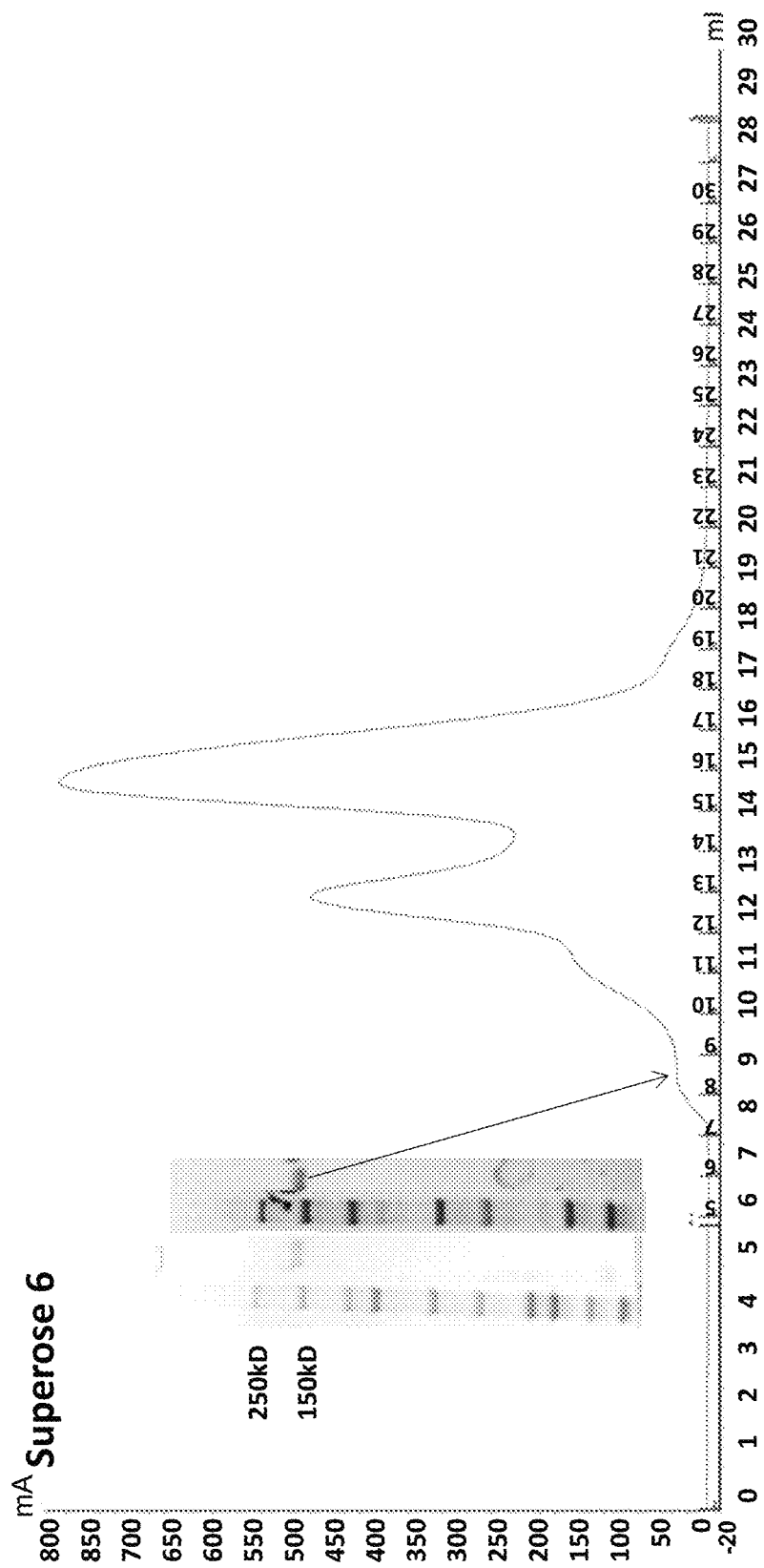
Figure 33B:
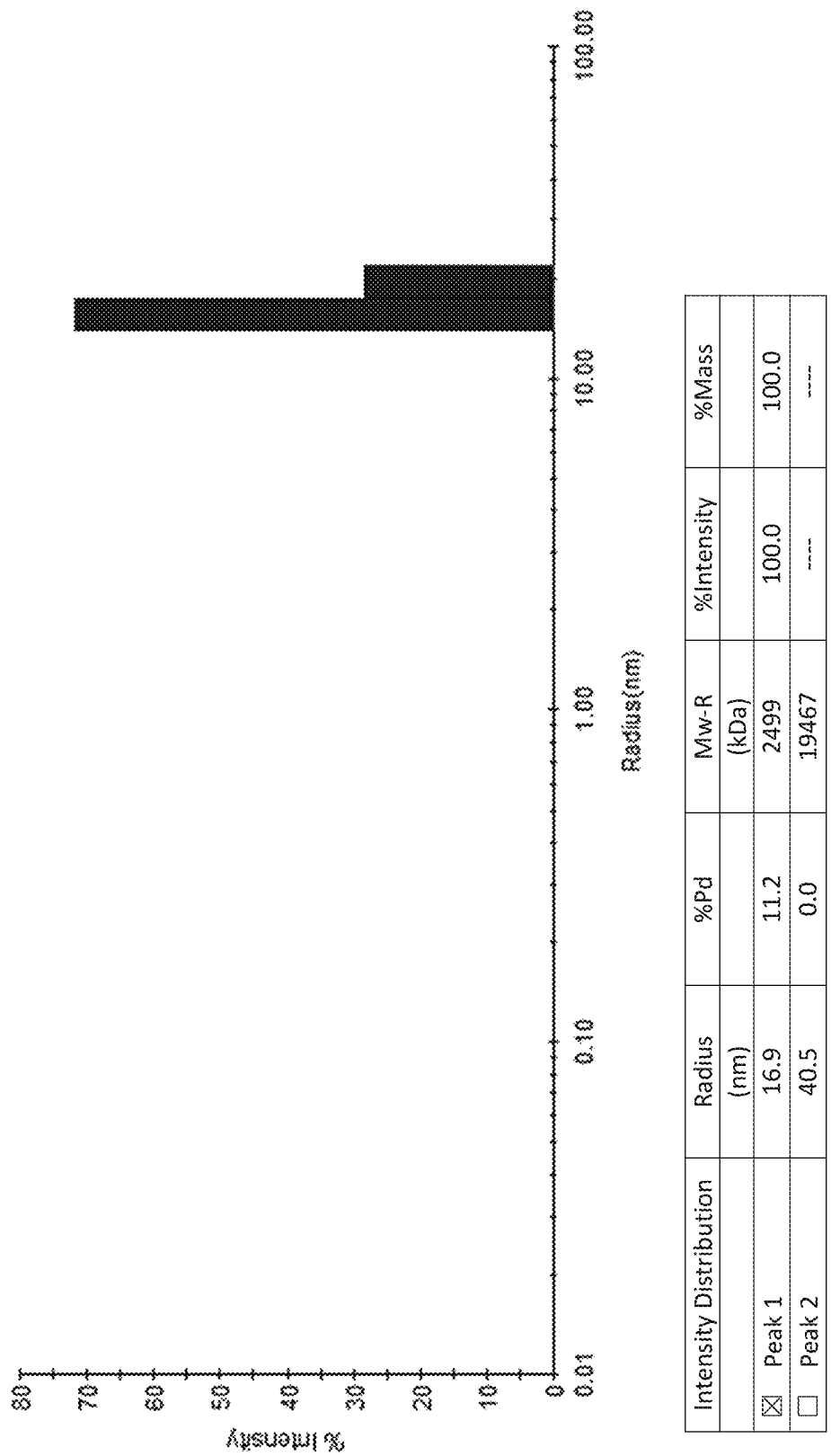

FIGS. 33A-B: FIG. 33A shows purification of gH/gL/gp42_NP_C14 (SEQ ID NO: 230) using the Superose 6 size exclusion chromatography. The arrow depicts the fractions collected from the peak with a denaturing coomassie gel analysis and a western blot analysis using anti-ferritin antibodies. FIG. 33B is a dynamic light scattering analysis of the sample in FIG. 33A, which shows the particle size radius of 16.9 nm.

Figure 34:
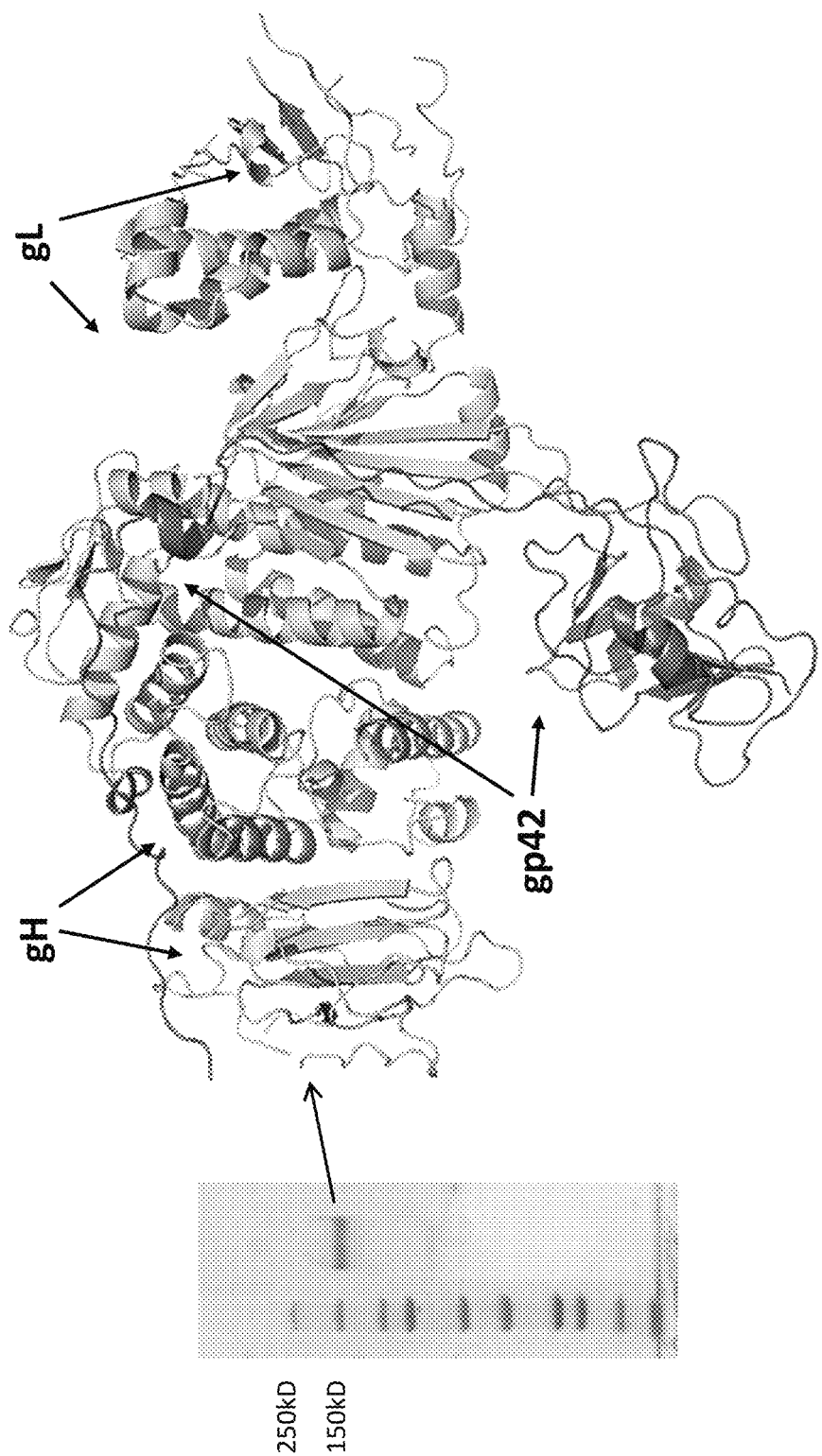

FIG. 34: An SDS reducing coomassie gel on the left shows the purified single-chain gH/gL/gp42-His product (SEQ ID NO: 226). The protein was purified using Nickel affinity chromatography. On the right is a 2.9 Angstrom crystal structure of the single-chain gH/gL/gp42-His product (SEQ ID NO: 226). Gp42 (in dark gray and indicated with arrows) interacts with the gH/gL heterodimer.

FIG. 35A-E: A cartoon of a single-chain construct of gH/gL/gp42 fused to ferritin (as in each of SEQ ID NOs: 227-231) is shown in FIG. 35A. The fusion between each protein is via a flexible amino acid linker or a rigid amino acid linker specified above. The single-chain gH/gL/gp42 molecule will assure a 1:1:1 ratio of heterotrimer formation on the nanoparticle. The crystal structure of this heterotrimer has been solved to show that the single-chain gH/gL/gp42 can adopt a heterotrimer formation similar to wild-type gH, gL, and gp42 proteins found in nature (FIG. 35B; see also FIG. 34). FIG. 35C is a model of how this single-chain gH/gL/gp42 heterotrimer is displayed on the nanoparticle through the fusion with ferritin. There are twenty-four copies of the single-chain gH/gL/gp42 displayed on a single nanoparticle. FIG. 35D shows the purification after expression of SEQ ID NOs: 227 in 293Expi cells. A denaturing SDS Coomassie gel shows the gH/gL/gp42 fused to ferritin to be above 150 kD with glycosylation. FIG. 35E shows negative stain electron microscopy analysis of the purified product, indicating that the single-chain gH/gL/gp42 fused to ferritin can successfully form nanoparticles displaying the gH/gL/gp42 antigens on the surface.

DETAILED DESCRIPTION

EBV polypeptides are provided, which can be antigenic when administered alone, with adjuvant as a separate molecule, and/or as part of a nanoparticle (e.g., ferritin particle or lumazine synthase particle), which can be self-adjuvanting. Such polypeptides and compositions comprising such polypeptides can be used to elicit antibody responses against Epstein Barr virus (EBV). The EBV polypeptide can comprise a gL, gH, gL/gH, gp220, or gp42 polypeptide, or combinations thereof, and a multimerization domain such as a ferritin. The ferritin may comprise a mutation replacing a surface-exposed amino acid with a cysteine, which can facilitate conjugating immune-stimulatory moieties to the ferritin via the cysteine. Such conjugation may eliminate or reduce the need for separately administered adjuvant, and may also potentially reduce the amount of adjuvant/immune-stimulatory moiety needed to elicit an immune response to the EBV polypeptide. In some embodiments, an antigenic EBV polypeptide comprising (i) an EBV polypeptide, and (ii-a) a ferritin comprising a surface-exposed cysteine, or (ii-b) a ferritin and an N- or C-terminal linker comprising a cysteine is provided. Any of the EBV polypeptides described herein can be combined with any of the ferritins described below. Nucleic acids that encode the polypeptides described herein are also provided.

A. Definitions

As used herein, an "EBV polypeptide" refers to a polypeptide comprising all or part of an amino acid sequence encoded by EBV. Similarly, gL, gH, gp42, and gp220 polypeptides refer to polypeptides comprising all or part of a gL, gH, gp42, or gp220 amino acid sequence, respectively, encoded by EBV. Polypeptides with, e.g., at least 80% identity to an EBV-encoded polypeptide will necessarily comprise part of the EBV-encoded polypeptide. The terms "gL polypeptide," "gH polypeptide," "gp42 polypeptide," and "gp220 polypeptide" are used interchangeably with "EBV gL polypeptide," "EBV gH polypeptide," "EBV gp42 polypeptide," and "EBV gp220 polypeptide," respectively. Immunization with an EBV polypeptide as part or all of an antigenic polypeptide may confer protection from infection with EBV. Unless the context dictates otherwise, any polypeptide disclosed herein comprising an EBV polypeptide can comprise all or part of multiple sequences encoded by EBV (for example, all or part or gL and gH of EBV, or all or part of gL, gH, and gp42 of EBV).

As used herein, a "monomer," or "monomer construct" refers to a construct expressed as a single-chain protein. A monomer may comprise gL and gH of EBV expressed in a single chain, or gL, gH, and gp42 of EBV expressed in a single chain.

As used herein, a "trimer," or "trimer construct" refers to a construct comprising gL and/or gH of EBV together with a trimerization domain, such as a foldon trimerization domain derived from T4 phage fibritin. Other trimerization domains, such as the human collagen XVIII trimerization domain (see, e.g., Alvarez-Cienfuegos et al., Scientific Reports 2016; 6:28643) and the L1ORF1p trimerization domain (see, e.g., Khazina et al., Proc Natl Acad Sci USA 2009 January 12; 106(3):731-36) are also known in the art and can be used in trimeric constructs.

"Ferritin" or "ferritin protein," as used herein, refers to a protein with detectable sequence identity to *H. pylon* ferritin (SEQ ID NO: 208 or 209) or another ferritin discussed herein, such as *P. furiosus* ferritin, *Trichoplusia ni* ferritin, or human ferritin, that serves to store iron, e.g., intracellularly or in tissues or to early iron in the bloodstream. Such exemplary ferritins, including those that occur as two polypeptide chains, known as the heavy and light chains (e.g., *T. ni* and human ferritin), are discussed in detail below. In some embodiments, a ferritin comprises a sequence with at least 15%, 20%, 30%, 40%, 50%, 60%, 70%, 75%, 80%, 85%, 90%, 95%, 97%, 98%, 99%, or 99.5% identity to a ferritin sequence disclosed herein, e.g., in Table 2 (Sequence Table). A ferritin may be a fragment of a full-length naturally-occurring sequence.

"Wild-type ferritin," as used herein, refers to a ferritin whose sequence consists of a naturally-occurring sequence. Ferritins also include full-length ferritin or a fragment of ferritin with one or more differences in its amino acid sequence from a wild-type ferritin.

As used herein, a "ferritin monomer" refers to a single ferritin molecule (or, where applicable, a single ferritin heavy or light chain) that has not assembled with other ferritin molecules. A "ferritin multimer" comprises multiple associated ferritin monomers. A "ferritin protein" includes monomeric ferritin and multimeric ferritin.

As used herein, "ferritin particle," refers to ferritin that has self-assembled into a globular form. Ferritin particles are sometimes referred to as "ferritin nanoparticles" or simply "nanoparticles". In some embodiments, a ferritin particle comprises 24 ferritin monomers (or, where applicable, 24 total heavy and light chains).

"Hybrid ferritin," as used herein, refers to ferritin comprising *H. pylori* ferritin with an amino terminal extension of bullfrog ferritin. An exemplary sequence used as an amino terminal extension of bullfrog ferritin appears as SEQ ID NO: 217. In hybrid ferritin, the amino terminal extension of bullfrog ferritin can be fused to *H. pylori* ferritin such that immune-stimulatory moiety attachment sites are distributed evenly on the ferritin particle surface. "Bullfrog linker" as used herein is a linker comprising the sequence of SEQ ID NO: 217. Hybrid ferritin is also sometimes referred to as "bfpFerr" or "bfp ferritin." Any of the constructs comprising a bullfrog sequence can be provided without the bullfrog sequence, such as, for example, without a linker or with an alternative linker. Exemplary bullfrog linker sequences are provided in Table 2. Where Table 2 shows a bullfrog linker, the same construct may be made without a linker or with an alternative linker.

"N-glycan," as used herein, refers to a saccharide chain attached to a protein at the amide nitrogen of an N (asparagine) residue of the protein. As such, an N-glycan is formed by the process of N-glycosylation. This glycan may be a polysaccharide.

"Glycosylation," as used herein, refers to the addition of a saccharide unit to a protein.

"Immune response," as used herein, refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a "protective immune response" refers to an immune response that protects a subject from infection (e.g., prevents infection or prevents the development of disease associated with infection). Methods of measuring immune responses are well known in the art and include, for example, by measuring proliferation and/or activity of lymphocytes (such as B or T cells), secretion of cytokines or chemokines, inflammation, antibody production and the like. An "antibody response" is an immune response in which antibodies are produced.

As used herein, an "antigen" refers to an agent that elicits an immune response, and/or an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism. Alternatively, or additionally, in some embodiments, an antigen elicits a cellular response (e.g., involving T-cells whose receptors specifically interact with the antigen) in an organism. A particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In some embodiments, an antigen reacts with the products of specific humoral or cellular immunity, including those induced by heterologous immunogens. Antigens include antigenic ferritin proteins comprising ferritin (e.g., comprising one or more mutations) and a non-ferritin polypeptide as described herein.

An "immune-stimulatory moiety," as used herein, refers to a moiety that is covalently attached to a ferritin or antigenic ferritin polypeptide and that can activate a component of the immune system (either alone or when attached to ferritin or antigenic ferritin polypeptide). Exemplary immune-stimulatory moieties include agonists of toll-like receptors (TLRs), e.g., TLR 4, 7, 8, or 9. In some embodiments, an immune-stimulatory moiety is an adjuvant.

"Adjuvant," as used herein, refers to a substance or vehicle that non-specifically enhances the immune response to an antigen. Adjuvants can include, without limitation, a suspension of minerals (e.g., alum, aluminum hydroxide, or phosphate) on which antigen is adsorbed; a water-in-oil or oil-in-water emulsion in which antigen solution is emulsified in mineral oil or in water (e.g., Freund's incomplete adjuvant). Sometimes killed mycobacteria is included (e.g., Freund's complete adjuvant) to further enhance antigenicity. Immuno-stimulatory oligonucleotides (e.g., a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants can also include biological molecules, such as Toll-Like Receptor (TLR) agonists and costimulatory molecules. An adjuvant may be administered as a separate molecule in a composition or covalently bound (conjugated) to ferritin or an antigenic ferritin polypeptide.

An "antigenic EBV polypeptide" is used herein to refer to a polypeptide comprising all or part of an EBV amino acid sequence of sufficient length that the molecule is antigenic with respect to EBV. Antigenicity may be a feature of the EBV sequence as part of a construct further comprising a heterologous sequence, such as a ferritin or lumazine synthase protein and/or immune-stimulatory moiety. That is, if an EBV sequence is part of a construct further comprising a heterologous sequence, then it is sufficient that the construct can serve as an antigen that generates anti-EBV antibodies, regardless of whether the EBV sequence without the heterologous sequence could do so.

"Antigenic ferritin polypeptide" and "antigenic ferritin protein" are used interchangeably herein to refer to a polypeptide comprising a ferritin and a non-ferritin polypeptide (e.g., an EBV polypeptide) of sufficient length that the molecule is antigenic with respect to the non-ferritin polypeptide. The antigenic ferritin polypeptide may further comprise an immune-stimulatory moiety. Antigenicity may be a feature of the non-ferritin sequence as part of the larger construct. That is, it is sufficient that the construct can serve as an antigen against the non-ferritin polypeptide, regardless of whether the non-ferritin polypeptide without the ferritin (and immune-stimulatory moiety if applicable) could do so. In some embodiments, the non-ferritin polypeptide is an EBV polypeptide, in which case the antigenic ferritin polypeptide is also an "antigenic EBV polypeptide." To be clear, however, an antigenic EBV polypeptide does not need to comprise ferritin. "Antigenic polypeptide" is used herein to refer to a polypeptide which is either or both of an antigenic ferritin polypeptide and an antigenic EBV polypeptide.

"Self-adjuvanting," as used herein, refers to a composition or polypeptide comprising a ferritin and an immune-stimulatory moiety directly conjugated to the ferritin so that the ferritin and immune-stimulatory moiety are in the same molecular entity. An antigenic ferritin polypeptide comprising a non-ferritin polypeptide may be conjugated to an immune-stimulatory moiety to generate a self-adjuvanting polypeptide.

A "surface-exposed" amino acid, as used herein, refers to an amino acid residue in a protein (e.g., a ferritin) with a side chain that can be contacted by solvent molecules when the protein is in its native three-dimensional conformation after multimerization, if applicable. Thus, for example, in the case of ferritin that forms a 24-mer, a surface-exposed amino acid residue is one whose side chain can be contacted by solvent when the ferritin is assembled as a 24-mer, e.g., as a ferritin multimer or ferritin particle.

As used herein, a "subject" refers to any member of the animal kingdom. In some embodiments, "subject" refers to humans. In some embodiments, "subject" refers to non-human animals. In some embodiments, subjects include, but are not limited to, mammals, birds, reptiles, amphibians, fish, insects, and/or worms. In certain embodiments, the non-human subject is a mammal (e.g., a rodent, a mouse, a rat, a rabbit, a monkey, a dog, a cat, a sheep, cattle, a primate, and/or a pig). In some embodiments, a subject may be a transgenic animal, genetically-engineered animal, and/or a clone. In certain embodiments of the present invention the subject is an adult, an adolescent or an infant. In some embodiments, terms "individual" or "patient" are used and are intended to be interchangeable with "subject".

As used herein, the term "vaccination" or "vaccinate" refers to the administration of a composition intended to generate an immune response, for example to a disease-causing agent. Vaccination can be administered before, during, and/or after exposure to a disease-causing agent, and/or to the development of one or more symptoms, and in some embodiments, before, during, and/or shortly after exposure to the agent. In some embodiments, vaccination includes multiple administrations, appropriately spaced in time, of a vaccinating composition.

The disclosure describes nucleic acid sequences and amino acid sequences having a certain degree of identity to a given nucleic acid sequence or amino acid sequence, respectively (a references sequence).

"Sequence identity" between two nucleic acid sequences indicates the percentage of nucleotides that are identical between the sequences. "Sequence identity" between two amino acid sequences indicates the percentage of amino acids that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Needleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions at which the sequences to be compared correspond, dividing this number by the number of positions compared (e.g., the number of positions in the reference sequence) and multiplying this result by 100.

In some embodiments, the degree of identity is given for a region which is at least about 50%, at least about 00%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments in continuous nucleotides. In some embodiments, the degree of identity is given for the entire length of the reference sequence.

Nucleic acid sequences or amino acid sequences having a particular degree of identity to a given nucleic acid sequence or amino acid sequence, respectively, may have at least one functional property of said given sequence, e.g., and in some instances, are functionally equivalent to said given sequence. One important property includes the ability to act as a cytokine, in particular when administered to a subject. In some embodiments, a nucleic acid sequence or amino acid sequence having a particular degree of identity to a given nucleic acid sequence or amino acid sequence is functionally equivalent to said given sequence.

As used herein, the term "kit" refers to a packaged set of related components, such as one or more compounds or compositions and one or more related materials such as solvents, solutions, buffers, instructions, or desiccants.

B. Antigenic EBV Polypeptides Comprising gL and gH Polypeptides

EBV has three glycoproteins, glycoprotein B (gB), gH, and gL, that form the core membrane fusion machinery to allow viral penetration into a cell. gL and gH have been previously described, for example, in Matsuura et al., Proc Natl Acad Sci USA. 2010 Dec. 28; 107(52):22641-6. Monomers and trimers of gL and gH for use as vaccines have been described, for example, in Cui et al., Vaccine. 2016 Jul. 25; 34(34):4050-5. The gH and gL proteins associate to form a heterodimeric complex considered necessary for efficient membrane fusion and binding to epithelial cell receptors required for viral entry.

Disclosed herein are antigenic polypeptides comprising EBV gL and EBV gH. In some embodiments, the polypeptide exists as a single-chain. In some embodiments, the polypeptide forms a trimer, e.g., through trimerization of a trimerization domain, such as a T4 phage fibritin trimerization domain. In some embodiments, the polypeptide forms a nanoparticle (e.g., ferritin or lumazine synthase particle), e.g., through multimerization of a ferritin or lumazine synthase. In some embodiments, an antigenic EBV polypeptide according to this disclosure comprises an EBV gL polypeptide and an EBV gH polypeptide, and a linker having a length of at least 15 amino acids separating the EBV gL polypeptide and the EBV gH polypeptide. It has been found that a relatively long linker can provide benefits such as improved expression and/or immunogenicity.

In some embodiments, the EBV gH and/or gL polypeptides are full-length gH and/or gL (for exemplary full-length sequences, see GenBank Accession Nos. CEQ35765.1 and YP_001129472.1, respectively). In some embodiments, the EBV gH and/or gL polypeptides are fragments of gH and/or gL. In some embodiments, the gL polypeptide is a gL (D7) construct with a 7-amino acid deletion at the end of the gL C terminus. In some embodiments, the gH polypeptide comprises a mutation at C137, such as a C137A mutation. In some embodiments, the C137 mutation removes a native, unpaired cysteine to avoid non-specific conjugation. In some embodiments, the gH polypeptide comprises a mutation to remove a cysteine corresponding to cysteine 137 of SEQ ID NO: 37, such as a C137A mutation. In some embodiments, the C137 mutation removes a native, unpaired cysteine to avoid non-specific conjugation.

In some embodiments, the EBV gL polypeptide comprises an amino acid sequence with at least 80%, 85%, 90%, 95%, 97%, 98%, 99%, or 100% identity to SEQ ID NO: 36. In some embodiments, the EBV gH polypeptide comprises an amino acid sequence with at least 80%, 85%, 90%, 95%, 97%, 98%, 99%, or 100% identity to SEQ ID NO: 37.

In some embodiments, a mammalian leader sequence (also known as a signal sequence) is appended N-terminally to an EBV polypeptide such as a gH or gL polypeptide, e.g., at the N-terminus of the polypeptide. In some embodiments, a mammalian leader sequence results in secretion of a protein when expressed in mammalian cells.

Native EBV gH and/or gL sequences are shown in GenBank Accession No. NC_009334.1 (Human herpesvirus 4, complete genome, dated 26 Mar. 2010). For some of the constructs disclosed herein, amino acids 23-137 of the gL amino acid sequence in NC_009334.1 was used as the gL polypeptide, and the native signal peptide (amino acids 1-22 of the NCBI sequence) was replaced with an IgG K leader sequence. For some of the constructs, amino acids 19-678 of the gH amino acid sequence in NC_009334.1 was used as the gH polypeptide. In some embodiments, the gL and gH were linked via a linker as shown in the table of sequences herein.

In some embodiments, gL and gH polypeptides are expressed as a single-chain monomer. In some embodiments, the monomer composition comprises or consists of a sequence shown in the Sequence Table and denoted in the description as "monomer". A single-chain comprising gL and gH polypeptides may be referred to as "gL/gH," which can be used interchangeably with "gH_gL," "gL_gH," or "gL/gH."

In some embodiments, gL and gH are provided as a trimer. In some embodiments, a trimerization domain is placed after (C-terminal to) the gH sequence and in some embodiments, this is followed by a His$_6$ (SEQ ID NO: 243) sequence. The foldon trimerization domain is exemplary, as any trimerization domain known in the art can be used, such as collagen or L1ORF1p trimerization domains referenced herein. A gL and gH trimer has been shown to induce higher serum neutralization titers relative to a gL and gH monomer using peripheral blood human naïve B cells (see, for example, Cui et al., Vaccine. 2016 Jul. 25; 34(34):4050-5).

In some embodiments, a gL/gH trimer has an amino acid sequence comprising or consisting of a sequence shown in the Sequence Table and denoted in the description as "trimer."

The gL/gH polypeptide can be combined with any of the ferritins or lumazine synthases discussed herein. For example, in some embodiments, an antigenic EBV polypeptide comprises a monomer or trimer gL/gH polypeptide (+/−gp42 and/or gp220) and i) a heavy or light chain ferritin (e.g., *T. ni* heavy or light chain ferritin); or ii) a ferritin, optionally comprising a surface-exposed cysteine.

Additionally, in some embodiments, any antigenic EBV polypeptide comprising an EBV gL/gH polypeptide and a ferritin can be present in a composition comprising another polypeptide disclosed herein.

C. Antigenic EBV Polypeptides Comprising a Gp220 Polypeptide

In some embodiments, an antigenic EBV polypeptide comprises a gp220 polypeptide. A gp220-hybrid bullfrog/*H. pylori* ferritin nanoparticle has been previously described in Kanekiyo Cell. 2015 Aug. 27; 162(5):1090-100. This nanoparticle did not comprise a mutation providing a surface-exposed cysteine or a linker comprising a cysteine, among other differences from certain ferritins described herein.

In some embodiments, the gp220 polypeptide comprises an amino acid sequence with at least 80%, 85%, 90%, 95%, 97%, 98%, 99%, or 100% identity to SEQ ID NO: 38.

In some embodiments, a mammalian leader sequence (also known as a signal sequence) is N-terminally appended to a gp220 polypeptide. In some embodiments, a mammalian leader sequence results in secretion of a protein when expressed in mammalian cells.

The gp220 polypeptide can be combined with any of the ferritins or lumazine synthases discussed herein. For example, in some embodiments, an antigenic EBV polypeptide comprises a gp220 polypeptide (+/−gL/gH and/or gp42) and i) a heavy or light chain ferritin (e.g., *T. ni* heavy or light chain ferritin); or ii) a ferritin, optionally comprising a surface-exposed cysteine as described herein.

Additionally, in some embodiments, any antigenic EBV polypeptide comprising a gp220 polypeptide and a ferritin can be present in a composition comprising another polypeptide disclosed herein.

D. Antigenic EBV Polypeptides Comprising a Gp42 Polypeptide

In some embodiments, an antigenic EBV polypeptide comprises a gp42 polypeptide. An exemplary gp42 sequence is provided as SEQ ID NO: 34. A further exemplary gp42 sequence, suitable for inclusion in fusions e.g. with gL and gH polypeptides, is provided as SEQ ID NO: 239. Another exemplary gp42 sequence, suitable for inclusion in fusions e.g. with gL and gH polypeptides, is provided as SEQ ID NO: 240.

In some embodiments, the gp42 polypeptide comprises an amino acid sequence with at least 80%, 85%, 90%, 95%, 97%, 98%, 99%, or 100% identity to SEQ ID NO: 34. In some embodiments, the gp42 polypeptide comprises an amino acid sequence with at least 80%, 85%, 90%, 95%, 97%, 98%, 99%, or 100% identity to SEQ ID NO: 239. In some embodiments, the gp42 polypeptide comprises an amino acid sequence with at least 80%, 85%, 90%, 95%, 97%, 98%, 99%, or 100% identity to SEQ ID NO: 240.

In some embodiments, a mammalian leader sequence (also known as a signal sequence) is N-terminally appended to a gp42 polypeptide. In some embodiments, a mammalian leader sequence results in secretion of a protein when expressed in mammalian cells. An exemplary leader sequence is amino acids 1-22 of SEQ ID NO: 226.

In some embodiments, an antigenic EBV polypeptide comprising a gH and/or gL polypeptide further comprises a gp42 polypeptide. Any of the EBV polypeptides comprising a gH and/or gL polypeptide described above can further comprise a gp42 polypeptide. In some embodiments, the gp42 polypeptide is located C-terminal to the gH and/or gL polypeptide(s), as exemplified in SEQ ID NOs: 21 and 226-231. In some embodiments, the gp42 polypeptide is located N-terminal to a ferritin, also as exemplified in SEQ ID NOs: 21 and 227-231. Thus, for example, an antigenic EBV polypeptide may comprise, in N- to C-terminal orientation, a gL polypeptide, a gH polypeptide, a gp42 polypeptide, and optionally a ferritin. Linkers such as those described herein can separate the gp42 polypeptide from EBV polypeptides and/or ferritins located N-terminal and/or C-terminal thereto. In some embodiments, a linker separates each EBV polypeptide in an antigenic ferritin polypeptide (e.g., a gL polypeptide, a gH polypeptide, and a gp42 polypeptide), and a further linker may be present between the ferritin if present and the EBV polypeptide proximal thereto (e.g., a gp42 polypeptide).

In some embodiments, a linker having a length of at least 15 amino acids separates the EBV gH polypeptide and the EBV gp42 polypeptide. Such a linker may have a length of 15 to 60 amino acids, 20 to 60 amino acids, 30 to 60 amino acids, 40 to 60 amino acids, 30 to 50 amino acids, or 40 to 50 amino acids. In some embodiments, the linker comprises an amino acid sequence with at least 80%, 85%, 90%, 95%, 97%, 98%, 99%, or 100% identity to SEQ ID NO: 234.

In some embodiments, where gp42 and ferritin are present in a polypeptide, a linker separates the EBV gp42 polypeptide and the ferritin. Such a linker may have a length of at least 15 amino acids or has a length of 15 to 60 amino acids, 20 to 60 amino acids, 30 to 60 amino acids, 40 to 60 amino acids, 30 to 50 amino acids, or 40 to 50 amino acids. In some embodiments, such a linker comprises an amino acid sequence with at least 80%, 85%, 90%, 95%, 97%, 98%, 99%, or 100% identity to any one of SEQ ID NOs: 233, 234, 235, 236, 237, or 238.

The gp42 polypeptide can be combined with any of the ferritins or lumazine synthases discussed herein. For example, in some embodiments, a polypeptide comprises a gp42 polypeptide (+/−gL/gH and/or gp220) and a heavy or light chain ferritin (e.g., T. ni heavy or light chain ferritin); or ii) ferritin, optionally comprising a surface-exposed cysteine as described herein.

In some embodiments, the antigenic EBV polypeptide comprises a sequence with at least 80%, 85%, 90%, 95%, 98%, or 99% identity to amino acids 23-1078 of SEQ ID NO: 226. In some embodiments, the antigenic EBV polypeptide comprises a sequence with 80%, 85%, 90%, 95%, 98%, or 99% identity to amino acids 1-1078 of SEQ ID NO: 226. In some embodiments, the antigenic EBV polypeptide comprises a sequence with at least 80%, 85%, 90%, 95%, 98%, or 99% identity to any one of SEQ ID NOs: 226, 227, 228, 229, 230, or 231, optionally lacking the leader sequence (e.g., lacking any or all of amino acids 1-22 of these sequences).

Additionally, in some embodiments, any antigenic EBV polypeptide comprising a gp42 polypeptide and a ferritin can be present in a composition comprising another polypeptide disclosed herein.

E. Linkers

In some embodiments, an antigenic EBV polypeptide comprises a linker between gL and gH polypeptides. In some embodiments, an antigenic EBV polypeptide comprises a linker between an EBV polypeptide and a ferritin or lumazine synthase. The following features are described with respect to either of such linkers, although the present invention provides that a relatively long linker between the gL and gH sequences may provide an increase in immunogenicity. Any linker may be used; for example, in some embodiments, the linker is 2, 3, 4, 5, 6, 7, 8, 9, or 10 amino acids in length. In some embodiments, the linker is about 2-4, 2-6, 2-8, 2-10, 2-12, or 2-14 amino acids in length. In some embodiments, the linker is a peptide linker, which can facilitate expression of the antigenic ferritin polypeptide as a fusion protein (e.g., from a single open reading frame). In some embodiments, the linker is a glycine-serine linker. In some embodiments, the glycine-serine linker is GS, GGGS (SEQ ID NO: 244), 2XGGGS (i.e., GGGSGGGS) (SEQ ID NO: 245), or 5XGGGS (SEQ ID NO: 246). In some embodiments, the linker between the EBV polypeptide and ferritin is GS, GGGS (SEQ ID NO: 244), 2XGGGS (i.e., GGGSGGGS) (SEQ ID NO: 245), or 5XGGGS (SEQ ID NO: 246).

In some embodiments, the linker is at least 15 amino acids in length. In some embodiments, the linker is at least 25 amino acids in length. In some embodiments, the linker is at least 30 amino acids in length. In some embodiments, the linker is at least 35 amino acids in length. In some embodiments, the linker is at least 40 amino acids in length. In some embodiments, the linker is less than or equal to 60 amino acids in length. In some embodiments, the linker is less than or equal to 50 amino acids in length. In some embodiments, the linker is about 16, 28, 40, 46, or 47 amino acids in length. In some embodiments, the linker is flexible. In some embodiments, the linker comprises a cysteine, e.g., for use as a site for conjugation of an immune-stimulatory moiety (e.g., adjuvant); an exemplary linker comprising a cysteine is provided as SEQ ID NO: 225. In some embodiments, the linker comprises a sequence with at least 75%, 80%, 85%, 90%, or 95% identity to SEQ ID NO: 225, and further comprises a cysteine corresponding to the cysteine in SEQ ID NO: 225. In some embodiments, the linker comprises at least 25 amino acids (e.g., 25 to 60 amino acids), wherein a cysteine is located at a position ranging from the $8^{th}$ amino acid from the N-terminus to the $8^{th}$ amino acid from the C-terminus, or within 10 amino acids of the central residue or bond of the linker.

In some embodiments, the linker comprises glycine (G) and/or serine (S) amino acids. In some embodiments, the linker comprises or consists of glycine (G), serine (S), asparagine (N), and/or alanine (A) amino acids, and optionally a cysteine as discussed above. In some embodiments, the linker comprises an amino acid sequence with at least 80%, 85%, 90%, 95%, 97%, 98%, 99%, or 100% identity to SEQ ID NO: 222. In some embodiments, the linker comprises GGGGSGGGGSGGGGSG (SEQ ID NO: 28), GGSGSGSNSSASSGASSGGASGGSGGSG (SEQ ID NO: 29), GGSGSASSGASASGSSNGSGSGSGSNSSASS-GASSGGASGGSGGSG (SEQ ID NO: 30), or GS. In some embodiments, the linker comprises FR1 (SEQ ID NO: 31) or FR2 (SEQ ID NO: 32). In some embodiments, the linker comprises SEQ ID NO: 233-238.

In some embodiments, a linker comprising a cysteine as a conjugation site for an immune-stimulatory moiety such as an adjuvant is used in a construct comprising a ferritin molecule lacking an unpaired, surface-exposed cysteine, or in a construct comprising a ferritin molecule comprising an unpaired, surface-exposed cysteine.

In some embodiments, the linker is a cysteine-thrombin-histidine linker. In some embodiments, this linker is used to directly conjugate an EBV polypeptide to ferritin via click chemistry. An exemplary sequence comprising a cysteine-thrombin-histidine linker is SEQ ID NO: 39. Click chemistry suitable for conjugation reactions involving the cysteine-thrombin-histidine linker is discussed herein.

In some embodiments, a construct does not comprise a linker. In some embodiments, a construct comprises one linker. In some embodiments, a construct comprises two or more than two linkers.

In some embodiments, the construct comprises a linker between gH and gL but not between the polypeptide and ferritin or vice versa. In some embodiments, the construct only comprises a linker between the polypeptide and ferritin.

F. Antigenic EBV Polypeptides Comprising an EBV Polypeptide and Ferritin or Lumazine Synthase In some embodiments, an antigenic EBV polypeptide is provided, comprising an EBV polypeptide and ferritin. The EBV polypeptide can be any of the EBV polypeptides described herein, such as a gL, gH, gL/gH, gp220, gp42 polypeptide, or combinations thereof. The ferritin component of the polypeptide may be a ferritin from any species, and may or may not have mutations, such as a mutation replacing a surface-exposed amino acid with a cysteine as described herein. In some embodiments, the polypeptide comprises the amino acids of any one of SEQ ID NOS: 1-27.

In some embodiments, the ferritin in the polypeptide is a wild-type ferritin. In some embodiments, the ferritin is bacterial, insect, fungal, bird, or mammalian. In some embodiments, the ferritin is human. In some embodiments, the ferritin is bacterial.

In some embodiments, the ferritin is a light chain and/or heavy chain ferritin. In some embodiments, the ferritin is an insect ferritin, such as *Trichoplusia ni* heavy chain ferritin (SEQ ID NO: 211) or *Trichoplusia ni* light chain ferritin (SEQ ID NO: 212). In some embodiments, the ferritin is a human ferritin, such as human heavy chain ferritin (SEQ ID NO: 214 or FTH1, GENE ID No: 2495) or human light chain ferritin (SEQ ID NO: 215 or FTL, GENE ID No: 2512). In some embodiments, a ferritin nanoparticle comprises 24 total subunits of heavy chain ferritin and light chain ferritin, such as in human or *Trichoplusia ni* ferritin nanoparticles. *T. ni* ferritin nanoparticles can comprise 12 subunits of heavy chain ferritin and 12 subunits of light chain ferritin.

In some embodiments, an antigenic EBV polypeptide comprises a light chain ferritin and an EBV polypeptide. In some embodiments, an antigenic EBV polypeptide comprises a heavy chain ferritin and an EBV polypeptide. In some embodiments, an antigenic EBV polypeptide comprising a light chain ferritin and an EBV polypeptide can assemble with a heavy chain ferritin that is not linked to an EBV polypeptide. In some embodiments, an antigenic EBV polypeptide comprising a heavy chain ferritin and an EBV polypeptide can assemble with a light chain ferritin that is not linked to an EBV polypeptide. A ferritin not linked to an EBV polypeptide (or, more generally, a non-ferritin polypeptide) may be referred as a "naked ferritin."

In some embodiments, an antigenic polypeptide comprising a heavy chain ferritin and a polypeptide can assemble with an antigenic polypeptide comprising a light chain ferritin and an EBV polypeptide to allow presentation of two of the same or different non-ferritin polypeptides on a single ferritin nanoparticle. In some embodiments, the two different non-ferritin polypeptides are EBV polypeptides. In some embodiments, the two different non-ferritin polypeptides are encoded by EBV and a different infectious agent. In some embodiments, the different non-ferritin polypeptide from a different infectious agent is from a virus or bacterium.

In some embodiments, an antigenic polypeptide comprising a heavy chain ferritin and a non-ferritin polypeptide can assemble with a polypeptide comprising a light chain ferritin and a non-ferritin polypeptide to produce a bivalent composition.

In some embodiments, an antigenic polypeptide comprises a light chain ferritin and a gp220 and/or gp42 polypeptide. In some embodiments, an antigenic polypeptide comprises a heavy chain ferritin and a gp220 and/or gp42 polypeptide.

In some embodiments, an antigenic polypeptide comprises a light chain ferritin and a single-chain gL and gH polypeptide. In some embodiments, an antigenic polypeptide comprises a heavy chain ferritin and a single-chain gL and gH polypeptide.

In some embodiments, an antigenic polypeptide comprising a light chain ferritin and a gp220 and/or gp42 polypeptide assembles with an antigenic polypeptide comprising a heavy chain ferritin and a single-chain gL and gH polypeptide.

In some embodiments, an antigenic polypeptide comprising a heavy chain ferritin and a gp220 and/or gp42 polypeptide assembles with an antigenic polypeptide comprising a light chain ferritin and a single-chain gL and 01 polypeptide. In some embodiments, twelve (12) gp220 and/or gp42 polypeptides and twelve (12) single-chain gL and gH polypeptides are comprised in an assembled ferritin nanoparticle, as in the case of an assembled *T. ni* ferritin nanoparticle.

Any type of terrain nanoparticle(s) that comprises both gp220 and/or gp42 and single-chain gL and gH polypeptides may be referred to as a "bivalent" or "bivalent EBV" particle or construct. A composition comprising a gL and gH trimer together with a ferritin that comprises gp220 and/or gp42 would also be a bivalent EBV composition.

In some embodiments, the ferritin is *H. pylori* ferritin (see SEQ ID NO: 208 or 209 for an exemplary *H. pylori* ferritin sequence), optionally with one or more mutations such as those described herein. In some embodiments, the lower sequence homology between *H. pylori* ferritin (or other bacterial ferritins) and human ferritin may decrease the potential for autoimmunity when used as a vaccine platform (see Kanekiyo et al., Cell 162, 1090-1100 (2015)).

In some embodiments, a nanoparticle is provided comprising an antigenic EBV polypeptide as disclosed herein comprising an EBV polypeptide and a ferritin.

1. Ferritin Mutations

In some embodiments, the ferritin comprises one or more mutations are disclosed herein. In some embodiments, the one or more mutations comprise changes to the amino acid sequence of a wild-type ferritin and/or an insertion, e.g., at the N- or C-terminus. In some embodiments, one, two, three, four, five, or more different amino acids are mutated in the ferritin as compared to wild-type ferritin (in some embodiments, in addition to any N-terminal insertion). The one or more mutations can change functional properties of the ferritin, e.g., as discussed in detail below. In general, a mutation simply refers to a difference in the sequence (such as a substituted, added, or deleted amino acid residue or residues) relative to the corresponding wild-type ferritin.

2. Cysteine for Conjugation

In some embodiments, ferritin is mutated to provide a chemical handle for conjugation of an immune-stimulatory moiety and/or EBV polypeptide. This can be achieved with a mutation replacing a surface-exposed non-cysteine amino acid with a cysteine. For the avoidance of doubt, language such as "replacing a surface-exposed amino acid with a cysteine" necessarily implies that the surface-exposed amino acid in the wild-type or pre-mutation sequence is not cysteine. Another approach for providing a chemical handle for conjugation of an immune-stimulatory moiety or EBV polypeptide is to include a segment of amino acids, such as a linker, N- or C-terminal to the ferritin, wherein the segment of amino acids comprises a cysteine. In some embodiments, this cysteine (whether replacing a surface-exposed amino acid or in an N- or C-terminal linker) is unpaired, which means that it does not have an appropriate partner cysteine to form a disulfide bond. In some embodiments, this cysteine does not change the secondary structure of ferritin. In some embodiments, this cysteine does not change the tertiary structure of ferritin.

In some embodiments, this cysteine can be used to conjugate agents, such as immune-stimulatory moieties, to ferritin. In some embodiments, this cysteine provides a free thiol group that is reactive. In some embodiments, agents conjugated to this cysteine on ferritin are exposed on the surface of an assembled ferritin particle. In some embodiments, this cysteine can interact with molecules and cells of the subject after administration while the ferritin particle is assembled.

In some embodiments, the presence of this cysteine allows conjugation of one or more immune-stimulatory moieties, e.g., adjuvants. In some embodiments, conjugation of the immune-stimulatory moiety would not occur in the absence of this cysteine.

In some embodiments, the non-cysteine amino acid that is replaced with a cysteine is selected from E12, S72, A75, K79, S100, and S111 of H. pylon ferritin. Thus, in some embodiments, the surface-exposed amino acid that is replaced in favor of cysteine is an amino acid residue that corresponds to E12, S26, S72, A75, K79, S100, or S111 of H. pylori ferritin. Analogous amino acids can be found in non-H. pylori ferritin by pair-wise or structural alignment. In some embodiments, the non-cysteine amino acid that is replaced with a cysteine can be selected from an amino acid that corresponds to S3, S19, S33, I82, A86, A102, and A120 of human light chain ferritin. In some embodiments, the surface-exposed amino acid to be replaced with a cysteine is selected based on the understanding that if the native amino acid were replaced with cysteine, it would be reactive in an assembled ferritin multimer or particle and/or that this cysteine does not disrupt the stability of the ferritin multimer or particle and/or that this cysteine does not lead to reduction in expression levels of ferritin.

In some embodiments, the ferritin comprises an E12C mutation. In some embodiments, the E12C residue can be used to conjugate agents (e.g., immune-stimulatory moieties and/or EBV polypeptides) to ferritin. In some embodiments, the E12C residue provides a free thiol group that is reactive. In some embodiments, agents conjugated to the E12C residue on ferritin monomers are expressed on the surface on an assembled ferritin multimer or particle. In some embodiments, twenty-four E12C residues (one from each monomer) are present on the surface of a ferritin multimer or particle.

In some embodiments, the ferritin comprises an S26C mutation. In some embodiments, the S26C residue can be used to conjugate agents (e.g., immune-stimulatory moieties and/or EBV polypeptides) to ferritin. In some embodiments, the S26C residue provides a free thiol group that is reactive. In some embodiments, agents conjugated to the S26C residue on ferritin monomers are expressed on the surface on an assembled ferritin multimer or particle. In some embodiments, twenty-four S26C residues (one from each monomer) are present on the surface of a ferritin multimer or particle.

In some embodiments, the ferritin comprises an S72C mutation. In some embodiments, the S72C residue can be used to conjugate agents (e.g., immune-stimulatory moieties and/or EBV polypeptides) to ferritin. In some embodiments, the S72C residue provides a free thiol group that is reactive. In some embodiments, agents conjugated to the S72C residue on ferritin monomers are expressed on the surface on an assembled ferritin multimer or particle. In some embodiments, twenty-four S72C residues (one from each monomer) are present on the surface of a ferritin multimer or particle.

In some embodiments, the ferritin comprises an A75C mutation. In some embodiments, the A75C residue can be used to conjugate agents (e.g., immune-stimulatory moieties and/or EBV polypeptides) to ferritin. In some embodiments, the A75C residue provides a free thiol group that is reactive. In some embodiments, agents conjugated to the A75C residue on ferritin monomers are expressed on the surface on an assembled ferritin multimer or particle. In some embodiments, twenty-four A75C residues (one from each monomer) are present on the surface of a ferritin multimer or particle.

In some embodiments, the ferritin comprises an K79C mutation. In some embodiments, the K79C residue can be used to conjugate agents (e.g., immune-stimulatory moieties and/or EBV polypeptides) to ferritin. In some embodiments, the K79C residue provides a free thiol group that is reactive. In some embodiments, agents conjugated to the K79C residue on ferritin monomers are expressed on the surface on an assembled ferritin multimer or particle. In some embodiments, twenty-four K79C residues (one from each monomer) are present on the surface of a ferritin multimer or particle.

In some embodiments, the ferritin comprises an S100C mutation. In some embodiments, the S100C residue can be used to conjugate agents (e.g., immune-stimulatory moieties and/or EBV polypeptides) to ferritin. In some embodiments, the S100C residue provides a free thiol group that is reactive. In some embodiments, agents conjugated to the S100C residue on ferritin monomers are expressed on the surface on an assembled ferritin multimer or particle. In some embodiments, twenty-four S100C residues (one from each monomer) are present on the surface of a ferritin multimer or particle.

In some embodiments, the ferritin comprises an S111C mutation. In some embodiments, the S111C residue can be used to conjugate agents (e.g., immune-stimulatory moieties and/or EBV polypeptides) to ferritin. In some embodiments, the S111C residue provides a free thiol group that is reactive. In some embodiments, agents conjugated to the S111C residue on ferritin monomers are expressed on the surface on an assembled ferritin multimer or particle. In some embodiments, twenty-four S111C residues (one from each monomer) are present on the surface of a ferritin multimer or particle.

3. Removal of Internal Cysteine

In some embodiments, the ferritin comprises a mutation replacing an internal cysteine with a non-cysteine amino acid. Removal of a native internal cysteine residue can ensure that there is only one unpaired cysteine per ferritin monomer and avoid undesired reactions such as disulfide formation and may result in a more stable and efficient result (e.g., adjuvant presentation). In some embodiments, C31 of *H. pylori* ferritin is replaced with a non-cysteine amino acid. In some embodiments, C31 of *H. pylori* ferritin is replaced with a serine (C31S), although any non-cysteine residue may be used, e.g., alanine, glycine, threonine, or asparagine. Analogous amino acids can be found in non-*H. pylori* ferritin by pair-wise or structural alignment. Thus, in some embodiments, the internal cysteine that is replaced in favor of non-cysteine is an amino acid residue that aligns with C31 of *H. pylori* ferritin. Exemplary ferritin sequences showing a C31S mutation are shown in SEQ ID NOS: 201-207. In some embodiments, when more than one internal cysteine is present in ferritin, two or more (e.g., each) internal cysteine is replaced with a non-cysteine amino acid, such as serine or an amino acid selected from serine, alanine, glycine, threonine, or asparagine.

4. Glycosylation

Human-compatible glycosylation can contribute to safety and efficacy in recombinant drug products. Regulatory approval may be contingent on demonstrating appropriate glycosylation as a critical quality attribute (see Zhang et al., Drug Discovery Today 21(5):740-765 (2016)). N-glycans can result from glycosylation of asparagine side chains and can differ in structure between humans and other organisms such as bacteria and yeast. Thus, it may be desirable to reduce or eliminate non-human glycosylation and/or N-glycan formation in ferritin according to the disclosure. In some embodiments, controlling glycosylation of ferritin improves the efficacy and/or safety of the composition, especially when used for human vaccination.

In some embodiments, ferritin is mutated to inhibit formation of an N-glycan. In some embodiments, a mutated ferritin has reduced glycosylation as compared to its corresponding wild type ferritin.

In some embodiments, the ferritin comprises a mutation replacing a surface-exposed asparagine with a non-asparagine amino acid. In some embodiments, the surface-exposed asparagine is N19 of *H. pylori* ferritin or a position that corresponds to position 31 of *H. pylori* ferritin as determined by pair-wise or structural alignment In some embodiments, mutating such an asparagine, e.g., N19 of *H. pylori* ferritin, decreases glycosylation of ferritin. In some embodiments, the mutation replaces the asparagine with a glutamine. In some embodiments, the ferritin is an *H. pylori* ferritin comprising an N19Q mutation. SEQ ID NOS: 201-207 are exemplary ferritin sequences comprising N19Q mutations.

A mammal exposed to a glycosylated protein produced in bacteria or yeast may generate an immune response to the glycosylated protein, because the pattern of glycosylation of a given protein in bacterial or yeast could be different from the pattern of glycosylation of the same protein in a mammal. Thus, some glycosylated therapeutic proteins may not be appropriate for production in bacteria or yeast.

In some embodiments, decreased glycosylation of ferritin by amino acid mutation facilitates protein production in bacteria or yeast. In some embodiments, decreased glycosylation of ferritin reduces the potential for adverse effects in mammals upon administration of mutated ferritin that is expressed in bacteria or yeast. In some embodiments, the reactogenicity in a human subject of a mutated ferritin produced in bacteria or yeast is lower because glycosylation is decreased. In some embodiments, the incidence of hypersensitivity responses in human subjects is lower following treatment with a mutated ferritin with reduced glycosylation compared to wildtype ferritin.

In some embodiments, degradation in a subject of a composition comprising a mutated ferritin with reduced glycosylation is slower compared with a composition comprising a wild-type ferritin, or a composition comprising a corresponding ferritin with wild-type glycosylation. In some embodiments, a composition comprising a mutated ferritin with reduced glycosylation has reduced clearance in a subject compared with a composition comprising a wild-type ferritin, or a composition comprising a corresponding ferritin with wild-type glycosylation. In some embodiments, a composition comprising a mutated ferritin with reduced glycosylation has a longer-serum half-life compared to wild-type ferritin, or a composition comprising a corresponding ferritin with wild-type glycosylation.

5. Combinations of Mutations

In some embodiments, a ferritin comprises more than one type of mutation described herein. In some embodiments, the ferritin comprises one or more mutations independently selected from: a mutation to decrease glycosylation, a mutation to remove an internal cysteine, and a mutation to generate a surface-exposed cysteine. In some embodiments, the ferritin comprises a mutation to decrease glycosylation, a mutation to remove an internal cysteine, and a mutation to generate a surface-exposed cysteine.

In some embodiments, the ferritin comprises an N19Q mutation, a C31S mutation, and a mutation to generate a surface-exposed cysteine. In some embodiments, the ferritin comprises an N19Q mutation, a C31S mutation, and an E12C mutation. In some embodiments, the ferritin comprises an N19Q mutation, a C31S mutation, and an S72C mutation. In some embodiments, the ferritin comprises an N19Q mutation, a C31S mutation, and an A75C mutation. In some embodiments, the ferritin comprises an N19Q mutation, a C31S mutation, and an K79C mutation. In some embodiments, the ferritin comprises an N19Q mutation, a C31S mutation, and an S100C mutation. In some embodiments, the ferritin comprises an N19Q mutation, a C31S mutation, and an S111C mutation. In some embodiments, the ferritin comprises mutations corresponding to any of the foregoing sets of mutations, wherein the corresponding mutations change an N to a Q, a C to an S, and a non-cysteine surface-exposed amino acid to a cysteine at positions determined by pair-wise alignment of the ferritin amino acid sequence to an *H. pylori* ferritin amino acid sequence (SEQ ID NO: 208 OR 209).

Exemplary ferritins comprising more than one type of mutation are provided in SEQ ID NOS: 201-207.

6. Structural Alignment

As discussed herein, positions of mutations corresponding to those described with respect to a given polypeptide (e.g., H. pylori ferritin) can be identified by pairwise or structural alignment. Structural alignment is relevant to large protein families such as ferritin where the proteins share similar structures despite considerable sequence variation and many members of the family have been structurally characterized, and can also be used to identify corresponding positions in different versions of other polypeptides described herein, such as EBV polypeptides (e.g., gL, gH, gp220, or gp42). The protein databank (PDB) comprises 3D structures for many ferritins, including those listed below with their accession numbers.

2jd6, 2jd7–PfFR-*Pyrococcus furiosus*. 2jd8-PfFR+Zn. 3a68-soFR from gene SferH4-soybean. 3a9q—soFR from gene SferH4 (mutant). 3egm, 3bvf, 3bvi, 3bvk, 3bv1-HpFR—Heliobacter *pylori*. 5c6f—HpFR (mutant)+Fe. 1z4a, 1v1g-FR-*Thermotoga* maritime. 1s3q, 1sq3, 310(9-FR—Archaeoglubus *fulgidus*. 1krq-FR-*Campylobacter jejuni*. leum—EcFR—*Escherichia coli*. 4reu—EcFR+Fe. 4×gs—EcFR (mutant)+Fe2O2. 4ztt—EcFR (mutant)+Fe2O+Fe2+Fe 4-02. lqgh—LiFR—*Listeria innocua*. 3qz3-VcFR—*Vibrio cholerae*. 3vnx-FR—Ulva pertusa. 4ism, 4isp, 4itt, 4itw, 4iwj, 4iwk, 4ixk, 3e6s-PnmFR—Pseudo-nitschia multiseries. 4zkh, 4zkw, 4zkx, 4z15, 4z16, 4z1w, 4zmc-PnmFR (mutant)+Fe. 1z6o-FR-*Trichoplusia ni*. 4cmy-FR+Fe-*Chlorobaculum tepidum*. Ferritin light chain (FTL). 11b3, 1h96-mFTL-mouse. lrcc, lrcd, lrci-bFTL+tartrate+Mg. lrce. lrcg-bFTL+tartrate+Mn. 3noz, 3np0, 3np2, 3o7r-hoFTL (mutant)—horse. 3o7s, 3u90-hoFTL. 4v 1w-hoFTL-cryo EM. 3rav, 3rd0-hoFTL+barbiturate. Ferritin light+heavy chains: 5gn8-hFTH+Ca.

Structural alignment involves identifying corresponding residues across two (or more) polypeptide sequences by (i) modeling the structure of a first sequence using the known structure of the second sequence or (ii) comparing the structures of the first and second sequences where both are known, and identifying the residue in the first sequence most similarly positioned to a residue of interest in the second sequence. Corresponding residues are identified in some algorithms based on alpha-carbon distance minimization in the overlaid structures (e.g., what set of paired alpha carbons provides a minimized root-mean-square deviation for the alignment). When identifying positions in a non-*H. pylori* ferritin corresponding to positions described with respect to *H. pylori* ferritin, *H. pylori* ferritin can be the "second" sequence. Where a non-*H. pylon* ferritin of interest does not have an available known structure, but is more closely related to another non-*H. pylori* ferritin that does have a known structure than to *H. pylori* ferritin, it may be most effective to model the non-*H. pylori* ferritin of interest using the known structure of the closely related non-*H. pylori* ferritin, and then compare that model to the *H. pylori* ferritin structure to identify the desired corresponding residue in the ferritin of interest. There is an extensive literature on structural modeling and alignment; representative disclosures include U.S. Pat. Nos. 6,859,736; 8,738,343; and those cited in Aslam et al., Electronic Journal of Biotechnology 20 (2016) 9-13. For discussion of modeling a structure based on a known related structure or structures, see, e.g., Bordoli et al., Nature Protocols 4 (2009) 1-13, and references cited therein.

7. Lumazine Synthase

In some embodiments, the antigenic polypeptide comprises a lumazine synthase protein. Lumazine synthases can form higher-order structures, e.g., a 60-subunit lumazine synthase particle. Exemplary lumazine synthases are *Aquifex aeolicus* lumazine synthase (SEQ ID NO: 40) and *E. coli* lumazine synthase (SEQ ID NO: 41). In some embodiments, the lumazine synthase has at least 85%, 90%, 95%, 97%, 98%, 99%, or 100% identity to the sequence of SEQ ID NOS: 40 or 41. The lumazine synthase can be located C-terminal to the EBV polypeptide and can be separated from the EBV polypeptide by a linker as discussed herein.

G. Mutations in gL, gH, Gp42, Linker, and/or Ferritin Sequences to Eliminate Potential Oxidation, Deamidation, or Isoaspartate Formation Sites In some embodiments, an antigenic EBV polypeptide comprises one or more mutations to eliminate potential oxidation, deamidation, or Isoaspartate formation sites, such as the exemplary mutations set forth in Table 1 below.

For example, in some embodiments, a gL sequence comprises one or more mutations to eliminate a potential succinimide/isoaspartate or deamidation site. For example, a gL sequence can comprise a G to A mutation at a position corresponding to position 36 of SEQ ID NO: 227; an N to Q mutation at a position corresponding to position 47 of SEQ ID NO: 227; or an N to Q mutation at a position corresponding to position 105 of SEQ ID NO: 227. A position in an amino acid sequence "corresponds" to a given position in SEQ ID NO: 227 if it aligns to that position according to a standard sequence alignment algorithm such as the Smith-Waterman algorithm using default parameters.

In some embodiments, a linker comprises one or more mutations to eliminate a potential deamidation site. For example, a linker sequence can comprise an N to G mutation at a position corresponding to position 132 or 141 of SEQ ID NO: 227.

In some embodiments, a gH sequence comprises one or more mutations to eliminate a potential succinimide/isoaspartate or oxidation site. For example, a gH sequence can comprise an M to L mutation at a position corresponding to position 189, 401, or 729 of SEQ ID NO: 227; a D to E mutation at a position corresponding to position 368 of SEQ ID NO: 227; an M to I mutation at a position corresponding to position 499 or 639 of SEQ ID NO: 227; or an N to Q mutation at a position corresponding to position 653 of SEQ ID NO: 227.

In some embodiments, a gp42 sequence comprises one or more mutations to eliminate a potential deamidation site. For example, a gp42 sequence can comprise an N to Q mutation at a position corresponding to position 959 or 990 of SEQ ID NO: 227; or an N to S mutation at a position corresponding to position 988 of SEQ ID NO: 227.

In some embodiments, a ferritin sequence comprises one or more mutations to eliminate a potential deamidation, oxidation, or isoaspartate formation site. For example, a ferritin sequence can comprise a Q to S mutation at a position corresponding to position 1150 of SEQ ID NO: 227; an M to I mutation at a position corresponding to position 1168 of SEQ ID NO: 227; an M to L mutation at a position corresponding to position 1177 of SEQ ID NO: 227; a G to A mutation at a position corresponding to position 1188 of SEQ ID NO: 227; or an N to Q mutation at a position corresponding to position 1253 or 1296 of SEQ ID NO: 227.

Exemplary mutations are shown below in Table 1. The position numbering corresponds to SEQ ID NO: 227.

TABLE 1

Exemplary mutations.

| Location | Modification | START | END | MOTIF | solvent expsoure | Mutation |
|---|---|---|---|---|---|---|
| gL | Succinimide/IsoAsp | 35 | 36 | DG | Exposed | G36A |
| gL | deamidation | 47 | 47 | N | likely exposed | N47Q |
| gL | deamidation | 105 | 105 | N | exposed | N105Q |
| linker | deamidation | 132 | 132 | N | exposed | N132G |
| linker | deamidation | 141 | 141 | N | exposed | N141G |
| gH | oxidation | 189 | 189 | M | exposed | M189L |
| gH | Succinimide/IsoAsp | 368 | 369 | DY | exposed | D368E |
| gH | oxidation | 401 | 401 | M | buried | M401L |
| gH | Succinimide/IsoAsp | 429 | 430 | DT | exposed | D429E |
| gH | oxidation | 499 | 499 | M | exposed | M499I |
| gH | oxidation | 639 | 639 | M | exposed | M639I |
| gH | oxidation | 653 | 653 | N | exposed | N653Q |
| gH | oxidation | 729 | 729 | M | exposed | M729L |
| gp42 | deamidation | 959 | 959 | N | exposed | N959Q |
| gp42 | deamidation | 988 | 988 | N | exposed | N988S |
| gp42 | deamidation | 990 | 990 | N | exposed | N990Q |
| ferritin | deamidation | 1150 | 1150 | Q | exposed | Q1150S |
| ferritin | oxidation | 1168 | 1168 | M | buried | M1168I |
| ferritin | deamidation | 1177 | 1177 | M | buried | M1177L |
| ferritin | IsoAsp | 1187 | 1188 | DG | buried | G1188A |
| ferritin | deamidation | 1253 | 1253 | N | exposed | N1253Q |
| ferritin | deamidation | 1296 | 1296 | N | exposed | N1296Q |

H. Immune-Stimulatory Moieties; Adjuvants; Conjugated EBV Polypeptides

In some embodiments, an EBV polypeptide and/or an immune-stimulatory moiety, such as an adjuvant, is attached to a surface-exposed amino acid. In some embodiments, the surface-exposed amino acid is a cysteine, e.g., resulting from a mutation discussed above. In some embodiments, the surface-exposed amino acid is a lysine, aspartate, or glutamate. Conjugation procedures using glutaraldehyde (for conjugation of a lysine with an amino-bearing linker or moiety) or a carbodiimide (e.g., 1-Cyclohexyl-3-(2-morpholin-4-yl-ethyl) carbodiimide or 1-Ethyl-3-(3-dimethyl-aminopropyl) carbodiimide (EDC; EDAC) for conjugating an aspartate or glutamate to an amino-bearing linker or moiety, or a lysine to a carboxyl-bearing linker or moiety) are described in, e.g., Chapter 4 of Holtzhauer, M., Basic Methods for the Biochemical Lab, Springer 2006, ISBN 978-3-540-32785-1, available from www.springer.com.

In some embodiments, an immune-stimulatory moiety, such as an adjuvant, is attached to a surface-exposed amino acid of ferritin. In some embodiments, more than one immune-stimulatory moiety, such as an adjuvant, is attached to a surface-exposed amino acid of ferritin. In some embodiments, twenty-four immune-stimulatory moieties are attached to a ferritin multimer or particle (e.g., one moiety for each monomer in the *H pylori* ferritin particle). In some embodiments with multiple immune-stimulatory moieties attached to a ferritin nanoparticle, all of the immune-stimulatory moieties are identical. In some embodiments with multiple immune-stimulatory moieties attached to a ferritin nanoparticle, all of the immune-stimulatory moieties are not identical.

1. Types of Immune-Stimulatory Moieties; Adjuvants

Any immune-stimulatory moiety that can be attached to a surface-exposed amino acid (e.g., cysteine) can be used in ferritins according to this disclosure. In some embodiments, the immune-stimulatory moiety is a B cell agonist.

In some embodiments, the immune-stimulatory moiety is not hydrophobic. In some embodiments, the immune-stimulatory moiety is hydrophilic. In some embodiments, the immune-stimulatory moiety is polar. In some embodiments, the immune-stimulatory moiety is capable of hydrogen bonding or ionic bonding, e.g., comprises a hydrogen bond donor, hydrogen bond acceptor, cationic moiety, or anionic moiety. A moiety is considered cationic or anionic if it would be ionized in aqueous solution at a physiologically relevant pH, such as pH 6, 7, 7.4, or 8.

In some embodiments, the immune-stimulatory moiety is an adjuvant. In some embodiments, the adjuvant comprises a pathogen associated molecular pattern (PAMP). In some embodiments, the adjuvant is a toll-like receptor (TLR) agonist or stimulator of interferon genes (STING) agonist. In some embodiments, the adjuvant activates TLR signaling in B and/or T cells. In some embodiments, the adjuvant regulates the adaptive immune response.

a) TLR2 Agonists

In some embodiments, the immune-stimulatory moiety is a TLR2 agonist. In some embodiments, the immune-stimulatory moiety stimulates TLR2 signaling. In some embodiments, the immune-stimulatory moiety is a synthetic small molecule ligand of TLR2. In some embodiments, the immune-stimulatory moiety is a synthetic small molecule agonist of TLR2 signaling.

In some embodiments, the TLR2 agonist is PAM2CSK4, FSL-1, or PAM3CSK4.

b) TLR7/8 Agonists

In some embodiments, the immune-stimulatory moiety is a TLR7 and/or TLR8 agonist (i.e., an agonist of at least one of TLR7 and TLR8). In some embodiments, the immune-stimulatory moiety stimulates TLR7 and/or TLR8 signaling. In some embodiments, the immune-stimulatory moiety is a synthetic small molecule ligand of TLR7 and/or TLR8. In some embodiments, the immune-stimulatory moiety is a synthetic small molecule agonist of TLR7 and/or TLR8 signaling.

In some embodiments, the TLR7 and/or TLR8 agonist is single-stranded (ssRNA). In some embodiments, the TLR7 and/or TLR8 agonist is an imidazoquinoline. In some embodiments, the TLR7 and/or TLR8 agonist is a nucleoside analog.

In some embodiments, the TLR7 and/or TLR8 agonist is an imidazoquinolinamine Toll-like receptor (TLR) agonist, such as 3M-012 (3M Pharmaceuticals). The structure of free 3M-012 is:

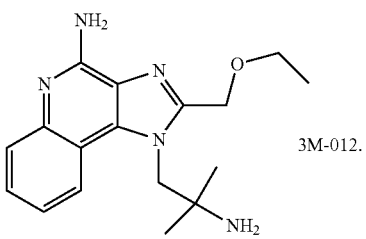 [SMILES: CCOCc1nc2c(N)nc3ccccc3c2n1CC(C)(C)N]

3M-012.

It is understood that an immune-stimulatory moiety such as 3M-012 or any moiety discussed herein can be conjugated to a ferritin by substituting an appropriate peripheral atom of the moiety (e.g., a hydrogen) with a bond to a ferritin described herein, e.g., at the sulfur of a surface-exposed cysteine or a linker attached to such a sulfur. Thus, when conjugated to a ferritin, the structure of the immune-stimulatory moiety will differ slightly from the structure of the free molecule.

In some embodiments the TLR7 and/or TLR8 agonist is SM 7/8a. The structure of free SM 7/8a is:

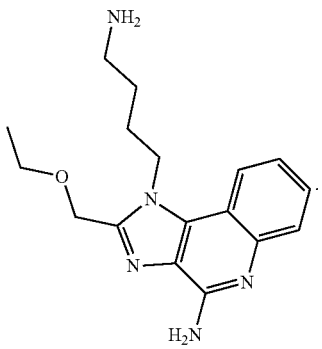 [SMILES: CCOCc1nc2c(N)nc3ccccc3c2n1CCCCN]

See, e.g., Nat Biotechnol. 2015 November; 33(11):1201-10. doi: 10.1038/nbt.3371.

c) TLR9 Agonists

In some embodiments, the immune-stimulatory moiety is a TLR9 agonist. In some embodiments, the immune-stimulatory moiety stimulates TLR9 signaling. In some embodiments, the immune-stimulatory moiety is a synthetic small molecule ligand of TLR9. In some embodiments, the immune-stimulatory moiety is a synthetic small molecule agonist of TLR9 signaling.

In some embodiments, the TLR9 agonist is a CpG oligodeoxynucleotide (ODN). In some embodiments, the TLR9 agonist is an unmethylated CpG ODN. In some embodiments, the CpG ODN comprises a partial or complete phosphorothioate (PS) backbone instead of the natural phosphodiester (PO) backbone found in ordinary DNA.

In some embodiments, the CpG ODN is a Class B ODN, which comprises one or more 6mer CpG motif comprising 5' Purine (Pu)—Pyrimidine (Py)-C-G-Py-Pu 3'; has a fully phosphorothioated (i.e., PS-modified) backbone; and has a length of 18-28 nucleotides. In some embodiments, the CpG ODN comprises the sequence of SEQ ID NO: 210, optionally comprising phosphorothioate linkages in the backbone.

In some embodiments, the TLR9 agonist comprises an immune-stimulatory sequence (ISS). In some embodiments the TLR9 agonist is ISS-1018 (Dynavax) (SEQ ID NO: 210).

d) STING Agonists

In some embodiments, the immune-stimulatory moiety is a STING (Stimulator of Interferon Genes Protein, also known as Endoplasmic Reticulum IFN Stimulator) agonist. In some embodiments, the immune-stimulatory moiety stimulates STING signaling. In some embodiments, the immune-stimulatory moiety is a synthetic small molecule ligand of STING. In some embodiments, the immune-stimulatory moiety is a synthetic small molecule agonist of STING signaling.

In some embodiments the STING agonist is a cyclic dinucleotide (CDN). See, e.g., Danilchanka et al., Cell 154:962-970 (2013). Exemplary CDNs include cdA, cdG, cAMP-cGMP, and 2'-5',3'-5' cGAMP (see Danilchanka et al. for structures). STING agonists also include synthetic agonists such as DMXAA

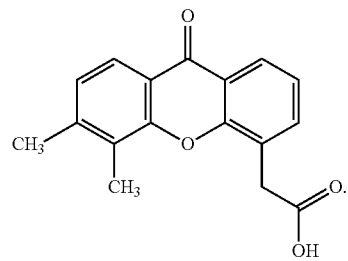 [SMILES: Cc1ccc2c(=O)c3cccc(CC(=O)O)c3oc2c1C]

2. Conjugated EBV Polypeptides

In some embodiments, an EBV polypeptide is conjugated to a surface-exposed amino acid of ferritin. In some embodiments, the EBV polypeptide renders the ferritin protein antigenic. In some embodiments, the EBV polypeptide is antigenic alone, whereas in some embodiments, the EBV polypeptide is antigenic because of its association with ferritin. In some embodiments, the EBV polypeptide is any one of the EBV polypeptides described herein.

3. Conjugation

In some embodiments, a surface-exposed cysteine (e.g., resulting from a mutation described herein) or a cysteine in a peptide linker attached to ferritin (e.g., N-terminally to ferritin) is used to conjugate an immune-stimulatory moiety, such as an adjuvant, or an EBV polypeptide to a ferritin. In some embodiments, a linker is conjugated to such a cysteine, which linker can be subsequently conjugated to an immune-stimulatory moiety, such as an adjuvant, or an EBV polypeptide. In some embodiments, such a cysteine creates a chemical handle for conjugation reactions to attach an adjuvant, linker, or an EBV polypeptide. In some embodiments, bioconjugates are produced, wherein an immune-stimulatory moiety, such as an adjuvant, or an EBV polypeptide is linked to a ferritin after reduction of such a cysteine. In some embodiments, the cysteine is an unpaired surface-exposed cysteine, i.e., that lacks a partner cysteine in an appropriate position to form a disulfide bond. In some embodiments, the cysteine is an unpaired cysteine that comprises a free thiol side chain.

a) Types of Conjugation Chemistries

Any type chemistry can be used to conjugate the immune-stimulatory moiety, such as an adjuvant, or an EBV polypeptide to the ferritin, e.g., via reaction a surface-exposed amino acid such as cysteine or another amino acid such as Lys, Glu, or Asp.

In some embodiments, the conjugation is performed using click chemistry. As used herein, "click chemistry" refers to a reaction between a pair of functional groups that rapidly and selective react (i.e., "click") with each other. In some embodiments, the click chemistry can be performed under mild, aqueous conditions. In some embodiments, a click chemistry reaction takes advantage of a cysteine on the surface of the ferritin, such as a cysteine resulting from mutation of a surface-exposed amino acid, to perform click chemistry using a functional group that can react with the cysteine.

A variety of reactions that fulfill the criteria for click chemistry are known in the field, and one skilled in the art could use any one of a number of published methodologies (see, e.g., Hein et al., Pharm Res 25(10):2216-2230 (2008)). A wide range of commercially available reagents for click chemistry could be used, such as those from Sigma Aldrich, Jena Bioscience, or Lumiprobe. In some embodiments, conjugation is performed using click chemistry as described in the Examples below.

In some embodiments, the click chemistry reaction occurs after reduction of the ferritin.

In some embodiments, the click chemistry may be a 1-step click reaction. In some embodiments, the click chemistry may be a 2-step click reaction.

In some embodiments, the reaction(s) comprises metal-free click chemistry. In some embodiments, the reaction(s) comprise thiol-maleimide and/or disulfide exchange.

Metal-Free Click Chemistry

Metal-free click chemistry can be used for conjugation reactions to avoid potential oxidation of proteins. Metal-free click chemistry has been used to form antibody conjugates (see van Geel et al., Bioconjugate Chem. 2015, 26, 2233-2242).

In some embodiments, metal-free click chemistry is used in reactions to attach adjuvant to ferritin. In some embodiments, copper-free conjugation is used in reactions to attach adjuvant to ferritin. In some embodiments, the metal-free click chemistry uses bicyclo[6.1.0]nonyne (BCN). In some embodiments, the metal-free click chemistry uses dibenzoazacyclooctyne (DBCO). In some embodiments BCN or DBCO reacts with an azide group.

DBCO has high specificity for azide groups via a strain-promoted click reaction in the absence of a catalyst, resulting in high yield of a stable triazole. In some embodiments, DBCO reacts with azide in the absence of copper catalyst.

In some embodiments, metal-free click chemistry is used in a 1-step click reaction. In some embodiments, metal-free click chemistry is used in a 2-step click reaction.

Thiol-Maleimide and Disulfide Exchange

Ferritins described herein can comprise a cysteine comprising a thiol, also known as a sulfhydryl, which is available for reaction with sulfhydryl-reactive chemical groups (or which can be made available through reduction). Thus, the cysteine allows chemoselective modification to add an immune-stimulatory moiety, such as an adjuvant, to the ferritin. Under basic conditions, the cysteine will be deprotonated to generate a thiolate nucleophile, which can react with soft electrophiles, such as maleimides and iodoacetamides. The reaction of the cysteine with a maleimide or iodoacetamide results in a carbon-sulfur bond.

In some embodiments, a sulfhydryl-reactive chemical group reacts with the surface-exposed cysteine or cysteine in the linker of the ferritin. In some embodiments, the sulfhydryl-reactive chemical group is a haloacetyl, maleimide, aziridine, acryloyl, arylating agent, vinylsulfone, pyridyl disulfide, or TNB-thiol.

In some embodiments, the sulfhydryl-reactive chemical group conjugates to the sulfhydryl of the cysteine by alkylation (i.e., formation of a thioether bond)). In some embodiments, the sulfhydryl-reactive chemical group conjugates to the sulfhydryl of the cysteine by disulfide exchange (i.e., formation of a disulfide bond).

In some embodiments, the reaction to conjugate an immune-stimulatory moiety, such as an adjuvant, to the ferritin is a thiol-maleimide reaction.

In some embodiments, the sulfhydryl-reactive chemical group is a maleimide. In some embodiments, reaction of a maleimide with the cysteine results in formation of a stable thioester linkage, e.g., that is not reversible. In some embodiments, the maleimide does not react with tyrosines, histidines, or methionines in the ferritin. In some embodiments, unreacted maleimides are quenched at the end of the reaction by adding a free thiol, e.g., in excess.

In some embodiments, the reaction to conjugate an immune-stimulatory moiety, such as an adjuvant, to the ferritin is a thiol-disulfide exchange, also known as a disulfide interchange. In some embodiments, the reaction involves formation of a mixed disulfide comprising a portion of the original disulfide. In some embodiments, the original disulfide is the cysteine introduced in the ferritin by mutation of a surface-exposed amino acid or addition of an N-terminal linker.

In some embodiments, the sulfhydryl-reactive chemical group is a pyridyl dithiol. In some embodiments, the sulfhydryl-reactive chemical group is a TNB-thiol group.

b) Linkers

In some embodiments, an immune-stimulatory moiety, such as an adjuvant, or an EBV polypeptide is attached to the ferritin via a linker that is covalently bound to a surface-exposed amino acid such as a cysteine. In some embodiments, the linker comprises a polyethylene glycol, e.g., a PEG linker. In some embodiments, the polyethylene glycol (e.g., PEG) linker increases water solubility and ligation efficiency of the ferritin linked to the immune-stimulatory moiety, such as an adjuvant. The PEG linker is between 2 and 18 PEGs long, e.g., PEG4, PEG5, PEG6, PEG7, PEG8, PEG9, PEG10, PEG11, PEG12, PEG13, PEG14, PEG15, PEG16, PEG17, and PEG18.

In some embodiments, the linker comprises a maleimide. In some embodiments, the linker comprises the components of immune-stimulatory moiety (ISM)—linker-maleimide. In some embodiments, the ISM-linker-maleimide is conjugated to ferritin in a 1-step click chemistry reaction by reaction of the maleimide with a cysteine of the ferritin. In some embodiments, the ISM of the adjuvant-linker-maleimide is SM7/8a. In some embodiments, the linker of the ISM-linker-maleimide is PEG4. In some embodiments, the ISM-linker-maleimide is SM7/8a-PEG4-maleimide.

In some embodiments, a 2-step click chemistry protocol is used with a linker comprising a sulfhydryl-reactive chemical group at one end and an amine-reactive group at the other end. In such a 2-step click chemistry protocol, a sulfhydryl-reactive chemical group reacts with a cysteine of the ferritin, while the amine-reactive group reacts with a reagent attached to the ISM. In this way, the ISM is conjugated to the ferritin via a set of 2 click chemistry reagents.

In some embodiments of the 2-step click chemistry protocol, the sulfhydryl-reactive chemical group is maleimide. In some embodiments of the 2-step click chemistry protocol, the maleimide reacts with the cysteine introduced in the ferritin by mutation of a surface-exposed amino acid or addition of an N-terminal linker.

In some embodiments of the 2-step click chemistry protocol, the amine-reactive group is DBCO. In some embodiments of the 2-step click chemistry protocol, the DBCO reacts with an azide group attached to an ISM.

In some embodiments, a maleimide-linker-DBCO is used. In some embodiments, the maleimide-linker-DBCO is conjugated to ferritin after the ferritin is reduced. In some embodiments, the maleimide-linker-reagent is conjugated to ferritin by reaction of the maleimide with the cysteine of the ferritin in a first step. In some embodiments, the DBCO is used to link to an ISM attached to azide. In some embodiments, the ISM coupled to azide is ISS-1018. In some embodiments, the adjuvant coupled to azide is 3M-012 or CpG.

In some embodiments, a linker with a reactive group is added to the ISM. In some embodiments, the linker is a PEG4-azide linker or a PEG4-maleimide linker.

In some embodiments, a PEG4-azide linker is conjugated to 3M-012. An exemplary structure of 3M-012 conjugated to a PEG4-azide linker is:

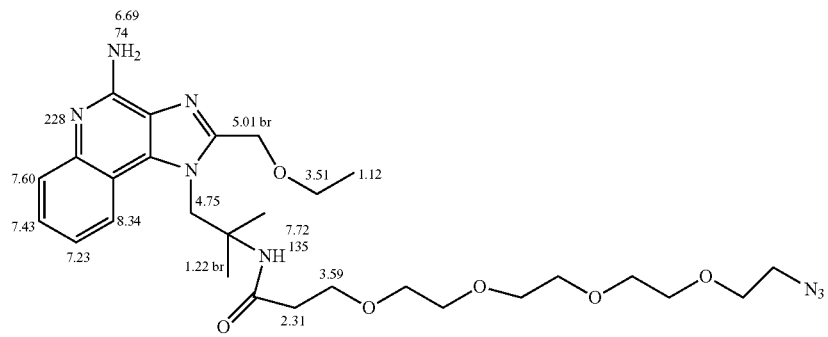 [SMILES: CCOCc1nc2c(N)nc3ccccc3c2n1CC(C)(C)NC(=O)CCOCCOCCOCCOCCN=[N+]=[N-]]

In some embodiments, a PEG4-azide linker is conjugated to SM7/8a. An exemplary structure of SM7/8a conjugated to a PEG4-azide linker is:

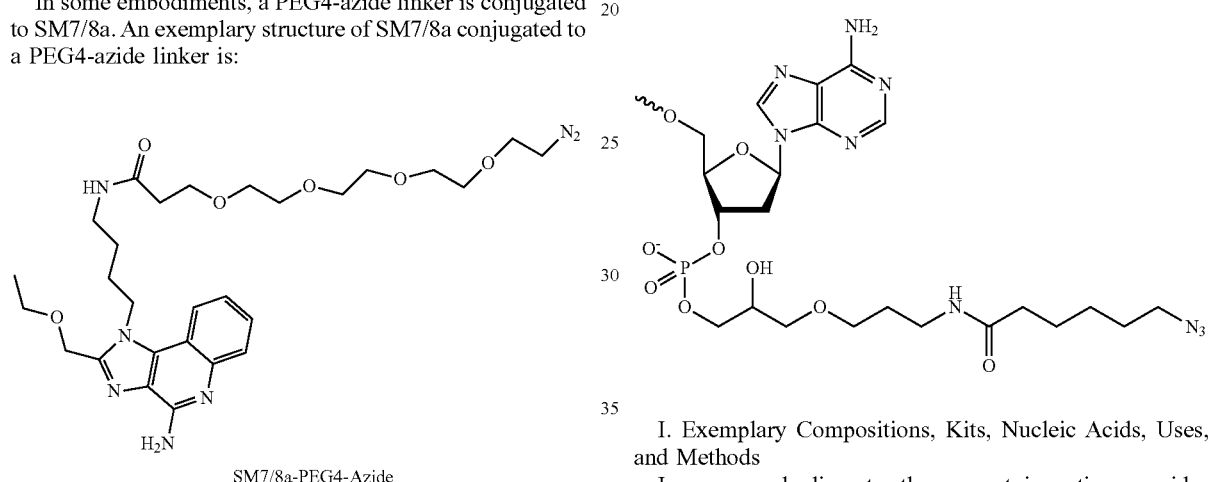

SM7/8a-PEG4-Azide

In some embodiments, a PEG4-maleimide linker is conjugated to SM7/8a. An exemplary structure of SM7/8a conjugated to a PEG4-maleimide linker is:

SM7/8a-PEG4-Maleimide

In some embodiments, an azide group is conjugated to ISS-1018. An exemplary structure of ISS-1018 conjugated to an NHS ester-azide linker is:

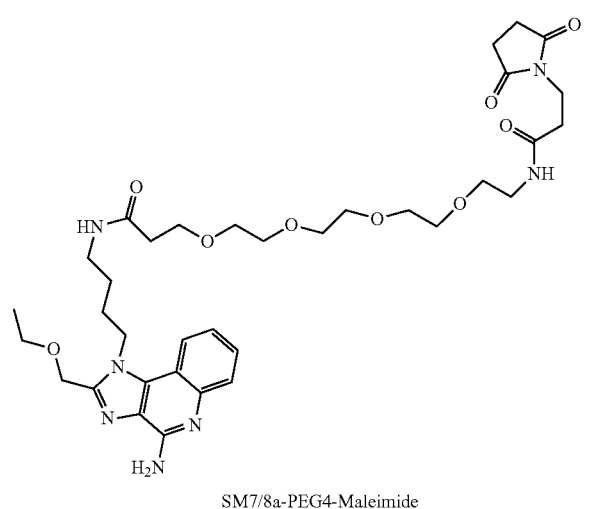 [SMILES: CCOCc1nc2c(N)nc3ccccc3c2n1CCCCNC(=O)CCOCCOCCOCCOCCNC(=O)CCN1C(=O)CCC1=O]

I. Exemplary Compositions, Kits, Nucleic Acids, Uses, and Methods

In some embodiments, the present invention provides methods of immunizing a subject against infection with EBV. The present invention further provides methods of eliciting an immune response against EBV in a subject. In some embodiments, the present methods comprise administering to the subject an effective amount of a pharmaceutical composition described herein to a subject. In some embodiments, the present methods comprises administering to the subject an effective amount of an antigenic EBV polypeptide or nanoparticle described herein to a subject.

In some embodiments, a composition comprising any one or more of the antigenic EBV polypeptides described herein and a pharmaceutically acceptable vehicle, adjuvant, or excipient is provided.

In some embodiments, an antigenic EBV polypeptide, nanoparticle, or composition described herein is administered to a subject, such as a human or any of the subjects discussed below, to immunize against infection caused by EBV. In some embodiments, an antigenic EBV polypeptide or nanoparticle described herein is administered to a subject, such as a human, to produce a protective immune response to future infection with EBV. In some embodiments, an antigenic EBV polypeptide is administered. In some embodiments, an antigenic EBV polypeptide comprising an EBV polypeptide and ferritin is administered, wherein the ferritin can have one or more mutations described herein. In some embodiments, an antigenic EBV polypeptide or nanoparticle comprising any one of SEQ ID NOS: 1-27 is administered.

In some embodiments, the protective immune response decreases the incidence of hospitalization. In some embodiments, the protective immune response decreases the incidence of EBV infection, mononucleosis, complications caused by mononucleosis (e.g. hepatitis, encephalitis, severe hemolytic anemia, or splenomegaly), nasopharyngeal cancer, gastric cancer, or B lymphoma (e.g., Burkitt's or Hodgkin's lymphoma).

In some embodiments, a composition comprises one antigenic EBV polypeptide (e.g., a monovalent composition). In some embodiments, a composition comprises an antigenic EBV polypeptide comprising a gH polypeptide. In some embodiments, a composition comprises an antigenic EBV polypeptide comprising a gL polypeptide. In some embodiments, a composition comprises an antigenic EBV polypeptide comprising a gp220 polypeptide.

In some embodiments, a composition comprises more than one antigenic EBV polypeptide. In some embodiments, a composition comprises one or more antigenic EBV polypeptides comprising more than one polypeptide encoded by EBV (i.e., a multivalent composition). In some embodiments, an EBV vaccine comprises nanoparticles comprising a gp220 polypeptide and, separately, nanoparticles comprising gH and gL polypeptides.

In some embodiments, any one or more of the antigenic EBV polypeptides, nanoparticles, or compositions described herein are provided for use in immunizing against infection caused by EBV. In some embodiments, any one or more of the polypeptides, nanoparticles, or compositions described herein are provided for use in producing a protective immune response to future infection with EBV.

1. Subjects

In some embodiments, the subject is a mammal. In some embodiments, the subject is a human.

In some embodiments, the subject is an adult (greater than or equal to 18 years of age). In some embodiments, the subject is a child or adolescent (less than 18 years of age). In some embodiments, the subject is elderly (greater than 60 years of age). In some embodiments, the subject is a non-elderly adult (greater than or equal to 18 years of age and less than or equal to 60 years of age).

In some embodiments, the composition is suitably formulated for an intended route of administration. Examples of suitable routes of administration include intramuscular, transcutaneous, subcutaneous, intranasal, oral, or transdermal.

In some embodiments, more than one administration of the composition is administered to the subject. In some embodiments, a booster administration improves the immune response.

In some embodiments, any one or more of the antigenic polypeptides, or compositions described herein are for use in a mammal, such as a primate (e.g., non-human primate, such as a monkey (e.g., a macaque, such as rhesus or cynomolgus) or ape), rodent (e.g., mouse or rat), or domesticated mammal (e.g., dog, rabbit, cat, horse, sheep, cow, goat, camel, or donkey).

2. Adjuvants

An adjuvant may be administered together with the antigenic EBV polypeptides and/or nanoparticles described herein to a subject, wherein administration of such a combination may produce a higher titer of antibodies against the EBV polypeptide(s) in the subject as compared to administration of the EBV poly peptide(s) without the adjuvant. An adjuvant may promote earlier, more potent, or more persistent immune response to the EBV polypeptide(s).

In some embodiments, a composition comprises one adjuvant. In some embodiments, a composition comprises more than one adjuvant. In some embodiments, a composition does not comprise an adjuvant.

In some embodiments, an adjuvant comprises aluminum. In some embodiments, an adjuvant is aluminum phosphate. In some embodiments, an adjuvant is Alum (Alyhydrogel '85 2%; Brenntag-Cat #21645-51-2).

In some embodiments, an adjuvant is an organic adjuvant. In some embodiments, an adjuvant is an oil-based adjuvant. In some embodiments, an adjuvant comprises an oil-in-water nanoemulsion.

In some embodiments, an adjuvant comprises squalene. In some embodiments, the adjuvant comprising squalene is Ribi (Sigma adjuvant system Cat #S6322-1v1), Addavax™ MF59, AS03, or AF03 (see U.S. Pat. No. 9,703,095). In some embodiments, the adjuvant comprising squalene is a nanoemulsion.

In some embodiments, an adjuvant comprises a polyacrylic acid polymer (PAA). In some embodiments, the adjuvant comprising PAA is SPA09 (see WO 2017218819).

In some embodiments, an adjuvant comprises non-metabolizable oils. In some embodiments, the adjuvant is Incomplete Freund's Adjuvant (IFA).

In some embodiments, an adjuvant comprises non-metabolizable oils and killed *Mycobacterium tuberculosis*. In some embodiments, the adjuvant is Complete Freund's Adjuvant (CFA).

In some embodiments, an adjuvant is a lipopolysaccharide. In some embodiments, an adjuvant is monophosphoryl A (MPL or MPLA).

3. Pharmaceutical Compositions

In various embodiments, a pharmaceutical composition comprising an antigenic EBV polypeptide described herein and/or related entities is provided. In some embodiments, the pharmaceutical composition is an immunogenic composition (e.g., a vaccine) capable of eliciting an immune response such as a protective immune response against a pathogen.

For example, in some embodiments, the pharmaceutical compositions may comprise one or more of the following: (1) an antigenic EBV polypeptide comprising an EBV polypeptide and a ferritin comprising a mutation replacing a surface-exposed amino acid with a cysteine; (2) an antigenic EBV polypeptide comprising an EBV polypeptide and a ferritin comprising a mutation replacing a surface exposed amino acid with a cysteine and an immune-stimulatory moiety linked to the cysteine; (3) an antigenic EBV polypeptide comprising an EBV polypeptide and a ferritin comprising (i) a surface-exposed cysteine, (ii) a peptide linker N-terminal to the ferritin protein, wherein the EBV polypeptide is N-terminal to the peptide linker; (4) an antigenic EBV polypeptide comprising an EBV polypeptide and a ferritin comprising (i) a mutation replacing a surface exposed amino acid with a cysteine and an immune-stimulatory moiety linked to the cysteine, (ii) a mutation replacing the internal cysteine at position 31 of *H. pylori* ferritin, or a mutation of an internal cysteine at a position that is analogous to position 31 of a non-*H. pylori* ferritin as determined by pair-wise or structural alignment, with a non-cysteine amino acid, and (iii) a mutation replacing a surface-exposed asparagine with a non-asparagine amino acid; or (5) a ferritin particle comprising any of the foregoing polypeptides. In some embodiments, the pharmaceutical compositions may comprise an antigenic EBV gL/gH polypeptide, e.g., wherein the polypeptide comprises a linker of at least 15 amino acids between the gL and gH polypeptide sequences.

In some embodiments, the present invention provides pharmaceutical compositions comprising antibodies or other agents related to the antigenic polypeptides described herein. In an embodiment, the pharmaceutical composition comprises antibodies that bind to and/or compete with an antigenic polypeptide described herein. Alternatively, the antibodies may recognize viral particles or bacteria comprising the non-ferritin polypeptide component of an antigenic polypeptide described herein.

In some embodiments, the pharmaceutical compositions as described herein are administered alone or in combination with one or more agents to enhance an immune response, e.g., an adjuvant described above. In some embodiments, a pharmaceutical composition further comprises an adjuvant described above.

In some embodiments, the pharmaceutical composition further comprises a pharmaceutically acceptable carrier or excipient. As used herein, the term "carrier" refers to a diluent, adjuvant, excipient, or vehicle with which a pharmaceutical composition is administered. In exemplary embodiments, carriers can include sterile liquids, such as, for example, water and oils, including oils of petroleum, animal, vegetable, or synthetic origin, such as, for example, peanut oil, soybean oil, mineral oil, sesame oil and the like. In some embodiments, carriers are or include one or more solid components. Pharmaceutically acceptable carriers can also include, but are not limited to, saline, buffered saline, dextrose, glycerol, ethanol, and combinations thereof. As used herein, an excipient is any non-therapeutic agent that may be included in a pharmaceutical composition, for example to provide or contribute to a desired consistency or stabilizing effect. Suitable pharmaceutical excipients include, but are not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In various embodiments, the pharmaceutical composition is sterile.

In some embodiments, the pharmaceutical composition contains minor amounts of wetting or emulsifying agents, or pH buffering agents. In some embodiments, the pharmaceutical compositions of may include any of a variety of additives, such as stabilizers, buffers, or preservatives. In addition, auxiliary, stabilizing, thickening, lubricating, and coloring agents can be included.

In various embodiments, the pharmaceutical composition may be formulated to suit any desired mode of administration. For example, the pharmaceutical composition can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. General considerations in the formulation and manufacture of pharmaceutical agents may be found, for example, in Remington's Pharmaceutical Sciences, 19th ed., Mack Publishing Co., Easton, Pa., 1995; incorporated herein by reference.

The pharmaceutical composition can be administered via any route of administration. Routes of administration include, for example, oral, intradermal, intramuscular, intraperitoneal, intravenous, subcutaneous, intranasal, mucosal, epidural, sublingual, intranasal, intracerebral, intravaginal, transdermal, rectally, by intratracheal installation, bronchial instillation, inhalation, or topically. Administration can be local or systemic. In some embodiments, administration is carried out orally. In another embodiment, the administration is by parenteral injection. In some instances, administration results in the release of the antigenic ferritin polypeptide described herein into the bloodstream. The mode of administration can be left to the discretion of the practitioner.

In some embodiments, the pharmaceutical composition is suitable for parenteral administration (e.g. intravenous, intramuscular, intraperitoneal, and subcutaneous). Such compositions can be formulated as, for example, solutions, suspensions, dispersions, emulsions, and the like. They may also be manufactured in the form of sterile solid compositions (e.g. lyophilized composition), which can be dissolved or suspended in sterile injectable medium immediately before use. For example, parenteral administration can be achieved by injection. In such embodiments, injectables are prepared in conventional forms, i.e., either as liquid solutions or suspensions, solid forms suitable for solution or suspension in liquid prior to injection, or as emulsions. In some embodiments, injection solutions and suspensions are prepared from sterile powders, lyophilized powders, or granules.

In a further embodiment, the pharmaceutical composition is formulated for delivery by inhalation (e.g., for direct delivery to the lungs and the respiratory system). For example, the composition may take the form of a nasal spray or any other known aerosol formulation. In some embodiments, preparations for inhaled or aerosol delivery comprise a plurality of particles. In some embodiments, such preparations can have a mean particle size of about 1, about 2, about 3, about 4, about 5, about 6, about 7, about 8, about 9, about 10, about 11, about 12, or about 13 microns. In some embodiments, preparations for inhaled or aerosol delivery are formulated as a dry powder. In some embodiments, preparations for inhaled or aerosol delivery are formulated as a wet powder, for example through inclusion of a wetting agent. In some embodiments, the wetting agent is selected from the group consisting of water, saline, or other liquid of physiological pH.

In some embodiments, the pharmaceutical composition in accordance with the invention are administered as drops to the nasal or buccal cavity. In some embodiments, a dose may comprise a plurality of drops (e.g., 1-100, 1-50, 1-20, 1-10, 1-5, etc.).

The present pharmaceutical composition may be administered in any dose appropriate to achieve a desired outcome. In some embodiments, the desired outcome is the induction of a long-lasting adaptive immune response against a pathogen, such as the source of a non-ferritin polypeptide present in an antigenic ferritin polypeptide present in the composition. In some embodiments, the desired outcome is a reduction in the intensity, severity, frequency, and/or delay of onset of one or more symptoms of infection. In some embodiments, the desired outcome is the inhibition or prevention of infection. The dose required will vary from subject to subject depending on the species, age, weight, and general condition of the subject, the severity of the infection being prevented or treated, the particular composition being used, and its mode of administration.

In some embodiments, pharmaceutical compositions in accordance with the invention are administered in single or multiple doses. In some embodiments, the pharmaceutical compositions are administered in multiple doses administered on different days (e.g., prime-boost vaccination strategies). In some embodiments, the pharmaceutical composition is administered as part of a booster regimen.

In various embodiments, the pharmaceutical composition is co-administered with one or more additional therapeutic agents. Co-administration does not require the therapeutic agents to be administered simultaneously, if the timing of their administration is such that the pharmacological activities of the additional therapeutic agent and the active ingredient(s) in the pharmaceutical composition overlap in time, thereby exerting a combined therapeutic effect. In general, each agent will be administered at a dose and on a time schedule determined for that agent.

4. Nucleic Acid/mRNA

Also provided is a nucleic acid encoding an antigenic EBV polypeptide described herein. In some embodiments, the nucleic acid is an mRNA. Any nucleic acid capable of undergoing translation resulting in a polypeptide is considered an mRNA for purposes of this disclosure.

5. Kits

Also provided herein are kits comprising one or more antigenic EBV polypeptides, nucleic acids, antigenic ferritin particles, antigenic lumazine synthase particles, compositions, or pharmaceutical compositions described herein. In some embodiments, a kit further comprises one or more of a solvent, solution, buffer, instructions, or desiccant.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. "About" indicates a degree of variation that does not substantially affect the properties of the described subject matter, e.g., within 10%, 5%, 2%, or 1%. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed considering the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items. The term "or" is used in the inclusive sense, i.e., equivalent to "and/or," unless the context dictates otherwise.

TABLE 2

(SEQUENCE TABLE): DESCRIPTION OF THE SEQUENCES

| Description | Sequences | SEQ ID NO |
|---|---|---|
| | Key for SEQ ID NOs: 1-41<br>Leader Sequence – underlined<br>gL – *Italicized*<br>Linker – double underlined<br>gH – Bold<br>bfpFerr (ferritin) – wavy underline<br>FR – *Italicized and double underline*<br>gp220 – Italicized and bold<br>gp42 – *Italicized and underlined*<br>T. ni ferritin heavy chain – double wavy underline<br>Foldon sequence: *Italicized and wavy underline*<br>Thrombin cleavage site: *Italicized and dashed underline*<br>6X His Tag (SEQ ID NO: 243): Bold, italicized and curvy underline | |
| SIB 7187 | MDSKGSSQKGSRLLLLLVSNLLPQGVL*ARAALLVCQYTIQSLIHLTGEDPGFFNVEIPEFPFYPTCNVCTADVNVTINFDVGGKKH*<br>*QLDLDFGQLTPHTKAVYQPRGAFGGSENATNLFILELLGAGELALTMRSKKLPINVTTGEEQQVSLESVDVYFQDVFGTMWCHHAEMQ*<br>*NPVYLIPETVPFYIKWDNCNSTNITAVVRAQGLDVTLPLSLPTSAQDSNFSVKTEMLGNEIDIECIMEDGEISQVLPGDNKFNITCSGY*<br>*ESHVPSGGIILTSTSPVATPIPGTYAYSLRLITPRPVSRFLGNNSILYVFYSGNGPKASGGDYCIQSNIVFSDEIPASQDMPTNTTDIT*<br>*YVGDNATYSVRMVTSEDANSPNVTVTAFWAWPNNTETDFKCKWTLTSGTPSGCENISGAFASNRTFDITVSGLGTARKTLIITRTATN*<br>*ATTTHKVIFSKAPE*GSESQVRQQFSKDIEKLLNEQVNKEMQSSNLIYMSMSWSYTHSLDGAGLFLFDHAABEYEHAKKLIIFLNENN<br>VPVQLTSISAPEHKFEGLTQIPQKAYEHEQHISESINNIVDHAIKCKDHATPNFLQWYVAEQHEEEVLFKDILDKIELIGNENHGLYLY<br>ADQYVKGIAKSRKS | 1 |
| leader sequence | MRAVGVPLAICLVTIFVLPTWGNWAYPCCHVTQLRAOHLLALENISDIYLVSNOTCDGFSLASLNSPKNGSNOLVISRCANGLNVVSF | 2 |
| gL(D7)_linker_gH | *FISILKRSSSALTGHLRELLITLETLYGSFSVEDLFGANLNRGGSGSASGSASGSSNGSGSGSGSNSSASSGASSGASSGGSGSG*<br>AASLSEVKLHLDIEGHASHYTIPWTELMAKVPGLSPEALWREANVTEDLASMLNRYKLIYKTSGTLGLALAEPVDIPAVSEGSMQVDA | |
| bfpFerr | SKVHPGVISGLNSPACMLSAPLEKQLFYYIGTMLPNTRPHSYVFYQLRCHLSYVALSINGDKFQTTGAMTSKFLMGTYKRVTEKGDEH<br>VLSLVFGKTKDLPDLRGPFSYPSLITSAQSGDYSLVIVTTFVHYANFHNYFVPNLKDMFSRAVTMTAASYARYVLQKLVLLEMKGGCRE<br>PELDTETLTTMFEVSVAFFKVGHAVGETGNGCVDLRWLAKSFFELTVLKDIIGICYGATVKGMQSYGLERLAAMLMATVKMEELGHLT | |
| Nanoparticle | TEKQEYALRLATVGYPKAGVYSGLIGGATSVLLSAYNRHPLFQPLHTVMRETLFIGSHVVLRELRLNVTTQGPNLALYLQLLSTALCSA<br>LEIGEVLRGLALGTESGLFSPCYLSLRFDLTRDKLLSMAPQEATLDQAAVSNAVDGFLGRLSLEREDRDAWHLPAYKCVDRLDKVLMI | |
| N19Q/C31S/S111C | IPLINVTFIISSDREVRGSALYEASTTYLSSSLFLSPVIMNKCSQQAVAGEPRQIPKIQNFTRTQKSCIFCGFALLSYDEKEGLETTT | |

TABLE 2-continued (SEQUENCE TABLE): DESCRIPTION OF THE SEQUENCES

| Description | Sequences | SEQ ID NO |
|---|---|---|
| SIB 7342 leader sequence gL(D7)_linker_gH bfpFerr Nanoparticle | NGTVMEIAGLYERASGGGSGGGSGGGSESQVRQQFSKDIEKLLNEQVNKEMQSSNLYMSMSSWSYTHSLDGAGLFLFDH<br>AAEEYEHAKKLIIFLNENNVPVQLTSISAPEHKFEGLTQIFQKAYEHEQHISESINNIVDHAIKCKDHATNFLQWYVAEQHEEEVLF<br>KDILDKIELIGNENHGLYLADQYVKGIAKSRKS | 3 |
| N19Q/C31S/S111C | METDLLLMVLLLMVPGSTGNWAYPCCHVTQLRAQHLLALENISDIYLVSNQTCDGFSLASLNSPKNGSNQLVISRCANGLNVVSFFI<br>SILKRSSSALTGHLRELITTLETLYGSFSVEDLFGANLNRGGSGSGSGGSGGSGGSGAASLSEVKLHLDIEGHASHYTIPWTELMAKV<br>PGLSPEALWREANVTEDLASMLNRYKLIYKTSGTLGIALAEPVDIPAVSEGSMQVDASKVHPGVISGLNSPACMLSAPLEKQLFYYIG<br>TMLPNTRPHSVTFYQLRCHLSYVALSINGDKFQYTGAMTSKFLMGTYKRVTEKGDEHVLSLVFGKTKDLPDLRGFPSYPSLTSAQSGD<br>YSLVIVTTFVHYANFHNYFVPNLKDMFSRAVTMTAASYARYVLQKIVLLEMKGGCREPELDTETLTTMFEVSVAFFKVGHAVGETGNG<br>CVDLRWLAKSFFELTVLKDIIGICYGATVKGMQSYGLERLAAMLMATVKMEELGHLTTEKQEYALRLATVGYPKAGVYSGLIGGATSV<br>LLSAYNRHPLFQPLHTVMRETLFIGSHVVLRELRLNVTTQGPNLALYQLLSTALCSALEIGEVLRGLALGTESGLFSPCYLSLRFDLT<br>RDKLLSMAPQEATLDQAAVSNAVDGFLGRLSLEREDRDAWHLPAYKCVDRLDKVLMIIPLINVTFIISSDREVRGSALYEASTTYLSS<br>SLFLSPVIMNKCSQGAVAGEPRQIPKIQNFTRTQKSCIFCGFALLSYDEKEGLETTYITSQEVQNSILSSNYFDFDNLHVHYLLLTT<br>NGTVMEIAGLYERASGGGSGGGSGGGSESQVRQQFSKDIEKLLNEQVNKEMQSSNLYMSMSSWSYTHSLDGAGLFLFDH<br>AAEEYEHAKKLIIFLNENNVPVQLTSISAPEHKFEGLTQIFQKAYEHEQHISESINNIVDHAIKCKDHATNFLQWYVAEQHEEEVLF<br>KDILDKIELIGNENHGLYLADQYVKGIAKSRKS | |
| SIB 7379 leader sequence gL(D7)_linker_gH Trimer | MRAVGVFLAICLVTIFVLPTWGNWAYPCCHVTQLRAQHLLALENISDIYLVSNQTCDGFSLASLNSPKNGSNQLVISRCANGLNVVSF<br>FISILKRSSSALTGHLRELITTLETLYGSFSVEDLFGANLNRGGSGSGASAGSSNGGSGSGSNSSASGASSGASSGASGGGSGSG<br>AASLSEVKLHLDIEGHASHYTIPWTELMAKVPGLSPEALWREANVTEDLASMLNRYKLIYKTSGTLGIALAEPVDIPAVSEGSMQVDA<br>SKVHPGVISGLNSPACMLSAPLEKQLFYYIGTMLPNTRPHSVTFYQLRCHLSYVALSINGDKFQYTGAMTSKFLMGTYKRVTEKGDEH<br>VLSLVFGKTKDLPDLRGFPSYPSLTSAQSGDYSLVIVTTFVHYANFHNYFVPNLKDMFSRAVTMTAASYARYVLQKIVLLEMKGGCRE<br>PELDTETLTTMFEVSVAFFKVGHAVGETGNGCVDLRWLAKSFFELTVLKDIIGICYGATVKGMQSYGLERLAAMLMATVKMEELGHLT<br>TEKQEYALRLATVGYPKAGVYSGLIGGATSVLLSAYNRHPLFQPLHTVMRETLFIGSHVVLRELRLNVTTQGPNLALYQLLSTALCSA<br>LEIGEVLRGLALGTESGLFSPCYLSLRFDLTRDKLLSMAPQEATLDQAAVSNAVDGFLGRLSLEREDRDAWHLPAYKCVDRLDKVLMI<br>IPLINVTFIISSDREVRGSALYEASTTYLSSSLFLSPVIMNKCSQGAVAGEPRQIPKIQNFTRTQKSCIFCGFALLSYDEKEGLETTT | 4 |

TABLE 2-continued (SEQUENCE TABLE): DESCRIPTION OF THE SEQUENCES

| Description | Sequences | SEQ ID NO |
|---|---|---|
| | YITSQEVQNSILSSNYFDFDNLHVHYLLLTTNGTVMEIAGLYEERASGSGYIPEAPRDGQAYVRKDGEWLLSTFLGSGSGLVPRG<br>SGAGGGHHHHHH | |
| SIB 7380<br>leader sequence<br>gL(D7)_linker_gH<br>Trimer | METDTLLLWVLLLWVPGSTGNWAYPCCHVTQLRAQHLLALENISDIYLVSNQTCDGFSLASLNSPKNGSQLVISRCANGLNVVSFFI<br>SILKRSSSALTGHLRELLTTLETLYGSFSVEDLFGANLNRGGSGGGGSGGGGSGAASLSEVKLHLDIEGHASHYTIPWTELMAKV<br>PGLSPEALWREANVTEDLASMLNRYKLIYKTSGTLGIALAEPVDIPAVSEGSMQVDASKVHPGVISGLNSPACMLSAPLEKQLFYYIG<br>TMLPNTRPHSVFYQLRCHLSYVALSINGDKFQYTGAMTSKFLMGTYKRVTEKGDEHVLSLVFGKTKDLPDLRGPFSYPSLTSAQSGD<br>YSLVIVTTFVHYANFHNYFVPNLKDMFSRAVTMTAASYARYVLQKLVLLEMKGGCREPELDTETLTTMFEVSVAFFKVGHAVGETGNG<br>CVDLRWLAKSFFELTVLKDIIGICYGATVKGMQSYGLERLAAMLMATVKMEELGHLTTEKQEYALRLATVGYPKAGVYSGLIGGATSV<br>LLSSAYNRHPLFQPLHTVMRETLFIGSHVVLRELRLNVTTQGPNLALIYQLLSTALCSALEIGEVLRGLALGTESGLFSPCYLSLRFDLT<br>RDKLLSMAPQEATLDQAAVSNAVDGFLGRLSLEREDRDAWHLPAYKCVDRLDKVLMIIPLINVTFIISSDREVRGSALYEASTTYLSS<br>SLFLSPVIMNKCSQGAVAGEPRQIPKIQNFTRTQKSCIFCGFALLSYDEKEGLETTYITSQEVQNSILSSNYFDFDNLHVHYLLLTT<br>NGTVMEIAGLYEERASGSGYIPEAPRDGQAYVRKDGEWLLSTFLGSGSGLVPRGSGAGGGHHHHHH | 5 |
| SIB 7381<br>leader sequence<br>gL(D7)_linker_gH<br>Monomer | MRAVGVPLAICLVTIFVLPTWGNWAYPCCHVTQLRAQHLLALENISDIYLVSNQTCDGFSLASLNSPKNGSNQLVISRCANGLNVVSF<br>FISILKRSSSALTGHLRELLTTLETLYGSFSVEDLFGANLNRGGSGSGSASSGASASGSNSGSGSGSNSSASSGASSGASGGSASGGSGSG<br>AASLSEVKLHLDIEGHASHYTIPWTELMAKVPGLSPEALWREANVTEDLASMLNRYKLIYKTSGTLGIALAEPVDIPAVSEGSMQVDA<br>SKVHPGVISGLNSPACMLSAPLEKQLFYYIGTMLPNTRPHSVFYQLRCHLSYVALSINGDKFQYTGAMTSKFLMGTYKRVTEKGDEH<br>VLSLVFGKTKDLPDLRGPFSYPSLTSAQSGDYSLVIVTTFVHYANFHNYFVPNLKDMFSRAVTMTAASYARYVLQKLVLLEMKGGCRE<br>PELDTETLTTMFEVSVAFFKVGHAVGETGNGCVDLRWLAKSFFELTVLKDIIGICYGATVKGMQSYGLERLAAMLMATVKMEELGHLT<br>TEKQEYALRLATVGYPKAGVYSGLIGGATSVLLSAYNRHPLFQPLHTVMRETLFIGSHVVLRELRLNVTTQGPNLALYQLLSTALCSA<br>LEIGEVLRGLALGTESGLFSPCYLSLRFDLTRDKLLSMAPQEATLDQAAVSNAVDGFLGRLSLEREDRDAWHLPAYKCVDRLDKVLMI<br>IPLINVTFIISSDREVRGSALYEASTTYLSSSLFLSPVIMNKCSQGAVAGEPRQIPKIQNFTRTQKSCIFCGFALLSYDEKEGLETTT<br>YITSQEVQNSILSSNYFDFDNLHVHYLLLTTNGTVMEIAGLYEERASGSGSGSGLVPRGSGAGGGHHHHHH | 6 |

TABLE 2-continued (SEQUENCE TABLE): DESCRIPTION OF THE SEQUENCES

| Description | Sequences | SEQ ID NO |
|---|---|---|
| SIB 7382 leader sequence gL(D7)_linker_gH Monomer | METDTLLLMWLLLWVPGSTGNWAYPCCHVTQLRAQHLLALENISDIYLVSNQTCDGFSLASLNSPKNGSNQLVISRCANGLNVVSFFI SILKRSSSALTGHLRELLITLETLYGSFSVEDLFGANLNRGGSGGGSGGGSGGGSGAASLSEVKLHLDIEGHASHYTIPWTELMAKV PGLSPEALWREANVTEDLASMLNRYKLIYKTSGTLGIALAEPVDIPAVSEGSMQVDASKVHPGVISGLNSPACMLSAPLEKQLFYYIG TMLPNTRPHSVVFYQLRCHLSVALSINGDKFQYTGAMTSKFLMGTYKRVTEKGDEHVLSLVFGKTKDLPLRGPFSYPSLTSAQSGD YSLVIVTTFVHYANFHNYFVPNLKDMFSRAVTMTAASYARYVLQKLVLLEMKGGCREPELDTETLTTMFEVSVAFFKVGHAVGETGNG CVDLRWLAKSFFELTVLKDIIGICYGATVKGMQSYGLERLAAMLMATVKMEELGHLTTEKQEYALRLATVGYPKAGVYSGLIGGATSV LLSAYNRHPLFQPLHTVMRETLFIGSHVVLRELRLNVTTQGPNLALYQLLSTALCSALEIGEVLRGLALGTESGLFSPCYLSLRFDLT RDKLLSMAPQEATLDQAAVSNAVDGFLGRLSLEREDRDAWHLPAYKCVDRLDKVLMIIPPLINVTFIISSDREVRGSALYEASTTYLSS SLFLSPVIMNKCSQGAVAGEPRQIPKIQNFTRTQKSCIFCGFALLSYDEKEGLETTTYITSQEVQNSILSSNYFDFDNLHVHYLLLTT NGTMEIAGLYEERASGSGSGSGLVPRGSGAGGGHHHHHH | 7 |
| SIB 7392 leader sequence gL_linker_gH Monomer | MRAVGVFLAICLVTIFVLPTWGNWAYPCCHVTQLRACHLLALENISDIYLVSNQTCDGESLASLNSPKNGNCLVISRCANGLNVVSF FISILKRSSSALTGHLRELLITLEYGSFSVEDLFGANLNRYAWHRGGGSGSGSGSASSGASASGSSNNGSGSGSGSNSSASSGGAS GGSGGGSGAASLSEVKLHLDIEGHASHYTIPWTELMAKVPGLSPEALWREANVTEDLASMLNRYKLIYKTSGTLGIALAEPVDIPAVSE GSMQVDASKVHPGVISGLNSPACMLSAPLEKQLFYYIGTMLPNTRPHSVVFYQLRCHLSVALSINGDKFQYTGAMTSKFLMGTYKRV TEKGDEHVLSLVFGKTKDLPLRGPFSYPSLTSAQSGDYSLVIVTTFVHYANFHNYFVPNLKDMFSRAVTMTAASYARYVLQKLVLLE MKGGCREPELDTETLTTMFEVSVAFFKVGHAVGETGNGCVDLRWLAKSFFELTVLKDIIGICYGATVKGMQSYGLERLAAMLMATVKM EELGHLTTEKQEYALRLATVGYPKAGVYSGLIGGATSVLLSAYNRHPLFQPLHTVMRETLFIGSHVVLRELRLNVTTQGPNLALYQLL STALCSALEIGEVLRGLALGTESGLFSPCYLSLRFDLTRDKLLSMAPQEATLDQAAVSNAVDGFLGRLSLEREDRDAWHLPAYKCVDR LDKVLMIIPPLINVTFIISSDREVRGSALYEASTTYLSSSLFLSPVIMNKCSQGAVAGEPRQIPKIQNFTRTQKSCIFCGFALLSYDEK EGLETTTYITSQEVQNSILSSNYFDFDNLHVHYLLLTTNGVFMETAGGLYEERASGSGSGSGLVPRGSGAGGGHHHHHH | 8 |
| SIB 7397 leader sequence gL_linker_gH Monomer | MRAVGVFLAICLVTIFVLPTWGNWAYPCCHVTQLRACHLLALENISDIYLVSNQTCDGESLASLNSPKNGNCLVISRCANGLNVVSF FISILKRSSSALTGHLRELLITLEYGSFSVEDLFGANLNRYAWHRGGGSGSGSGSNSSASSGGASSGGAGGSGGGSGAASLSEVKLHL DIEGHASHYTIPWTELMAKVPGLSPEALWREANVTEDLASMLNRYKLIYKTSGTLGIALAEPVDIPAVSEGSMQVDASKVHPGVISGL NSPACMLSAPLEKQLFYYIGTMLPNTRPHSVVFYQLRCHLSVVALSINGDKFQYTGAMTSKFLMGTYKRVTEKGDEHVLSLVFGKTKD | 9 |

TABLE 2-continued (SEQUENCE TABLE): DESCRIPTION OF THE SEQUENCES

| Description | Sequences | SEQ ID NO |
|---|---|---|
| SIB 7400 | LPDLRGPFSYPSLTSAQSGDYSLIVTTFVHYANFHNYFVPNLKDMFSRAVTMTAASYARYVLQKIVLLEMKGGCREPELDTETLTTM<br>FEVSVAFFKVGHAVGETGNGCVDLRWLAKSFFELTVLKDIIGICYGATVKGMQSYGLERLAAMLMATVKMEELGHLTTEKQEYALRLA<br>TVGYPKAGVYSGLIGGATSVLLSAYNRHPLFQPLHTVMRETLFIGSHVVLRELRLNVTTQGPNLALYQLLSTALCSALEIGEVLRGLA<br>LGTESGLFSPCYLSLRFDLTRDKLLSMAPQEATLDQAAVSNAVDGFLGRLSLEREDRDAWHLPAYKCVDRLDKVLMIIPLINVTFIIS<br>SDREVRGSALYEASTTYLSSSLFLSPVIMNKCSQGAVAGEPRQIPKIQNFTRTQKSCIFCGFALLSYDEKEGLETTYITSQEVQNSI<br>LSSNYFDFDLHVHYLLLTTNGTVMEIAGLYEERASGSGSGSGSLVPRGSAGGGHHHHHH | 10 |
| leader sequence<br>gL_linker_gH<br>bfpFerr<br>Nanoparticle<br>N19Q/C31S/S111C | METDTLLLWVLLLWVPGSTGNWAYPCCHVTQLRACHLLALENISDIYLVSNQTCDGESLASLNSPKNGSNCLVISRCANGLNVSFFI<br>SILKRSSSALTGHLRELLITLETLYGSFSVEDLFGANLNRYAWHRGGGSGGSGGSGGSGAASLSEVKLHLDIEGHASHYTIPWT<br>ELMAKVPGLSPEALWREANVTEDLASMLNRYKLIYKTSGTLGIALAEPVDIPAVSEGSMQVDASKVHPGVISGLNSPACMLSAPLEKQ<br>LFYYIGTMLPNTRPHSVFYQLRCHLSYVALSINGDKFQYTGAMTSKFLMGTYKRVTEKGDEHVLSLVFGKTKDLPDLRGPFSYPSLT<br>SAQSGDYSLIVTTFVHYANFHNYFVPNLKDMFSRAVTMTAASYARYVLQKIVLLEMKGGCREPELDTETLTTMFEVSVAFFKVGHAV<br>GETGNGCVDLRWLAKSFFELTVLKDIIGICYGATVKGMQSYGLERLAAMLMATVKMEELGHLTTEKQEYALRLATVGYPKAGVYSGLI<br>GGATSVLLSAYNRHPLFQPLHTVMRETLFIGSHVVLRELRLNVTTQGPNLALYQLLSTALCSALEIGEVLRGLALGTESGLFSPCYLS<br>LRFDLTRDKLLSMAPQEATLDQAAVSNAVDGFLGRLSLEREDRDAWHLPAYKCVDRLDKVLMIIPLINVTFIISSDREVRGSALYEAS<br>TTYLSSSLFLSPVIMNKCSQGAVAGEPRQIPKIQNFTRTQKSCIFCGFALLSYDEKEGLETTYITSQEVQNSILSSNYFDFDNLHVH<br>YLLLTTNGTVMEIAGLYEERASGGGSGGSGGSGGSGGSGGSGESQVRQFSKDIEKLLNEQVNKEMQSSNLYMSMSWSYTHSLDGAG<br>LFLFDHAAEEYEHAKKLIIFLNENNVPVQLTSISAPEHKFEGLTQIFQKAYEHEQHISESINNIVDHAIKCKDHAIFNFLQWYVAEQH<br>EEEVLPKDILDKIELIGNENHGLYLADQYVKGIAKSRKS | |
| SIB 7402<br>leader sequence<br>gL_linker_gH_<br>trimer | MRAVGVFLAICLVTIFVLPTWGNWAYPCCHVTQLRACHLLALENISDIYLVSNQTCDGESLASLNSPKNGSNQLVISRCANGLNVSF<br>FISILKRSSSALTGHLRELLITTLETLYGSFSVEDLFGANLNRYAWHRGGGSGGSGGSGGSNSSASSGASSGGGASSGGGGSASSGGGSGASSGMQVDASKVHPGVISGL<br>DIEGHASHYTIPWTELMAKVPGLSPEALWREANVTEDLASMLNRYKLIYKTSGTLGIALAEPVDIPAVSEGSMQVDASKVHPGVISGL<br>NSPACMLSAPLEKQLFYYIGTMLPNTRPHSVFYQLRCHLSYVALSINGDKFQYTGAMTSKFLMGTYKRVTEKGDEHVLSLVFGKTKD<br>LPDLRGPFSYPSLTSAQSGDYSLIVTTFVHYANFHNYFVPNLKDMFSRAVTMTAASYARYVLQKIVLLEMKGGCREPELDTETLTTM<br>FEVSVAFFKVGHAVGETGNGCVDLRWLAKSFFELTVLKDIIGICYGATVKGMQSYGLERLAAMLMATVKMEELGHLTTEKQEYALRLA | 11 |

TABLE 2-continued (SEQUENCE TABLE): DESCRIPTION OF THE SEQUENCES

| Description | Sequences | SEQ ID NO |
|---|---|---|
| | TVGYPKAGVYSGLIGGATSVLLSAYNRHPLFQPLHTVMRETLFIGSHVVLRELRLNVTTQGPNLALYQLLSTALCSALEIGEVLRGLA | |
| | LGTESGLFSPCYLSLRFDLTRDKLLSMAPQEATLDQAAVSNAVDGFLGRLSLEREDRDAWHLPAYKCVDRLDKVLMIIPLINVTFIIS | |
| | SDREVRGSALYEASTTYLSSSLFLSPVIMNKCSQGAVAGEPRQIPKIQNFTRTQKSCIFCGFALLSYDEKEGLETTYIITSQEVQNSI | |
| | LSSNYFDFDNLHVHYLLLTTNGTVMEIAGLYEERA*SGSGYIPEAPRDGQAYVRKDGEWLLSTFLGSSGSGSGSLVPRGSGAGGHHHHHH* | 12 |
| SIB 7403 | MRAVGVFLAICLVTIFVLPTWGNWAYPCCHVTQLRACHLLALENISDIYLVSNQTCDGESLASLNSPKNGSNQLVISRCANGLNVVSF | |
| leader sequence | *FISILKRSSSALTGHLRELLITLETLYGSFSVEDLFGANLNRYAWHRGGGSGSASSGASSGSNGSGSGSNSSASSGASSGAS* | |
| gL_linker_gH_trimer | GGSGGSGAASLSEVKLHLDIEGHASHYTIPWTELMAKVPGLSPEALWREANVTEDLASMLNRYKLIYKTSGTLGIALAEPVDIPAVSE | |
| | GSMQVDASKVHPGVISGLNSPACMLSAPLEKQLFYYIGTMLPNTRPHSYVFYQLRCHLSVALSINGDKFQYTGAMTSKFLMGTYKRV | |
| | TEKGDEHVLSLVFGKTKDLPDLRGPFSYPSLTSAQSGDYSLVIVTTFVHYANFHNYFVPNLKDMFSRAVTMTAASYARVVLQKLVLLE | |
| | MKGGCREPELDTETLTTMFEVSVAFFKVGHAVGETGNGCVDLRWLAKSFFELTVLKDIIGICYGATVKGMQSYGLERLAAMLMATVKM | |
| | EELGHLTTEKQEYALRLATVGYPKAGVYSGLIGGATSVLLSAYNRHPLFQPLHTVMRETLFIGSHVVLRELRLNVTTQGPNLALYQLL | |
| | STALCSALEIGEVLRGLALGTESGLFSPCYLSLRFDLTRDKLLSMAPQEATLDQAAVSNAVDGFLGRLSLEREDRDAWHLPAYKCVDR | |
| | LDKVLMIIPLINVTFIISSDREVRGSALYEASTTYLSSSLFLSPVIMNKCSQGAVAGEPRQIPKIQNFTRTQKSCIFCGFALLSYDEK | |
| | EGLETTYIITSQEVQNSILSSNYFDFDNLHVHYLLLTTNGTVMEIAGLYEERA*SGSGYIPEAPRDGQAYVRKDGEWLLSTFLGSSGSG* | |
| | *SGLVPRGSGAGGHHHHHH* | |
| SIB 7404 | MRAVGVFLAICLVTIFVLPTWGNWAYPCCHVTQLRACHLLALENISDIYLVSNQTCDGESLASLNSPKNGSNQLVISRCANGLNVVSF | 13 |
| leader sequence | *FISILKRSSSALTGHLRELLITLETLYGSFSVEDLFGANLNRYAWHRGGGSGSGSGSGSGSGGGSGSGSGSGGSGAASLSEVKLHL* | |
| gL_linker_gH | DIEGHASHYTIPWTELMAKVPGLSPEALWREANVTEDLASMLNRYKLIYKTSGTLGIALAEPVDIPAVSEGSMQVDASKVHPGVISGL | |
| bfpFerr | NSPACMLSAPLEKQLFYYIGTMLPNTRPHSYVFYQLRCHLSVALSINGDKFQYTGAMTSKFLMGTYKRVTEKGDEHVLSLVFGKTKD | |
| Nanoparticle | LPDLRGPFSYPSLTSAQSGDYSLVIVTTFVHYANFHNYFVPNLKDMFSRAVTMTAASYARVVLQKLVLLEMKGGCREPELDTETLTTM | |
| N19Q/C31S/S111C | FEVSVAFFKVGHAVGETGNGCVDLRWLAKSFFELTVLKDIIGICYGATVKGMQSYGLERLAAMLMATVKMEELGHLTTEKQEYALRLA | |
| | TVGYPKAGVYSGLIGGATSVLLSAYNRHPLFQPLHTVMRETLFIGSHVVLRELRLNVTTQGPNLALYQLLSTALCSALEIGEVLRGLA | |
| | LGTESGLFSPCYLSLRFDLTRDKLLSMAPQEATLDQAAVSNAVDGFLGRLSLEREDRDAWHLPAYKCVDRLDKVLMIIPLINVTFIIS | |

TABLE 2-continued (SEQUENCE TABLE): DESCRIPTION OF THE SEQUENCES

| Description | Sequences | SEQ ID NO |
|---|---|---|
| SIB 7406 leader sequence gL_linker_gH bfpFerr Nanoparticle N19Q/C31S/S111C | SDREVRGSALYEASTYLSSSLFLSPVIMNKCSQGAVAGEPRQIPKIQNFTRTQKSCIFCGFALLSYDEKEGLETTYITSQEVQNSI<br>LSSNYFDFDNLHVHYLLLTTNGTVMEIAGLYEERASGGGGSGGGGSGGGGSESQVRQQFSKDIEKLLNEQVNKEMQSSNLYMS<br>MSSWSYTHSLDGA TABLE 2-continued (SEQUENCE TABLE): DESCRIPTION OF THE SEQUENCES

| Description | Sequences | SEQ ID NO |
|---|---|---|
| SIB 7429 | TTYLSSSLFLSPVIMNKCSQGAVAGEPRQIPKIQNFTRTQKSCIFCGFALLSYDEKEGLETTYYITSQEVQNSILSSNYFDFDNLHVH<br>YLLLTTNGTVMEIAGLYEERASGSGSGSGLVPRGSGAGG<u>HHHHHH</u> | 16 |
| leader sequence<br>gL_linker_gH_trimer | *METDTLLLMVLLLWVPGSTGNWAYPCCHVTQLRACHLLALENISDIYLVSNQTCDGFSLASLNSPKNGSNQLVISRCANGLNVVSFFI*<br>*SILKRSSSALTGHLRELLTTLETLYGSFSVEDLFGANLNRYAWHRG*GGGGSGGGGSGGGGSGAASLSEVKLHLDIEGHASHYTIPWT<br>ELMAKVPGLSPEALWREANVTEDLASMLNRYKLIYKTSGTLGIALAEPVDIPAVSEGSMQVDASKVHPGVISGLNSPACMLSAPLEKQ<br>LFYYIGTMLPNTRPHSYVFYQLRCHLSYVALSINGDKFQYTGAMTSKFLMGTYKRVTEKGDEHVLSLVFGKTKDLPDLRGPFSYPSLT<br>SAQSGDYSLVIVTTFVHYANFHNYFVPNLKDMFSRAVTMTAASYARYVLQKLVLLEMKGGCREPELDTETLTTMFEVSVAFFKVGHAV<br>GETGNGCVDLRWLAKSFFELTVLKDIIGICYGATVKGMQSYGLERLAAMLMATVKMEELGHLTTEKQEYALRLATVGYPKAGVYSGLI<br>GGATSVLLSAYNRHPLFQPLHTVMRETLFIGSHVVLRELRLNVTTQGPNLALYQLLSTALCSALEIGEVLRGLALGTESGLFSPCYLS<br>LRFDLTRDKLLSMAPQEATLDQAAVSNAVDGFLGRLSLEREDRDAWHLPAYKCVDRLDKVLMIIPLINVTFIISSDREVRGSALYEAS<br>TTYLSSSLFLSPVIMNKCSQGAVAGEPRQIPKIQNFTRTQKSCIFCGFALLSYDEKEGLETTYYITSQEVQNSILSSNYFDFDNLHVH<br>YLLLTTNGTVMEIAGLYEERA<u>SGSGSGSGLVSTFLGSGSGSGLVPRGSGAGGHHHHHH</u> | |
| SIB 15000 | <u>MRAVGVFLAICLVTIFVLPTWGNWAYPCCHVTQLRACHLLALENISDIYLVSNQTCDGESLASLNSPKNGSNQLVISRCANGLNVVSF</u> | 17 |
| leader sequence<br>gL_FR1_gH | *FISILKRSSSALTGHLRELLTTLETLYGSFSVEDLFGANLNRYAWHRG*GGGSGSASAEAAAKEAAAKAGGSGGSASAEAAAKEAAAKAGGSGGSAAEEAAAKEAAAKAGGSGGSAASLSEVKLHLDI*<br>EGHASHYTIPWTELMAKVPGLSPEALWREANVTEDLASMLNRYKLIYKTSGTLGIALAEPVDIPAVSEGSMQVDASKVHPGVISGLNS<br>PACMLSAPLEKQLFYYIGTMLPNTRPHSYVFYQLRCHLSVVALSINGDKFQYTGAMTSKFLMGTYKRVTEKGDEHVLSLVFGKTKDLP<br>DLRGPFSYPSLTSAQSGDYSLVIVTTFVHYANFHNYFVPNLKDMFSRAVTMTAASYARYVLQKLVLLEMKGGCREPELDTETLTTMFE<br>VSVAFFKVGHAVGETGNGCVDLRWLAKSFFELTVLKDIIGICYGATVKGMQSYGLERLAAMLMATVKMEELGHLTEKQEYALRLATV<br>GYPKAGVYSGLIGGATSVLLSAYNRHPLFQPLHTVMRETLFIGSHVVLRELRLNVTTQGPNLALYQLLSTALCSALEIGEVLRGLALG<br>TESGLFSPCYLSLRFDLTRDKLLSMAPQEATLDQAAVSNAVDGFLGRLSLEREDRDAWHLPAYKCVDRLDKVLMIIPLINVTFIISSD<br>REVRGSALYEASTTYLSSSLFLSPVIMNKCSQGAVAGEPRQIPKIQNFTRTQKSCIFCGFALLSYDEKEGLETTYYITSQEVQNSILS | | bfpFerr<br>Nanoparticle<br>N19Q/C31S/S111C

TABLE 2-continued (SEQUENCE TABLE): DESCRIPTION OF THE SEQUENCES

| Description | Sequences | SEQ ID NO |
|---|---|---|
| SIB 15001 | SNYFDFDNLHVHYLLLTTNGTVMEIAGLYEERASGGGSGGGSGGGSGGGSGGGSESQVRQQFSKDIEKLLNEQVNKEMQSSNLYMSMS SWSYTHSLDGAGLFLFDHAAEEYEHAKKLIIFLNENNVPVQLTSISAPEHRKEGLTQIFQKAYEHEQHISESINNIVDHAIKCKDHAT FNFLQWYVAEQHEEEVLFKDILDKIELIGNENHGLYLADQVKGIAKSRKS | 18 |
| leader sequence gL_FR2_gH bfpFerr Nanoparticle N19Q/C31S/S111C | MRAVGVFLAICLVTIFVLPT TABLE 2-continued (SEQUENCE TABLE): DESCRIPTION OF THE SEQUENCES

| Description | Sequences | SEQ ID NO |
|---|---|---|
| SIB 15003 | EGLETTYITSQEVQNSILSSNYFDFDNLHVHYLLLTTNGTVMEIAGLYEERASGGGSASSGGSGASSGGASGSGSGSGSGSGSSSASSGASS<br>EGLETTYITSQEVQNSILSSNYFDFDNLHVHYLLLTTNGTVMEIAGLYEERASGGGSASSGGSGASSGGASGSGSGSGSGSGSSSASSGASS<br>GGASGGGSGGGESQVRQQFSKDIEKLLNEQVNKEMQSSNLYMSMSWSYTHSLDGAGLFLFDHAAEEYEHAKKLIIFLNENNVPVQL<br>TSISAPEHKFEGLTQIFQKAYEHEQHISESINNIVDHAIKCKDHAITFNFLQWYVAEQHEEEVLFKDILDKIELIGNENHGLYLADQYV<br>KGIAKSRKS | 20 |
| Construct 7<br>gL_linker_gH_linker_bfpFerr<br>Nanoparticle<br>N19Q/C31S | MRAVGVFL TABLE 2-continued (SEQUENCE TABLE): DESCRIPTION OF THE SEQUENCES

| Description | Sequences | SEQ ID NO |
|---|---|---|
| SIB 15005 leader sequence Construct 5 gL_gH_C137A_bfpFer TABLE 2-continued (SEQUENCE TABLE): DESCRIPTION OF THE SEQUENCES

| Description | Sequences | SEQ ID NO |
|---|---|---|
| SIB 15006 leader sequence Construct 7 gL_gH_C137A_bfpFerr Nanoparticle N19Q/C31S | MRAVGVFLAICLVTIFVLPTWGNWAYPCCHVTQLRACHLLALENISDIYLVSNQTCDGFSLASLNSPKNGSNQLIVISRCANGLNVVSF<br>FISILKRSSALTGHLRELLITLETLYGSFSVEDLFGANLNRYAWHRGGGSGSASSGASASGSSNGSGSGSGSNSSASSGASSGAS<br>GGSGGGSGAASLSEVKLHLDIEGHASHYTIPWTELMAKVPGLSPEALWREANVTEDLASMLNRYKLIYKTSGTLGIALAEPVDIPAVSE<br>GSMQVDASKVHPGVISGLNSPACMLSAPLEKQLFYYIGTMLPNTRPHSYVFYQLRAHLSVVALSINGDKFQYTGAMTSKFLMGTYKRV<br>TEKGDEHVLSLVFGKTKDLPDLRGPFSYPSLITSAQSGDYSLVIVTTFVHYANFHNTFVPNLKDMFSRAVTMTAASYARYVLQKLVLLE<br>MKGGCREPELDTETLTTMFEVSVAFFKVGHAVGETGNGCVDLRWLAKSFFELTVLKDIIGICYGATVKGMQSYGLERLAAMLMATVKM<br>EELGHLTTEKQEYALRLLATVGYPKAGVYSGLIGGATSVLLSAYNRHPLFQPLHTVMRETLFIGSHVVLRELRLNVTTQGPNLALYQLL<br>STALCSALEIGEVLRGLALGTESGLFSPCYLSLRFDLTRDKLLSMAPQEATLDQAAVSNAVDGFLGRLSLEREDRDAWHLPAYKCVDR<br>LDKVLMLIIPLINVTFIISSDREVRGSALYRASTTYLSSSLFLSPVIMNKCSQGAVAGEPRQIPKIQNFTRTQKSCIFCGFALLSYDEK<br>EGLETTYITSQEVQNSILSNYFDFDNLHVHYLLLTTNGTVMEIAGLYEERASGGGSGSASSGASASGSSCSGSGSGSSSASSGASS<br>GGASGGGSGGSGESQVRQQFSKDIEKLLNEQVNKEMQSSNLYMSMSSWSYTHSLDGAGLFLFDHAAEEYEHAKKLIIFLNENNVPVQL<br>TSISAPEHKFEGLTQIFQKAYEHEQHISESINNIVDHAIKSKDHATFNFLQWYVAEQHEEEVLFKDILDKIELIGNENHGLYLADQYV<br>KGIAKSRKS | 23 |
| SIB 17395 leader sequence gp220-T.ni ferritin heavy chain | MDSKGSSQKGSRLLLLLVVSNLLLPQGVLAEAALLVCQYTIQSLIHLTGEDPGFFNVEIPEPFPFYPTCNVCTADVNVTINFDVGGKKH<br>QLDLDFGQLTPHTKAVVQPRGAFGGSENATNLFLLELLGAGELALTMRSKKLPINVTTGEEQQVSLESVDYFQDVFGTMWCHHAEMQ<br>NPVYLIPETVPVIKWDNCNSTNITAVVRAQGLDVTLPLSLPTSAQDSNFSVKTEMLGNEIDIECIMEDGEISQVLPGDNKFNITCSGY<br>ESHVPSGGILTSTSPVATPIPGTGYAYSLRLTPRPVSRFIGNNSILYVFYSGNGPKASGGDYCIQSNIVFSDEIPASQDMPTNTTDIT<br>YVGDNATYSVPMVTSEDANSPNVTVTAFWAWPNNTETDFKCKWTLTSGTPSGCENISGAFASNRTFDITVSGLGTARKTLIITRTATN<br>ATTTHKVIFSKAPEGSTQCNVNPVQIPKDMITMHRSCRNSMRQQIQMEVGASLQYLAMGAHFSKDVVNRPGFAQLFFDAASEEREHA<br>MKLIEYLLMRGELTNDVSSLLQVRPPTRSSWKGGVEALEHALSMESDVTKSIRNVIKACEDDSEENDYHLVDYLTGDFLEEQYKGQRD<br>LAGKASTLKKLMDRHERALGEFIFDKKLLGIDV | 24 |

TABLE 2-continued (SEQUENCE TABLE): DESCRIPTION OF THE SEQUENCES

| Description | Sequences | SEQ ID NO |
|---|---|---|
| SIB 17396 leader sequence gL_linker_gH-T. ni ferritin heavy chain | MRAVGVFLAICLVTIFVLPTWGNWAYPCCHVTQLRACHLLALENISDIYLVSNQTCDGFSLASLNSPKNGSNQLVISRCANGLNVVSF FISILKRSSSALTGHLRELLITLETLYGSFSVEDLFGANLNRYAWHRGGGSGSASSGASASGSSNGSGSGSNSSASSGASSGGAS GGSGGSGAASLSEVKLHLDIEGHASHYTIPWTELMAKVPGLSPEALWREANVTEDIASMLNRYKLIYKTSGTLGIALAEPVDIPAVSE GSMQVDASKVHPGVISGLNSPACMLSAPLEKQLFYYIGTMLPNTRPHSYVFYQLRCHLSYVALSINGDKFQYTGAMTSKFLMGTYKRV TEKGDEHVLSLVFGKTKDLPDLRGPPFSYPSLTS TABLE 2-continued (SEQUENCE TABLE): DESCRIPTION OF THE SEQUENCES

| Description | Sequences | SEQ ID NO |
|---|---|---|
| SIB 17398 | MRAVGVFLAICLVTIFVLPTWGNWAYPCCHVTQLRACHLLALENISDIYLVSNQTCDGFSLASLNSPKNGSNQLVISRCANGLNVVSF FISILKRSSSALTGHLRELLITTLETLYGSFSVEDLFGANLNRYAWHRGGGSGSASSGASASGSSGSSGSSNSSASSGASSGGAS GGSGGGSGAASLSEVKLHLDIEGHASHYTIPWTELMAKVPGLSPEALWREANVTEDLASMLNRYKLIYKTSGTLGIALAEPVDIPAVSE GSMQVDASKVHPGVISGLNSPACMLSAPLEKQLFYYIGTMLPNTRPHSYVFYQLRCHLSVVALSINGDKFQYTGAMTSKFLMGTYKRV TEKGDEHVLSLVFGKTKDLPDLRGPFSYPSLTSAQSGDYSLVIVTTFVHYANFHNTFVPNLKDMFSRAVTMTAASYARYVLQKLVLLE MKGGCREPELDTETLITMFEVSVAFFKVGHAVGETGNGCVDLRWLAKSFFELTVLKDIIGICYGATVKGMQSYGLERLAAMLMATVKM EELGHLTTEKQEYALRLATVGYPKAGVYSGLIGGATSVLLSAYNRHPLFQPLHTVMRETLFIGSHVVLRELRLNVTTQGPNLALYQLL STALCSALEIGEVLRGLALGTESGLFSPCYLSLRFDLTRDKLLSMAPQEATLDQAAVSNAVDGFLGRLSLEREDRDAWHLPAYKCVDR LDKVLMLIIPLLNVTFIISSDREVRGSALYRASTTYLSSSLFLSPVIMNKCSQGAVAGEPRQIPKIQNFTRTQKSCIFCGFALLSYDEK EGLETTYITSQEVQNSILSSNYFDFDNLHVHYLLLTTNGTVMEIAGLYEERASGSADTCYNDVALDCGITSNSLALPRCNAVYGEYG SHGNVATELQAYAKLHLERSYDYLLSAAYFNNYQTNRAGFSKLFKKLSDRAWSKTIDIIKHVTKRGDKMNFDQHSTMKTERKNYTAEN HELEALAKALDTQKELAERAFYIHREATRNSQHLHDPEIAQYLEEEFIEDHAEKIRTLAGHTSDLKKFITANNGHDLSLALYVEDEYL | 27 |
| leader sequence | | |
| gL_linker_gH-T.ni ferritin | | |
| light chain | | |
| | QKTV | |
| 16 amino acid linker | GGGGSGGGGSGGGGSG | 28 |
| 28 amino acid linker | GGSGSGSNSSASSGASSGGASGGGSGGSG | 29 |
| 46 amino acid linker | GGSGSGSASSGASASGSSGSSGSSNSSASSGASSGGASGASGGSGGSG | 30 |
| FR1 | GGSGSAEAAAKEAAAKAGGSGGSG | 31 |
| FR2 | GGSGSAEAAAKEAAAKEAAAKASGGSGGSG | 32 |
| 47 amino acid linker comprising a C for conjugation | SGGGGSGGSGSASSGASASGSSCSGSGSSSASSGASSGGASGGGSGGSG | 33 |
| Gp42 | DSKGSSQKGSRLLLLVVSNLLLPQGVLAYFLPPRVRGGRVAAAAITWVPKPNVEVWPVDPPPPVNFNKTAEQEYGDKEVKLPHWTP TLHTFQVPQNYTKANCTYCNTREYTPFSYKGCCFYFKKKHTWNGCFQACAELYPCTYFYGPTPDILPVVTRNLNAIESLWVGVYRVGE GNWTSLDGGTFKVYQIFGSHCTYVSKFSTVSHHECSFLKPCLCVSQRSNS | 34 |

TABLE 2-continued (SEQUENCE TABLE): DESCRIPTION OF THE SEQUENCES

| Description | Sequences | SEQ ID NO |
|---|---|---|
| CpG (phosphorothioate modifications where * is shown) | T*G*A*C*T*G*T*G*A*A*C*G*T*T*C*G*A*G*A*T*G*A | 35 |
| Exemplary gL polypeptide | NWAYPCCHVTQLRAQHLLALENISDIYLVSNQTCDGFSLASLNSPKNGSNQLVISRCANGLNVVSFFISILKRSSSALTGHLRELLTT LETLYGSFSVEDLFGANLNRYAWHRGG | 36 |
| Exemplary gH polypeptide | AASLSEVKLHLDIEGHASHYTIPWTELMAKVPGLSPEALWREANVTEDLASMLNRYKLIYKTSGTLGIALAEPVDIPAVSEGSMQVDA SKVHPGVISGLNSPACMLSAPLEKQLFYYIGTMLPNTRPHSYVFYQLRCHLSYVALSINGDKFQYTGAMTSKFLMGTYKRVTEKGDEH VLSLVFGKTKDLPLRGPFSYPSLITSAQSGDYSLVIVTTFVHYANFHNYFVPNLKDMFSRAVTMTPAASYARYVLQKIVLLEMKGGCRE PELDTETLTTMPEVSVAFFKVGHAVGETGNGCVDLRMLAKSFFELTVLKDIIGICYGATVKGMQSYGLERLAAMLMATVKMEELGHLT TEKQEYALRLATVGYPKAGVVSGLIGGATSVLLSAYNRHPLFQPLHTVMRETLFIGSHVVLRELRLNVTTQGPNLALYQLLSTALCSA LEIGEVLRGLALGTESGLFSPCYLSLRFDLTRDKLLSMAPQEATLDQAAVSNAVDGFLGRLSLEREDRDAWHLPAYKCVDRLDKVLMI IPLINVTFISSDREVRGSALYEASTYLSSSLFLSPVIMNKCSQGAVAGEPRQIPKIQNFTRTQKSCIFCGFALLSYDEKEGLETTT YITSQEVQNSILSSNYPDFDNLHVHYLLLTNGTVMEIAGLYEERA | 37 |
| Exemplary gp220 polypeptide | EAALLVCQYTIQSLIHLTGEDPGFFNVEIPEFPFYPTCNVCTADVNVTINFDVGGKKHQLDLDFGQLTPHTKAVYQPRGAFGGSENAT NLFLLELLGAGELALTMRSKKLPINVTTGEEQQVSLESVDYFQDVFGTMWCHHAEMQNPVYLIPETVPYIKWDNCNSTNITAVVRAQ GLDVTLPLSLPTSAQDSNFSVKTEMLGNEIDIECIMEDGEISQVLPGDNKFNITCSGYESHVPSGGILTSTPSPVATPIPGTGYAYSLR LTPRPVSRFLGNNSILYVFYSGNGPKASGGDYCIQSNIVFSDEIPASQDMPTNTDITYVGDNATYSVPMVTSEDANSPNVTVTAFWA WPNNTETDFKCKWTLTSGTPSGCENISGAPASNRTFDITVSGLGTAPKTLIITRATANATTTHKVIFSKAPE | 38 |
| Cysteine-Thrombin-His Linker | <u>C</u>LVPRGSLEHHHHHH | 39 |
| Lumazine synthase of Aquifex aeolicus (strain VF5) | MQIYEGKLTAEGLRFGIVASRFNHALVDRLVEGAIDCIVRHGGREEDITLVRVPGSWEIPVAAGELARKEDIDAVIAIGVLIRGATPH FDYIASEVSKGLANLSLELRKPITFGVITADTLEQAIERAGTKHGNKGWEAALSAIEMANLFKSLR | 40 |

TABLE 2-continued (SEQUENCE TABLE): DESCRIPTION OF THE SEQUENCES

| Description | Sequences | SEQ ID NO |
|---|---|---|
| E. coli 6,7-dimethyl-8-ribityllumazine synthase | MNIIEANVATPDARVAITIARFNNFINDSLLEGAIDALKRIGQVKDENITVVWVPGAYELPLAAGALAKTGKYDAVIALGTVIRGTA HPEYVAGGASNGLAHVAQDSEIPVAFGVLTTESIEQAIERAGTKAGNKGAEAALTALEMINVLKAIKA | 41 |
| | Not Used | 42-200 |
| bfpFerritin- | ESQVRQQFSKDIEKLLNEQVNKEMQSSNLYMCMSSWSYTHSLDGAGLFLFDHAAEEYEHAKKLIIFLNENNVPVQLTSISAPEHKFEG | 201 |
| N19Q/C31S/S26C | LTQIFQKAYEHEQHISESINNIVDHAIKSKDHATFNFLQWYVAEQHEEEVLFKDILDKIELIGNENHGLYLADQYVKGIAKSRKS | |
| bfpFerritin- | ESQVRQQFSKDIEKLLNEQVNKEMQSSNLYMSMSSWSYTHSLDGAGLFLFDHAAEEYEHAKKLIIFLNENNVPVQLTCISAPEHKFEG | 202 |
| N19Q/C31S/S72C | LTQIFQKAYEHEQHISESINNIVDHAIKSKDHATFNFLQWYVAEQHEEEVLFKDILDKIELIGNENHGLYLADQYVKGIAKSRKS | |
| bfpFerritin- | ESQVRQQFSKDIEKLLNEQVNKEMQSSNLYMSMSSWSYTHSLDGAGLFLFDHAAEEYEHAKKLIIFLNENNVPVQLTSISCPEHKFEG | 203 |
| N19Q/C31S/A75C | LTQIFQKAYEHEQHISESINNIVDHAIKSKDHATFNFLQWYVAEQHEEEVLFKDILDKIELIGNENHGLYLADQYVKGIAKSRKS | |
| bfpFerritin- | ESQVRQQFSKDIEKLLNEQVNKEMQSSNLYMSMSSWSYTHSLDGAGLFLFDHAAEEYEHAKKLIIFLNENNVPVQLTSISAPEHCFEG | 204 |
| N19Q/C31S/K79C | LTQIFQKAYEHEQHISESINNIVDHAIKSKDHATFNFLQWYVAEQHEEEVLFKDILDKIELIGNENHGLYLADQYVKGIAKSRKS | |
| bfpFerritin- | ESQVRQQFSKDIEKLLNEQVNKEMQSSNLYMSMSSWSYTHSLDGAGLFLFDHAAEEYEHAKKLIIFLNENNVPVQLTSISAPEHKFEG | 205 |
| N19Q/C31S/S100C | LTQIFQKAYEHEQHISECINNIVDHAIKSKDHATFNFLQWYVAEQHEEEVLFKDILDKIELIGNENHGLYLADQYVKGIAKSRKS | |
| bfpFerritin- | ESQVRQQFSKDIEKLLNEQVNKEMQSSNLYMSMSSWSYTHSLDGAGLFLFDHAAEEYEHAKKLIIFLNENNVPVQLTSISAPEHKFEG | 206 |
| N19Q/C31S/S111C | LTQIFQKAYEHEQHISESINNIVDHAIKCKDHATFNFLQWYVAEQHEEEVLFKDILDKIELIGNENHGLYLADQYVKGIAKSRKS | |
| bfpFerritin- | ESQVRQQFSKDIEKLLNCQVNKEMQSSNLYMSMSSWSYTHSLDGAGLFLFDHAAEEYEHAKKLIIFLNENNVPVQLTSISAPEHKFEG | 207 |
| N19Q/C31S/E12C | LTQIFQKAYEHEQHISESINNIVDHAIKSKDHATFNFLQWYVAEQHEEEVLFKDILDKIELIGNENHGLYLADQYVKGIAKSRKS | |
| Exemplary H. pylori Ferritin with bullfrog linker | ESQVRQQFSKDIEKLLNEQVNKEMNSSNLYMSMSSWCYTHSLDGAGLFLFDHAAEEYEHAKKLIIFLNENNVPVQLTSISAPEHKFEG LTQIFQKAYEHEQHISESINNIVDHAIKSKDHATFNFLQWYVAEQHEEEVLFKDILDKIELIGNENHGLYLADQYVKGIAKSRKS | 208 |
| Exemplary wild-type H. pylori ferritin (GenBank Accession AAD06160.1) (without bullfrog linker or N-terminal Met) | LSKDIIKLLNEQVNKEMNSSNLYMSMSSWCYTHSLDGAGLFLFDHAAEEYEHAKKLIIFLNENNVPVQLTSISAPEHKFEGLTQIFQK AYEHEQHISESINNIVDHAIKSKDHATFNFLQWYVAEQHEEEVLFKDILDKIELIGNENHGLYLADQYVKGIAKSRKS | 209 |

TABLE 2-continued (SEQUENCE TABLE): DESCRIPTION OF THE SEQUENCES

| Description | Sequences | SEQ ID NO |
|---|---|---|
| CpG (ISS-1018) | TGACTGTGAACGTTCGAGATGA | 210 |
| Trichoplusia ni heavy chain ferritin | TQCNVNPVQIPKDWITMHRSCRNSMEQQIQMEVGASLQYLAMGAHFSKDVVNRPGFAQLFPDAASEREHAMKLIEYLLMRGELTNDV SSLLQVRPPTRSSWKGGVEALEHALSMESDVTKSIRNVIKACEDDSEFNDYHLVDYLTGDFLEEQYKGQRDLAGKASTLKKLMDRHEA LGEFIFDKKLLGIDV | 211 |
| Trichoplusia ni light chain ferritin | ADTCYNDVALDCGITSNSLALPRCNAVYGEYGSHGNVATELQAYAKLHLERSYDYLLSAAYFNNYQTNRAGFSKLFKKLSDEAWSKTI DIIKHVTKRGDKMNFDQHSTMKTERKNYTAENHELEALAKALDTQKELAERAFYIHREATRNSQHLHDPEIAQYLEEEFIEDHABKIR TLAGHTSDLKKFITANNGHDLSLALYVFDEYLQKTV | 212 |
| Pyrococcus furiosus ferritin | MLSERMLKALNDQLNRELYSAYLYFAMAAYFEDLGLEGFANWMKAQAEEEIGHALRFYNY IYDRNGRVELDEIPKPPKEWESPLKAFEAAYEHEKFISKSIYELAALAEEEKDYSTRAFL EWFINEQVEEEASVKKILDKLLKFAKDSPQILFMLDKELSARAPKLPGLLMQGGE | 213 |
| human heavy chain ferritin | MTTASTSQVRQNYHQDSEAAINRQINLELYASYVYLSMSYYFDRDDVALKNFAKYFLHQSHEEREHAEKLMKLQNQRGGRIFLQDIKK PDCDDWESGLNAMECALHLEKNVQQSLLELHKLATDKNDPHLCDFIETHYLNEQVKAIKELGDHVTNLRKMGAPESGLAEYLFDKHTL GDSDQES | 214 |
| human light chain ferritin(signal peptide is underlined) | <u>MDSKGSSQKGSRLLLLIVVSNLLLPQGVLA</u>SSQIRQNYSTDVEAAVNSLVNLYLQASYTYLSLGFYFDRDDVALEGVSHFFRELAEEK REGYERLLKMQNQRGGRALFQDIKKPAEDEWGKTPDAMKAAMALEKKLNQALLDLHALGSARTDPHLCDFLETHFLDEEVKLIKKMGD HLTNLHRLGGPEAGLGEYLFERLTLKHD | 215 |
| lumazine synthase from Aquifex aeolicus | MQIYEGKLTAEGLRFGIVASRFNHALVDRLVEGAIDCIVRHGGREEDITLVRVPGSWEIPVAAGELARKEDIDAVIAIGVLIRGATPH FDYIASEVSKGLANLSLELRKPITFGVITADTLEQAIERAGTKHGNKGWEAALSAIEMANLFKSLR | 216 |
| bullfrog linker | ESQVRQF | 217 |
| Cysteine-Thrombin-His Linker | CLVPRGSLEHHHHHH | 218 |
| E. coli 6,7-dimethyl-8-ribityllumazine synthase | MNITEANVATPDARVAITIARPNNFINDSLLEGAIDALKRIGQVKDENITVVWVPGAYELPLAAGALAKTGKYDAVIALGTVIRGGTA HPEYVAGGASNGLAHVAQDSEIPVARGVLTTESIEQATERAGTKAGNKGAEAALTALEMINVLKAIKA | 219 |
| 16 amino acid linker | GGGGSGGGGSGGGGSG | 220 |
| 28 amino acid linker | GGSGSGNSSASSGASSGGASSGGSGSG | 221 |

TABLE 2-continued (SEQUENCE TABLE): DESCRIPTION OF THE SEQUENCES

| Description | Sequences | SEQ ID NO |
|---|---|---|
| 46 amino acid linker | GGSGSASGSASGSNGSGSGSSNSSASSGASSGEASGSGSG | 222 |
| FR1 | GGSGSASAEAAAKEAAAKAGGSGGSG | 223 |
| FR2 | GGSGSASAEAAAKEAAAKASGSGGSG | 224 |
| 47 amino acid linker comprising a C for conjugation | SGGGSGSASSGASASGSCSGSGSSASSGASSGASGGGGSGG | 225 |
| SIB 15007 | MRAVGVFLAICLVTIFVLPTWGNWAYPCCHVTQLRACHLLALENISDIYLVSNQTCDGESLASLNSPKNGSNCLVISRCANGLNVVSF FISILKRSSSALTGHLRELLITLETLYGSFSVEDLFGANLNRYAWHRGGGSGSASGSASGSNGSGSGSSNSSASSGASSGGAS GGSGGSGAASLSEVKLHLDIEGHASHYTIPWTELMAKVPGLSPEALWREANVTEDLASMLNRYKLIYKTSGTLGIALAEPVDIPAVSE GSMQVDASKVHPGVISGLNSPACMLSAPLEKQLFYYIGTMLPNTRPHSYVFYQLRAHLSVVALSINGDKFQYTGAMTSKFLMGTYKRV TEKGDEHVLSLVFGKTKDLPLRGPFSYPSLTSAQSGDYSLVIVTTFVHYANFHNYFVPNLKDMFSRAVTMTAASYARYVLQKLVLLE MKGGCREPELDTETLTTMFEVSVAFFKVGHAVGETGNGCVDLRWLAKSFFELTVLKDIIGICYGATVKGMQSYGLERLAAMLMATVKM EELGHLTTEKQEYALRLATVGYPKAGVYSGLIGGATSVLLSAYNRHPLFQPLHTVMRETLFIGSHVVLRELRLNVTTQGPNLALYQLL STALCSALEIGEVLRGLALGTESGLFSPCYLSPCVLSLRFPDLTRDKLLSMAPQEATLDQAAVSNAVDGFLGRLSLEREDRDAWHLPAYKCVDR LDKVLMIIPLINVTFIISSDREVRGSALYEASTTYLSSSLFLSPVIMNKCSQGAVAGEPRQIPKIQNFTRTQKSCIFCGFALLSYDEK EGLETTYITSQEVQNSILSSNYFDEDNLHVHYLLLTTNGTVMEIAGLYEERASGGGSGASASGSSGGSGGSGSGSSASSGLAY FLPPRVRGGGRVAAAAITWVPKPNVEVWPVDPPPPVNENKTAEQEYGDKEVKLPHWTPTLHTFQVPQNYTKANCTYCNTREYTESYKG CCFYFTKKKHTWNGCFQACAELYPCTYFYGPTPDILPVVTRNLNAIESLWVGVYRVGEGMWTSLDGGTEKVYQIEGSHCTVSKESTV PVSHHECSFLKPCLCVSQRSNSGSHHHHHH | 226 |
| SIB 15008 gH/gL/gp42 NP | MRAVGVFLAICLVTIFVLPTWGNWAYPCCHVTQLRAQHLLALENISDIYLVSNQTCDGESLASLNSPKNGSNQLVISRCANGLNVVSF FISILKRSSSALTGHLRELLITLETLYGSFSVEDLFGANLNRYAWHRGGGSGSASGSASGSNGSGSGSSNSSASSGASSGGAS GGSGGSGAASLSEVKLHLDIEGHASHYTIPWTELMAKVPGLSPEALWREANVTEDLASMLNRYKLIYKTSGTLGIALAEPVDIPAVSE GSMQVDASKVHPGVISGLNSPACMLSAPLEKQLFYYIGTMLPNTRPHSYVFYQLRAHLSVVALSINGDKFQYTGAMTSKFLMGTYKRV TEKGDEHVLSLVFGKTKDLPLRGPFSYPSLTSAQSGDYSLVIVTTFVHYANFHNYFVPNLKDMFSRAVTMTAASYARYVLQKLVLLE MKGGCREPELDTETLTTMFEVSVAFFKVGHAVGETGNGCVDLRWLAKSFFELTVLKDIIGICYGATVKGMQSYGLERLAAMLMATVKM EELGHLTTEKQEYALRLATVGYPKAGVYSGLIGGATSVLLSAYNRHPLFQPLHTVMRETLFIGSHVVLRELRLNVTTQGPNLALYQLL | 227 |

TABLE 2-continued (SEQUENCE TABLE): DESCRIPTION OF THE SEQUENCES

| Description | Sequences | SEQ ID NO |
|---|---|---|
| | STALCSALEIGEVLRGLALGTESGLFSPCYISLRFDLTRDKLLSMAPQEATLDQAAVSNAVDGFLGRLSLEREDRDAWHLPAYKCVDR<br>LDKVLMIIPLINVTFIISSDREVRGSALYEASTTYLSSSLFLSPVIMNKCSQGAVAGEPRQIPKLQNFTRTQKSCIFCGFALLSYDEK<br>EGLETTYIITSQEVQNSILSSNYFDEDNLHVYLLLTTNGTVMEIAGLYEERASGGGSGSASSGASASGSSGSASGSSSASSGLAY<br>FLPPRVRGGGRVAAAAITWVPKNVEWPVDPPPVNENKTAEQEYGDKEVKLPHWTPTLHTFQVPQNYTKANCTYCNTREYTESYKG<br>CCFYFTKKKHTWNGCFQACAELYPCYFYGPTPDILPVVTRNLNAIESLWVGVYRVGEGNWTSLDGGTEKVYQIEGSHCTYVSKESTV<br>PVSHHECSFLKPCLCVSQRSNSGGSSGSSGGSSGSGGSGESQVRQQFSKDIEKLLNEQVNKEMQSSNLYMSMSSWSYTHSLDGAGLFLFDHAAEEYEHAKKLIIF<br>LNENNVPVQLTISISAPEHKFEGLTQIFQKAYEHEQHISESINNIVDHAIKCKDHAITFNFLQWYVAEQHEEEVLFKDILDKIELIGNEN<br>HGLYLADQYVKGIAKSRKS | |
| SIB 15009<br>gH/gL/gp42_NP_C12 | MRAVGVFLAICLVTIFVLPTWGNWAYPCCHVTQLRAQHLLALENISDIYLVSNQTCDGESLASLNSPKNGSNQLVISRCANGLNVVSF<br>FISILKRSSALTGHLRELLITTLETLYGSFSVEDLFGANLNRYAWHRGGGSGSASGASASGSSNGSGSGSNSSASGASSGGAS<br>GGSGGSGAASLSEVKLHLDIEGHASHYTIPWTELMAKVPGLSPEALWREANVTEDLASMLNRYKLIYKTSGTLGIALAEPVDIPAVSE<br>GSMQVDASKVHPGVISGLNSPACMLSAPLEKQLFYYIGTMLPNTRPHSYVFYQLRAHLSVVALSINGDKFQYTGAMTSKFLMGTYKRV<br>TEKGDEHVLSLVEGKTKDLPDLRGPFSYPSLLTSAQSGDYSLVIVTTFVHYANFHNYFVPNLKDMESRAVTMTAASYARYVLQKLVLLE<br>MKGGCREPELDTETLTTMFEVSVAFFKVGHAVGETGNGCVDLRWLAKSFFELTVLKDIIGICYGATVKGMQSYGLERLAAMLMATVKM<br>EELGHLTTEKQEYALRLATVGYPKAGVYSGLLIGGATSVLLSAYNRHPLFQPLHTVMRETLFIGSHVVLRELRLNVTTQGPNLALYQLL<br>STALCSALEIGEVLRGLALGTESGLFSPCYISLRFDLTRDKLLSMAPQEATLDQAAVSNAVDGFLGRLSLEREDRDAWHLPAYKCVDR<br>LDKVLMIIPLINVTFIISSDREVRGSALYEASTTYLSSSLELSPVIMNKCSQGAVAGEPRQIPKLQNFTRTQKSCIFCGFALLSYDEK<br>EGLETTYIITSQEVQNSILSSNYFDEDNLHVYLLLTTNGTVMEIAGLYEERASGGGSGSASGASASGSSGSASSGSSSASSGLAY<br>FLPPRVRGGGRVAAAAITWVPKNVEWPVDPPPVNENKTAEQEYGDKEVKLPHWTPTLHTFQVPQNYTKANCTYCNTREYTESYKG<br>CCFYFTKKKHTWNGCFQACAELYPCYFYGPTPDILPVVTRNLNAIESLWVGVYRVGEGNWTSLDGGTEKVYQIEGSHCTYVSKESTV<br>PVSHHECSFLKPCLCVSQRSNSGGSSGSSGGSSGSGGSGESQVRQQFSKDIEKLLNEQVNK<br>EMQSSNLYMSMSSWSYTHSLDGAGLFLFDHAAEEYEHAKKLIIFFLNENNVPVQLTISAPEHKFEGLTQIFQKAYEHEQHISESINNI<br>VDHAIKCKDHAITFNFLQWYVAEQHEEEVLFKDILDKIELIGNENHGLYLADQYVKGIAKSRKS | 228 |

TABLE 2-continued (SEQUENCE TABLE): DESCRIPTION OF THE SEQUENCES

| Description | Sequences | SEQ ID NO |
|---|---|---|
| SIB 15010 gH/gL/gp42_NP_C13 | MRAVGVFLAICLVTIFVLPTWGNWAYPCCHVTQLRAQHLLALENISDIYLVSNQTCDGESLASLNSPKNGSNQLVISRCANGLNVVSF<br>FISILKRSSSALTGHLRELLITLETLYGSFSVEDLFGANLNRYAWHRGGGSGSASSGASASGSSNGSGSGSNSSASSGASSGGAS<br>GGSGGSGAASLSEVKLHLDIEGHASHYTIPWTELMAKVPGLSPEALWREANVTEDLASMLNRYKLIYKTSGTLGIALAEPVDIPAVSE<br>GSMQVDASKVHPGVISGLNSPACMLSAPLEKQLFYYIGTMLPNTRPHSYVEYQLRAHLSVVALSINGDKFQYTGAMTSKFLMGTYKRV<br>TEKGDEHVLSLVEGKTKDLPLRGPFSYPSLTSAQSGDYSLVIVTTFVHYANFHNYFVPNLKDMESRAVTMTAASYARYVLQKLVILE<br>MKGGCREPELDTETLTTMFEVSVAFPKVGHAVGETGNGCVDLRWLAKSFFELTVLKDIIGICYGATVKGMQSYGLERLAAMLMATVKM<br>EELGHLTTEKQEYALRLATVGFLIGGATVSVLLGGATSVLLSAYNRHPLFQPLHTVMRETLFIGSHVVLRELRLNVTTQGPNLALYQLL<br>STALCSALEIGEVLRGLALGTESGLFSPCYLSLRFDLTRDKLLSMAPQEATLDQAAVSNAVDGFLGRLSLEREDRDAWHLPAYKCVDR<br>LDKVLMLIPLINVTFIISSDREVRGSALYRASTTYLSSSLELSPVIMNKCSQGASASGSSGSGSASGSGSGSSSASSGLAY<br>EGLETTYITSQEVQNSILSSNYFDFDNLHVHYLLLTTNGTVMEIAGLYEERASGGGSGSASGSSGSGSASGSGSGSSSASSGLAY<br>FLPPRVRGGGRVAAAAITWVEPKNVEVWPVDPEPPVNENKTAEQEYGDKEVKLPHWTPTLHTFQVEQNYTKANCTYCNTREYTESYKG<br>CCFYFTKKKHTWNGCFQACAELYPCTYFYGPTPDILPVVTRNLNAIESLWGVYRVGEGNWTSLDGGTEKVYQIFGSHCTYVSKESTV<br>PVSHHECSFLKPCLCVSQRSNSEPEPEPEPEGGESQVRQQPSKDIEKLLNEQVNKEMQSSNLYMSMSSWSYTHSLDGAGLFLPDHAA<br>EEYEHAKKLLIFLNENNVPVQLTSISAPEHKPEGLITQIFQKAYEHEQHISESINNIVDHAIKCKDHATFNFLQWYAEQHEEVLFKD<br>ILDKIELIGNENHGLYLADQVVKGIAKSRKS | 229 |
| SIB 15011 gH/gL/gp42_NP_C14 | MRAVGVFLAICLVTIFVLPTWGNWAYPCCHVTQLRACHLLALENISDIYLVSNQTCDGESLASLNSPKNGSNQLVISRCANGLNVVSF<br>FISILKRSSSALTGHLRELLITLETLYGSFSVEDLFGANLNRYAWHRGGGSGSASSGASASGSSNGSGSGSNSSASSGASSGGAS<br>GGSGGSGAASLSEVKLHLDIEGHASHYTIPWTELMAKVPGLSPEALWREANVTEDLASMLNRYKLIYKTSGTLGIALAEPVDIPAVSE<br>GSMQVDASKVHPGVISGLNSPACMLSAPLEKQLFYYIGTMLPNTRPHSYVEYQLRAHLSVVALSINGDKFQYTGAMTSKFLMGTYKRV<br>TEKGDEHVLSLVFGKTKDLPLRGPFSYPSLTSAQSGDYSLVIVTTFVHYANFHNYFVPNLKDMFSRAVTMTAASYARYVLQKLVILE<br>MKGGCREPELDTETLTTMFEVSVAFPKVGHAVGETGNGCVDLRWLAKSFFELTVLKDIIGICYGATVKGMQSYGLERLAAMLMATVKM<br>EELGHLTTEKQEYALRLATVGPKAGVYSGLIGGATSVLLSAYNRHPLFQPLHTVMRETLFIGSHVVLRELRLNVTTQGPNLALYQLL<br>STALCSALEIGEVLRGLALGTESGLFSPCYLSLRFDLTRDKLLSMAPQEATLDQAAVSNAVDGFLGRLSLEREDRDAWHLPAYKCVDR<br>LDKVLMLIPLINVTFIISSDREVRGSALYEASTTYLSSSLELSPVIMNKCSQGAVAGEPRQIPKIQNFTRTQKSCIFCGFALLSYDEK | 230 |

TABLE 2-continued (SEQUENCE TABLE): DESCRIPTION OF THE SEQUENCES

| Description | Sequences | SEQ ID NO |
|---|---|---|
| | EGLETTYITSQEVQNSILSSNYFDEDNLHVHYLLLTTNGTVMEIAGLYEERASGGGSGSASSGASASGSGSGSGSSSASSGLAY | |
| | FLPPRVRGGGRVAAAAITWVPKPNVEWPVDPPPVNENKTAEQEYGDKEVKLPHWTPTLHTFQVPCNYTKANCTYCNTREYTESYKG | |
| | CCFYFTKKKHTWNGCFQACAELYPCTYFYGPTPDILPVVTRNLNAIESLWVGVYRVGEGNWTSLDGGTEKVYQIEGSHCTVSKESTV | |
| | PVSHHECSFLKPCLCVSQRSNSGGGESQVRQQFSKDIEKLLNEQVNKEMQSSNLYMSMSWSYTHSLDGAGLFLFDHAAEEYEHAKK | |
| | LIIFLNENNVPVQLTSISAPEHKFEGLTQIFQKAYEHEQHISESINNIVDHAIKCKDHATFNFLQWYVAEQHEEEVLFKDILDLIELI | |
| | GNENHGLYLADQYVKGIAKSRKS | |
| SIB 15012 gH/gL/gp42_NP_C16 | MDSKGSSQKGSRLLLLLVSNLLPQGVLANWAYPCCHVTQLRACHLLALENISDIYLVSNQTCDAFSLASLNSPKGGSNCLVISRCA | 231 |
| | NGLNVVSFFISILKRSSSALTGHLRELLITTLETLYGSFSVEDLFGAGLNRYAWHRGGGSGSASSGASASGSGSGSGSSSASS | |
| | GASSGGASGGSGGSGGAASLSEVKLHLDIEGHASHYTIPWTELLAKVPGLSPEALWREANVTEDLASMLNRYKLIYKTSGTLIGIALAEP | |
| | VDIPAVSEGSMQVDASKVHPGVISGLNSPACMLSAPLEKQLFYYIGTMLPNTRPHSYVEYQLRCHLSYVALSINGDKFQYTGAMTSKF | |
| | LMGTYKRVTEKGDEHVLSLVFGKTKDLPDLRGPFSYPSLLTSAQSGEYSLVIVTTFVHYANFHNYFVPNLKDMFSRAVTMTAASYARYV | |
| | LQKLVLLEMKGGCREPELETELTTMFEVSVAFFKVGHAVGETGNGCVDLRWLAKSFFELTVLKDIIGICYGATVKGMQSYGLERLAA | |
| | ILMATVKMEEELGHLTEKQEYALRLARATVGYPKAGVYSGLIGGATSVLLSAYNRHPLFQPLHTVMRETLFIGSHVVLRELRLNVTTQGP | |
| | NLALYQLLSTALCSALEIGEVLRGLALGTESGLFSPCYLSRFDLTRDKLLSIAPQEATLDQAAVSQAVDGPFLGRLSLEREDRDAWHL | |
| | PAYKCVDRLDKVLMIIPLINVTFIISSDREVRGSALYEASTTYLSSSLELSPVILNKCSQGAVAGEPRQIPKIQNFTRTQKSCIFCGF | |
| | ALLSYDEKEGLETTYITSQEVQNSILSSNYFDEDNLHVHYLLLTTNGTVMEIAGLYEERASGGGGSASSGASASGSGSGSGSGSGSS | |
| | SASSGAITWVPKPNVEWPVDPPPVNENKTAEQEYGDKEVKLPHWTPTLHTFQVPQNYTKANCTYCNTREYTESYKGCCFYFTKKKH | |
| | TWQGCFQACAELYPCTYFYGPTPDILPVVTRSLQAIESLWVGVYRVGEGNWTSLDGGTEKVYQIFGSHCTVSKESTVPVSHHECSFL | |
| | KPCLCVSQRSNSGGGASSGGGESQVRSQFSKDIEKLLNEQVNKEMQSSNLYMSMSWSYTHSLDGAGLFLFDHAAEEYEHAKKLIIFLNENNVPVQL | |
| | SGGAASGGSGGGSGGASSGGASASGSSGGGSASSGGASASGSSGGSGGGSASSGGASASGSSGGGSASSGGASASGSSGGSSSASSGGAS | |
| | TSISAPEHKFEGLTQIFQKAYEHEQHISESINQIVDHAIKCKDHATFNFLQWYVAEQHEEEVLFKDILDKIELIGQENHGLYLADQYV | |
| | KGIAKSRKS | |
| SIB 15013 gH/gL_rigid_NP | MRAVGVPLAICLVTIFVLPTWGNWAYPCCHVTQLRAQHLLALENISDIYLVSNQTCDGFSLASLNSPKNGSNQLVISRCANGLNVVSF | 232 |
| | FISILKRSSSALTGHLRELLITTLETLYGSFSVEDLFGANLNRYAWHRGGGSGSASSGASASGSSGGSGSNSSASSGGASSGGAS | |

TABLE 2-continued (SEQUENCE TABLE): DESCRIPTION OF THE SEQUENCES

| Description | Sequences | SEQ ID NO |
|---|---|---|
| | GGSGGSGGAASLSEVKLHLDIEGHASHYTIPWTELMAKVPGLSPEALWREANVTEDLASMLNRYKLIYKTSGTLGIALAEPVDIPAVSE<br>GSMQVDASKVHPGVISGLNSPACMLSAPLEKQLFYYIGTMLPNTRPHSYVFYIQLRAHLSVVALSINGDKFQYTGAMTSKFLMGTYKRV<br>TEKGDEHVLSLVFGKTKDLPDLRGPFSYPSLTSAQSGDYSLVIVTTFVHYANFHNYFVPNLKDMFSRAVTMTAASYARYVLQKLVLLE<br>MKGGCREPELDTETLTTMFEVSVAFFKVGHAVGETGNGCVDLRWLAKSFFELTVLKDIIGICYGATVKGMQSYGLERLAAMLMATVKM<br>EELGHLTTEKQEYALRLIATVGYPKAGVYSGLIGGATSVLLSAYNRHPLFQPLHTVMRETLFIGSHVVLRELRLNVTTQGPNLALYQLL<br>STALCSALEIGEVLRGLALGTESGLFSPCYLSLRFDLTRDKLLSMAPQEATLDQAAVSNAVDGFLGRLSLREDRDAWHLPAYKCVDR<br>LDKVLMIIPLINVTFIISSDREVRGSALYRASTTYLSSSLFLSPVIMNKCSQGAVAGEPRQIPKIQNFTRTQKSCIFCGFALLSYDEK<br>EGLETTYITSQEVQNSILSSNYFDEDNLHVHYLLLTTNGTVMEIAGLYEERA<u>SGEPEPEPEPEPEPEPEPEPEPEPEPEPEPEPEPE</u><br><u>PEPEPEPEPEPEPEPESQVRQQFSKDIEKLLNEQVNKEMQSSNLYMSMSWSYTHSLDGAGLFLFDHAAEEYEHAKKLLIFLNENNVPVQ</u><br><u>LTSISAPEHKFEGLTQIFQKAYEHEQHISESINNIVDHAIKCKDHATFNFLQWYVAEQHEEEVLFKDILDKIELIGNENHGLYLADQY</u><br><u>VKGIAKSRKS</u> | 233 |
| 46 amino acid linker | <u>GGSGSASSGASASGSSGGSGSSGSASSGGASGGSGSG</u> | 234 |
| 32 amino acid linker | <u>SGGGSGSASSGASASGSSGSSGSSSASSG</u> | 235 |
| 88 amino acid linker | <u>GGSGSASSGASASGSSGSGSSGSASSGASASGGAGSSGGSGSSGSASSGASASGGAGSSGSSGSASSGGASGGSGSG</u> | 236 |
| 44 amino acid linker | <u>GGSGSASSGASASGSSGSGSSGSASSGASASGGAGSSGGSGSG</u> | 237 |
| 12 amino acid rigid linker | <u>EPEPEPEPEPGG</u> | 238 |
| 48 amino acid rigid linker | <u>SGEPEPEPEPEPEPEPEPEPEPEPEPEPEPEPEPEPEPEPEPEPEPEP</u> | 239 |
| gp42 fusion segment | LAYFLPRVRGGGRVAAAAITWVPKPNVEVWPVDPPPVNENKTAEQEYGDKEVKLPHWTPTLHTFQVPQNYTKANCTYCNTREYTES<br>YKGCCFYFTKKKHTWNGCFQACAELYPCTYFYGPTDILPVVTRNLNAIESLWVGVYRVGEGNWTSLDGGTEKVYQIFGSHCTYVSKF<br><u>STVPVSHHECSFLKPCLCVSQRSNS</u> | 240 |
| gp42 fusion segment 2 | AITWVPKPNVEVWPVDPPPVNENKTAEQEYGDKEVKLPHWTPTLHTFQVPQNYTKANCTYCNTREYTESYKGCCFYFTKKKHTWQGC<br>FQACAELYPCTYFYGPTDILPVVTRSLQAIESLWVGVYRVGEGNWTSLDGGTFKVYQIFGSHCTYVSKESTVPVSHHECSFLKPCLC<br><u>VSQRSNS</u> | |

TABLE 2-continued (SEQUENCE TABLE): DESCRIPTION OF THE SEQUENCES

| Description | Sequences | SEQ ID NO |
|---|---|---|
| SIB 15014<br>gH/gL/gp42_NP_C17 | MDSKGSSQKGSRLLLLLVVSNLLLPQGVLANWAYPCCHVTQLRAQHLLALENISDIYLVSNQTCDAFSLASLNSPKQGSNQLVISRCA<br>NGLNVVSFFISILKRSSSALTGHLRELLTTLETLYGSFSVEDLFGAQLNRYAWHRGGGSGSASSGASASGSGGGSGSGSSASS<br>NPGASSGGASGGSGGSGAASLSEVKLHLDIEGHASHYTIPWTELIAKVPGLSPEALWREANVTEDLASMLNRYKLIYKTSGTLGIALAEP<br>VDIPAVSEGSMQVDASKVHPGVISGLNSPACMLSAPLEKQLFYYIGTMLPNTRPHSYVFYQLRCHLSYVALSINGDKFQYTGAMTSKF<br>LMGTYKRVTEKGDEHVLSLVFGKTKDLPDLRGPFSYPSLTSAQSGEYSLVIVTTFVHYANFHNYFVPNLKDMFSRAVTMTAASYARYV<br>LQKLVLLEMKGGCREPELETETLTTMFEVSVAFFKVGHAVEGETGNGCVDLRWLAKSFFELTVLKDIIGICYGATVKGMQSYGLERLAA<br>ILMATVKMEELGHLTTEKQEYALRLATVGYPKAGVYSGLIGGATSVLLSAYNRHPLFQPLHTVMRETLFIGSHVVLRELRLNVTTQGP<br>NLALYQLLSTALCSALEIGEVLRGLALGTESGLFSPCYLSLRFDLTRDKLLSIAPQEATLDQAAVSQAVDGFLGRLSLEREDRDAWHL<br>PAYKCVDRLDKVLMIIPPLINVTFIISSDREVRGSALYEASTTYLSSSLFLSPVIMNKCSQGAVAGEPRQIPKIQNFTRTQKSCIFCGF<br>ALLSYDEKEGLETTYITSQEVQNSILSSNYFDFDNLHVHYLLLTTNGTVMEIAGLYEERASGGGSGSASSGASASGSGGGSGSGSSS<br>SASSGAITWVPKPNVEVWPVDPPPVNENKTAEQEYGDKEVKLPHWTPTLHTFQVPQNYTKANCTYCNTREYTESYKGCCFYFTKKKH<br>TWQGCFQACAELYPCTYFYGPTPDILPVVTRNLNAIESLWVGVYRVGEGNWTSLDGGTEKVYQIFGSHCTVVSKESTVPVSHHECSFL<br>KPCLCVSQRSNSGGSASGGSGGSGAASGGSGGASSGASGGSGGSGASSGASASGGSGGSASSGASASGGSGSSSSASSGAS<br>SGGASGGSGGSGESQVRSQFSKDIEKLLNEQVNKEMQSSNLYMSMSWSYTHSLDGAGLFLFPDHAAEEYEHAKKLLIFLNENNVPVQL<br>TSISAPEHKFEGLTQIFQKAYEHEQHISESINQIVDHAIKCKDHATPNFLQWYVAEQHEEEVLFKDILDKIELIGQENHGLYLADQYV<br>KGIAKSRKS | 241 |
| SIB 15015<br>gH/gL/gp42_NP_C18 | MDSKGSSQKGSRLLLLLVVSNLLLPQGVLANWAYPCCHVTQLRAQHLLALENISDIYLVSNQTCDAFSLASLNSPKQGSNQLVISRCA<br>NGLNVVSFFISILKRSSSALTGHLRELLTTLETLYGSFSVEDLFGAQLNRYAWHRGGGSGSASSGASASGSGGGSGSGSSASS<br>GASSGGASGGSGGSGAASLSEVKLHLDIEGHASHYTIPWTELIAKVPGLSPEALWREANVTEDLASMLNRYKLIYKTSGTLGIALAEP<br>VDIPAVSEGSMQVDASKVHPGVISGLNSPACMLSAPLEKQLFYYIGTMLPNTRPHSYVFYQLRCHLSYVALSINGDKFQYTGAMTSKF | 242 |

TABLE 2-continued (SEQUENCE TABLE): DESCRIPTION OF THE SEQUENCES

| Description | Sequences | SEQ ID NO |
|---|---|---|
| | LMGTYKRVTEKGDEHVLSLVFGKTKDLPDLRGPFSYPSLTSAQSGEYSLVIVTTFVHYANFHNYFVPNLKDMFSRAVTMTAASYARYV | |
| | LQKLVLLEMKGGCREPELETETLTTMFEVSVAFFKVGHAVGETGNGCVDLRWLAKSFFELTVLKDIIGICYGATVKGMQSYGLERLAA | |
| | MLMATVKMEELGHLTEKQEYALRLATVGYPKAGVYSGLIGGATSVLLSAYNRHPLFQPLHTVMRETLFIGSHVVLRELRLNVTTQGP | |
| | NLALYQLLSTALCSALEIGEVLRGLALGTESGLFSPCYLSLRFDLTRDKLLSMAPQEATLDQAAVSNAVDGFLGRLSLEREDRDAWHL | |
| | PAYKCVDRLDKVLMIIPLINVTFIISSDREVRGSALYEASTTYLSSSLFLSPVIMNKCSQGAVAGEPRQIPKIQNFTRTQKSCIFCGF | |
| | ALLSYDEKEGLETTTYITSQEVQNSILSSNYFDFDNLHVHYLLLTTNGTVMEIAGLYEERASGGGSGSASSGASASGSSGSGSGSS | |
| | SASSGAITWVPKPNVEVWPVDPPPVNENKTAEQEYGDKEVKLPHWTPTLHTFQVPQNYTKANCTYCNTREYTESYKGCCFYFTKKKH | |
| | TWNGCFQACAELYPCTYFYGPTPDILPVVTRNLNAIESLWVGVYRVGEGNWTSLDGGTEKVYQIFGSHCTYVSKESTVPVSHHECSFL | |
| | KPCLCVSQRSNSGGGSGASSGASASGSSSSASSGASGGSGGGSASGGSGGGSGASGGASGGSASSGASASGSSGGSGSSSASSGAS | |
| | SGGASGSGGSGGESGQVRSQFSKDIEKLLNEQVNKEMQSSNLYMSMSWSYTHSLDGAGLFLFDHAAEEYEHAKKLIIFLNENNVPVQL | |
| | TSISAPEHKFEGLTQIPQKAYEHEQHISESINQIVDHAIKCKDHATFNFLQWYVAEQHEEEVLFKDILDKIELIGQENHGLYLADQYV | |
| | KGIAKSRKS | |

EXAMPLES

The following examples are provided to illustrate certain disclosed embodiments and are not to be construed as limiting the scope of this disclosure in any way.

1. Antigenic EBV Polypeptides for Eliciting Antibodies Against EBV

Antigenic polypeptides that elicit antibodies against EBV were developed. Self-assembling ferritin nanoparticles were developed that display EBV gL and gH polypeptides as a single-chain, and the immunogenicity of these nanoparticles in mice was evaluated.

Figure 1A:
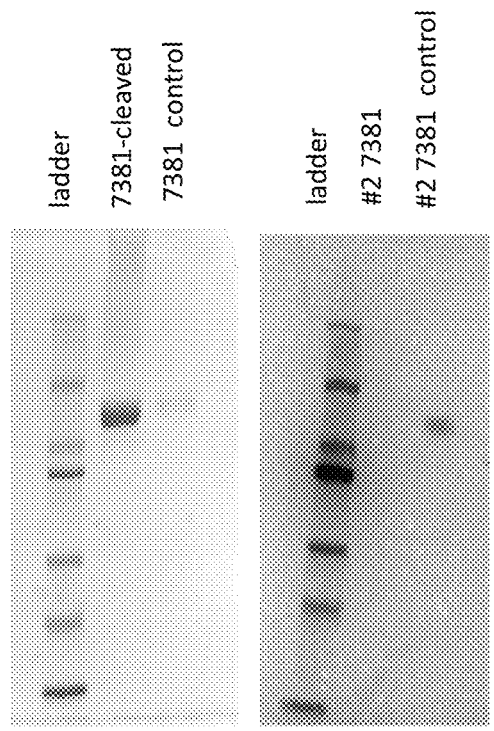
FIGS. 1A-1B show purified single-chain gL and gH monomer (FIG. 1A) (SEQ ID NO: 6) and trimer (FIG. 1B) (SEQ ID NO: 11) with and without removal of the His-tag by Coomassie and Western blot analysis.
Figure 1B:
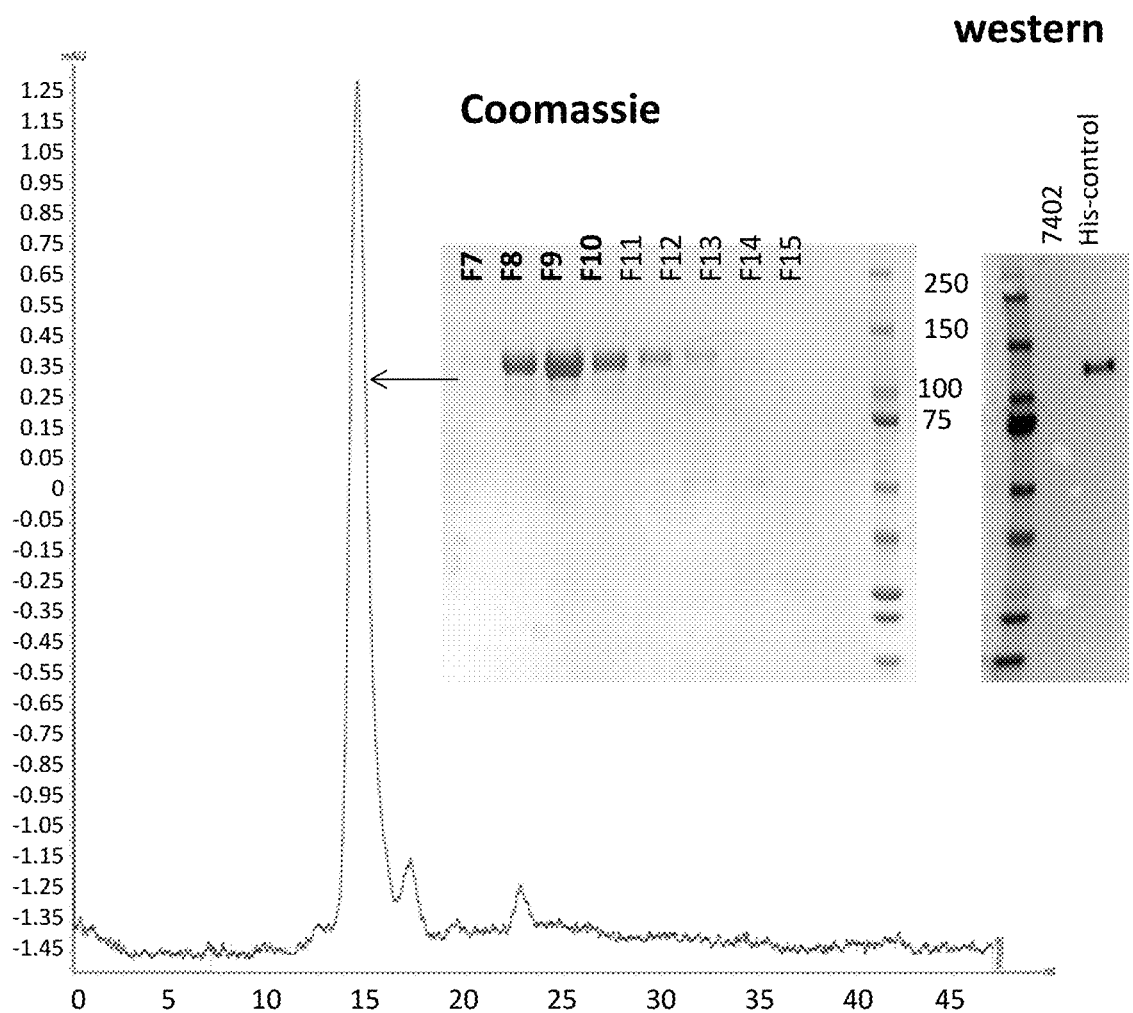
Figure 2B:
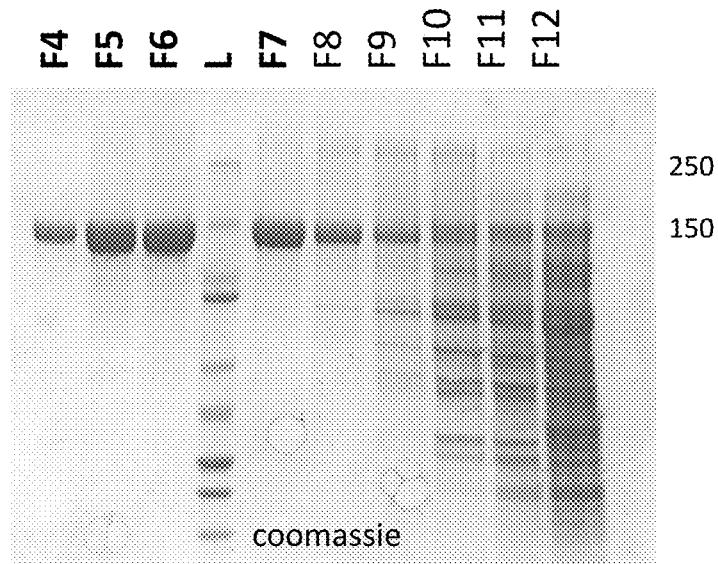
Figure 2C:
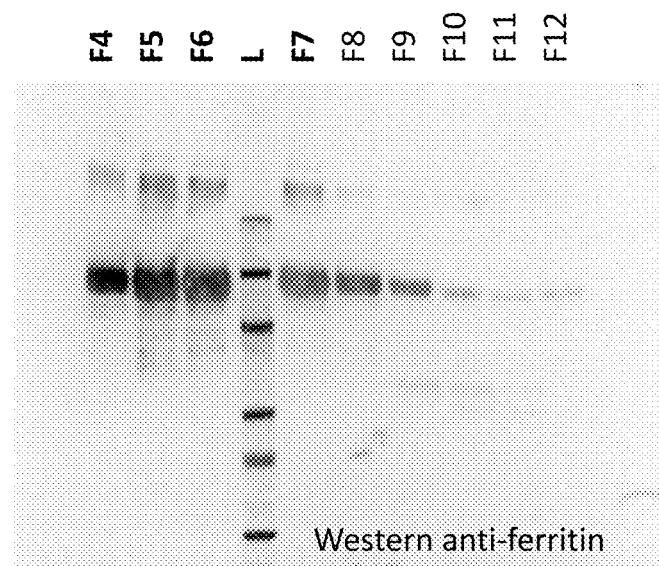
Figure 2D:
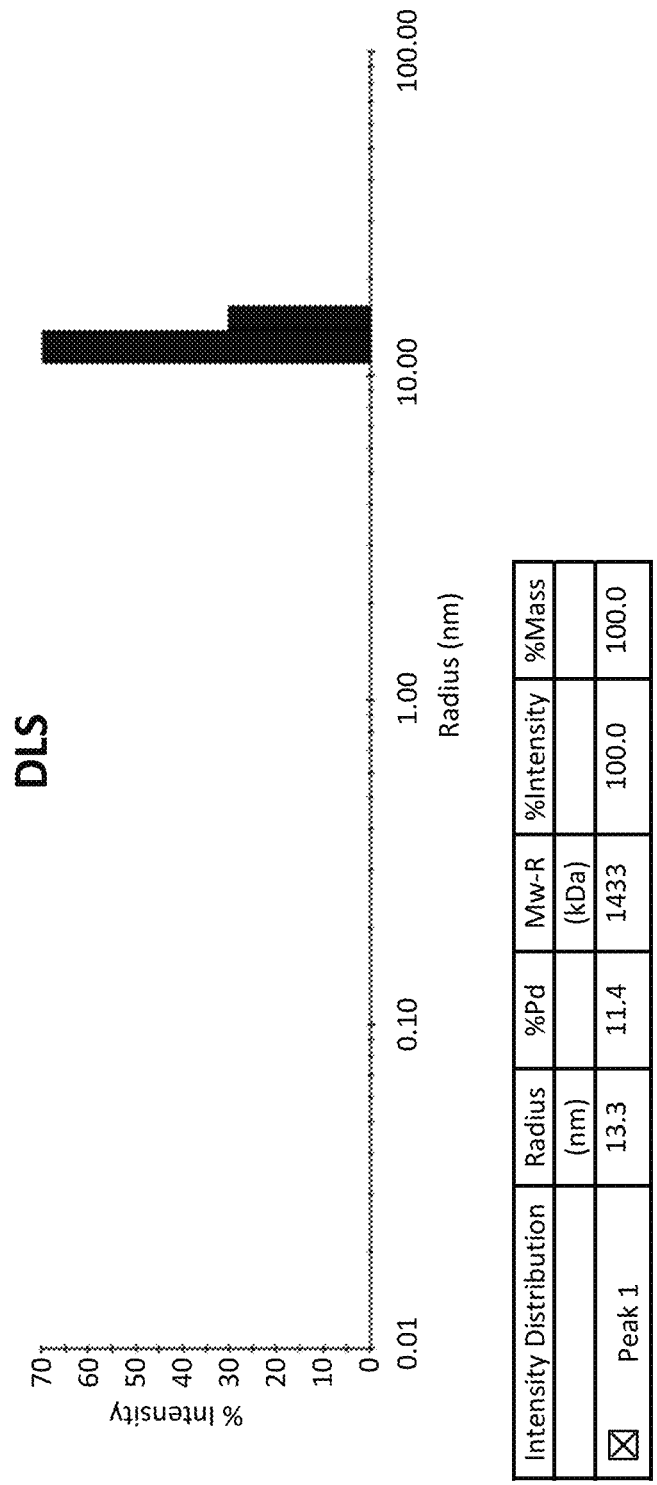
Figure 2E:
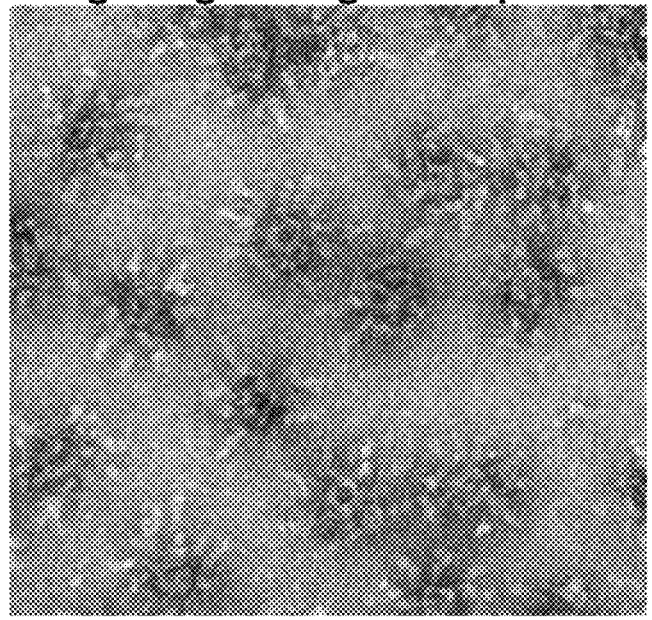

Monomeric and trimeric gL/gH constructs were expressed and purified. FIG. 1A shows single-chain gL and gH monomer (SEQ ID NO: 6) +/−His-tag cleavage by Coomassie and western blot (anti-His) analysis. FIG. 1B shows fractionation of a gL and gH trimer (SEQ ID NO: 11) on a Superose® SEC column as an absorbance trace and by Coomassie, along with a western blot to confirm His-tag cleavage by thrombin protease. The final concentration of samples was 1 mg/mL, the total volume was 15 mL, and the endotoxin level was 1.48 EU/mL for the SEQ ID NO: 6 construct.

Single-chain gL/gH ferritin nanoparticles (SEQ ID NO: 14) were expressed and purified. FIGS. 2A-2E show purification and characterization thereof by Superose® 6 SEC fractionation (2A), Coomassie of SEC fractions (2B), western blot of SEC fractions with anti-ferritin primary Ab (2C), dynamic light scattering (DLS, 2D), and electron microscopy (2E).

Figure 3:
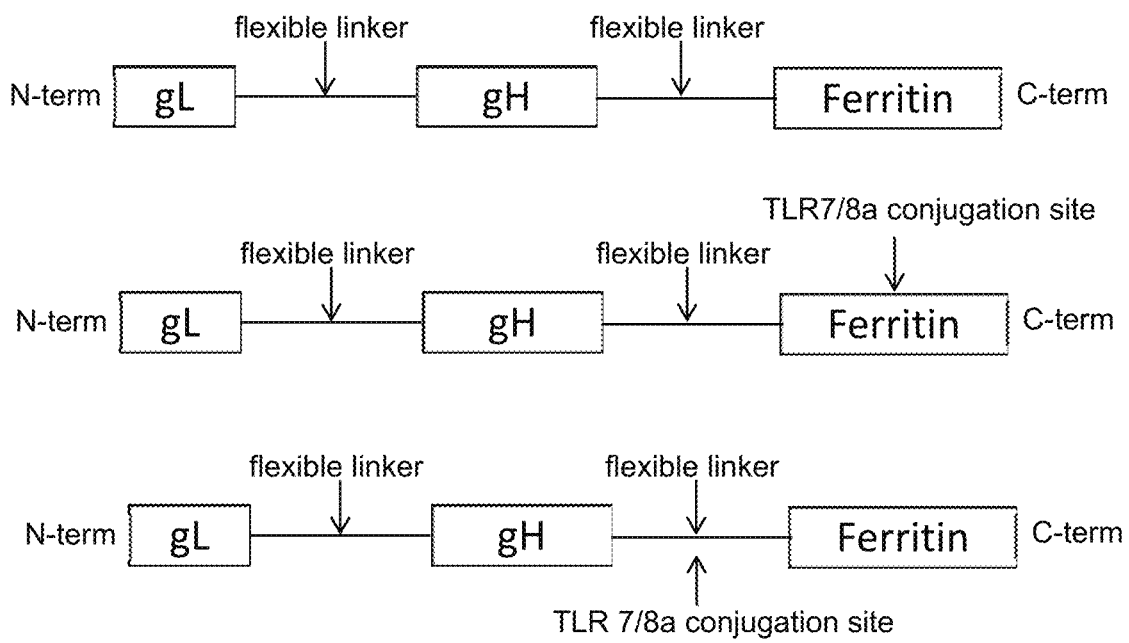
FIG. 3 shows different representative single-chain gL/gH-ferritin constructs.
Figure 4:
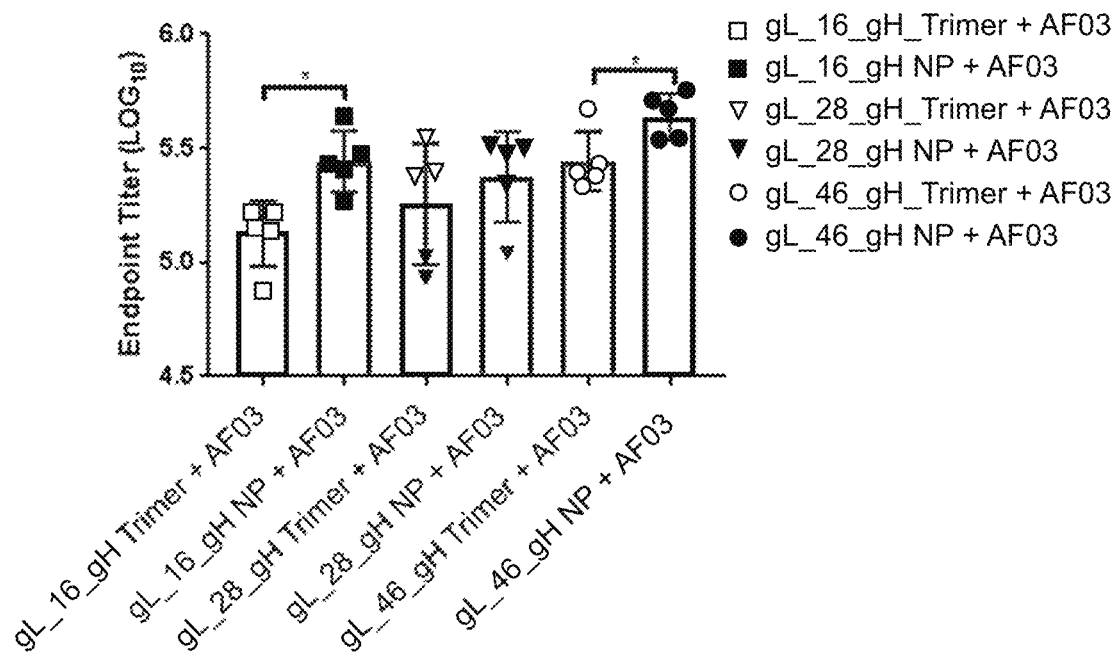
FIG. 4 shows antibody titers following immunization of mice with single-chain gL/gH trimers or nanoparticles (NP) admixed with AF03 adjuvant, which is a squalene emulsion-based adjuvant. *p-value=<0.05 when comparing the NP construct with its corresponding trimer construct. From left to right, constructs were SEQ ID NOs: 16, 10, 11, 13, 12, and 14.

Exemplary constructs of single-chain EBV gL and gH fused to ferritin are shown in FIG. 3. A conjugation site for an immune-stimulatory moiety, such as a toll-like receptor 7/8 agonist (TLR7/8a), can be present either on the ferritin or in the linker (see, e.g., SEQ ID NOS: 14, 19, 22, 20, 23, and 33 for exemplary sequences).

gL/gH trimers or nanoparticles with different linkers were injected into mice and immune sera were assessed (FIG. 4). Mice were given two 2-µg injections with adjuvant AF03, a squalene emulsion-based adjuvant, with a 3-week interval between doses. Anti-gL/gH antibody endpoint titers were measured by ELISA at week 6. For gH_16_gL, a nanoparticle (SEQ ID NO: 10) outperformed a trimer construct (SEQ ID NO: 16). The gL_28_gH nanoparticle (SEQ ID NO: 13) did not perform significantly differently from the trimer construct (SEQ 1D NO: 11). The gL_46_gH nanoparticle (SEQ ID NO: 14) outperformed the gL_46_gH trimer (SEQ ID NO: 12).

These data indicate that single-chain gL/gH nanoparticles can elicit a robust immune response against EBV 2. Bivalent Immunization Against gL/gH and Gp220

Figure 5A:
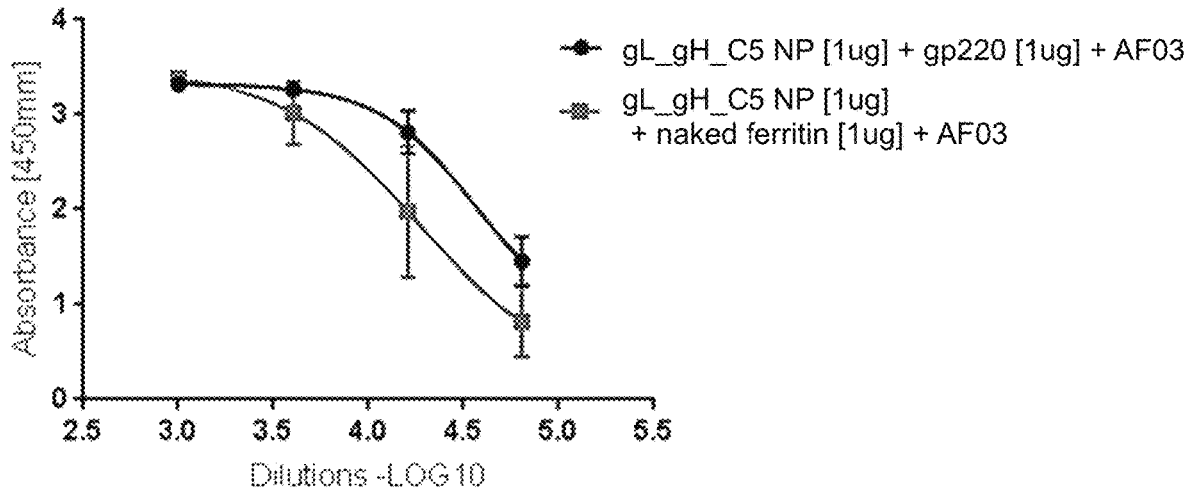
FIGS. 5A-5B show anti-gL/gH antibody response in mice to a bivalent composition comprising both gp220 nanoparticles (SEQ ID NO: 1) and a single-chain gL/gH nanoparticle ("gL_gH_C5 NP," SEQ ID NO: 19) compared to the single-chain gL/gH nanoparticle and negative control naked ferritin (i.e., ferritin not conjugated to any non-ferritin polypeptide or immune-stimulatory moiety). The results indicate that using the bivalent composition did not result in interference with the anti-gL/gH antibody response relative to the results with single-chain gL/gH with negative control naked ferritin. Both compositions included AF03 adjuvant. ELISA results at individual dilutions (FIG. 5A) and binding titer (FIG. 5B) are shown.
Figure 5B:
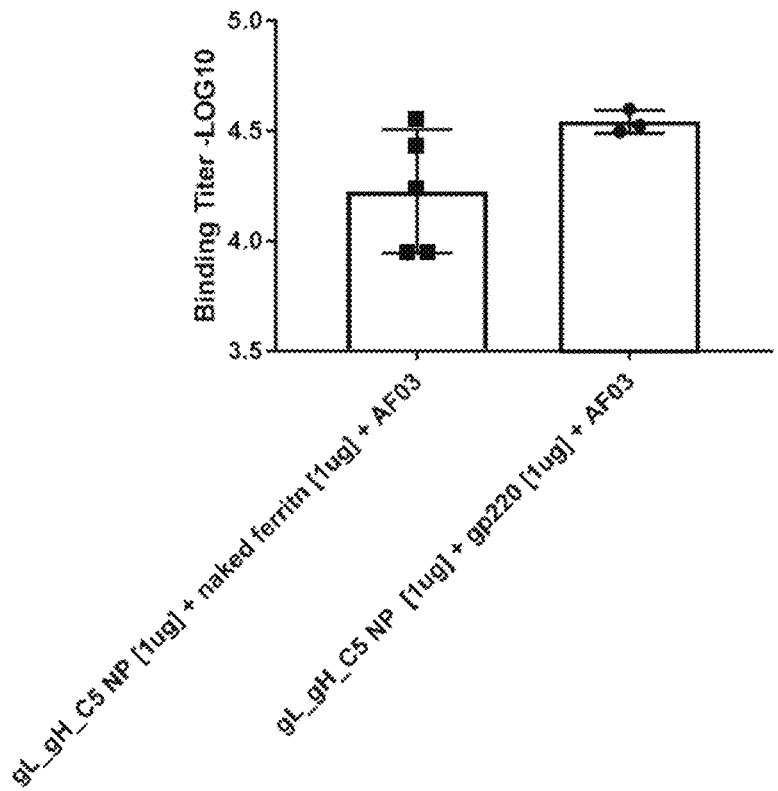
Figure 6A:
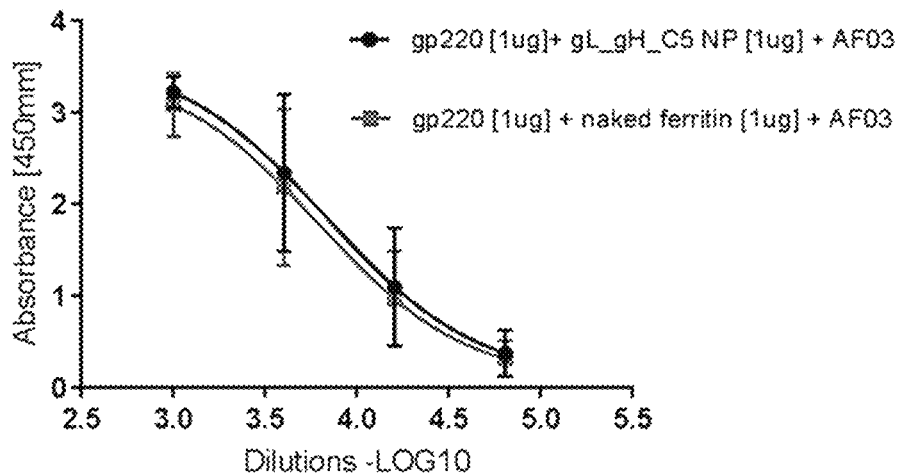
FIGS. 6A-6B show anti-gp220 antibody response to a bivalent composition comprising both gp220 nanoparticles and single-chain gL/gH nanoparticles as described for FIGS. 5A-B. The results indicate that using the bivalent composition did not result in interference with the anti-gp220 antibody response relative to the results with gp220 nanoparticles with negative control naked ferritin. Both compositions included AF03 adjuvant. ELISA results at individual dilutions (FIG. 6A) and binding titer (FIG. 6B) are shown.
Figure 6B:
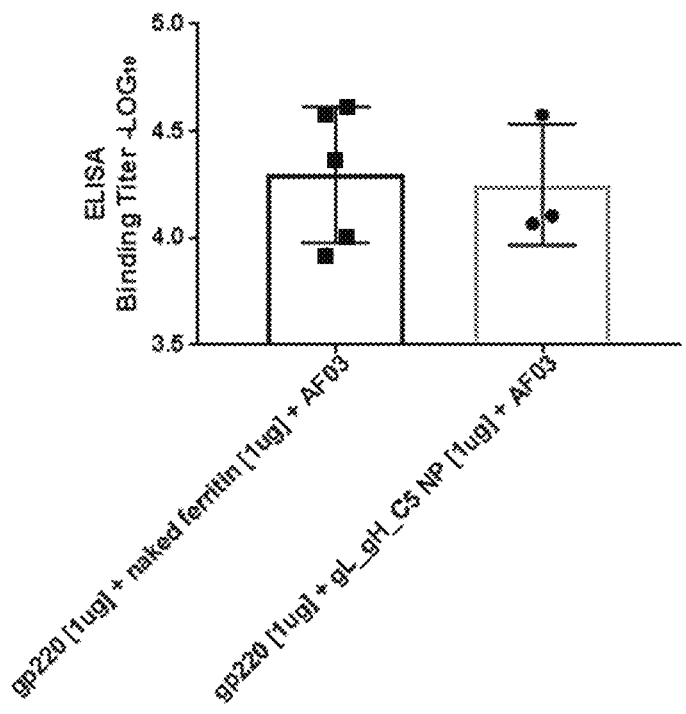

Bivalent immunization was performed using compositions comprising single-chain gL/gH nanoparticles and gp220 nanoparticles. Including the gp220 nanoparticles (SEQ ID NO: 1) had no significant interfering effect on the immune response elicited by single-chain gL/gH nanoparticles (gL-gH_C5 NP [SEQ ID NO: 19]), as measured by an ELISA binding assay using sera from mice vaccinated as described above (FIGS. 5A-5B, showing measurements at individual dilutions and binding titers, respectively). Similarly, no interference was observed in the response to the immune response to gp220 nanoparticles when administered in combination with the single-chain gL/gH nanoparticles, as measured by ELISA (FIGS. 6A-6B, showing measurements at individual dilutions and binding titers, respectively).

Thus, immunization with both a single-chain gL/gH nanoparticle and a gp220 nanoparticle did not decrease the immune response to either polypeptide.

3. Conjugation of Adjuvant to Ferritin Nanoparticles

Figure 7A:
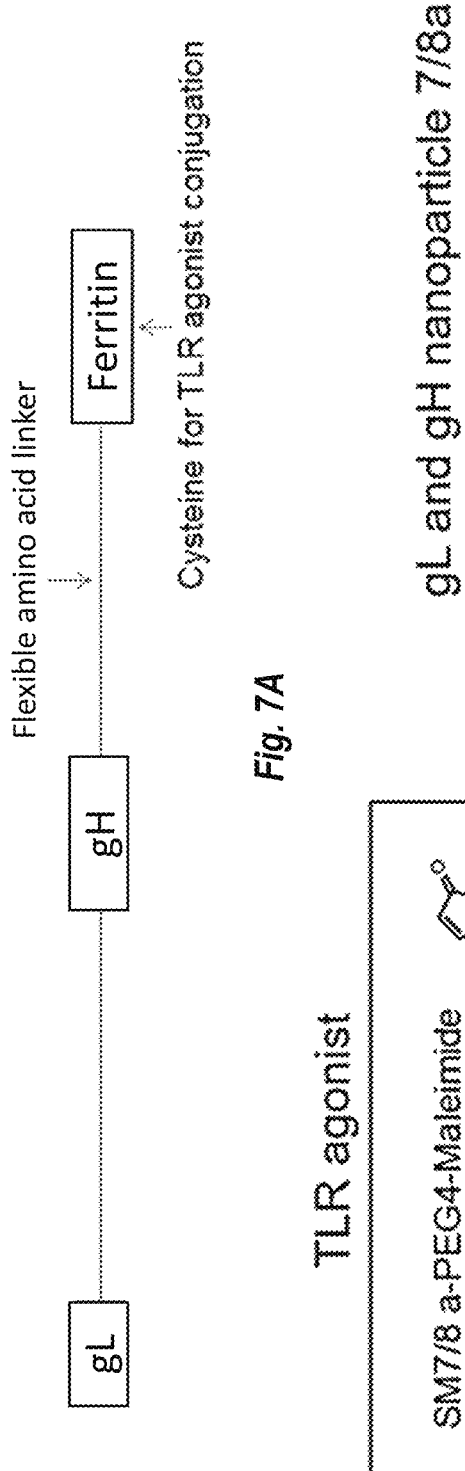
FIG. 7A shows the design of a nanoparticle comprising an EBV polypeptide and ferritin comprising a mutation replacing a surface-exposed amino acid with a cysteine for conjugation to an immune-stimulatory moiety such as a toll-like receptor (TLR) agonist. For an exemplary sequence corresponding to this design, see SEQ ID NO: 14, in which a single-chain gL/gH antigen is linked to ferritin by a flexible 46 amino acid linker.
Figure 7C:
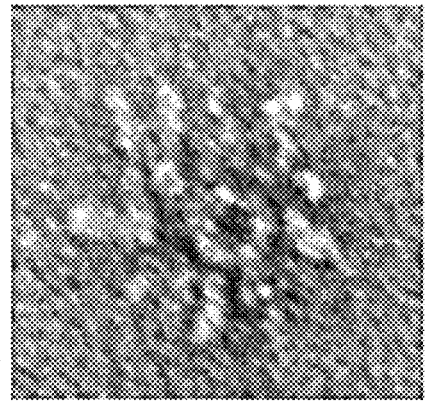
FIG. 7C shows an electron micrograph (EM) image of a gL/gH nanoparticle with SM7/8a conjugated thereto via the cysteine on the ferritin surface and a PEG4-maleimide linker
Figure 7B:
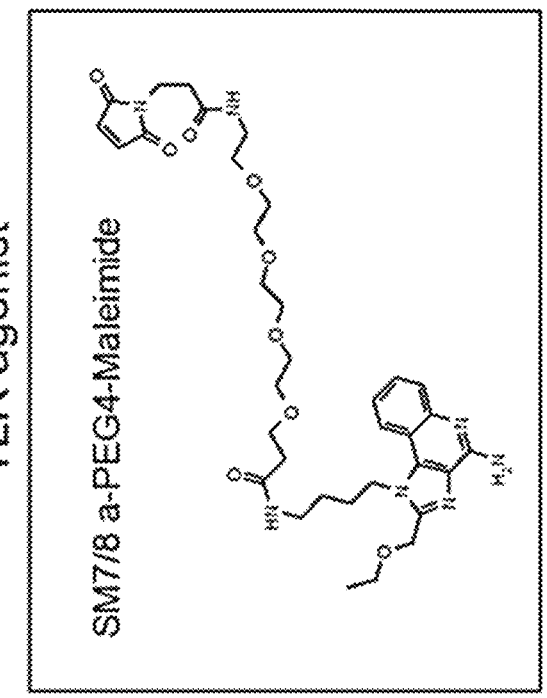
FIG. 7B shows a representative toll-like receptor (TLR) agonist (SM7/8a with a PEG4-maleimide linker) suitable for conjugation to a construct according to FIG. 7A.

Next, conjugation of adjuvants to ferritin nanoparticles was assessed. FIG. 7A illustrates a construct in which the ferritin comprises a mutation replacing a surface-exposed amino acid with a cysteine, which is available for conjugation. FIG. 7B shows an exemplary immune-stimulatory moiety (SM7/8a, a TLR-7/8 agonist) linked to a PEG4 linker and maleimide. This maleimide can be used to covalently conjugate the linker (itself attached to SM7/8a) to the surface-exposed cysteine of the ferritin. A polypeptide comprising a single-chain gL/gH polypeptide fused to ferritin conjugated to SM7/8a is shown in the electron micrograph of FIG. 7C.

Figure 8B:
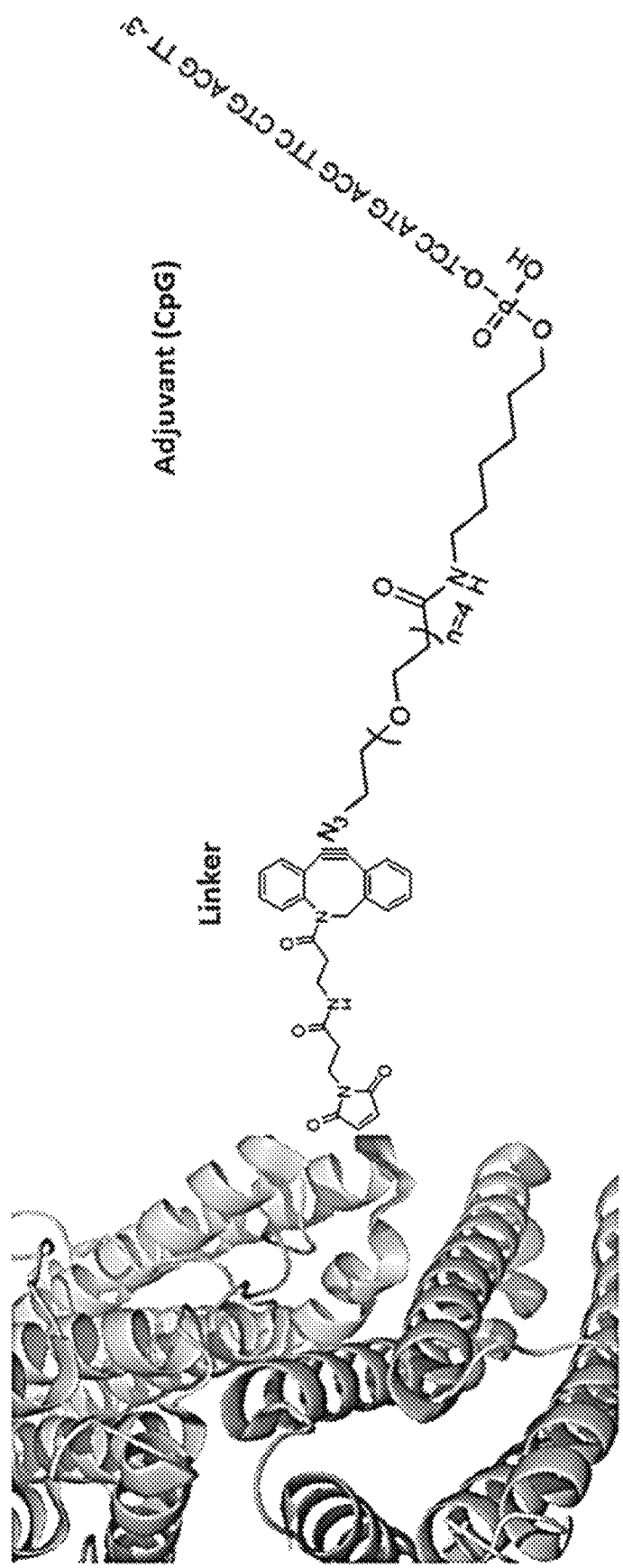
FIG. 8B illustrates conjugation of a CpG adjuvant (SEQ ID NO: 247) to ferritin by juxtaposing the ferritin, linker, and CpG adjuvant, oriented to show the parts of each moiety that become attached to each other in proximity.

A cysteine resulting from mutation of a surface-exposed amino acid is illustrated in the structure a ferritin molecule in FIG. 8A. Conjugation of a CpG adjuvant (SEQ ID NO: 230) to ferritin is illustrated in FIG. 8B by juxtaposing the ferritin, linker, and CpG adjuvant, oriented to show the parts of each moiety that become attached to each other in proximity.

Figure 9A:
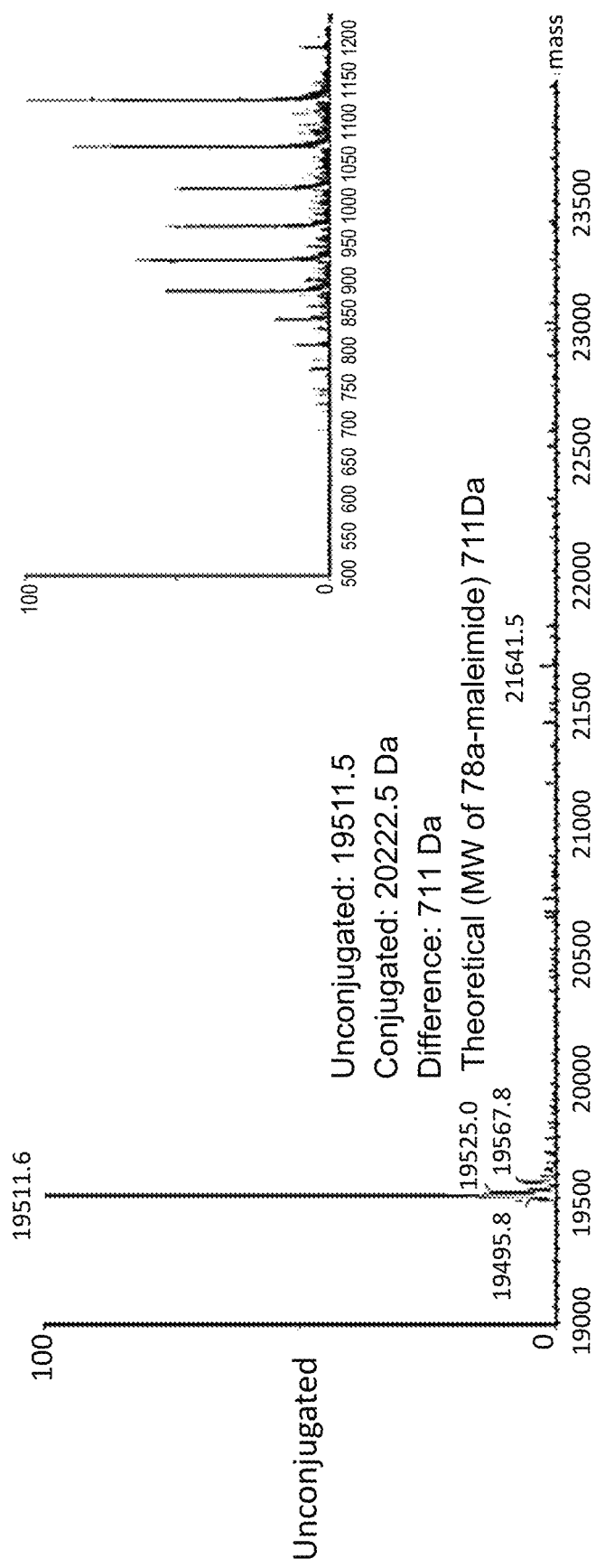
FIGS. 9A-9B show mass spectrometry (MS) spectra of the unconjugated (FIG. 9A) and SM7/8a-conjugated (FIG. 9B) forms of a gL/gH-ferritin. The difference in mass of the main peaks was 711 Da, which approximately corresponds to the predicted difference from conjugating the SM7/8a with linker.
Figure 9B:
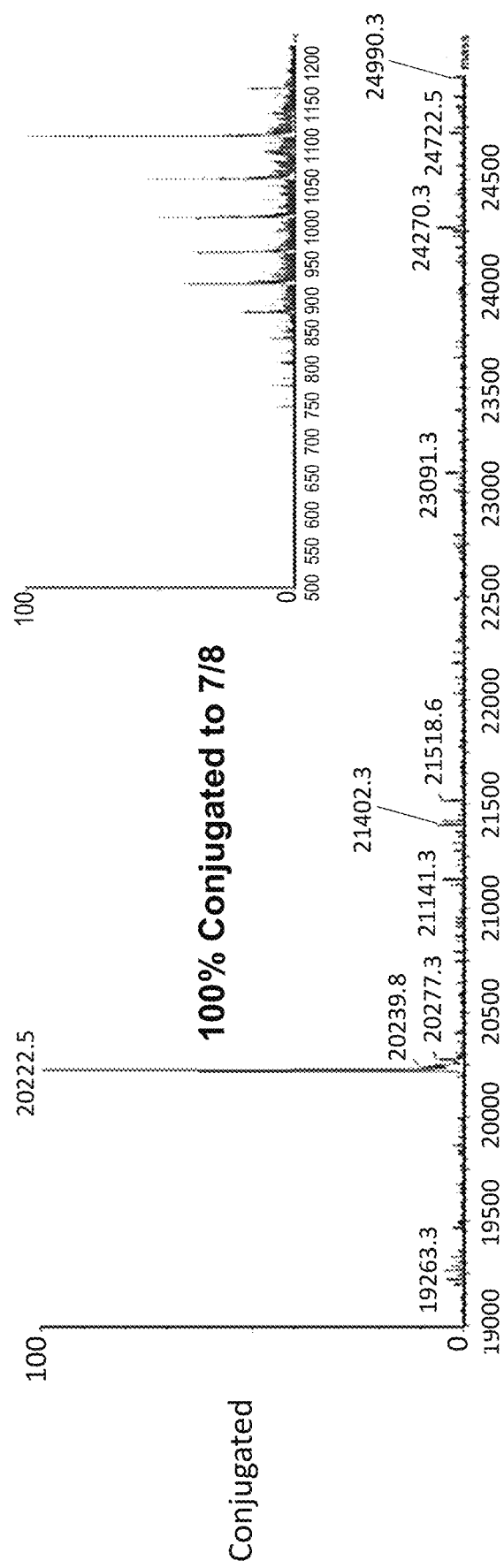

A gL/gH nanoparticle (SEQ ID NO: 19) was reduced using 2 mM TCEP and then oxidized via the addition of 1×PBS and using a 100 kD microspin column to remove TCEP. SM7/8a was then incubated with the gL/gH nanoparticle for conjugation. Excess SM7/8a was removed from the reaction via a 100 kD microspin column. Mass spectrometry (MS) data indicated that about 100% of the polypeptide comprising single-chain gL/gH and ferritin (SEQ ID NO: 19) was conjugated to SM7/8a (FIG. 9B) based on shift of the main MS peak relative to the spectrum of the unconjugated polypeptide (FIG. 9A). The difference between the mass of the conjugated and unconjugated polypeptide corresponds to the molecular weight of the SM7/8a-linker-maleimide adduct (711 Da).

Figure 10A:
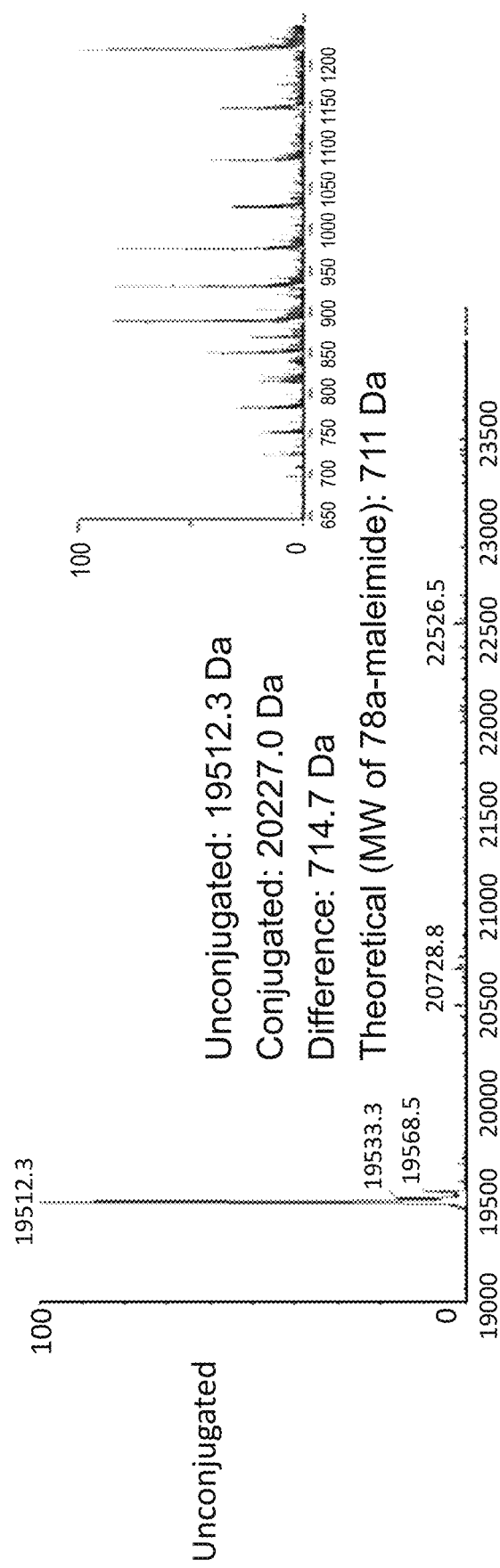
FIGS. 10A-10B show mass spectrometry (MS) spectra of the unconjugated (FIG. 10A) and SM7/8a-conjugated (FIG. 10B) forms of a gp220-ferritin. The difference in mass of the main peaks was 714.7 Da, which approximately corresponds to the predicted difference from conjugating the SM7/8a with linker.
Figure 10B:
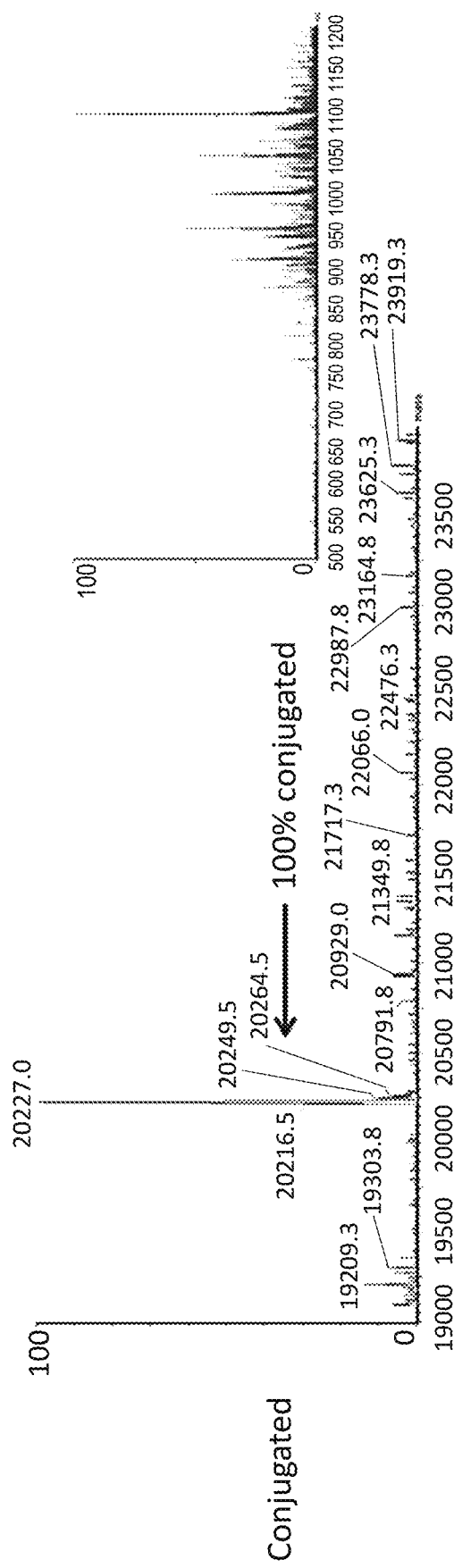

A gp220 nanoparticle (SEQ ID NO: 1) was reduced using 2 mM TCEP and then oxidized via the addition of 1×PBS and using a 100 kD microspin column to remove TCEP. The SM7/8a was then incubated with the gL/gH nanoparticle for conjugation. Excess SM7/8a was removed from the reaction via a 100 kD microspin column. MS data indicated that about 100% of a conjugated polypeptide comprising gp220 and ferritin (SEQ ID NO: 1) is conjugated to SM7/8a (FIG. 10B) based on shift of the main MS peak relative to the spectrum of the unconjugated polypeptide (FIG. 10A).

Figures 11A, 11B, 11C, 11D:
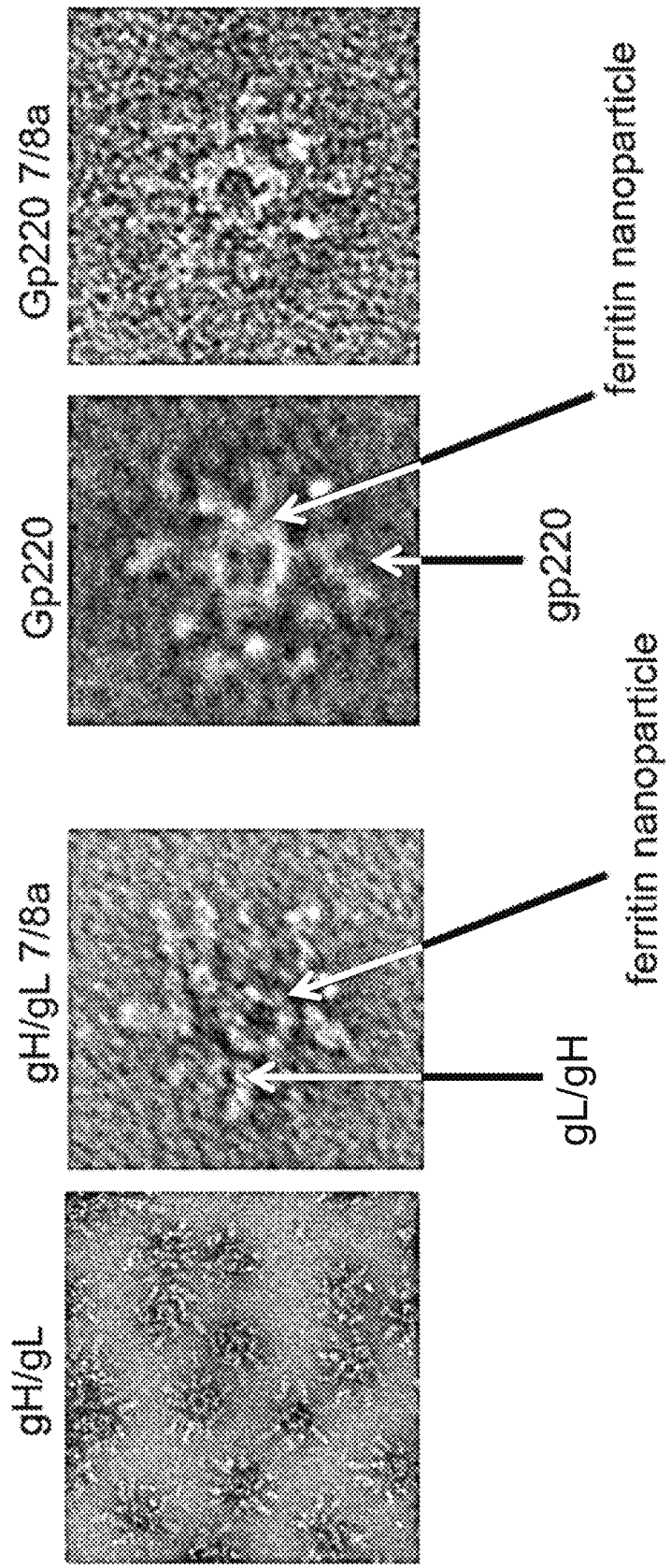
FIGS. 11A-11D show electron microscopy (EM) images of unconjugated (FIGS. 11A, C) and conjugated (FIGS. 11B, D) single-chain gL/gH (FIGS. 11A, B) and gp220 (FIGS.

Electron microscopy (EM) data also confirmed that conjugation of SM7/8a to polypeptides comprising single-chain gL/gH and ferritin (FIG. 11B in comparison to unconjugated sample in FIG. 11A) or comprising gp220 and ferritin (FIG. 11D in comparison to unconjugated sample in FIG. 11C) did not disrupt nanoparticle assembly.

Antibody responses were assayed by ELISA following immunization with 1 jig of nanoparticles comprising single-chain gL/gH (gL_gH_CS NP, FIGS. 12A and 12B) or nanoparticles comprising gp220 (FIGS. 13A and 13B). Nanoparticles were in combination with 1 µg of naked ferritin and were unconjugated or conjugated to SM7/8a. Unconjugated nanoparticles were administered with or without admixed AF03 adjuvant. Each mouse received 100 µL of the nanoparticle composition as described above. For mice receiving AF03 adjuvant, a 1:1 volume of AF03 was mixed with the nanoparticles. BALB/c mice (n=5/group) were immunized twice with a 3-week interval between doses. A bleed was taken for ELISA analysis at week 5. The most robust ELISA responses were seen for nanoparticles administered in the AF03 adjuvant. Conjugation to SM7/8a produced a more robust ELISA response compared to unconjugated nanoparticles without adjuvant.

The effect of coadministration of 1 µg each of gL_gH_C5 nanoparticles conjugated to SM7/8a and gp220 nanoparticles conjugated to SM7/8a was also assessed, as compared to single administration of either nanoparticle accompanied by naked ferritin nanoparticles in FIGS. 14A-14B and 15A-15B. No interference was observed on the immune response to either single-chain gL/gH (FIGS. 14A-14B, without and with AF03, respectively) or gp220 (FIGS. 15A-15B, without and with AF03, respectively).

4. Long-Term Immunogenicity Studies

Studies were performed to assess immunogenicity at 3 months after dosing with nanoparticles comprising single-chain gL/gH (gL/gH_C5, SEQ ID NO: 19). BALB/c mice (n=5/group) were immunized twice with a 3-week interval between doses. Naked ferritin (i.e., ferritin not conjugated to any polypeptide or adjuvant) was administered at 1 µg with the 1 µg nanoparticles comprising single-chain gL/gH, and the nanoparticles were formulated in the presence or absence of admixed AF03 adjuvant. A bleed was taken for ELISA analysis at week 13. For mice receiving AF03 adjuvant, a 1:1 volume of AF03 was mixed with the nanoparticle composition. Each mouse received 100 µL of the nanoparticle composition described above. Some mice received nanoparticles comprising single-chain gL/gH in which the ferritin was conjugated to SM7/8a ("7/8a" in FIGS. 16-17).

Figure 16:
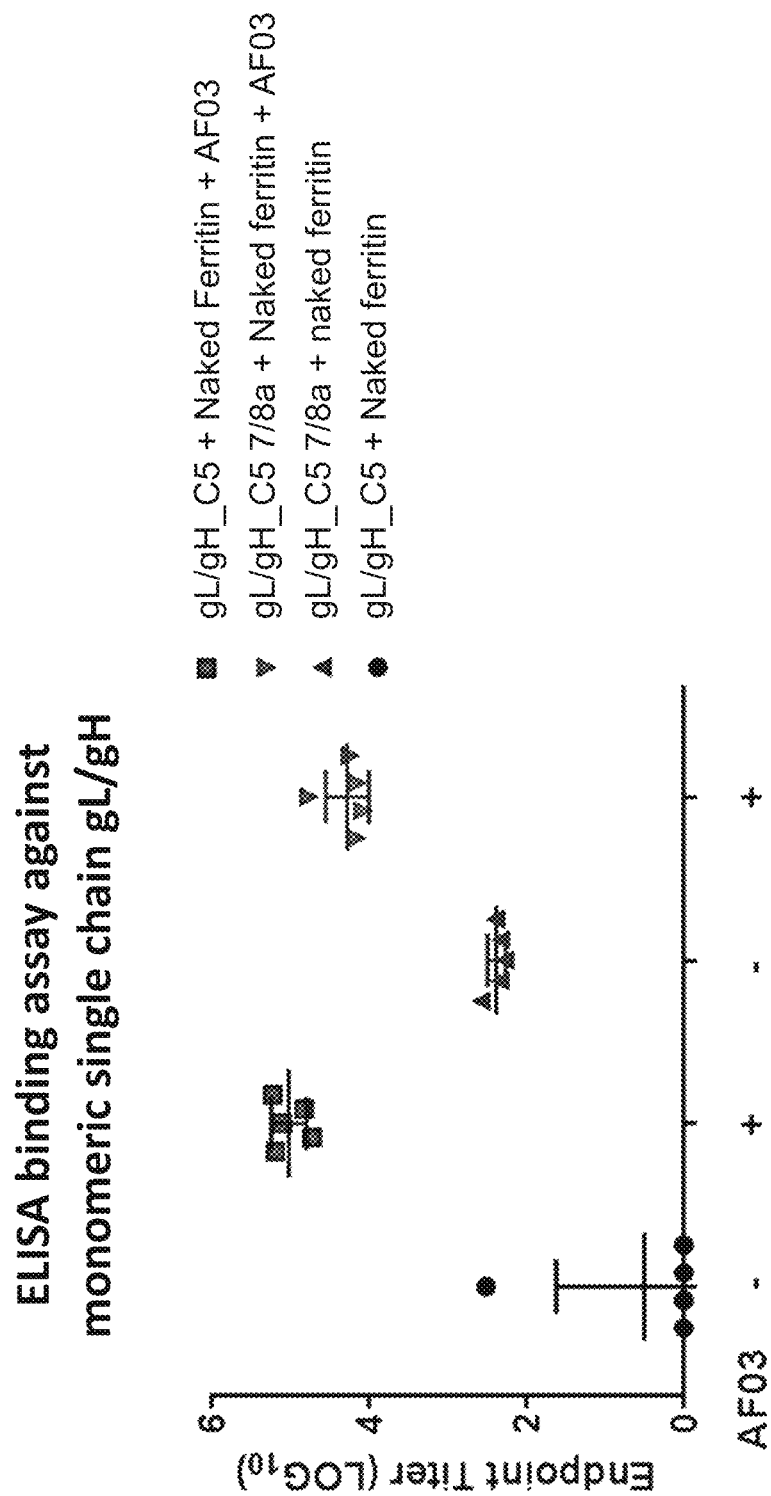

As shown in FIG. 16, nanoparticles comprising single-chain gL/gH conjugated to SM7/8a produced the greatest immune response when formulated in AF03. A robust immune response was also seen for these nanoparticles without AF03.

Figure 17:
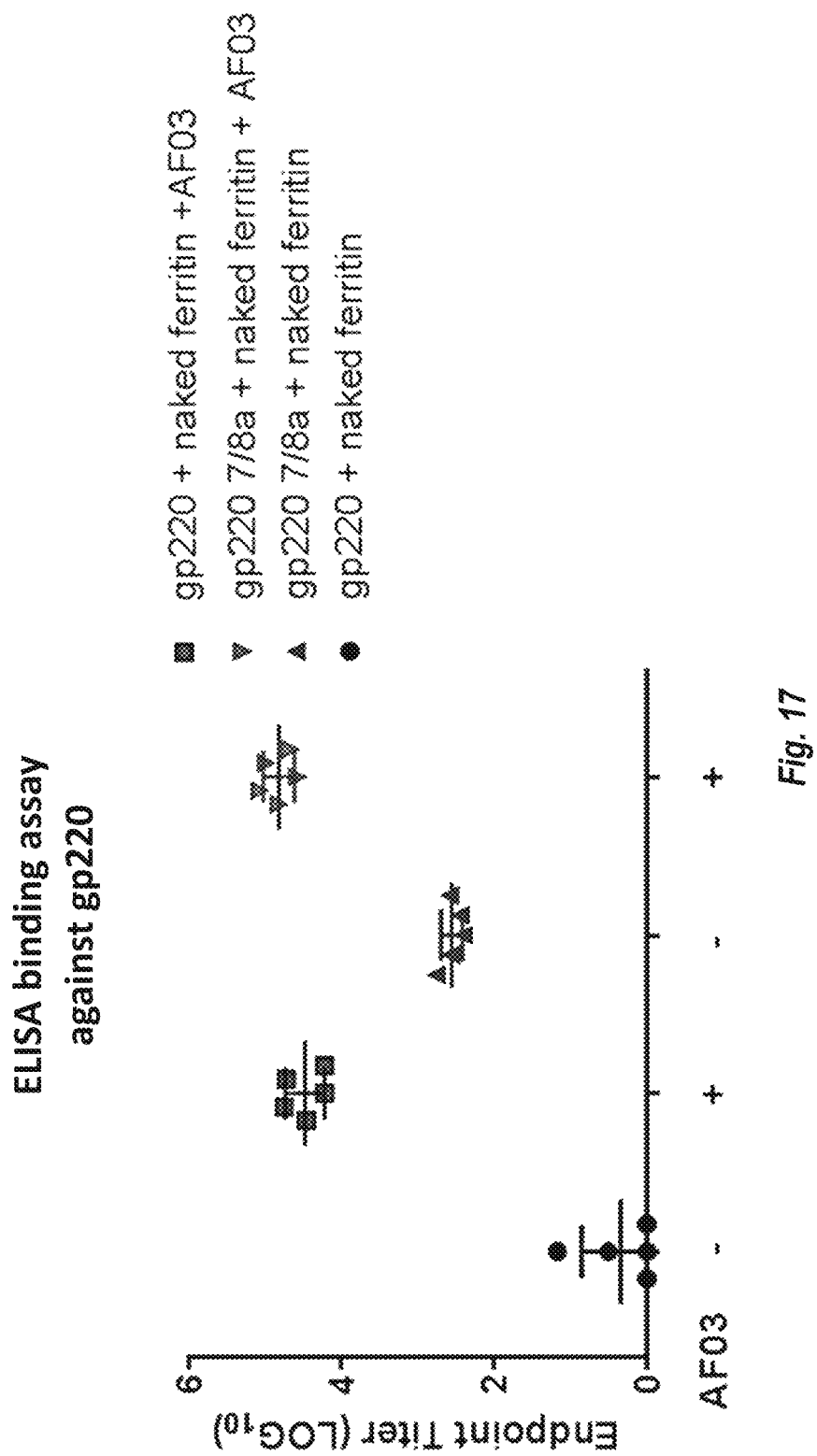

A parallel experiment was performed using gp220 nanoparticles (SEQ ID NO: 1) (with or without conjugation to SM7/8a) in place of the nanoparticles comprising single-chain gL/gH. Similar results were seen for these nanoparticles, wherein the formulation including admixed AF03 produced the most robust response, and a robust immune response was also seen for these nanoparticles without AF03 (FIG. 17).

Figure 18:
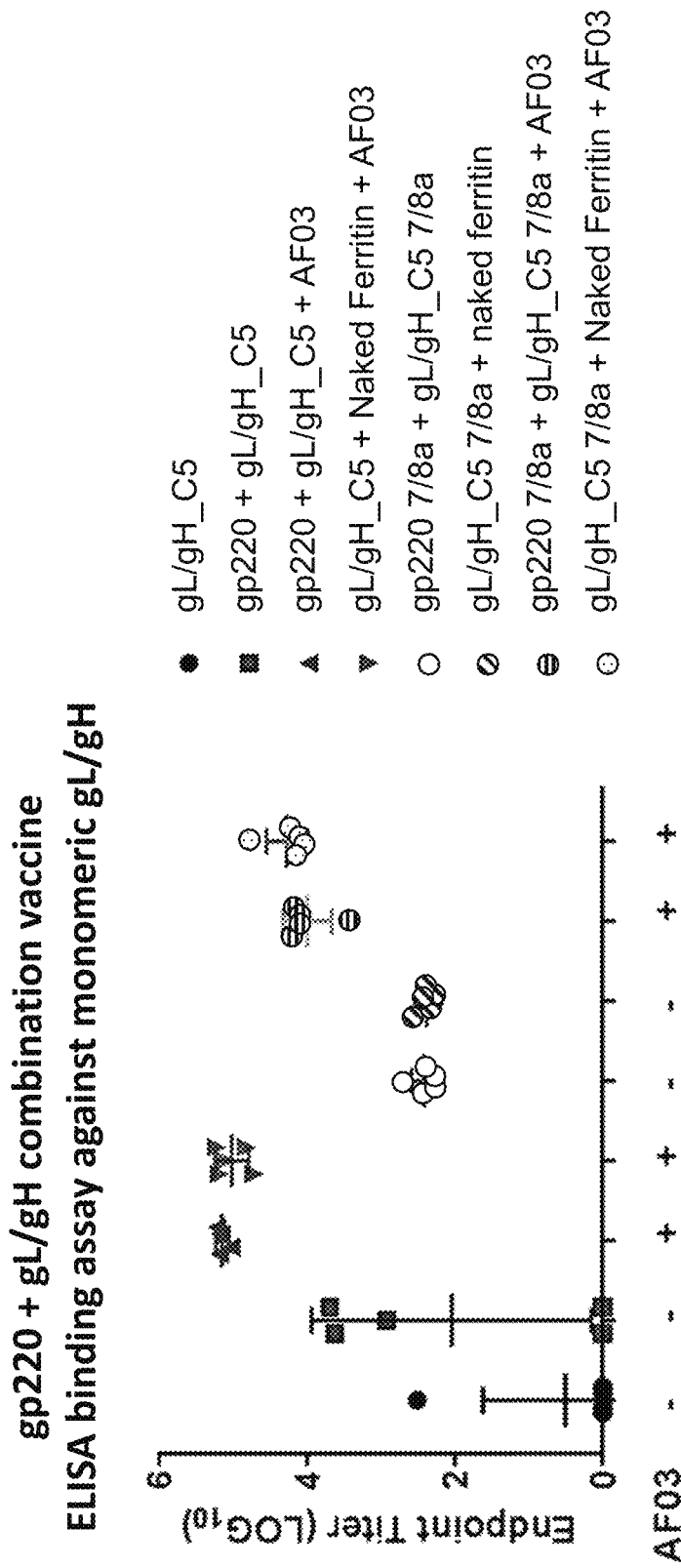
Figure 19:
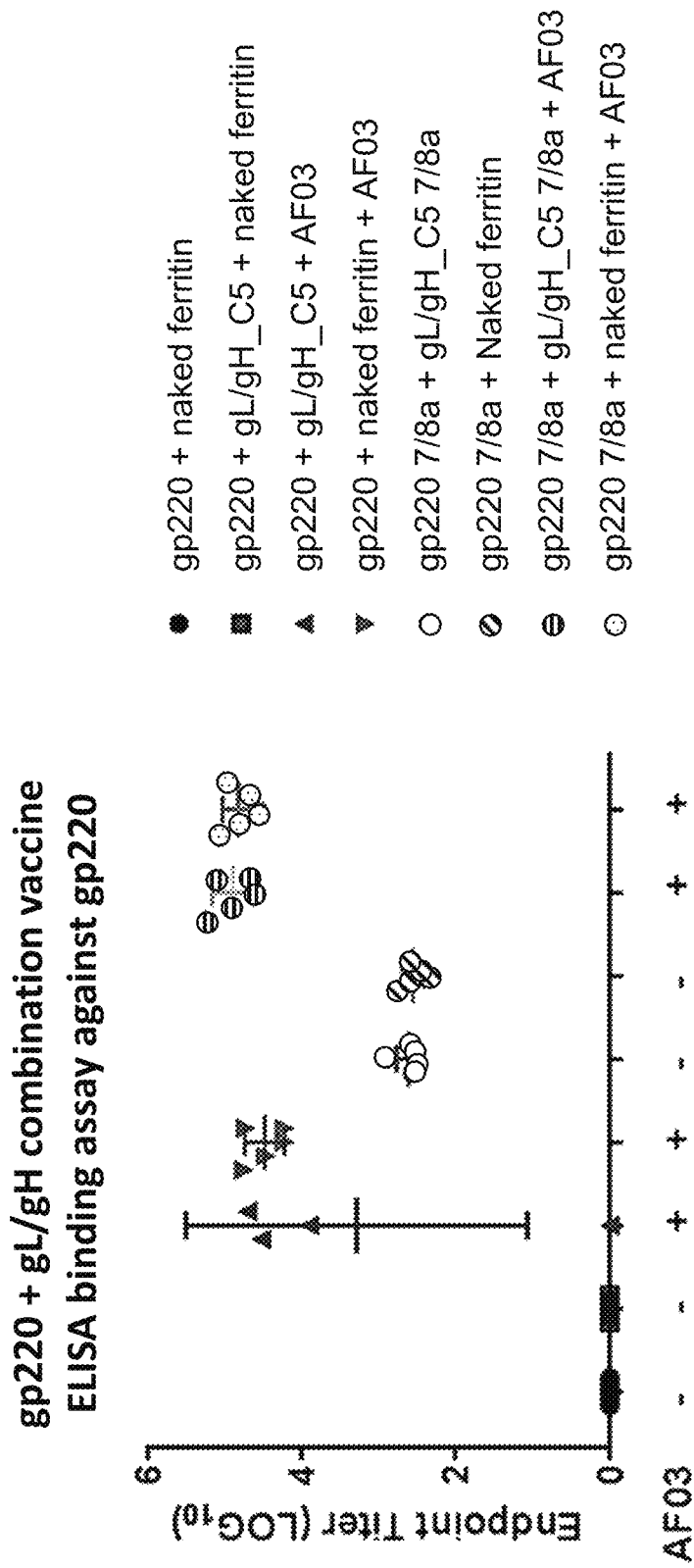

The immune response elicited by a bivalent composition comprising nanoparticles comprising single-chain gL/gH (gL/gH_C5; SEQ ID NO: 19) and nanoparticles comprising gp220 (SEQ ID NO: 1) was assessed. BALB/c mice (n=5/group) were immunized with a 3-week interval between doses. 100 µL of the nanoparticle composition containing 1 µg of each nanoparticle was administered. For mice receiving AF03 adjuvant, a 1:1 volume of AF03 was mixed with vaccine. A terminal week 13 bleed was taken for ELISA analysis. For immune responses against both single-chain gL/gH (FIG. 18) and gp220 (FIG. 19), no interference was seen due to administration of the nanoparticles in combination, as compared to administration of either nanoparticle in combination with naked ferritin.

Figure 21:
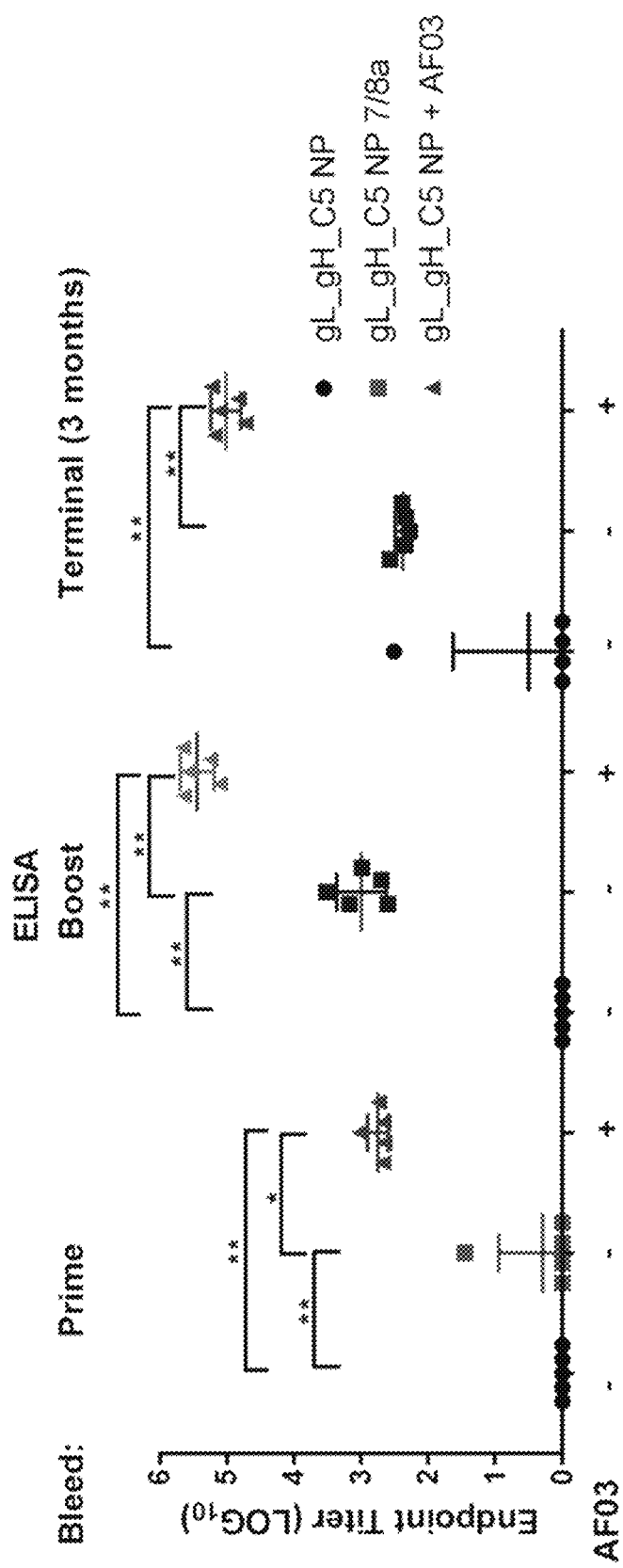
Figure 22:
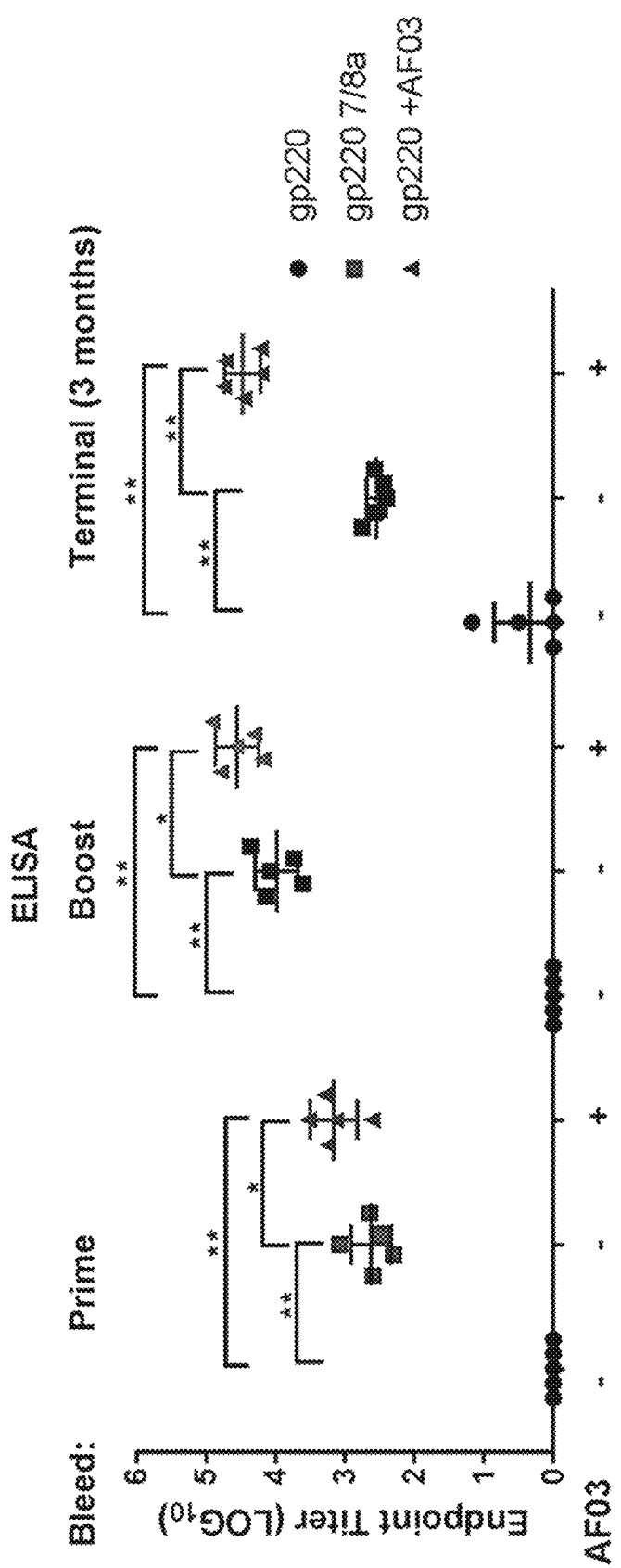

Further experiments with the gL/gH_C5 nanoparticle (SEQ ID NO: 19) confirmed that long-term immune responses were seen when the nanoparticle was conjugated to SM7/8a (7/8a) or when the nanoparticle was formulated in AF03 (FIG. 21). BALB/c mice (n=5/group) were immunized with a 3-week interval between doses. 100 µL of the nanoparticle composition containing 1 µg of nanoparticles was administered. For mice receiving AF03 adjuvant, a 1:1 volume of AF03 was mixed with vaccine. Week 2 (Prime), 5 (Boost), and 13 (Terminal) bleeds were taken for ELISA analysis. A parallel experiment was performed using gp220 nanoparticles (SEQ ID NO: 1) and a similar long-term response was also seen for gp220 nanoparticles (FIG. 22).

A different nanoparticle comprising single-chain gL/gH (gL_gH_C7: SEQ ID NO: 20) was also assessed. The gL_gH_C7 construct comprises a flexible linker between the gH polypeptide and the ferritin with a cysteine as a conjugation site for an immune-stimulatory moiety. The linker may be used with a ferritin lacking a surface-exposed cysteine (as shown in SEQ ID NO: 20). SM7/8a was conjugated to gL_gH_C7 by reducing the protein using 2 mM TCEP and then oxidizing by adding 1×PBS and using a 100 kD microspin column to remove TCEP. The SM7/8a was then incubated with the gL/gH nanoparticle. Following conjugation, excess SM7/8a was removed from the reaction via a 100 kD microspin column.

Figure 20A:
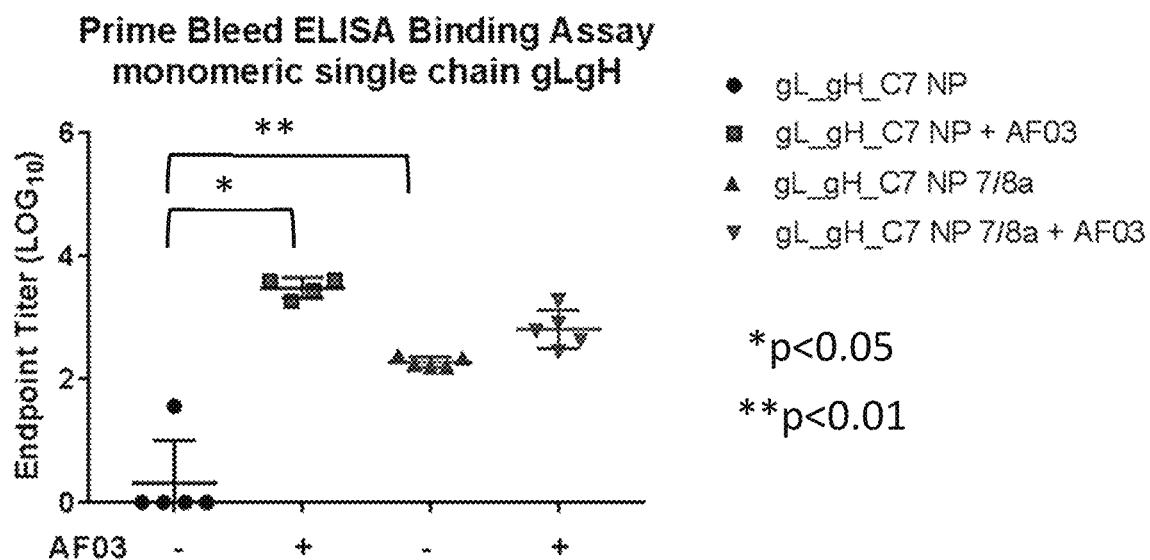
Figure 20B:
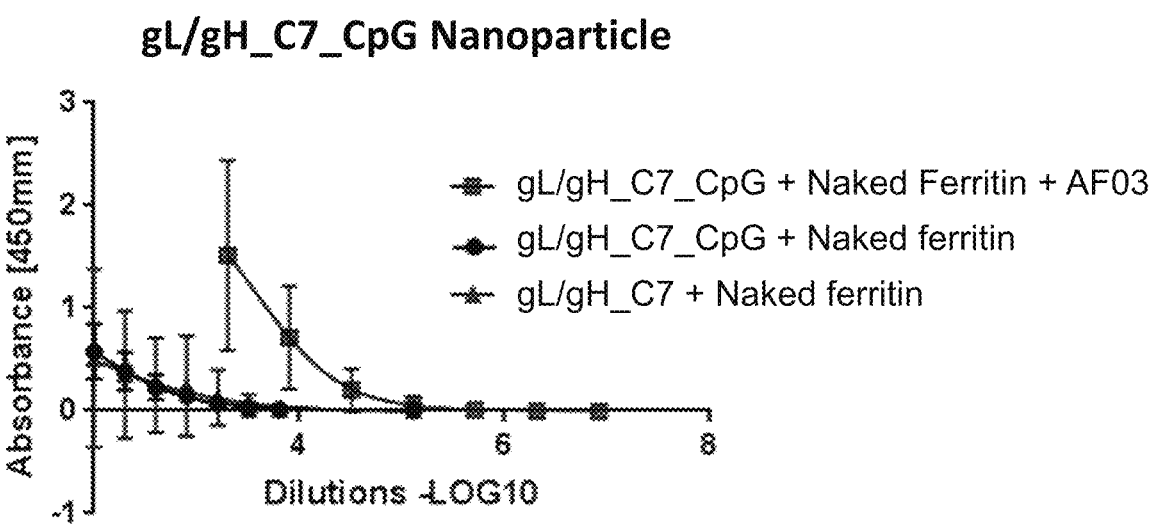
Figure 20C:
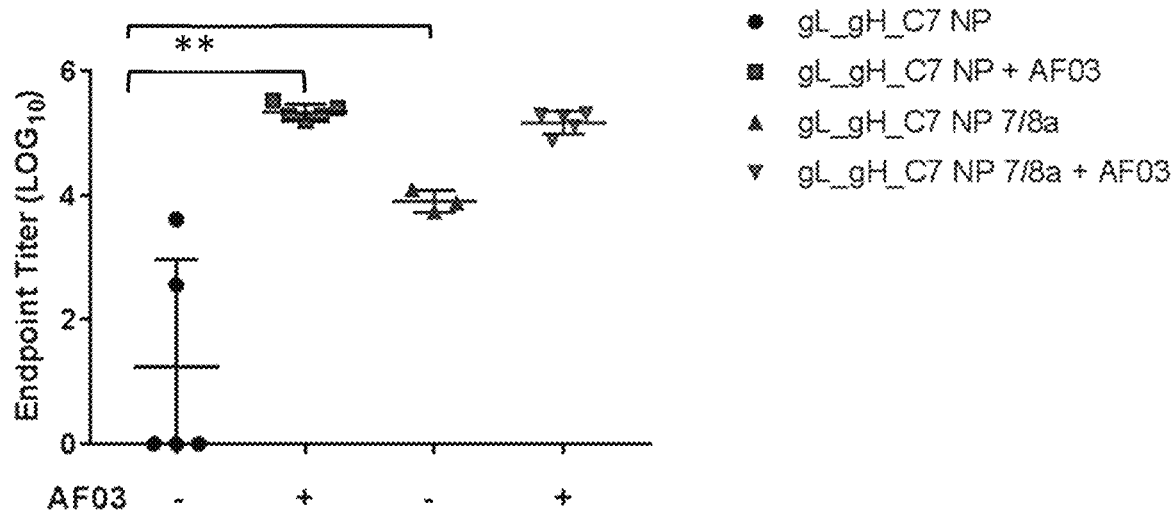
Figure 20D:
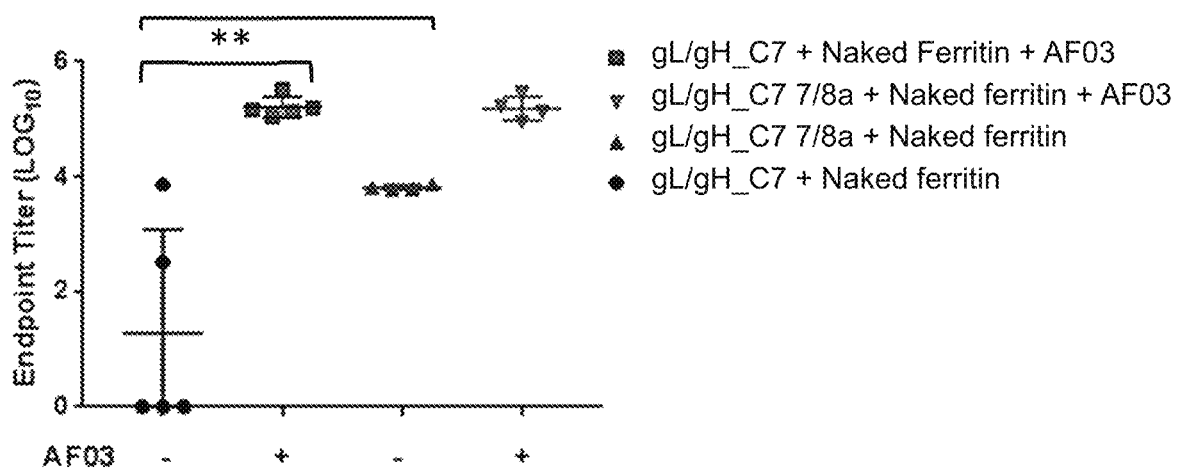

Mice received 1 µg of these gL/gH nanoparticles, either conjugated to 7/8a or unconjugated, plus 1 µg of naked ferritin. 100 µL of the nanoparticle composition containing 1 µg of nanoparticles was administered. BALB/c mice (n=5/group) were immunized with a 3-week interval between doses. For mice receiving AF03 adjuvant, a 1:1 volume of AF03 was mixed with the nanoparticle composition. Week 2 (prime), 5 (booster), and 13 (terminal) bleeds were taken for ELISA analysis. These nanoparticles elicited immune responses when formulated in AF03 or when conjugated to SM7/8a as measured by ELISA endpoint titer at prime bleed (FIG. 20A). Similar results were seen with booster bleed (FIG. 20C) or terminal bleed (FIG. 20D) samples. These nanoparticles were also conjugated to a CpG oligodeoxynucleotide, and administered in the same way. Results for the CpG conjugate were similar to unconjugated nanoparticles (FIG. 20B) at week 5.

5. Characterization of Nanoparticles Comprising *Trichoplusia ni* Ferritin

Nanoparticles were also developed comprising *Trichoplusia ni* ferritin and gp220 and/or gL/gH polypeptides. *Trichoplusia ni* ferritin nanoparticles contain heavy and light chains self-assembled at a 1:1 ratio. It was found that combining one non-ferritin polypeptide with the light chain and another non-ferritin polypeptide on the heavy chain allowed presentation of two distinct polypeptides on the surface of individual nanoparticles. Thus, for example, a self-assembled *Trichoplusia ni* ferritin nanoparticle could present both gp220 and gL/gH.

Figure 23A:
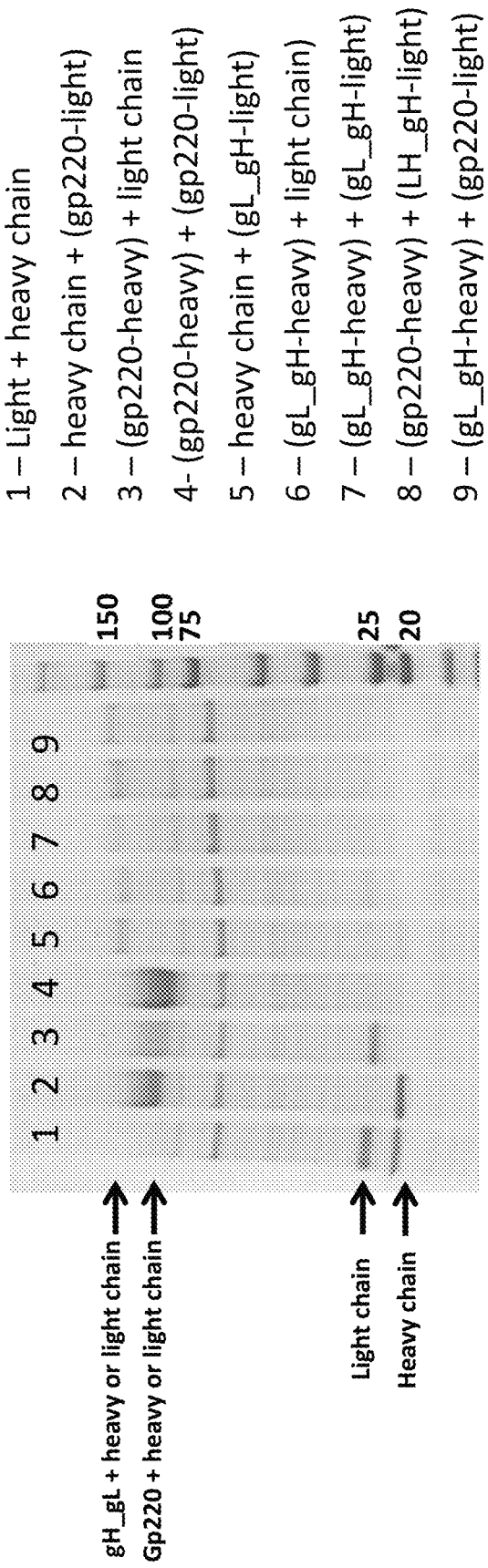
Figure 23B:
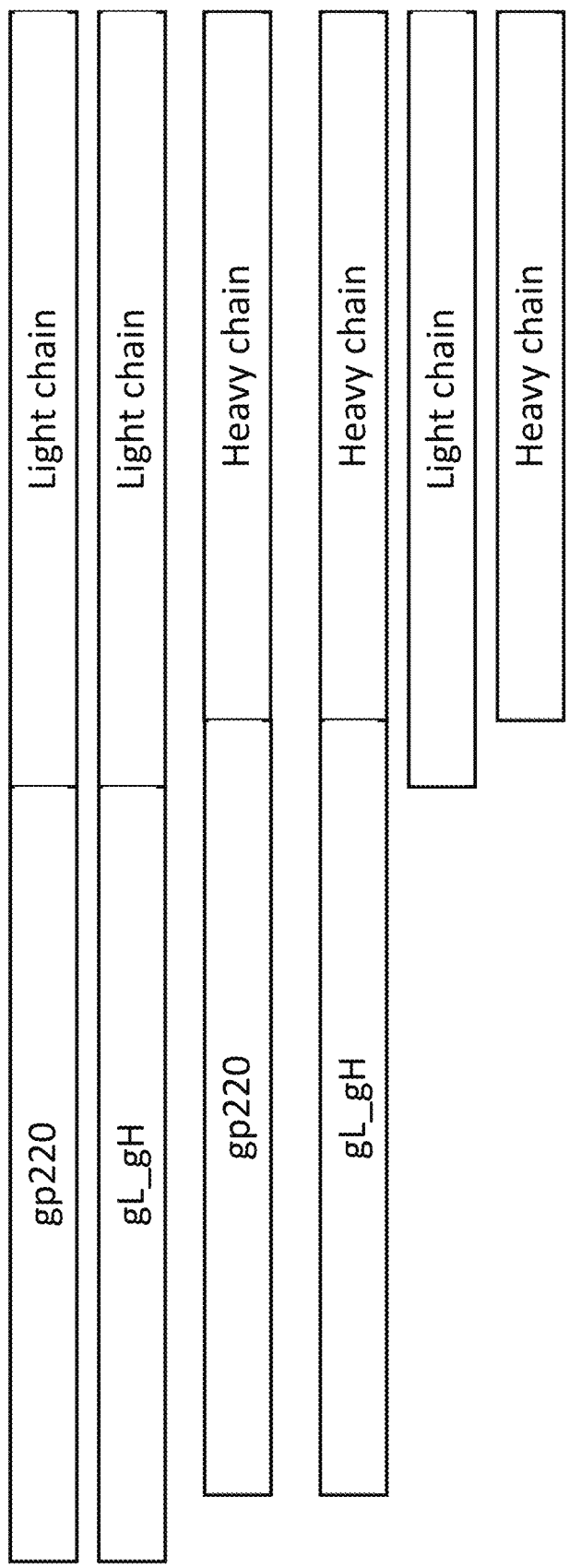

A *Trichoplusia ni* ferritin nanoparticle was produced and purified with the heavy chain fused to either gp220 (SEQ ID NO: 24) or single-chain gL/gH (SEQ ID NO: 25) and the light chain fused to either gp220 (SEQ ID NO: 26) or single-chain gL/gH (SEQ ID NO: 27) (constructs illustrated in FIG. 23B and visualized by Coomassie gel staining in FIG. 23A, showing the expected increase in molecular weight relative to light and heavy chains alone). The combination of a light chain and a heavy chain fused to gL/gH and gp220, respectively or vice versa, generated an individual multivalent nanoparticle that can present two different EBV polypeptides.

Figure 24A:
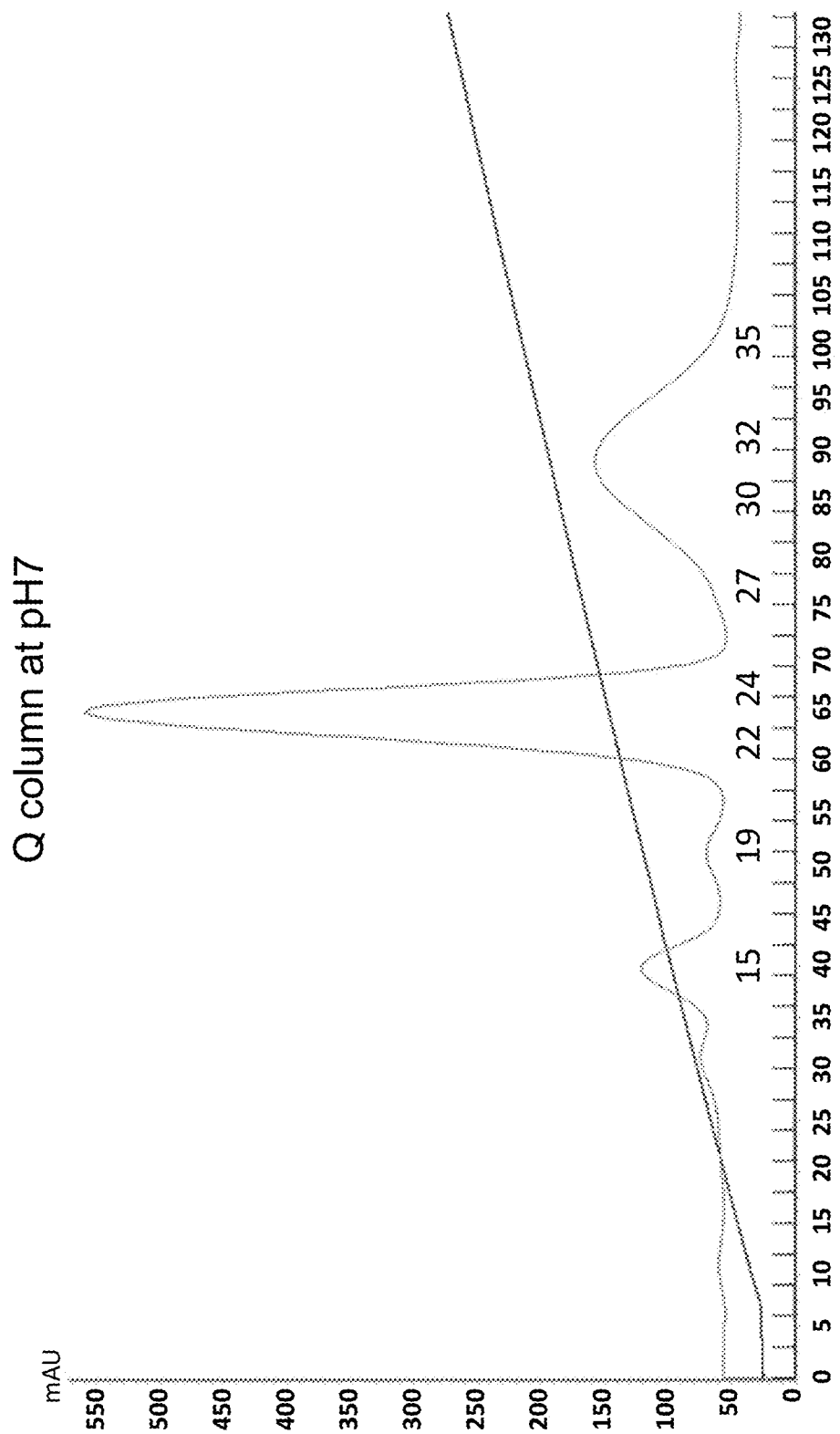
Figure 24B:
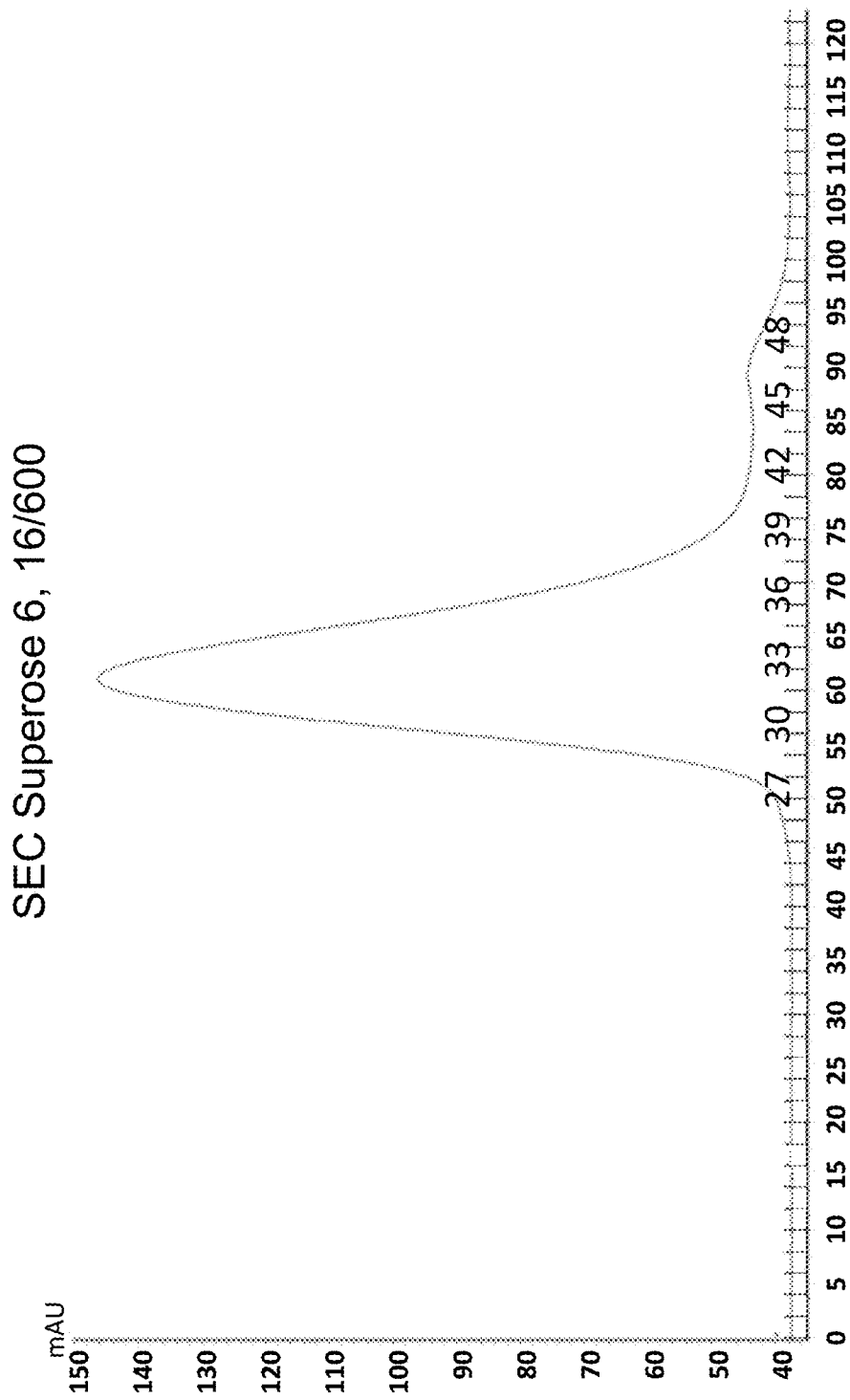
Figure 25A:
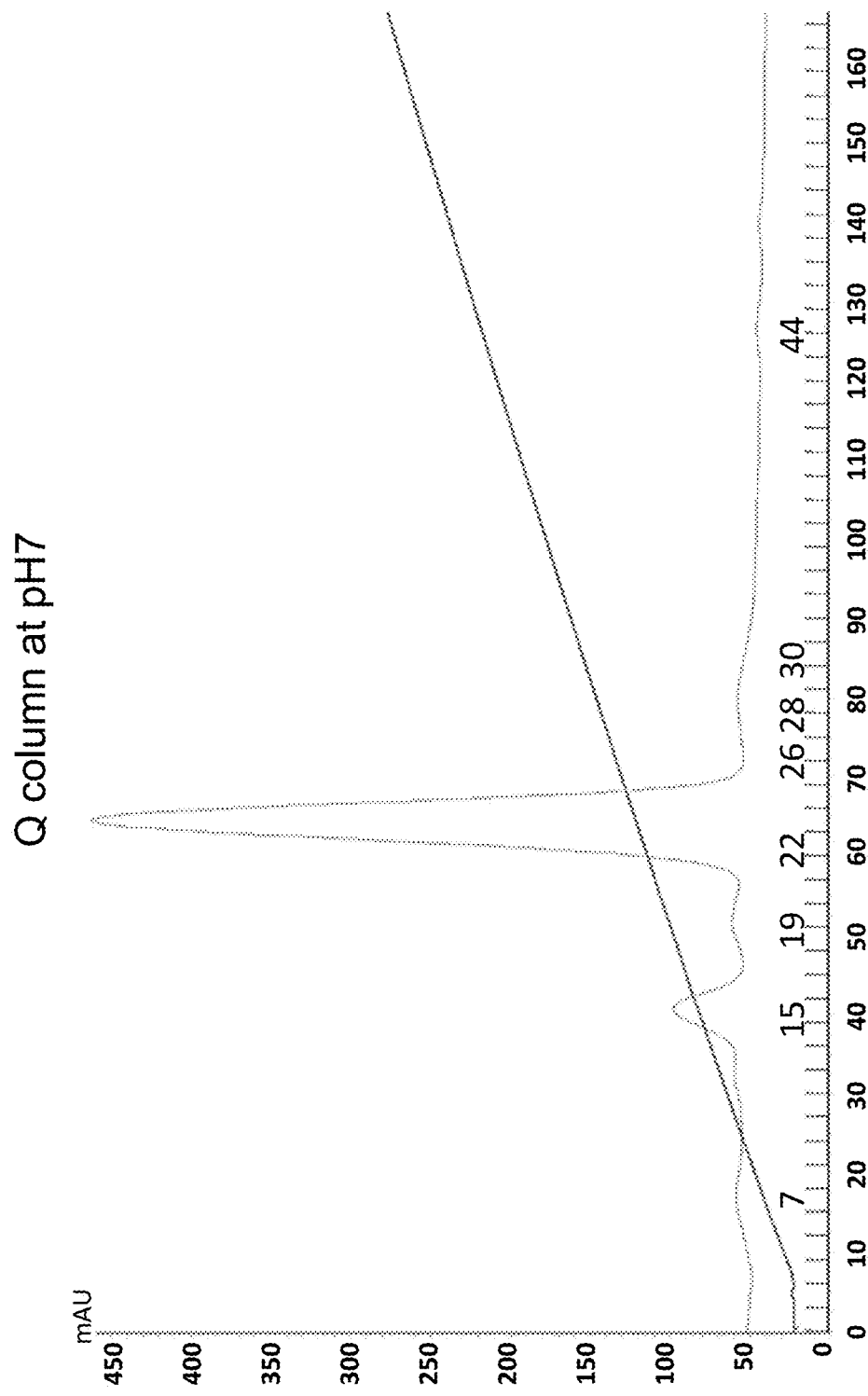
Figure 25B:
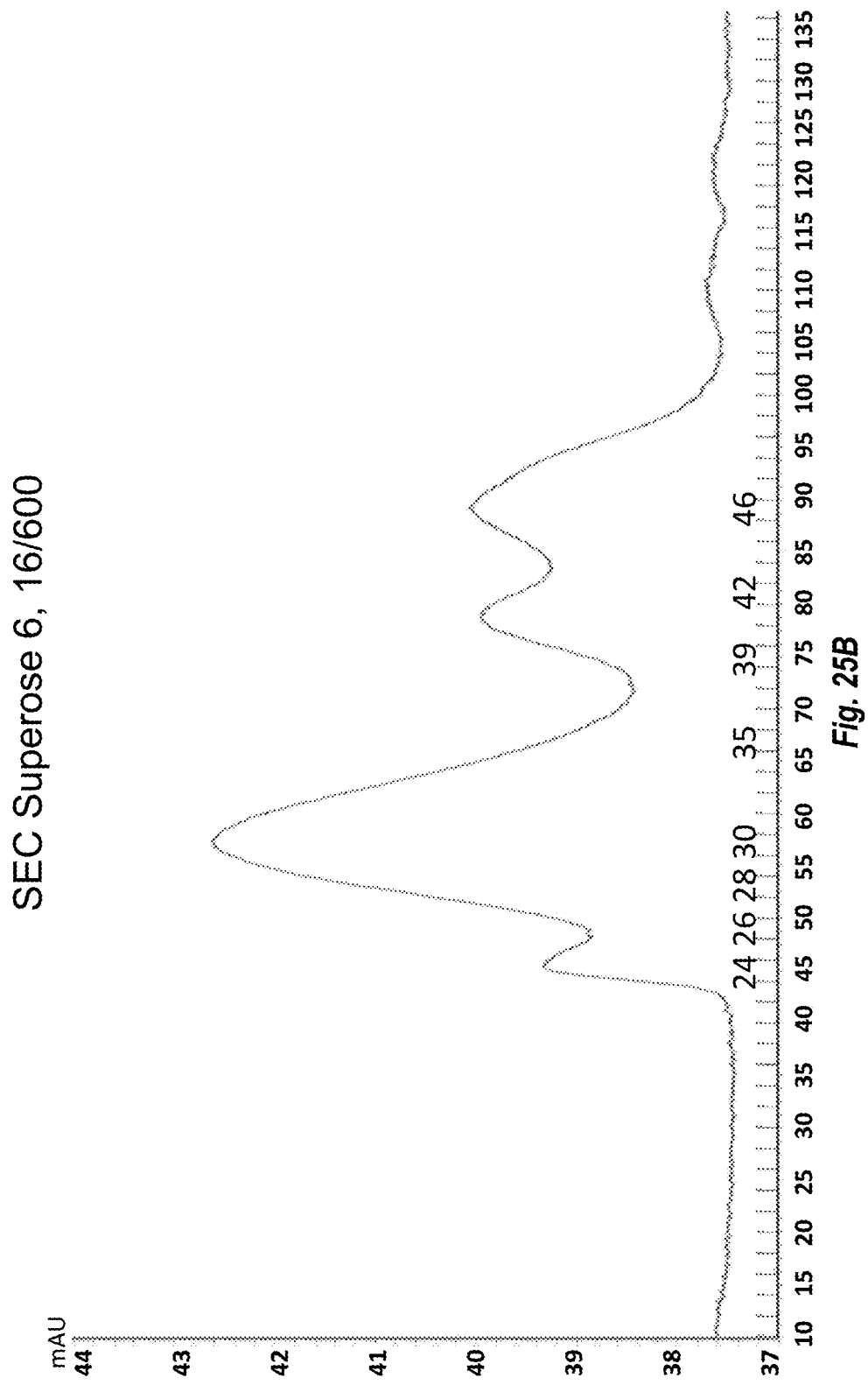
Figure 26D:
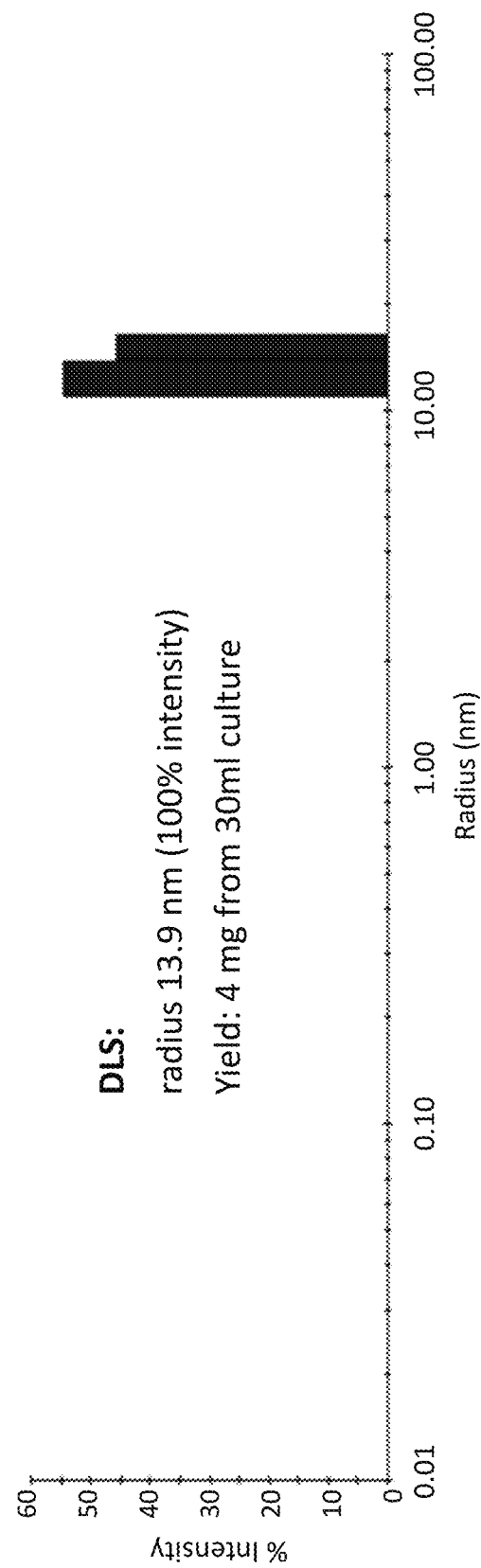
Figure 26H:
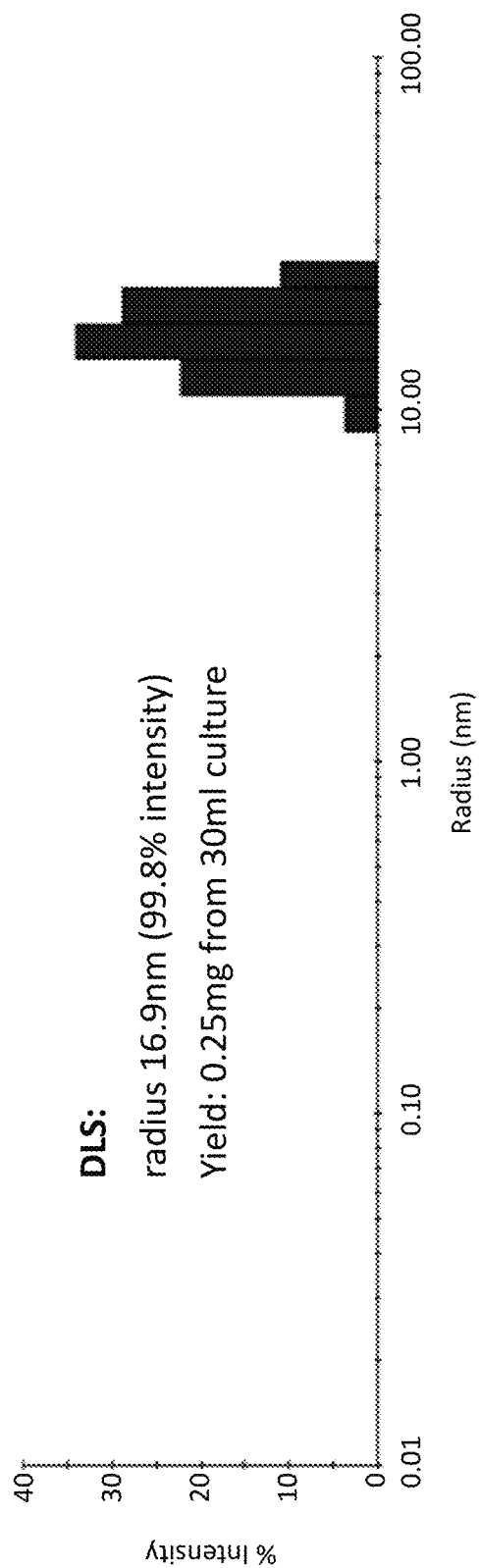
Figure 27B:
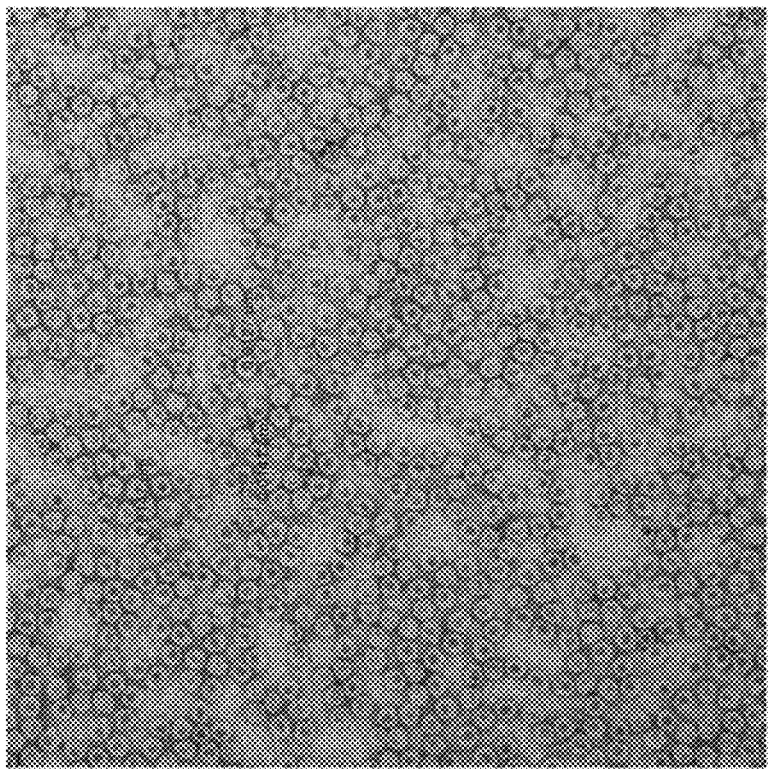
Figure 27A:
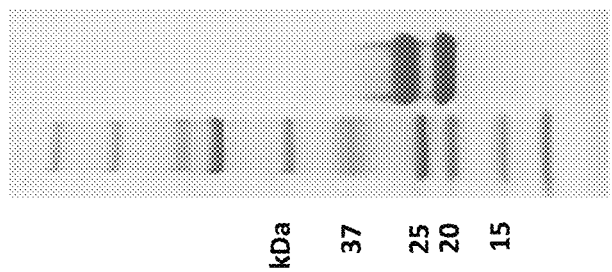
Figure 27C:
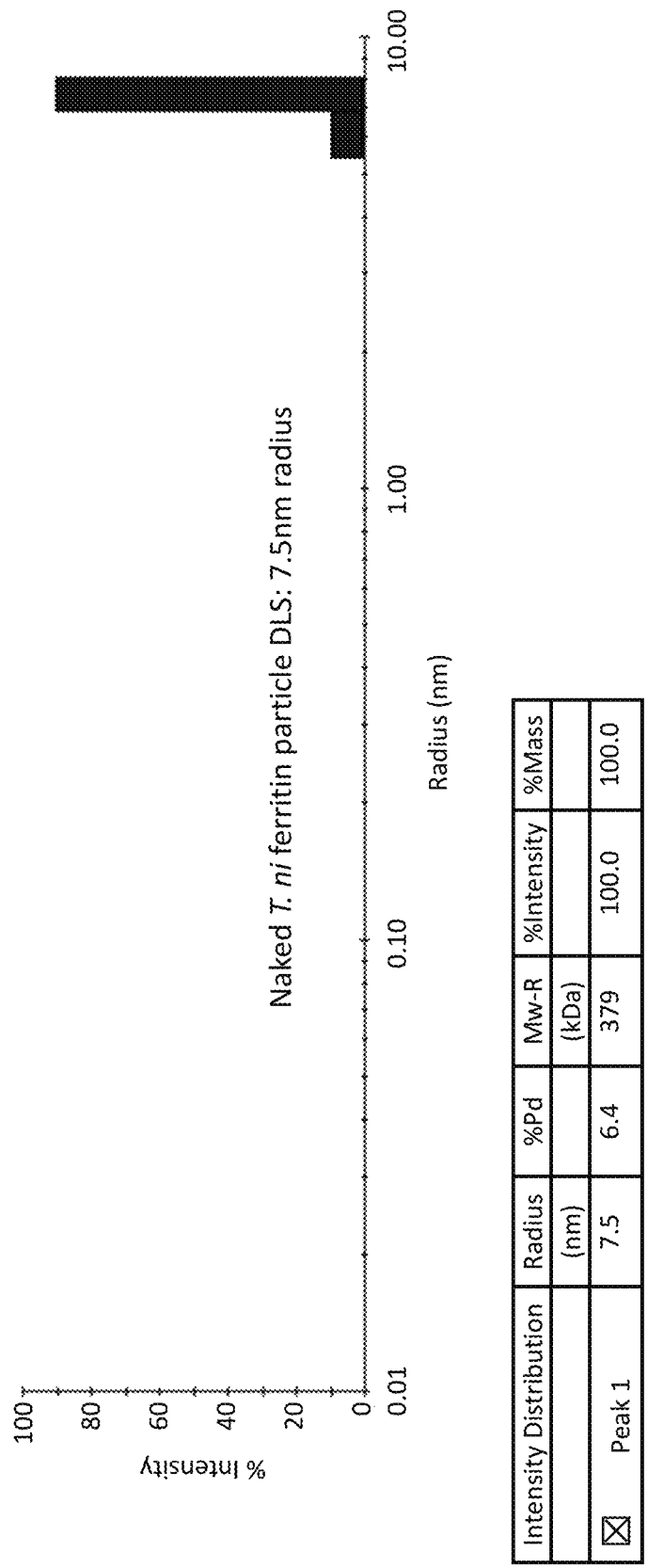
Figure 28A:
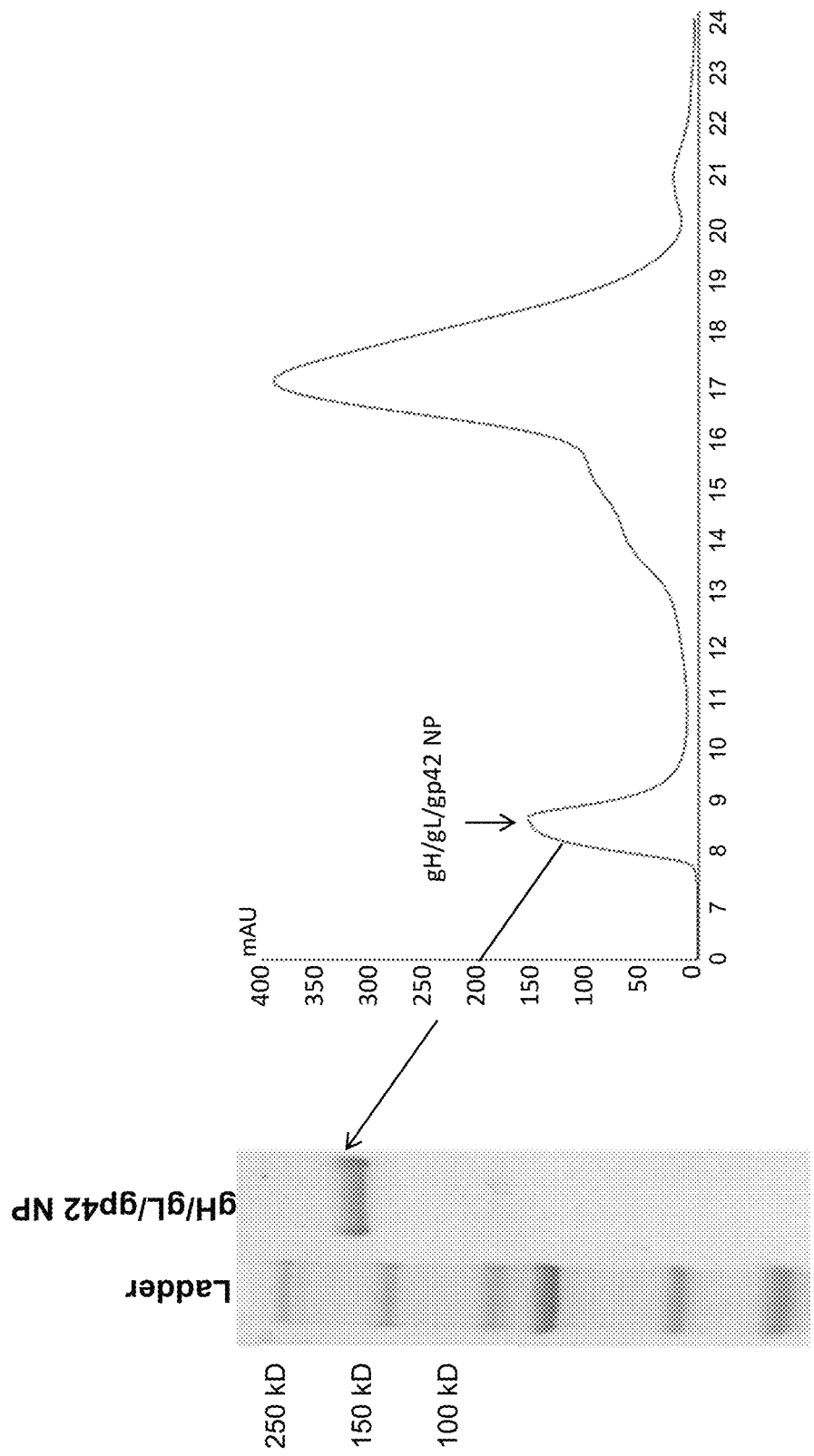
Figure 28B:
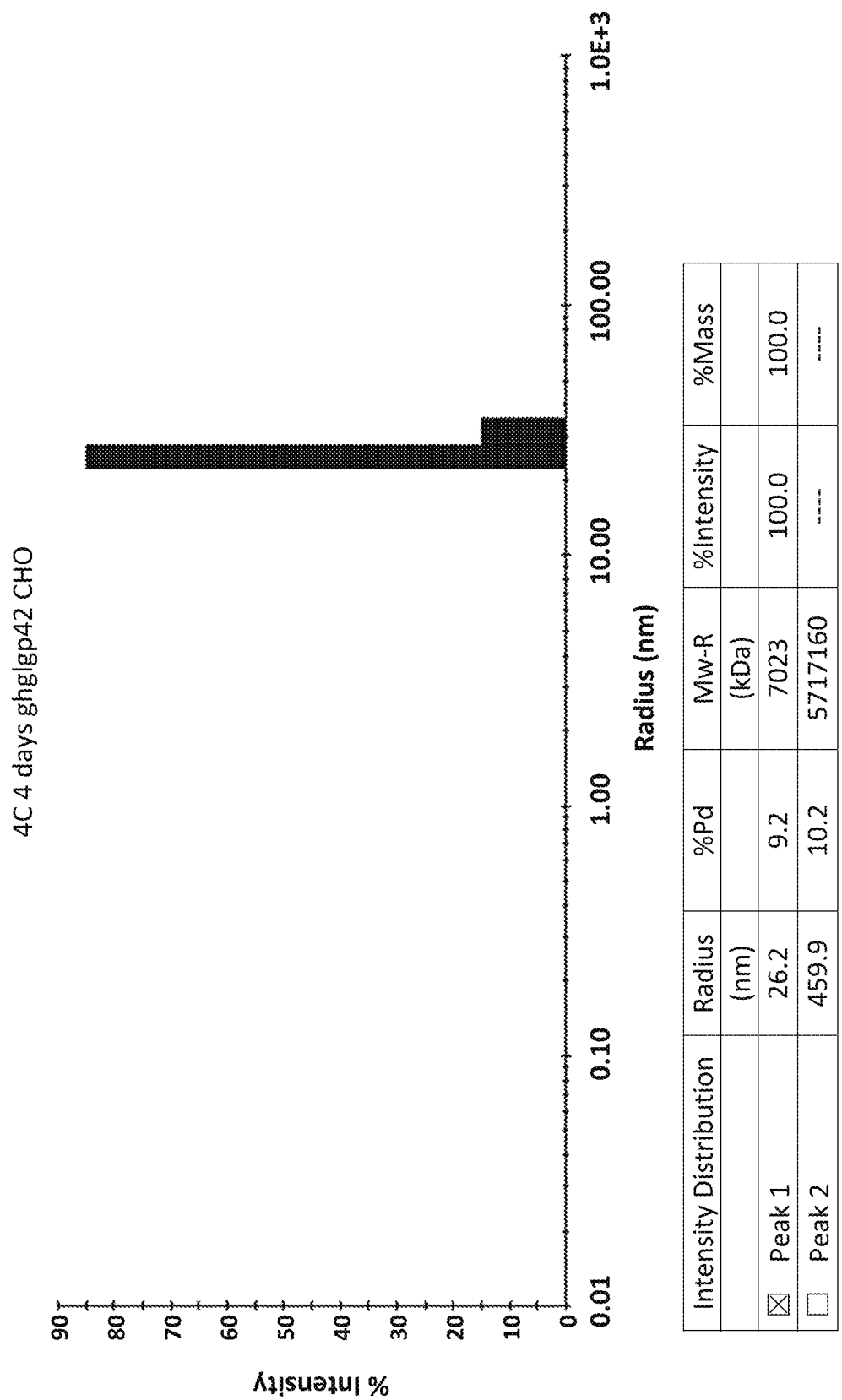

Two *T. ni* ferritin nanoparticles with either only gp220 in both the heavy and light chains (as shown in FIG. 24E) or gp220 in the heavy chain and gH_gL in the light chain (as shown in FIG. 25E) were also produced. The purification followed two steps: The first purification step was an ion exchange chromatographic step (Q column, see FIG. 24A with Coomassie results in FIG. 24C and FIG. 25A with Coomassie results shown in FIG. 25C). This step was followed by size exclusion chromatography (see FIG. 24B with Coomassie results in FIGS. 24D and 25B with Coomassie results in FIG. 25D).

Nanoparticles comprising *Trichoplusia ni* light and heavy chain fused to gp220 (SEQ ID NOs: 24 and 26; illustrated in FIG. 26B) showed a profile consistent with formation of a nanoparticle comprising the heterologous gp220 polypeptide, based on Coomassie staining (FIG. 26A), an increase in DLS radius (FIG. 26D) relative to naked *T ni* ferritin (FIG. 27C), and EM analysis (FIG. 26C) in which additional peripheral density around the nanoparticle core appeared relative to the naked nanoparticles (FIG. 27B). Similar results indicative of the presence of heterologous gL/gH and gp220 polypeptides in the nanoparticles were seen for SEQ ID NOs: 24 and 27 (*Trichoplusia ni* light chains with a gL/gH polypeptide and heavy chains with a gp220 polypeptide; see FIGS. 26E-26H for visualization by Coomassie staining, an illustration of the construct, an electron micrograph, and characterization by DLS, respectively). For comparison, FIGS. 27A-27C show Coomassie staining (FIG. 27A), DLS radius (FIG. 27B), and EM analysis (FIG. 27C) for naked *T. ni* ferritin (i.e., not conjugated to any polypeptide).

Thus, use of *T. ni* ferritin allows presentation of 2 polypeptides on individual nanoparticles.

6. gH/gL/Gp42 Constructs

A cartoon of a single-chain construct of gH/gL/gp42 fused to ferritin (as in each of SEQ ID NOs: 227-231 and 241-242) is shown in FIG. 35A. The fusion between each protein is via a flexible amino acid linker or a rigid amino acid linker. The single-chain gH/gL/gp42 molecule provides a 1:1:1 ratio of heterotrimer formation on the nanoparticle.

The crystal structure of a gH/gL/gp42 His-tagged fusion (SEQ ID NO: 226) has been solved to show that the single-chain gH/gL/gp42 can adopt a heterotrimer conformation similar to wild-type gH, gL, and gp42 proteins found in nature (FIGS. 34 and 35B). In FIGS. 34 and 35B, Gp42 (in dark gray and indicated with arrows in FIG. 34) interacts with the gH/gL heterodimer. FIG. 35C is a model of how this single-chain gH/gL/gp42 heterotrimer fused to ferritin is displayed on a nanoparticle. There are twenty-four copies of the single-chain gH/gL/gp42 that will be displayed on a single nanoparticle.

A gH/gL/gp42 NP construct (SEQ ID NO: 227) was expressed in 293 expi cells and purified (FIG. 28A). gH/gL/gp42 NP purified from CHO pools had a dynamic light scattering radius of around 26.2 nm (FIG. 28B).

The immune responses elicited by a monovalent (gH/gL/gp42 NP+naked ferritin nanoparticle) or bivalent (gH/gL/gp42 NP+gp220 NP) composition were assessed. The gH/gL/gp42 NP had the sequence of SEQ ID NO: 227 and the gp220 NP had the sequence of SEQ ID NO: 1. BALB/c mice (n=5/group) were immunized with a 3-week interval between doses. 100 μL of the nanoparticle composition containing 1 μg of each nanoparticle was administered with an AF03 adjuvant (1:1 volume of AF03 mixed with vaccine). The boost indicates the sera collected at week 5 after the second immunization. EBV viral neutralizing assay analysis in B cells (FIG. 29A) and in epithelial cells (FIG. 29B) was done using sera collected at week 5 from the mice. No interference was seen due to administration of the nanoparticles in bivalent formulation, as compared to administration of the monovalent form (gH/gL/gp42 with naked ferritin).

Bivalent immunization of ferrets was performed using compositions comprising single-chain gL/gH nanoparticles (gL_gH_C137A_bfpFerr Nanoparticle N19Q/C31S/S111C [SEQ ID NO: 22]) and gp220 nanoparticles (SEQ ID NO: 1) in the presence of adjuvant AF03 (FIGS. 30A-30B) or gL/gH/gp42 NP (SEQ ID NO: 227) and gp220 nanoparticles (SEQ ID NO: 1) in the presence of adjuvant AF03 (FIGS. 30C-30E). Inj. 1=injection one (sera collected from 6 ferrets at week 2 post Inj. 1). Inj. 2=injection 2 (sera collected from 6 ferrets at week 2 post Inj. 2). An ELISA binding assay measured endpoint binding titers against the antigens indicated in FIGS. 30A-30E. FIGS. 30F-G shows an EBV viral neutralizing assay (in B cells and epithelial cells, respectively) of sera from ferrets receiving bivalent vaccination of gL/gH/gp42 NP (SEQ ID NO: 227) and gp220 nanoparticles (SEQ ID NO: 1) in the presence of adjuvant AF03. Prime=Inj. 1 and Boost=Inj. 2.

gH/gL/gp42_NP_C12 (SEQ ID NO: 228) was expressed and purified using Superose 6 size exclusion chromatography (FIG. 31A). A dynamic light scattering analysis of the sample in FIG. 31A showed a particle size radius of 20.6 nm (FIG. 31B).

gH/gL/gp42_NP_C13 (SEQ ID NO: 229) was expressed and purified using Superose 6 size exclusion chromatography (FIG. 32A). A dynamic light scattering analysis of the sample in FIG. 32A showed a particle size radius of 17.1 nm (FIG. 32B).

gH/gL/gp42_NP_C14 (SEQ ID NO: 230) was expressed and purified using Superose 6 size exclusion chromatography (FIG. 33A). A dynamic light scattering analysis of the sample in FIG. 33A showed a particle size radius of 16.9 nm (FIG. 33B).

FIG. 35D shows the purification of SEQ ID NO: 227 after expression in 293Expi cells. A denaturing SDS coomassie gel shows the gH/gL/gp42 fused to ferritin to be above 150 kD with glycosylation. Negative stain electron microscopy analysis of the purified product shows the single-chain gH/gL/gp42 fused to ferritin can successfully form nanoparticles displaying the gH/gL/gp42 antigens on the surface (FIG. 35E). Through temperature, oxidation, and/or deamidation stress test on days 0, 3, 7, or 14, potential labile sequences have been identified via sequence analysis or mass spectrometry for the single-chain gH/gL/gp42 nanoparticle of SEQ ID NO: 227. To improve vaccine stability, expression, and/or immunogenicity of this vaccine construct, conservative amino acid substitution mutations will be made to SEQ ID NO: 227 in different combinations, particularly at the sites listed in Table 1. Conservative amino acid mutations at the respective location in the particular gene will also be tested in SEQ ID NOs: 228-230, which differ from SEQ ID NOs. 227 only by the linker sequence that fuses the C-terminus of gp42 with the N-terminus of the ferritin sequence.

We claim:

1. An antigenic single-chain EBV polypeptide comprising an Epstein Barr Virus (EBV) gL polypeptide; an EBV gH polypeptide; an EBV gp42 polypeptide; and ferritin, wherein a linker having a length of at least 15 amino acids separates the EBV gL polypeptide and the EBV gH polypeptide, wherein the antigenic single-chain EBV polypeptide comprises a sequence with at least 80% identity to any one of SEQ ID NOs: 226-231 or 241-242, optionally lacking the leader sequence.

2. The antigenic single-chain EBV polypeptide of claim 1, wherein the gH polypeptide is C-terminal to the gL polypeptide, and wherein the gp42 polypeptide is C-terminal to the gH polypeptide.

3. The antigenic single-chain EBV polypeptide of claim 1, wherein the gp42 polypeptide comprises an amino acid sequence of SEQ ID NO: 239 or 240.

4. The antigenic single-chain EBV polypeptide of claim 1, wherein a linker having a length of at least 15 amino acids separates the EBV gH polypeptide and the EBV gp42 polypeptide, optionally wherein the linker comprises an amino acid sequence of SEQ ID NO: 234.

5. The antigenic single-chain EBV polypeptide or composition of claim 1, wherein the linker has a length of 15 to 60 amino acids.

6. The antigenic single-chain EBV polypeptide of claim 1, wherein the EBV polypeptide comprises an amino acid sequence of SEQ ID NO: 36 or SEQ ID NO: 37, or SEQ ID NO: 3S.

7. The antigenic single-chain EBV polypeptide of claim 1, wherein the linker comprises an amino acid sequence of SEQ ID NO: 30.

8. The antigenic single-chain EBV polypeptide of claim 1, wherein the antigenic EBV polypeptide comprises a sequence of amino acids 23-1078 of SEQ ID NO: 226.

9. The antigenic single-chain EBV polypeptide of claim 1, wherein the antigenic single-chain EBV polypeptide comprises a sequence with at least 90% identity to SEQ ID NO: 242.

10. A composition comprising the antigenic single-chain EBV polypeptide(s) of claim 1 and a pharmaceutically acceptable carrier.

11. A method of eliciting an immune response to EBV or protecting a subject against infection with EBV comprising administering the antigenic single-chain EBV polypeptide of claim 1 to a human subject.

12. A nucleic acid encoding the antigenic single-chain EBV polypeptide of claim 1, wherein the nucleic acid is an mRNA or DNA.

13. The antigenic single-chain EBV polypeptide of claim 1, further comprising a ferritin polypeptide, wherein the ferritin polypeptide comprises a mutation replacing a surface-exposed amino acid with a cysteine.

14. The antigenic single-chain EBV polypeptide of claim 13, wherein the ferritin polypeptide comprises one or more of E12C, S26C, S72C, A75C, K79C, S100C, and S111C mutations of H. pylori ferritin.

15. The antigenic single-chain EBV polypeptide of claim 1, further comprising a ferritin polypeptide, wherein the ferritin polypeptide comprises a mutation replacing a surface-exposed asparagine with a non-asparagine amino acid, optionally wherein the asparagine is at position 19 of H. pylori ferritin.

16. The antigenic single-chain EBV polypeptide of claim 1, further comprising a ferritin polypeptide, wherein the ferritin comprises a mutation replacing an internal cysteine with a non-cysteine amino acid, optionally wherein the internal cysteine is at position 31 of H. pylori ferritin.

17. The antigenic single-chain EBV polypeptide of claim 2, wherein each polypeptide is separated by a linker.

* * * * *

UNITED STATES PATENT AND TRADEMARK OFFICE
CERTIFICATE OF CORRECTION

| | | |
|---|---|---|
| PATENT NO. | : 11,617,780 B2 | Page 1 of 1 |
| APPLICATION NO. | : 17/061146 | |
| DATED | : April 4, 2023 | |
| INVENTOR(S) | : Gary J. Nabel et al. | |

It is certified that error appears in the above-identified patent and that said Letters Patent is hereby corrected as shown below:

In the Claims

In Claim 6, Column 349, Lines 48-49, "sequence of SEQ ID NO: 36 or SEQ ID NO: 37, or SEQ ID NO: 3S." should read --sequence of SEQ ID NO: 36 or SEQ ID NO: 37.--

Signed and Sealed this
Twenty-seventh Day of June, 2023

*Katherine Kelly Vidal*

Katherine Kelly Vidal
*Director of the United States Patent and Trademark Office*